US012797601B2

(12) United States Patent
Tuval et al.

(10) Patent No.: US 12,797,601 B2
(45) Date of Patent: Nov. 17, 2026

(54) THRUST BEARING FOR BLOOD PUMPS

(71) Applicant: MAGENTA MEDICAL LTD, Kadima (IL)

(72) Inventors: Yosi Tuval, Even Yehuda (IL); Gad Lubinsky, Ein Vered (IL); Yuri Sudin, Modiin-Makkabim-Reut (IL); Avi Rozenfeld, Haifa (IL); Shaul Mustacchi, Rosh Haayin (IL); Ran Tamir, Ramat Gan (IL)

(73) Assignee: MAGENTA MEDICAL LTD, Kadima (IL)

( * ) Notice: Subject to any disclaimer, the term of this patent is extended or adjusted under 35 U.S.C. 154(b) by 264 days.

(21) Appl. No.: 18/639,087

(22) Filed: Apr. 18, 2024

(65) Prior Publication Data

US 2024/0359000 A1 Oct. 31, 2024

Related U.S. Application Data

(63) Continuation of application No. PCT/IB2023/059141, filed on Sep. 14, 2023.
(Continued)

(51) Int. Cl.
*A61M 60/17* (2021.01)
*A61M 60/13* (2021.01)
(Continued)

(52) U.S. Cl.
CPC .......... *A61M 60/178* (2021.01); *A61M 60/13* (2021.01); *A61M 60/139* (2021.01);
(Continued)

(58) Field of Classification Search
CPC .... A61L 29/02; F16C 1/02; F16C 1/08; F16C 1/26; F16C 2316/10; A61M 2039/1077;
(Continued)

(56) References Cited

U.S. PATENT DOCUMENTS 3,592,183 A 7/1971 Watkins et al.
3,932,068 A 1/1976 Zimmermann
(Continued)

FOREIGN PATENT DOCUMENTS

AU 2008219653 A1 9/2008
AU 2013205145 A1 5/2013
(Continued)

OTHER PUBLICATIONS

Examination Report for European Application No. 21158196.2 mailed May 28, 2024.
(Continued)

*Primary Examiner* — Amanda K Hulbert
(74) *Attorney, Agent, or Firm* — Ballard Spahr LLP

(57) ABSTRACT

Apparatus and methods are described including a blood pump that includes an axial shaft configured for insertion into, and rotation within, a body of a subject. An impeller is coupled to the axial shaft such that, as the axial shaft rotates, the impeller pumps blood of the subject. A thrust bearing includes a proximally-facing ceramic surface disposed distally from the axial shaft so as to inhibit distal movement of the axial shaft beyond the thrust bearing, and a distally-facing ceramic cover that covers a distal end of the axial shaft, such that the ceramic cover contacts the ceramic surface as the axial shaft rotates. Other applications are also described.

25 Claims, 66 Drawing Sheets

Related U.S. Application Data

(60) Provisional application No. 63/470,259, filed on Jun. 1, 2023, provisional application No. 63/443,519, filed on Feb. 6, 2023, provisional application No. 63/432,496, filed on Dec. 14, 2022, provisional application No. 63/406,427, filed on Sep. 14, 2022.

(51) Int. Cl.

| | |
|---|---|
| ***A61M 60/139*** | (2021.01) |
| ***A61M 60/178*** | (2021.01) |
| ***A61M 60/237*** | (2021.01) |
| ***A61M 60/414*** | (2021.01) |
| ***A61M 60/825*** | (2021.01) |
| ***A61M 60/857*** | (2021.01) |
| ***A61M 60/865*** | (2021.01) |

(52) U.S. Cl.
CPC ........ *A61M 60/237* (2021.01); *A61M 60/414* (2021.01); *A61M 60/825* (2021.01); *A61M 60/857* (2021.01); *A61M 60/865* (2021.01); *A61M 2207/00* (2013.01)

(58) Field of Classification Search
CPC ...... A61M 2205/02; A61M 2205/0211; A61M 2205/0222; A61M 2205/0233; A61M 2205/025; A61M 2205/0266; A61M 2205/0294; A61M 2205/04; A61M 2205/103; A61M 2205/3303; A61M 2205/3306; A61M 2205/3327; A61M 2205/3331; A61M 2205/3365; A61M 2205/3606; A61M 2205/50; A61M 2205/502; A61M 2207/00; A61M 2207/10; A61M 2210/125; A61M 2210/127; A61M 2230/30; A61M 39/10; A61M 60/122; A61M 60/13; A61M 60/17; A61M 60/174; A61M 60/178; A61M 60/216; A61M 60/226; A61M 60/237; A61M 60/242; A61M 60/295; A61M 60/408; A61M 60/414; A61M 60/419; A61M 60/497; A61M 60/508; A61M 60/531; A61M 60/538; A61M 60/554; A61M 60/585; A61M 60/806; A61M 60/808; A61M 60/81; A61M 60/816; A61M 60/818; A61M 60/825; A61M 60/829; A61M 60/833; A61M 60/855; A61M 60/857; A61M 60/859; A61M 60/865; A61M 60/888; A61M 60/90
See application file for complete search history.

(56) References Cited

U.S. PATENT DOCUMENTS 4,407,271 A 10/1983 Schiff
4,625,712 A 12/1986 Wampler
4,753,221 A 6/1988 Kensey et al.
4,771,765 A 9/1988 Choy et al.
4,909,787 A 3/1990 Danforth
4,919,647 A 4/1990 Nash
4,944,722 A 7/1990 Carriker et al.
4,954,055 A 9/1990 Raible et al.
4,957,504 A 9/1990 Chardack
4,964,864 A 10/1990 Summers et al.
4,969,865 A 11/1990 Hwang et al.
4,985,014 A 1/1991 Orejola
5,011,469 A 4/1991 Buckberg et al.
5,037,403 A 8/1991 Garcia
5,061,256 A 10/1991 Wampler
5,141,338 A * 8/1992 Asada .................. F16C 33/107 384/114
5,169,378 A 12/1992 Figuera
5,275,580 A 1/1994 Yamazaki
5,330,484 A 7/1994 Guenther et al.
5,348,545 A 9/1994 Shani et al.
5,453,076 A 9/1995 Kiyota et al.
5,507,629 A * 4/1996 Jarvik ................ A61M 60/419 417/423.12
5,531,789 A 7/1996 Yamazaki et al.
5,533,987 A 7/1996 Pray et al.
5,569,275 A 10/1996 Kotula et al.
5,613,935 A 3/1997 Jarvik
5,692,882 A 12/1997 Bozeman et al.
5,713,730 A 2/1998 Nose et al.
5,749,855 A 5/1998 Reitan
5,772,693 A 6/1998 Brownlee
5,843,158 A 12/1998 Lenker et al.
5,863,179 A 1/1999 Westphal et al.
5,876,385 A 3/1999 Ikari et al.
5,879,499 A 3/1999 Corvi
5,911,685 A 6/1999 Siess et al.
5,911,715 A 6/1999 Berg et al.
5,928,132 A 7/1999 Leschinsky
5,947,892 A 9/1999 Benkowski et al.
5,957,672 A 9/1999 Aber
5,964,694 A 10/1999 Siess et al.
6,007,478 A 12/1999 Siess et al.
6,059,760 A 5/2000 Sandmore et al.
6,086,527 A 7/2000 Talpade
6,110,163 A 8/2000 Voda
6,116,862 A 9/2000 Rau et al.
6,135,729 A 10/2000 Aber
6,136,025 A 10/2000 Barbut et al.
6,162,017 A 12/2000 Raible
6,176,848 B1 1/2001 Rau et al.
6,183,220 B1 2/2001 Ohara et al.
6,217,541 B1 4/2001 Yu
6,247,892 B1 6/2001 Kazatchkov et al.
6,270,477 B1 8/2001 Bagaoisan et al.
6,355,001 B1 3/2002 Quinn et al.
6,413,222 B1 7/2002 Pantages et al.
6,482,228 B1 11/2002 Norred
6,485,501 B1 11/2002 Green
6,506,146 B1 1/2003 Mohl
6,520,983 B1 2/2003 Colgan et al.
6,533,716 B1 3/2003 Schmutz-Rode et al.
6,533,770 B1 3/2003 Lepulu et al.
6,537,315 B2 3/2003 Yamazaki et al.
6,544,216 B1 4/2003 Sammler et al.
6,592,567 B1 7/2003 Levin et al.
6,616,624 B1 9/2003 Kieval
6,709,429 B1 3/2004 Schaefer et al.
6,884,210 B2 4/2005 Nose et al.
6,949,066 B2 9/2005 Bearnson et al.
6,974,436 B1 12/2005 Aboul-Hosn et al.
7,004,925 B2 2/2006 Navia et al.
7,010,954 B2 3/2006 Siess et al.
7,011,620 B1 3/2006 Siess
7,022,100 B1 4/2006 Aboul-hosn et al.
7,027,875 B2 4/2006 Siess et al.
7,070,555 B2 7/2006 Siess
7,144,364 B2 12/2006 Barbut et al.
7,159,593 B2 1/2007 Mccarthy et al.
7,201,772 B2 4/2007 Schwammenthal et al.
7,258,679 B2 8/2007 Moore et al.
7,335,192 B2 2/2008 Keren et al.
7,338,521 B2 3/2008 Antaki et al.
7,341,570 B2 3/2008 Keren et al.
7,393,181 B2 7/2008 Mcbride et al.
7,485,104 B2 2/2009 Kieval
7,717,952 B2 5/2010 Case et al.
7,744,642 B2 6/2010 Rittgers et al.
7,762,941 B2 7/2010 Jarvik
7,766,853 B2 8/2010 Lane
7,766,892 B2 8/2010 Keren et al.
7,766,961 B2 8/2010 Patel et al.
7,780,628 B1 8/2010 Keren et al.
7,811,221 B2 10/2010 Gross

(56) References Cited

U.S. PATENT DOCUMENTS 7,841,976 B2 11/2010 McBride et al.
7,878,967 B1 2/2011 Khanal
7,914,436 B1 3/2011 Kung
7,914,503 B2 3/2011 Goodson et al.
7,927,068 B2 4/2011 Mcbride et al.
8,012,121 B2 9/2011 Goodson et al.
8,079,948 B2 12/2011 Shifflette
8,118,723 B2 2/2012 Richardson et al.
8,123,669 B2 2/2012 Siess et al.
8,157,758 B2 4/2012 Pecor et al.
8,192,451 B2 6/2012 Cambronne et al.
8,216,122 B2 7/2012 Kung
8,221,492 B2 7/2012 Case et al.
8,235,933 B2 8/2012 Keren et al.
8,277,470 B2 10/2012 Demarais et al.
8,376,707 B2 2/2013 Mcbride et al.
8,439,859 B2 5/2013 Pfeffer et al.
8,449,443 B2 5/2013 Rodefeld et al.
8,485,961 B2 7/2013 Campbell et al.
8,489,190 B2 7/2013 Pfeffer et al.
8,512,262 B2 8/2013 Gertner
8,535,211 B2 9/2013 Walters et al.
8,538,535 B2 9/2013 Ariav et al.
8,579,858 B2 11/2013 Reitan et al.
8,591,393 B2 11/2013 Walters et al.
8,591,539 B2 11/2013 Gellman
8,597,170 B2 12/2013 Walters et al.
8,617,239 B2 12/2013 Reitan
8,672,868 B2 3/2014 Simons
8,684,904 B2 4/2014 Campbell et al.
8,690,749 B1 4/2014 Nunez
8,721,516 B2 5/2014 Scheckel
8,721,517 B2 5/2014 Zeng et al.
8,727,959 B2 5/2014 Reitan et al.
8,734,331 B2 5/2014 Evans et al.
8,734,508 B2 5/2014 Hastings et al.
8,777,832 B1 7/2014 Wang et al.
8,814,543 B2 8/2014 Liebing
8,814,776 B2 8/2014 Hastie et al.
8,814,933 B2 8/2014 Siess
8,827,887 B2 9/2014 Curtis et al.
8,849,398 B2 9/2014 Evans
8,864,642 B2 10/2014 Scheckel
8,888,728 B2 11/2014 Aboul-hosn et al.
8,900,060 B2 12/2014 Liebing
8,926,492 B2 1/2015 Scheckel
8,932,141 B2 1/2015 Liebing
8,944,748 B2 2/2015 Liebing
8,979,493 B2 3/2015 Roehn
8,992,163 B2 3/2015 Mcbride et al.
8,998,792 B2 4/2015 Scheckel
9,028,216 B2 5/2015 Schumacher et al.
9,067,006 B2 6/2015 Toellner
9,072,825 B2 7/2015 Pfeffer et al.
9,089,634 B2 7/2015 Schumacher et al.
9,138,518 B2 9/2015 Campbell et al.
9,162,017 B2 10/2015 Evans et al.
9,162,019 B2 10/2015 Horvath et al.
9,217,442 B2 12/2015 Wiessler et al.
9,259,521 B2 2/2016 Simons
9,278,189 B2 3/2016 Corbett
9,314,558 B2 4/2016 Er
9,327,067 B2 5/2016 Zeng et al.
9,328,741 B2 5/2016 Liebing
9,339,596 B2 5/2016 Roehn
9,345,824 B2 5/2016 Mohl et al.
9,358,329 B2 6/2016 Fitzgerald et al.
9,358,330 B2 6/2016 Schumacher
9,364,592 B2 6/2016 Mcbride et al.
9,364,593 B2 6/2016 Mcbride et al.
9,370,613 B2 6/2016 Hsu et al.
9,381,288 B2 7/2016 Schenck et al.
9,393,384 B1 7/2016 Kapur et al.
9,402,942 B2 8/2016 Hastie et al.
9,404,505 B2 8/2016 Scheckel
9,416,783 B2 8/2016 Schumacher et al.
9,416,791 B2 8/2016 Toellner
9,421,311 B2 8/2016 Tanner et al.
9,446,179 B2 9/2016 Keenan et al.
9,474,840 B2 10/2016 Siess
9,512,839 B2 12/2016 Liebing
9,533,082 B2 1/2017 Reichenbach et al.
9,533,084 B2 1/2017 Siess et al.
9,545,468 B2 1/2017 Aboul-hosn et al.
9,550,017 B2 1/2017 Spanier et al.
9,561,314 B2 2/2017 Aboul-hosn et al.
9,572,915 B2 2/2017 Heuring et al.
9,597,205 B2 3/2017 Tuval
9,597,437 B2 3/2017 Aboul-hosn et al.
9,603,983 B2 3/2017 Roehn et al.
9,611,743 B2 4/2017 Toellner et al.
9,616,159 B2 4/2017 Anderson et al.
9,623,161 B2 4/2017 Medvedev et al.
9,669,142 B2 6/2017 Spanier et al.
9,669,144 B2 6/2017 Spanier et al.
9,675,738 B2 6/2017 Tanner et al.
9,675,740 B2 6/2017 Zeng et al.
9,713,663 B2 7/2017 Medvedev et al.
9,717,833 B2 8/2017 Mcbride et al.
9,750,860 B2 9/2017 Schumacher
9,750,861 B2 9/2017 Hastie et al.
9,759,237 B2 9/2017 Liebing
9,764,113 B2 9/2017 Tuval et al.
9,771,801 B2 9/2017 Schumacher et al.
9,789,238 B2 10/2017 Aboul-hosn et al.
9,795,727 B2 10/2017 Schumacher
9,814,814 B2 11/2017 Corbett et al.
9,821,146 B2 11/2017 Tao et al.
9,827,356 B2 11/2017 Muller et al.
9,833,550 B2 12/2017 Siess
9,835,550 B2 12/2017 Kakuno et al.
9,850,906 B2 12/2017 Ozaki et al.
9,872,947 B2 1/2018 Keenan et al.
9,872,948 B2 1/2018 Siess
9,878,079 B2 1/2018 Pfeffer et al.
9,889,242 B2 2/2018 Pfeffer et al.
9,895,475 B2 2/2018 Toellner et al.
9,903,384 B2 2/2018 Roehn
9,907,890 B2 3/2018 Muller
9,907,891 B2 3/2018 Wiessler et al.
9,919,087 B2 3/2018 Pfeffer et al.
9,962,475 B2 5/2018 Campbell et al.
9,964,115 B2 5/2018 Scheckel
9,974,893 B2 5/2018 Toellner
9,999,714 B2 6/2018 Spanier et al.
10,029,037 B2 7/2018 Muller et al.
10,029,040 B2 7/2018 Taskin
10,039,872 B2 8/2018 Zeng et al.
10,039,874 B2 8/2018 Schwammenthal et al.
10,052,419 B2 8/2018 Er
10,052,420 B2 8/2018 Medvedev et al.
10,071,192 B2 9/2018 Zeng
10,086,121 B2 10/2018 Fitzgerald et al.
10,105,475 B2 10/2018 Muller
10,107,299 B2 10/2018 Scheckel
10,117,980 B2 11/2018 Keenan et al.
10,119,550 B2 11/2018 Bredenbreuker et al.
10,149,932 B2 12/2018 Mcbride et al.
10,172,985 B2 1/2019 Simon et al.
10,179,197 B2 1/2019 Kaiser et al.
10,183,104 B2 1/2019 Anderson et al.
10,196,899 B2 2/2019 Toellner et al.
10,207,037 B2 2/2019 Corbett et al.
10,208,763 B2 2/2019 Schumacher et al.
10,215,187 B2 2/2019 Mcbride et al.
10,221,866 B2 3/2019 Liebing
10,231,838 B2 3/2019 Chin et al.
10,232,099 B2 3/2019 Peters et al.
10,238,783 B2 3/2019 Aboul-hosn et al.
10,245,363 B1 4/2019 Rowe
10,265,447 B2 4/2019 Campbell et al.
10,265,448 B2 4/2019 Liebing
10,279,095 B2 5/2019 Aboul-hosn et al.
10,300,185 B2 5/2019 Aboul-hosn et al.

(56) References Cited

U.S. PATENT DOCUMENTS

| | | | |
|---|---|---|---|
| 10,300,186 | B2 | 5/2019 | Aboul-hosn et al. |
| 10,316,853 | B2 | 6/2019 | Toellner |
| 10,322,175 | B2 | 6/2019 | Cully et al. |
| 10,330,101 | B2 | 6/2019 | Toellner |
| 10,342,904 | B2 | 7/2019 | Schumacher |
| 10,342,906 | B2 | 7/2019 | D'ambrosio et al. |
| 10,363,349 | B2 | 7/2019 | Muller et al. |
| 10,369,260 | B2 | 8/2019 | Smith et al. |
| 10,376,162 | B2 | 8/2019 | Edelman et al. |
| 10,413,646 | B2 | 9/2019 | Wiessler et al. |
| 10,449,276 | B2 | 10/2019 | Pfeffer et al. |
| 10,449,279 | B2 | 10/2019 | Muller |
| 10,478,538 | B2 | 11/2019 | Scheckel et al. |
| 10,478,539 | B2 | 11/2019 | Pfeffer et al. |
| 10,478,540 | B2 | 11/2019 | Scheckel et al. |
| 10,495,101 | B2 | 12/2019 | Scheckel |
| 10,557,475 | B2 | 2/2020 | Roehn |
| 10,583,231 | B2 | 3/2020 | Schwammenthal et al. |
| 10,584,589 | B2 | 3/2020 | Schumacher et al. |
| 10,589,012 | B2 | 3/2020 | Toellner et al. |
| 10,617,808 | B2 | 4/2020 | Hastie et al. |
| 10,662,967 | B2 | 5/2020 | Scheckel |
| 10,669,855 | B2 | 6/2020 | Toellner et al. |
| 10,765,789 | B2 | 9/2020 | Zeng et al. |
| 10,792,406 | B2 | 10/2020 | Roehn et al. |
| 10,799,624 | B2 | 10/2020 | Pfeffer et al. |
| 10,799,626 | B2 | 10/2020 | Siess et al. |
| 10,801,511 | B2 | 10/2020 | Siess et al. |
| 10,806,838 | B2 | 10/2020 | Er |
| 10,835,653 | B2 | 11/2020 | Liebing |
| 10,842,922 | B2 | 11/2020 | Roehn et al. |
| 10,857,272 | B2 | 12/2020 | Liebing |
| 10,864,309 | B2 | 12/2020 | Mcbride et al. |
| 10,864,310 | B2 | 12/2020 | Schwammenthal et al. |
| 10,865,801 | B2 | 12/2020 | Mcbride et al. |
| 10,874,783 | B2 | 12/2020 | Pfeffer et al. |
| 10,881,770 | B2 | 1/2021 | Tuval et al. |
| 10,881,845 | B2 | 1/2021 | Siess et al. |
| 10,894,115 | B2 | 1/2021 | Pfeffer et al. |
| 10,898,629 | B2 | 1/2021 | Siess et al. |
| 10,907,646 | B2 | 2/2021 | Bredenbreuker et al. |
| 10,920,596 | B2 | 2/2021 | Toellner et al. |
| 10,926,013 | B2 | 2/2021 | Schumacher et al. |
| 10,926,060 | B2 | 2/2021 | Stern et al. |
| 10,935,038 | B2 | 3/2021 | Siess |
| 10,980,927 | B2 | 4/2021 | Pfeffer et al. |
| 10,994,120 | B2 | 5/2021 | Tuval et al. |
| 11,007,350 | B2 | 5/2021 | Tao et al. |
| 11,020,584 | B2 | 6/2021 | Siess et al. |
| 11,027,114 | B2 | 6/2021 | D'ambrosio et al. |
| 11,033,729 | B2 | 6/2021 | Scheckel et al. |
| 11,040,187 | B2 | 6/2021 | Wiessler et al. |
| RE48,649 | E | 7/2021 | Siess |
| 11,077,294 | B2 | 8/2021 | Keenan et al. |
| 11,107,626 | B2 | 8/2021 | Siess et al. |
| 11,116,960 | B2 | 9/2021 | Simon et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,168,705 | B2 | 11/2021 | Liebing |
| 11,185,679 | B2 | 11/2021 | Tuval et al. |
| 11,185,680 | B2 | 11/2021 | Tuval et al. |
| 11,191,944 | B2 | 12/2021 | Tuval et al. |
| 11,197,690 | B2 | 12/2021 | Fantuzzi et al. |
| 11,219,755 | B2 | 1/2022 | Siess et al. |
| 11,229,786 | B2 | 1/2022 | Zeng et al. |
| 11,253,692 | B2 | 2/2022 | Schumacher |
| 11,253,693 | B2 | 2/2022 | Pfeffer et al. |
| 11,260,212 | B2 | 3/2022 | Tuval et al. |
| 11,260,213 | B2 | 3/2022 | Zeng et al. |
| 11,260,215 | B2 | 3/2022 | Scheckel et al. |
| 11,266,824 | B2 | 3/2022 | Er |
| 11,268,521 | B2 | 3/2022 | Toellner |
| 11,273,301 | B2 | 3/2022 | Pfeffer et al. |
| 11,278,711 | B2 | 3/2022 | Liebing |
| 11,280,345 | B2 | 3/2022 | Bredenbreuker et al. |
| 11,285,309 | B2 | 3/2022 | Tuval et al. |
| 11,291,825 | B2 | 4/2022 | Tuval et al. |
| 11,298,523 | B2 | 4/2022 | Tuval et al. |
| 11,298,525 | B2 | 4/2022 | Jahangir |
| 11,305,105 | B2 | 4/2022 | Corbett et al. |
| 11,313,228 | B2 | 4/2022 | Schumacher et al. |
| 11,338,124 | B2 | 5/2022 | Pfeffer et al. |
| 11,351,358 | B2 | 6/2022 | Nix et al. |
| 11,364,373 | B2 | 6/2022 | Corbett et al. |
| 11,413,446 | B2 | 8/2022 | Siess et al. |
| 11,421,701 | B2 | 8/2022 | Schumacher et al. |
| 11,434,922 | B2 | 9/2022 | Roehn |
| 11,471,663 | B2 | 10/2022 | Tuval et al. |
| 11,708,833 | B2 | 7/2023 | Mcbride et al. |
| 11,833,278 | B2 | 12/2023 | Siess et al. |
| 11,839,754 | B2 | 12/2023 | Tuval et al. |
| 11,883,274 | B2 | 1/2024 | Schwammenthal et al. |
| 11,986,602 | B2 | 5/2024 | Corbett et al. |
| 12,070,382 | B2 | 8/2024 | Goslau et al. |
| 12,090,314 | B2 | 9/2024 | Tuval et al. |
| 12,127,820 | B2 | 10/2024 | Tuval et al. |
| 12,186,545 | B2 | 1/2025 | Tuval et al. |
| 12,220,570 | B2 | 2/2025 | Hildebrand et al. |
| 12,329,957 | B2 | 6/2025 | Tuval et al. |
| 2001/0031210 | A1 | 10/2001 | Antaki et al. |
| 2001/0031981 | A1 | 10/2001 | Evans et al. |
| 2001/0041934 | A1 | 11/2001 | Yamazaki et al. |
| 2002/0107536 | A1 | 8/2002 | Hussein |
| 2002/0151799 | A1 | 10/2002 | Pantages et al. |
| 2003/0055486 | A1 | 3/2003 | Adams et al. |
| 2003/0088310 | A1 | 5/2003 | Hansen et al. |
| 2003/0100816 | A1 | 5/2003 | Siess |
| 2003/0135086 | A1 | 7/2003 | Khaw et al. |
| 2003/0149473 | A1 | 8/2003 | Chouinard et al. |
| 2003/0171650 | A1 | 9/2003 | Tartaglia et al. |
| 2003/0187322 | A1 | 10/2003 | Siess |
| 2003/0208097 | A1 | 11/2003 | Aboul-hosn et al. |
| 2004/0064090 | A1 | 4/2004 | Keren et al. |
| 2004/0064091 | A1 | 4/2004 | Keren et al. |
| 2004/0111006 | A1 | 6/2004 | Alferness et al. |
| 2004/0116769 | A1 | 6/2004 | Jassawalla et al. |
| 2004/0167415 | A1 | 8/2004 | Gelfand et al. |
| 2004/0210236 | A1 | 10/2004 | Allers et al. |
| 2004/0260389 | A1 | 12/2004 | Case et al. |
| 2005/0033406 | A1 | 2/2005 | Barnhart et al. |
| 2005/0049692 | A1 | 3/2005 | Numamoto et al. |
| 2005/0079274 | A1 | 4/2005 | Palasis et al. |
| 2005/0085848 | A1 | 4/2005 | Johnson et al. |
| 2005/0107657 | A1 | 5/2005 | Carrier et al. |
| 2005/0107870 | A1 | 5/2005 | Wang et al. |
| 2005/0119682 | A1 | 6/2005 | Nguyen et al. |
| 2005/0137680 | A1 | 6/2005 | Ortiz et al. |
| 2005/0180854 | A1 | 8/2005 | Grabau et al. |
| 2005/0250975 | A1 | 11/2005 | Carrier et al. |
| 2006/0024182 | A1 | 2/2006 | Akdis et al. |
| 2006/0062672 | A1 | 3/2006 | Mcbride et al. |
| 2006/0064059 | A1 | 3/2006 | Gelfand et al. |
| 2006/0106449 | A1 | 5/2006 | Ben |
| 2006/0135961 | A1 | 6/2006 | Rosenman et al. |
| 2006/0155322 | A1 | 7/2006 | Sater et al. |
| 2006/0265051 | A1 | 11/2006 | Caro et al. |
| 2007/0073271 | A1 | 3/2007 | Brucker et al. |
| 2007/0100415 | A1 | 5/2007 | Licata et al. |
| 2007/0100435 | A1 | 5/2007 | Case et al. |
| 2007/0142729 | A1 | 6/2007 | Pfeiffer et al. |
| 2007/0162103 | A1 | 7/2007 | Case et al. |
| 2007/0208291 | A1 | 9/2007 | Patel |
| 2007/0244550 | A1 | 10/2007 | Eidenschink |
| 2007/0260327 | A1 | 11/2007 | Case et al. |
| 2007/0282243 | A1 | 12/2007 | Pini et al. |
| 2007/0282413 | A1 | 12/2007 | Tockman et al. |
| 2007/0293808 | A1 | 12/2007 | Williams et al. |
| 2008/0009668 | A1 | 1/2008 | Cohn |
| 2008/0086027 | A1 | 4/2008 | Siess et al. |
| 2008/0103591 | A1 | 5/2008 | Siess |
| 2008/0114339 | A1 | 5/2008 | McBride et al. |
| 2008/0114374 | A1 | 5/2008 | Soma et al. |
| 2008/0132747 | A1 | 6/2008 | Shifflette |

(56) References Cited

U.S. PATENT DOCUMENTS

| | | | |
|---|---|---|---|
| 2008/0132748 | A1 | 6/2008 | Shifflette |
| 2008/0140189 | A1 | 6/2008 | Nguyen et al. |
| 2008/0154236 | A1 | 6/2008 | Elkins et al. |
| 2008/0183280 | A1 | 7/2008 | Agnew et al. |
| 2008/0219653 | A1 | 9/2008 | Shioda |
| 2008/0306327 | A1 | 12/2008 | Shifflette |
| 2008/0306328 | A1 | 12/2008 | Ercolani et al. |
| 2009/0024157 | A1 | 1/2009 | Anukhin |
| 2009/0024195 | A1 | 1/2009 | Rezai et al. |
| 2009/0062597 | A1 | 3/2009 | Shifflette |
| 2009/0093764 | A1 | 4/2009 | Pfeffer et al. |
| 2009/0093796 | A1 | 4/2009 | Pfeffer et al. |
| 2009/0264991 | A1 | 10/2009 | Paul et al. |
| 2009/0287299 | A1 | 11/2009 | Tabor et al. |
| 2009/0318857 | A1 | 12/2009 | Goodson et al. |
| 2010/0030098 | A1 | 2/2010 | Fojtik |
| 2010/0048793 | A1 | 2/2010 | Baekelandt et al. |
| 2010/0049313 | A1 | 2/2010 | Alon et al. |
| 2010/0076247 | A1 | 3/2010 | Zilbershlag et al. |
| 2010/0130810 | A1 | 5/2010 | Mohl |
| 2010/0152523 | A1 | 6/2010 | Macdonald et al. |
| 2010/0185043 | A1 | 7/2010 | Woodard et al. |
| 2010/0217261 | A1 | 8/2010 | Watson |
| 2010/0222632 | A1 | 9/2010 | Poirier |
| 2010/0268017 | A1 | 10/2010 | Siess |
| 2010/0285084 | A1 | 11/2010 | Yang et al. |
| 2011/0004046 | A1 | 1/2011 | Campbell et al. |
| 2011/0034874 | A1 | 2/2011 | Reitan et al. |
| 2011/0106244 | A1 | 5/2011 | Ferrari et al. |
| 2011/0112567 | A1 | 5/2011 | Lenker et al. |
| 2011/0144633 | A1 | 6/2011 | Govari |
| 2011/0152999 | A1 | 6/2011 | Hastings et al. |
| 2011/0190874 | A1 | 8/2011 | Celermajer et al. |
| 2011/0213408 | A1 | 9/2011 | Gross et al. |
| 2011/0230949 | A1 | 9/2011 | Haverkost et al. |
| 2011/0257462 | A1 | 10/2011 | Rodefeld et al. |
| 2011/0264075 | A1 | 10/2011 | Leung et al. |
| 2011/0282128 | A1 | 11/2011 | Reitan et al. |
| 2011/0282274 | A1 | 11/2011 | Fulton |
| 2011/0301662 | A1 | 12/2011 | Bar-yoseph et al. |
| 2012/0022579 | A1 | 1/2012 | Fulton |
| 2012/0059460 | A1 | 3/2012 | Reitan |
| 2012/0089047 | A1 | 4/2012 | Ryba et al. |
| 2012/0089225 | A1 | 4/2012 | Akkerman et al. |
| 2012/0093628 | A1 | 4/2012 | Liebing |
| 2012/0116382 | A1 | 5/2012 | Ku et al. |
| 2012/0130469 | A1 | 5/2012 | Cragg et al. |
| 2012/0143141 | A1 | 6/2012 | Verkaik et al. |
| 2012/0172654 | A1 | 7/2012 | Bates |
| 2012/0172655 | A1 | 7/2012 | Campbell et al. |
| 2012/0172656 | A1 | 7/2012 | Walters et al. |
| 2012/0178985 | A1 | 7/2012 | Walters et al. |
| 2012/0178986 | A1 | 7/2012 | Campbell et al. |
| 2012/0224970 | A1 | 9/2012 | Schumacher et al. |
| 2012/0234411 | A1 | 9/2012 | Scheckel |
| 2012/0237353 | A1 | 9/2012 | Schumacher et al. |
| 2012/0237357 | A1 | 9/2012 | Schumacher et al. |
| 2012/0245680 | A1 | 9/2012 | Masuzawa et al. |
| 2012/0303112 | A1 | 11/2012 | Armstrong et al. |
| 2012/0316586 | A1 | 12/2012 | Demarais et al. |
| 2012/0328460 | A1 | 12/2012 | Horvath et al. |
| 2013/0041202 | A1 | 2/2013 | Toellner |
| 2013/0046376 | A1 | 2/2013 | Hassan et al. |
| 2013/0053623 | A1 | 2/2013 | Evans et al. |
| 2013/0053732 | A1 | 2/2013 | Heuser |
| 2013/0060077 | A1 | 3/2013 | Liebing |
| 2013/0066140 | A1 | 3/2013 | Mcbride et al. |
| 2013/0079874 | A1 | 3/2013 | Doss et al. |
| 2013/0085318 | A1 | 4/2013 | Toellner |
| 2013/0085319 | A1 | 4/2013 | Evans et al. |
| 2013/0177409 | A1 | 7/2013 | Schumacher et al. |
| 2013/0177432 | A1 | 7/2013 | Toellner et al. |
| 2013/0237744 | A1 | 9/2013 | Pfeffer et al. |
| 2013/0245360 | A1 | 9/2013 | Schumacher |
| 2013/0253328 | A1 | 9/2013 | Zelenka et al. |
| 2013/0303830 | A1 | 11/2013 | Zeng et al. |
| 2013/0303831 | A1 | 11/2013 | Evans |
| 2013/0303969 | A1 | 11/2013 | Keenan et al. |
| 2013/0331639 | A1 | 12/2013 | Campbell et al. |
| 2014/0018840 | A1 | 1/2014 | Morgan et al. |
| 2014/0025041 | A1 | 1/2014 | Fukuoka et al. |
| 2014/0039375 | A1 | 2/2014 | Jimenez et al. |
| 2014/0107399 | A1 | 4/2014 | Spence |
| 2014/0128659 | A1 | 5/2014 | Heuring et al. |
| 2014/0223724 | A1 | 8/2014 | Scheckel |
| 2014/0255176 | A1 | 9/2014 | Bredenbreuker et al. |
| 2014/0275720 | A1 | 9/2014 | Ferrari |
| 2014/0275722 | A1 | 9/2014 | Zimmermann et al. |
| 2014/0276051 | A1 | 9/2014 | Hoffman |
| 2014/0350523 | A1 | 11/2014 | Dehdashtian et al. |
| 2015/0005570 | A1 | 1/2015 | Fritz et al. |
| 2015/0018597 | A1 | 1/2015 | Fierens et al. |
| 2015/0031937 | A1 | 1/2015 | Kearsley et al. |
| 2015/0051435 | A1 | 2/2015 | Siess et al. |
| 2015/0119633 | A1 | 4/2015 | Haselby et al. |
| 2015/0157777 | A1 | 6/2015 | Tuval et al. |
| 2015/0164372 | A1 | 6/2015 | Navab et al. |
| 2015/0164662 | A1 | 6/2015 | Tuval |
| 2015/0176582 | A1 | 6/2015 | Liebing |
| 2015/0258262 | A1 | 9/2015 | Pfeffer et al. |
| 2015/0290370 | A1 | 10/2015 | Crunkleton et al. |
| 2015/0290372 | A1 | 10/2015 | Muller et al. |
| 2015/0306291 | A1 | 10/2015 | Bonde et al. |
| 2015/0328382 | A1 | 11/2015 | Corbett et al. |
| 2015/0343136 | A1 | 12/2015 | Nitzan et al. |
| 2015/0343179 | A1 | 12/2015 | Schumacher et al. |
| 2015/0343186 | A1 | 12/2015 | Nitzan et al. |
| 2016/0022890 | A1 | 1/2016 | Schwammenthal et al. |
| 2016/0051741 | A1 | 2/2016 | Schwammenthal et al. |
| 2016/0053768 | A1 | 2/2016 | Schumacher et al. |
| 2016/0064117 | A1 | 3/2016 | Romero et al. |
| 2016/0106896 | A1 | 4/2016 | Pfeffer et al. |
| 2016/0129170 | A1 | 5/2016 | Siess |
| 2016/0136341 | A1 | 5/2016 | Pfeffer et al. |
| 2016/0136342 | A1 | 5/2016 | Pfeffer et al. |
| 2016/0136343 | A1 | 5/2016 | Anagnostopoulos |
| 2016/0144089 | A1 | 5/2016 | Woo et al. |
| 2016/0184500 | A1 | 6/2016 | Zeng |
| 2016/0206425 | A1 | 7/2016 | Madrid et al. |
| 2016/0213827 | A1 | 7/2016 | Tanner et al. |
| 2016/0256619 | A1 | 9/2016 | Throckmorton et al. |
| 2016/0256620 | A1 | 9/2016 | Scheckel et al. |
| 2016/0258248 | A1 | 9/2016 | MacDonald |
| 2016/0279310 | A1 | 9/2016 | Scheckel et al. |
| 2016/0303299 | A1 | 10/2016 | Muller |
| 2016/0331378 | A1 | 11/2016 | Nitzan et al. |
| 2016/0354525 | A1 | 12/2016 | Mcbride et al. |
| 2017/0007403 | A1 | 1/2017 | Wildhirt et al. |
| 2017/0014562 | A1 | 1/2017 | Liebing |
| 2017/0028115 | A1 | 2/2017 | Muller |
| 2017/0035954 | A1 | 2/2017 | Muller et al. |
| 2017/0049946 | A1 | 2/2017 | Kapur et al. |
| 2017/0071769 | A1 | 3/2017 | Mangiardi |
| 2017/0087286 | A1 | 3/2017 | Spanier et al. |
| 2017/0087288 | A1 | 3/2017 | Groß-hardt et al. |
| 2017/0100527 | A1 | 4/2017 | Schwammenthal et al. |
| 2017/0173237 | A1 | 6/2017 | Pfeifer et al. |
| 2017/0197021 | A1 | 7/2017 | Nitzan et al. |
| 2017/0215918 | A1 | 8/2017 | Tao et al. |
| 2017/0232168 | A1 | 8/2017 | Reichenbach et al. |
| 2017/0232171 | A1 | 8/2017 | Roehn et al. |
| 2017/0258981 | A1 | 9/2017 | Franano et al. |
| 2017/0274128 | A1 | 9/2017 | Tamburino et al. |
| 2017/0290964 | A1 | 10/2017 | Barry |
| 2017/0333067 | A1 | 11/2017 | Wilson |
| 2017/0333607 | A1 | 11/2017 | Zarins |
| 2017/0340787 | A1 | 11/2017 | Corbett et al. |
| 2017/0340791 | A1 | 11/2017 | Aboul-hosn et al. |
| 2017/0348470 | A1 | 12/2017 | D'ambrosio et al. |
| 2018/0050139 | A1 | 2/2018 | Siess et al. |
| 2018/0050142 | A1 | 2/2018 | Siess et al. |
| 2018/0055979 | A1 | 3/2018 | Corbett et al. |
| 2018/0064861 | A1 | 3/2018 | Dur et al. |
| 2018/0064862 | A1 | 3/2018 | Keenan et al. |

(56) References Cited

U.S. PATENT DOCUMENTS

2018/0078159 A1 3/2018 Edelman et al.
2018/0080326 A1 3/2018 Schumacher et al.
2018/0100507 A1 4/2018 Wu et al.
2018/0104453 A1 4/2018 Tao et al.
2018/0126130 A1 5/2018 Nitzan et al.
2018/0149164 A1 5/2018 Siess
2018/0149165 A1 5/2018 Siess et al.
2018/0169312 A1 6/2018 Barry
2018/0169313 A1 6/2018 Schwammenthal et al.
2018/0207334 A1 7/2018 Siess
2018/0228952 A1 8/2018 Pfeffer et al.
2018/0228953 A1 8/2018 Siess et al.
2018/0264182 A1 9/2018 Spanier et al.
2018/0264183 A1 9/2018 Jahangir
2018/0280598 A1 10/2018 Curran et al.
2018/0289877 A1 10/2018 Schumacher et al.
2018/0303990 A1 10/2018 Siess et al.
2018/0303992 A1 10/2018 Taskin
2018/0303993 A1 10/2018 Schwammenthal et al.
2018/0311422 A1 11/2018 Greatrex et al.
2018/0353667 A1 12/2018 Moyer et al.
2019/0015570 A1 1/2019 Muller
2019/0030228 A1 1/2019 Keenan et al.
2019/0046702 A1 2/2019 Siess et al.
2019/0060539 A1 2/2019 Siess et al.
2019/0070345 A1 3/2019 Mcbride et al.
2019/0076167 A1 3/2019 Fantuzzi et al.
2019/0083690 A1 3/2019 Siess et al.
2019/0101130 A1 4/2019 Bredenbreuker et al.
2019/0105437 A1 4/2019 Siess et al.
2019/0117865 A1 4/2019 Walters et al.
2019/0134287 A1 5/2019 Demou
2019/0143018 A1 5/2019 Salahieh et al.
2019/0143019 A1 5/2019 Mehaffey et al.
2019/0170153 A1 6/2019 Scheckel
2019/0175802 A1 6/2019 Tuval et al.
2019/0175803 A1 6/2019 Pfeffer et al.
2019/0175805 A1 6/2019 Tuval et al.
2019/0175806 A1 6/2019 Tuval et al.
2019/0209753 A1 7/2019 Tuval et al.
2019/0209755 A1 7/2019 Nix et al.
2019/0209757 A1 7/2019 Tuval et al.
2019/0209758 A1 7/2019 Tuval et al.
2019/0211836 A1 7/2019 Schumacher et al.
2019/0216994 A1 7/2019 Pfeffer et al.
2019/0224391 A1 7/2019 Liebing
2019/0224392 A1 7/2019 Pfeffer et al.
2019/0224393 A1 7/2019 Pfeffer et al.
2019/0239998 A1 8/2019 Tuval et al.
2019/0262518 A1 8/2019 Molteni et al.
2019/0269840 A1 9/2019 Tuval et al.
2019/0274812 A1 9/2019 Groh et al.
2019/0275224 A1 9/2019 Hanson et al.
2019/0282741 A1 9/2019 Franano et al.
2019/0290817 A1 9/2019 Guo et al.
2019/0307561 A1 10/2019 Gosal et al.
2019/0316591 A1 10/2019 Toellner
2019/0321527 A1 10/2019 King et al.
2019/0321530 A1 10/2019 Cambronne et al.
2019/0321531 A1 10/2019 Cambronne et al.
2019/0328948 A1 10/2019 Salahieh et al.
2019/0336664 A1 11/2019 Liebing
2019/0344001 A1* 11/2019 Salahieh ............. A61M 60/824
2019/0351118 A1 11/2019 Graichen et al.
2019/0365975 A1 12/2019 Muller et al.
2020/0000542 A1 1/2020 McFall et al.
2020/0038567 A1 2/2020 Siess et al.
2020/0078506 A1 3/2020 Schwammenthal et al.
2020/0086022 A1 3/2020 El Katerji et al.
2020/0087199 A1 3/2020 Gimblet
2020/0093973 A1 3/2020 Gandhi et al.
2020/0114053 A1 4/2020 Salahieh et al.
2020/0155739 A1 5/2020 Siess et al.
2020/0197585 A1 6/2020 Scheckel et al.
2020/0237981 A1 7/2020 Tuval et al.
2020/0237982 A1 7/2020 Tuval et al.
2020/0237984 A1 7/2020 Tuval et al.
2020/0237985 A1 7/2020 Tuval et al.
2020/0237986 A1 7/2020 Tuval et al.
2020/0246527 A1 8/2020 Hildebrand et al.
2020/0268952 A1 8/2020 Nitzan et al.
2020/0276369 A1 9/2020 Nitzan et al.
2020/0276370 A1 9/2020 Keen et al.
2020/0288988 A1 9/2020 Goldvasser
2020/0289136 A1 9/2020 Chou et al.
2020/0376183 A1 12/2020 El Katerji et al.
2020/0405926 A1 12/2020 Alexander et al.
2021/0008261 A1 1/2021 Calomeni et al.
2021/0008264 A1 1/2021 Radman
2021/0023285 A1 1/2021 Brandt
2021/0023286 A1 1/2021 Tuval et al.
2021/0038794 A1 2/2021 Tuval et al.
2021/0069394 A1 3/2021 Tuval et al.
2021/0069395 A1 3/2021 Tuval et al.
2021/0077676 A1 3/2021 Tuval et al.
2021/0077692 A1 3/2021 Tanner et al.
2021/0085955 A1 3/2021 Singru
2021/0121617 A1 4/2021 Harjes et al.
2021/0145475 A1 5/2021 Tao et al.
2021/0162199 A1 6/2021 Tuval et al.
2021/0170081 A1 6/2021 Kanz
2021/0178145 A1 6/2021 Tuval et al.
2021/0213273 A1 7/2021 Spanier et al.
2021/0236797 A1 8/2021 D'ambrosio et al.
2021/0260361 A1 8/2021 Charafeddine et al.
2021/0299433 A1 9/2021 Siess et al.
2022/0072297 A1 3/2022 Tuval et al.
2022/0079457 A1 3/2022 Tuval et al.
2022/0088368 A1 3/2022 Tuval et al.
2022/0134085 A1 5/2022 Siess et al.
2022/0161018 A1 5/2022 Mitze et al.
2022/0161019 A1 5/2022 Mitze et al.
2022/0161021 A1 5/2022 Mitze et al.
2022/0184376 A1 6/2022 Tuval et al.
2022/0226632 A1 7/2022 Tuval et al.
2022/0241574 A1 8/2022 Tuval et al.
2022/0249830 A1 8/2022 Kanz
2022/0313980 A1 10/2022 Hildebrand et al.
2022/0355096 A1 11/2022 Tuval et al.
2023/0001180 A1 1/2023 Boensch et al.
2023/0052997 A1 2/2023 Skrzypczak et al.
2023/0063196 A1 3/2023 Spanier et al.
2023/0071248 A1 3/2023 Keenan et al.
2023/0130285 A1 4/2023 Malone et al.
2023/0137473 A1 5/2023 Zipory et al.
2023/0211142 A1 7/2023 Gong
2023/0218887 A1 7/2023 Tuval et al.
2023/0226342 A1 7/2023 Tuval et al.
2023/0390545 A1 12/2023 D'Ambrosio et al.
2024/0189571 A1 6/2024 Tuval et al.
2024/0252812 A1 8/2024 Tuval et al.
2024/0261562 A1 8/2024 Tuval et al.
2024/0277997 A1 8/2024 Tuval et al.
2025/0387612 A1 12/2025 van Dort et al.

FOREIGN PATENT DOCUMENTS

CA 2701809 A1 4/2009
CA 2927346 A1 4/2009
CN 101448535 A 6/2009
CN 101820933 A 9/2010
CN 101854964 A 10/2010
CN 102365105 A 2/2012
CN 102805885 A 12/2012
CN 104185481 A 12/2014
CN 104703532 A 6/2015
CN 103182105 B 1/2016
CN 105214153 A 1/2016
CN 105682602 A 6/2016
CN 107050544 A 8/2017
CN 107137796 A 9/2017
CN 109069716 A 12/2018
CN 109641089 A 4/2019
CN 109821085 A 5/2019

(56) References Cited

FOREIGN PATENT DOCUMENTS

| | | | |
|---|---|---|---|
| CN | 113457006 | A | 10/2021 |
| CN | 114259646 | A | 4/2022 |
| CN | 114588533 | A | 6/2022 |
| CN | 115040778 | A | 9/2022 |
| CN | 116036463 | A | 5/2023 |
| CN | 116328174 | A | 6/2023 |
| CN | 116474257 | A | 7/2023 |
| CN | 116867541 | A | 10/2023 |
| DE | 1033690 | B | 7/1958 |
| DE | 10336902 | B3 | 8/2004 |
| EP | 0228787 | A1 | 7/1987 |
| EP | 0256683 | A2 | 2/1988 |
| EP | 0807447 | A1 | 11/1997 |
| EP | 0916359 | A1 | 5/1999 |
| EP | 1339443 | A1 | 9/2003 |
| EP | 0925801 | B1 | 11/2004 |
| EP | 1651290 | A1 | 5/2006 |
| EP | 1827531 | A1 | 9/2007 |
| EP | 1871441 | A2 | 1/2008 |
| EP | 2047872 | A1 | 4/2009 |
| EP | 2047873 | A1 | 4/2009 |
| EP | 2109394 | A2 | 10/2009 |
| EP | 2217300 | A1 | 8/2010 |
| EP | 2218469 | A1 | 8/2010 |
| EP | 2234658 | A2 | 10/2010 |
| EP | 2282070 | A1 | 2/2011 |
| EP | 2298374 | A1 | 3/2011 |
| EP | 2299119 | A1 | 3/2011 |
| EP | 2301598 | A1 | 3/2011 |
| EP | 2308524 | A1 | 4/2011 |
| EP | 2314331 | A1 | 4/2011 |
| EP | 2345440 | A1 | 7/2011 |
| EP | 2366412 | A2 | 9/2011 |
| EP | 2376788 | A1 | 10/2011 |
| EP | 2408489 | A1 | 1/2012 |
| EP | 2424587 | A1 | 3/2012 |
| EP | 2475415 | A1 | 7/2012 |
| EP | 2607712 | A1 | 6/2013 |
| EP | 2040639 | B1 | 2/2014 |
| EP | 1207934 | B1 | 8/2014 |
| EP | 2662099 | B1 | 9/2014 |
| EP | 2427230 | B1 | 12/2014 |
| EP | 2396050 | B1 | 1/2015 |
| EP | 2835141 | A1 | 2/2015 |
| EP | 2840954 | A1 | 3/2015 |
| EP | 2841122 | A1 | 3/2015 |
| EP | 2841124 | A1 | 3/2015 |
| EP | 2860849 | A1 | 4/2015 |
| EP | 2868331 | A2 | 5/2015 |
| EP | 2868332 | A1 | 5/2015 |
| EP | 2999496 | A2 | 3/2016 |
| EP | 3000492 | A1 | 3/2016 |
| EP | 3000493 | A1 | 3/2016 |
| EP | 3055922 | A1 | 8/2016 |
| EP | 3062730 | A1 | 9/2016 |
| EP | 3115070 | A1 | 1/2017 |
| EP | 3127562 | A1 | 2/2017 |
| EP | 2922486 | B1 | 5/2017 |
| EP | 3216467 | A1 | 9/2017 |
| EP | 3222302 | A1 | 9/2017 |
| EP | 3236079 | A1 | 10/2017 |
| EP | 3287154 | A1 | 2/2018 |
| EP | 3287155 | A1 | 2/2018 |
| EP | 3326567 | A1 | 5/2018 |
| EP | 3329951 | A1 | 6/2018 |
| EP | 3338825 | A1 | 6/2018 |
| EP | 3205360 | B1 | 8/2018 |
| EP | 3359214 | A1 | 8/2018 |
| EP | 3359215 | A1 | 8/2018 |
| EP | 3398624 | A1 | 11/2018 |
| EP | 3398625 | A1 | 11/2018 |
| EP | 3407930 | A1 | 12/2018 |
| EP | 3446729 | A1 | 2/2019 |
| EP | 3446730 | A1 | 2/2019 |
| EP | 3545983 | A1 | 10/2019 |
| EP | 3606575 | A1 | 2/2020 |
| EP | 3698820 | A1 | 8/2020 |
| EP | 3737436 | A1 | 11/2020 |
| EP | 3782665 | A1 | 2/2021 |
| EP | 3848089 | A1 | 7/2021 |
| EP | 3858421 | A1 | 8/2021 |
| EP | 3897814 | A1 | 10/2021 |
| EP | 4218899 | A1 | 8/2023 |
| EP | 4252825 | A2 | 10/2023 |
| GB | 2239675 | A | 7/1991 |
| GB | 2451161 | A | 1/2009 |
| GB | 2504175 | A | 1/2014 |
| GB | 2504177 | A | 1/2014 |
| JP | 2003504091 | A | 2/2003 |
| JP | 2004202006 | A | 7/2004 |
| JP | 2008519624 | A | 6/2008 |
| JP | 4159781 | B2 | 10/2008 |
| JP | 2009530041 | A | 8/2009 |
| JP | 2012505038 | A | 3/2012 |
| JP | 2012527269 | A | 11/2012 |
| JP | 2015500666 | A | 1/2015 |
| JP | 2015516267 | A | 6/2015 |
| JP | 2016509950 | A | 4/2016 |
| JP | 2017196495 | A | 11/2017 |
| JP | 2018509223 | A | 4/2018 |
| JP | 2018528804 | A | 10/2018 |
| JP | 2018-536447 | A | 12/2018 |
| JP | 2018535727 | A | 12/2018 |
| JP | 2020503083 | A | 1/2020 |
| JP | 2021-510318 | A | 4/2021 |
| WO | 9001972 | A1 | 3/1990 |
| WO | 90/13321 | | 11/1990 |
| WO | 1994/01148 | A1 | 1/1994 |
| WO | 99/34847 | | 7/1999 |
| WO | 2001/083016 | A2 | 5/2000 |
| WO | 2000043053 | A1 | 7/2000 |
| WO | 0062838 | A2 | 10/2000 |
| WO | 2002/070039 | A2 | 3/2001 |
| WO | 2002/038085 | | 5/2002 |
| WO | 03/006096 | | 1/2003 |
| WO | 03103745 | A2 | 12/2003 |
| WO | 2004073796 | A2 | 9/2004 |
| WO | 2005020848 | A2 | 3/2005 |
| WO | 2007081818 | A2 | 7/2007 |
| WO | 2007112033 | A2 | 10/2007 |
| WO | 2007127477 | A2 | 11/2007 |
| WO | 2008005747 | A2 | 1/2008 |
| WO | 2008005990 | A2 | 1/2008 |
| WO | 2008055301 | A1 | 5/2008 |
| WO | 2008104858 | A2 | 9/2008 |
| WO | 2009010963 | A2 | 1/2009 |
| WO | 2009046096 | A1 | 4/2009 |
| WO | 2009046790 | A2 | 4/2009 |
| WO | 2009064879 | A2 | 5/2009 |
| WO | 2009129481 | A1 | 10/2009 |
| WO | 2010042546 | | 4/2010 |
| WO | 2010063494 | A1 | 6/2010 |
| WO | 2010105854 | A1 | 9/2010 |
| WO | 2010127871 | A1 | 11/2010 |
| WO | 2010133567 | A1 | 11/2010 |
| WO | 2010150208 | A2 | 12/2010 |
| WO | 2011035926 | A1 | 3/2011 |
| WO | 2011047884 | A1 | 4/2011 |
| WO | 2011076441 | A1 | 6/2011 |
| WO | 2011089022 | A1 | 7/2011 |
| WO | 2011160858 | A1 | 12/2011 |
| WO | 2012007141 | A1 | 1/2012 |
| WO | 2012094535 | A2 | 7/2012 |
| WO | 2013032849 | A1 | 3/2013 |
| WO | 2013070186 | A1 | 5/2013 |
| WO | 2013093001 | A2 | 6/2013 |
| WO | 2013119752 | A2 | 8/2013 |
| WO | 2013148697 | A1 | 10/2013 |
| WO | 2013173239 | A1 | 11/2013 |
| WO | 2013183060 | A2 | 12/2013 |
| WO | 2014063119 | A1 | 4/2014 |
| WO | 2014141284 | A2 | 9/2014 |
| WO | 2014164292 | A1 | 10/2014 |
| WO | 2015063277 | A2 | 5/2015 |

(56) References Cited

FOREIGN PATENT DOCUMENTS

| | | | |
|---|---|---|---|
| WO | 2015160943 | A1 | 10/2015 |
| WO | 2015177793 | A2 | 11/2015 |
| WO | 2016001218 | A1 | 1/2016 |
| WO | 2016005803 | A2 | 1/2016 |
| WO | 2016185473 | A1 | 11/2016 |
| WO | 2016207293 | A1 | 12/2016 |
| WO | 2017032751 | A1 | 3/2017 |
| WO | 2017053361 | A1 | 3/2017 |
| WO | 2017060254 | A1 | 4/2017 |
| WO | 2017081561 | A1 | 5/2017 |
| WO | 2017137604 | A1 | 8/2017 |
| WO | 2017147291 | A1 | 8/2017 |
| WO | 2017159849 | A1 | 9/2017 |
| WO | 2017162618 | A1 | 9/2017 |
| WO | 2017196271 | A1 | 11/2017 |
| WO | 2018033920 | A1 | 2/2018 |
| WO | 2018036927 | A1 | 3/2018 |
| WO | 2018045299 | A1 | 3/2018 |
| WO | 2018061001 | A2 | 4/2018 |
| WO | 2018061002 | A1 | 4/2018 |
| WO | 2018067410 | A1 | 4/2018 |
| WO | 2018078615 | A1 | 5/2018 |
| WO | 2018096531 | A1 | 5/2018 |
| WO | 2018158636 | A1 | 9/2018 |
| WO | 2018172848 | A2 | 9/2018 |
| WO | 2018220589 | A1 | 12/2018 |
| WO | 2018226991 | A1 | 12/2018 |
| WO | 2018234454 | A1 | 12/2018 |
| WO | 2019079342 | A1 | 4/2019 |
| WO | 2019094963 | A1 | 5/2019 |
| WO | 2019125899 | A1 | 6/2019 |
| WO | 2019138350 | A2 | 7/2019 |
| WO | 2019152875 | A1 | 8/2019 |
| WO | 2019158996 | A1 | 8/2019 |
| WO | 2019229223 | A1 | 12/2019 |
| WO | 2020152611 | A2 | 7/2020 |
| WO | 2021055826 | A1 | 3/2021 |
| WO | 2021062265 | A1 | 4/2021 |
| WO | 2021152012 | A1 | 8/2021 |
| WO | 2021159147 | A1 | 8/2021 |
| WO | 2021198881 | A1 | 10/2021 |
| WO | 2021205346 | A2 | 10/2021 |
| WO | 2022189932 | A1 | 9/2022 |
| WO | 2023014742 | A1 | 2/2023 |
| WO | 2023062453 | A1 | 4/2023 |
| WO | 2024057252 | A1 | 3/2024 |
| WO | 2024057253 | A2 | 3/2024 |
| WO | 2024057254 | A1 | 3/2024 |
| WO | 2024057255 | A2 | 3/2024 |
| WO | 2024057256 | A2 | 3/2024 |
| WO | 2024057257 | A2 | 3/2024 |
| WO | 2025141457 | A1 | 7/2025 |
| WO | 2025141460 | A1 | 7/2025 |
| WO | 2025141461 | A2 | 7/2025 |

OTHER PUBLICATIONS

Final Office Action for U.S. Appl. No. 17/528,807 mailed Apr. 24, 2024.
Issue Notification for U.S. Appl. No. 17/173,944 mailed Jun. 12, 2024.
Non-Final Office Action for U.S. Appl. No. 17/609,589 mailed Jul. 1, 2024.
Notice of Allowance for U.S. Appl. No. 16/952,327 mailed Apr. 29, 2024.
Notice of Allowance for U.S. Appl. No. 17/069,570 mailed Jun. 24, 2024.
Notice of Allowance for U.S. Appl. No. 17/070,670 mailed Jun. 13, 2024.
Notice of Allowance for U.S. Appl. No. 17/574,701 mailed Jun. 26, 2024.
U.S. Appl. No. 18/639,079, filed Apr. 18, 2024.
U.S. Appl. No. 18/639,094, filed Apr. 18, 2024.
U.S. Appl. No. 18/639,098, filed Apr. 18, 2024.
U.S. Appl. No. 18/640,222, filed Apr. 19, 2024.
U.S. Appl. No. 18/640,260, filed Apr. 19, 2024.
U.S. Appl. No. 18/640,285, filed Apr. 19, 2024.
U.S. Appl. No. 18/640,303, filed Apr. 19, 2024.
U.S. Appl. No. 18/652,930, filed May 2, 2024.
U.S. Appl. No. 18/652,956, filed May 2, 2024.
U.S. Appl. No. 18/652,959, filed May 2, 2024.
U.S. Appl. No. 18/652,962, filed May 2, 2024.
U.S. Appl. No. 18/654,336, filed May 3, 2024.
Corrected Notice of Allowance for U.S. Appl. No. 16/952,327 mailed Sep. 20, 2024.
Corrected Notice of Allowance for U.S. Appl. No. 17/069,570 mailed Jul. 16, 2024.
Corrected Notice of Allowance for U.S. Appl. No. 17/528,807 mailed Sep. 19, 2024.
Corrected Notice of Allowance for U.S. Appl. No. 17/857,402 mailed Nov. 7, 2024.
Examination Report for European Application No. 21158903.1 mailed Jul. 9, 2024.
Extended Search Report for European Application No. 24170573.0 mailed Jul. 29, 2024.
Final Office Action for U.S. Appl. No. 17/078,472 mailed Aug. 9, 2024.
Hearing Notice for Indian Application No. 202147033522 mailed Jul. 24, 2024.
Issue Notification for U.S. Appl. No. 16/952,327 mailed Oct. 9, 2024.
Issue Notification for U.S. Appl. No. 17,574,701 mailed Aug. 28, 2024.
Issue Notification for U.S. Appl. No. 17/528,807 mailed Oct. 9, 2024.
Non-Final Office Action for U.S. Appl. No. 17/528,015 mailed Oct. 21, 2024.
Non-Final Office Action for U.S. Appl. No. 17/532,318 mailed Jul. 18, 2024.
Non-Final Office Action for U.S. Appl. No. 17/677,571 mailed Aug. 15, 2024.
Non-Final Office Action for U.S. Appl. No. 17/678,812 mailed Sep. 26, 2024.
Non-Final Office Action for U.S. Appl. No. 17/682,073 mailed Aug. 29, 2024.
Non-Final Office Action for U.S. Appl. No. 17/682,104 mailed Sep. 30, 2024.
Non-Final Office Action for U.S. Appl. No. 18/511,532 mailed Aug. 27, 2024.
Notice of Allowance for U.S. Appl. No. 16/952,327 mailed Aug. 6, 2024.
Notice of Allowance for U.S. Appl. No. 17/070,670 mailed Sep. 11, 2024.
Notice of Allowance for U.S. Appl. No. 17/528,807 mailed Sep. 9, 2024.
Notice of Allowance for U.S. Appl. No. 17/857,402 mailed Oct. 8, 2024.
Office Action for Japanese Application No. 2023-156391 mailed Jun. 3, 2024.
Office Action for Japanese Application No. 2023-191120 mailed Oct. 1, 2024.
Restriction Requirement for U.S. Appl. No. 17/722,752 mailed Sep. 12, 2024.
Restriction Requirement for U.S. Appl. No. 17/723,150 mailed Sep. 11, 2024.
Restriction Requirement for U.S. Appl. No. 17/723,656 mailed Sep. 12, 2024.
U.S. Appl. No. 18/882,984, filed Sep. 12, 2024.
U.S. Appl. No. 18/889,744, filed Sep. 19, 2024.
U.S. Appl. No. 18/933,729, filed Oct. 31, 2024.
U.S. Appl. No. 18/933,745, filed Oct. 31, 2024.
U.S. Appl. No. 18/933,749, filed Oct. 31, 2024.
U.S. Appl. No. 18/933,759, filed Oct. 31, 2024.
"Peripheral Interventions 2015 Product Catalog", Boston Scientific, 2015, 7 pages.

(56) References Cited

OTHER PUBLICATIONS

Alsafarr , et al., "Hydrodynamic Effects on Flow Through Screens at Intakes", Water Research vol. 8, Issue 9, Sep. 1974, pp. 617-622.
Brückler , et al., "Flow Design and Optimization of a Percutaneously Implantable Miniature Blood Pump", Medical technology in cardiology, 2002, 11 pages.
Fox , et al., "Introduction to Fluid Mechanics", Sixth Edition, pp. 341-343.
Kapur , et al., "Mechanical Left Ventricular Unloading to Reduce Infarct Size During Acute Myocardial Infarction: Insight from Preclinical and Clinical Studies", Journal of Cardiovascular Translational Research, Apr. 23, 2019, pp. 1-8.
Kaufman , "Invasive Vascular Diagnosis", Radiology Key Fastest Radiology Insight Engine, Chapter 3, Dec. 23, 2015, 12 pages.
Schmitz-Rode , "Percutaneously implantable, self-expanding left heart support pump", Clinic for Radiological Diagnostics, 2001, 19 Pages.
Siess , et al., "Basic Design Criteria for Rotary Blood Pumps", Rotary Blood Pumps, 2000, pp. 69-83.
Corrected Notice of Allowance for U.S. Appl. No. 16/275,559 mailed Nov. 8, 2023.
Corrected Notice of Allowance for U.S. Appl. No. 16/279,352 mailed Nov. 3, 2021.
Corrected Notice of Allowance for U.S. Appl. No. 16/281,237 mailed Mar. 31, 2021.
Corrected Notice of Allowance for U.S. Appl. No. 16/810,116 mailed Apr. 7, 2023.
Corrected Notice of Allowance for U.S. Appl. No. 16/810,121 mailed Jun. 28, 2022.
Corrected Notice of Allowance for U.S. Appl. No. 16/810,121 mailed Sep. 20, 2022.
Corrected Notice of Allowance for U.S. Appl. No. 16/810,172 mailed Feb. 2, 2022.
Corrected Notice of Allowance for U.S. Appl. No. 16/952,389 mailed Feb. 20, 2024.
Corrected Notice of Allowance for U.S. Appl. No. 16/952,389 mailed Mar. 4, 2024.
Corrected Notice of Allowance for U.S. Appl. No. 16/952,444 mailed Mar. 13, 2024.
Corrected Notice of Allowance for U.S. Appl. No. 17/069,570 mailed Apr. 10, 2024.
Corrected Notice of Allowance for U.S. Appl. No. 17/070,323 mailed Jun. 1, 2023.
Corrected Notice of Allowance for U.S. Appl. No. 17/070,323 mailed Oct. 4, 2023.
Corrected Notice of Allowance for U.S. Appl. No. 17/077,769 mailed Nov. 15, 2023.
Corrected Notice of Allowance for U.S. Appl. No. 17/077,769 mailed Nov. 6, 2023.
Corrected Notice of Allowance for U.S. Appl. No. 17/077,769 mailed Oct. 4, 2023.
Corrected Notice of Allowance for U.S. Appl. No. 17/180,041 mailed Jun. 30, 2023.
Corrected Notice of Allowance for U.S. Appl. No. 17/180,041 mailed Oct. 4, 2023.
Corrected Notice of Allowance for U.S. Appl. No. 17/182,482 mailed Feb. 7, 2023.
Examination Report for Australian Patent Application No. 2017349920 mailed Jun. 2, 2022.
Examination Report for Australian Patent Application No. 2017349920 mailed Nov. 4, 2022.
Examination Report for Australian Patent Application No. 2019206421 mailed Sep. 29, 2023.
Examination Report for European Application No. 21718229.4 mailed Mar. 17, 2022.
Examination Report for Indian Patent Application No. 201917018651 mailed Jun. 30, 2021.
Examination Report for Indian Patent Application No. 202047017397 mailed May 4, 2022.
Examination Report for Indian Patent Application No. 202147033522 mailed May 24, 2023.
Extended Search Report and Preliminary Opinion for European Application No. 23159720.4 mailed Jun. 27, 2023.
Extended Search Report for European Application No. 19172327.9 mailed Aug. 23, 2019.
Extended Search Report for European Application No. 20159714.3 mailed Jul. 3, 2020.
Extended Search Report for European Application No. 20159716.8 mailed Jul. 3, 2020.
Extended Search Report for European Application No. 20159718.4 mailed Jul. 9, 2020.
Extended Search Report for European Application No. 20195082.1 mailed Nov. 5, 2020.
Extended Search Report for European Application No. 20195084.7 mailed Nov. 5, 2020.
Extended Search Report for European Application No. 20195085.4 mailed Nov. 4, 2020.
Extended Search Report for European Application No. 20195987.1 mailed Nov. 5, 2020.
Extended Search Report for European Application No. 21156647.6 mailed May 21, 2021.
Extended Search Report for European Application No. 21158196.2 mailed Apr. 8, 2021.
Extended Search Report for European Application No. 21158902.3 mailed Apr. 29, 2021.
Extended Search Report for European Application No. 21158903.1 mailed Apr. 9, 2021.
Extended Search Report for European Application No. 21208803.3 mailed Apr. 13, 2022.
Extended Search Report for European Application No. 21209256.3 mailed Mar. 2, 2022.
Extended Search Report for European Application No. 22155936.2 mailed Jul. 8, 2022.
Extended Search Report for European Application No. 22163640.0 mailed Jun. 29, 2022.
Extended Search Report for European Application No. 22163648.3 mailed Aug. 10, 2022.
Extended Search Report for European Application No. 22163653.3 mailed Jul. 1, 2022.
Extended Search Report for European Application No. 22197511.3 mailed Dec. 5, 2022.
Extended Search Report for European Application No. 23159721.2 mailed Jun. 26, 2023.
Extended Search Report for European Application No. 23159724.6 mailed Jun. 26, 2023.
Extended Search Report for European Application No. 23159725.3 mailed Jun. 28, 2023.
Extended Search Report for European Application No. 23189145.8 mailed Nov. 27, 2023.
Extended Search Report for European Application No. 23189147.4 mailed Dec. 13, 2023.
Extended Search Report for European Application No. 23189148.2 mailed Dec. 13, 2023.
Extended Search Report for European Application No. 23189149.0 mailed Dec. 13, 2023.
Final Office Action for U.S. Appl. No. 16/275,559 mailed Jan. 4, 2021.
Final Office Action for U.S. Appl. No. 16/275,559 mailed May 17, 2022.
Final Office Action for U.S. Appl. No. 16/275,559 mailed Oct. 20, 2021.
Final Office Action for U.S. Appl. No. 16/276,965 mailed Apr. 13, 2021.
Final Office Action for U.S. Appl. No. 16/277,411 mailed Jun. 21, 2021.
Final Office Action for U.S. Appl. No. 16/279,352 mailed May 3, 2021.
Final Office Action for U.S. Appl. No. 16/952,327 mailed Jun. 8, 2023.
Final Office Action for U.S. Appl. No. 16/952,389 mailed Jul. 18, 2023.

(56) References Cited

OTHER PUBLICATIONS

Final Office Action for U.S. Appl. No. 16/952,444 mailed Jul. 5, 2023.
Final Office Action for U.S. Appl. No. 17/069,064 mailed May 25, 2022.
Final Office Action for U.S. Appl. No. 17/069,570 mailed Apr. 28, 2023.
Final Office Action for U.S. Appl. No. 17/070,670 mailed Jun. 2, 2023.
Final Office Action for U.S. Appl. No. 17/077,769 mailed Jun. 7, 2023.
Final Office Action for U.S. Appl. No. 17/078,472 mailed Oct. 23, 2023.
Final Office Action for U.S. Appl. No. 17/176,344 mailed Apr. 12, 2024.
Final Office Action for U.S. Appl. No. 17/176,344 mailed Oct. 12, 2022.
Final Office Action for U.S. Appl. No. 17/574,701 mailed Feb. 8, 2024.
Hearing Notice for Indian Patent Application No. 201917018651 mailed Dec. 11, 2023.
International Search Report and Written Opinion from International Application No. PCT/IB2019/050186 mailed Jul. 18, 2019.
International Search Report and Written Opinion from International Application No. PCT/IB2020/050515 mailed Sep. 9, 2020.
International Search Report and Written Opinion from International Application No. PCT/IB2021/052590 mailed Sep. 14, 2021.
International Search Report and Written Opinion from International Application No. PCT/IB2021/052857 mailed Oct. 5, 2021.
International Search Report and Written Opinion from International Application No. PCT/IB2022/051990 mailed Aug. 10, 2022.
International Search Report and Written Opinion from International Application No. PCT/IB2022/058101 mailed Feb. 20, 2023.
International Search Report and Written Opinion from International Application No. PCT/IB2023/059136 mailed Jan. 2, 2024.
International Search Report and Written Opinion from International Application No. PCT/IB2023/059137 mailed Mar. 21, 2024.
International Search Report and Written Opinion from International Application No. PCT/IB2023/059138 mailed Feb. 7, 2024.
International Search Report and Written Opinion from International Application No. PCT/IB2023/059141 mailed Mar. 22, 2024.
International Search Report and Written Opinion from International Application No. PCT/IB2023/059142 mailed Apr. 16, 2024.
International Search Report and Written Opinion from International Application No. PCT/IB2023/059143 mailed Mar. 14, 2024.
International Search Report and Written Opinion from International Application No. PCT/IL2017/051158 mailed Jan. 17, 2018.
Invitation to Pay Additional Fees for International Application No. PCT/IB2020/050515 mailed Mar. 31, 2020.
Invitation to Pay Additional Fees for International Application No. PCT/IB2021/052590 mailed Jul. 23, 2021.
Invitation to Pay Additional Fees for International Application No. PCT/IB2021/052857 mailed Jul. 7, 2021.
Invitation to Pay Additional Fees for International Application No. PCT/IB2022/051990 mailed May 13, 2022.
Invitation to Pay Additional Fees for International Application No. PCT/IB2023/059134 mailed Dec. 21, 2023.
Invitation to Pay Additional Fees for International Application No. PCT/IB2023/059137 mailed Jan. 2, 2024.
Invitation to Pay Additional Fees for International Application No. PCT/IB2023/059138 mailed Dec. 8, 2023.
Invitation to Pay Additional Fees for International Application No. PCT/IB2023/059141 mailed Dec. 22, 2023.
Invitation to Pay Additional Fees for International Application No. PCT/IB2023/059142 mailed Jan. 2, 2024.
Issue Notification for U.S. Appl. No. 16/275,559 mailed Nov. 22, 2023.
Issue Notification for U.S. Appl. No. 16/276,965 mailed Mar. 16, 2022.
Issue Notification for U.S. Appl. No. 16/277,411 mailed Feb. 9, 2022.
Issue Notification for U.S. Appl. No. 16/278,482 mailed Jan. 13, 2021.
Issue Notification for U.S. Appl. No. 16/279,352 mailed Nov. 10, 2021.
Issue Notification for U.S. Appl. No. 16/280,566 mailed Nov. 10, 2021.
Issue Notification for U.S. Appl. No. 16/281,237 mailed Apr. 14, 2021.
Issue Notification for U.S. Appl. No. 16/281,264 mailed Dec. 16, 2020.
Issue Notification for U.S. Appl. No. 16/750,354 mailed Nov. 17, 2021.
Issue Notification for U.S. Appl. No. 16/810,086 mailed Mar. 9, 2022.
Issue Notification for U.S. Appl. No. 16/810,116 mailed May 17, 2023.
Issue Notification for U.S. Appl. No. 16/810,172 mailed Mar. 23, 2022.
Issue Notification for U.S. Appl. No. 16/810,270 mailed Oct. 12, 2022.
Issue Notification for U.S. Appl. No. 16/952,389 mailed Mar. 13, 2024.
Issue Notification for U.S. Appl. No. 16/952,444 mailed Mar. 20, 2024.
Issue Notification for U.S. Appl. No. 17/069,321 mailed Mar. 16, 2022.
Issue Notification for U.S. Appl. No. 17/070,323 mailed Oct. 18, 2023.
Issue Notification for U.S. Appl. No. 17/077,769 mailed Nov. 29, 2023.
Issue Notification for U.S. Appl. No. 17/078,439 mailed Apr. 3, 2024.
Issue Notification for U.S. Appl. No. 17/177,296 mailed Mar. 13, 2024.
Issue Notification for U.S. Appl. No. 17/180,041 mailed Oct. 18, 2023.
Non-Final Office Action for U.S. Appl. No. 16/275,559 mailed Jan. 19, 2023.
Non-Final Office Action for U.S. Appl. No. 16/275,559 mailed Jan. 26, 2022.
Non-Final Office Action for U.S. Appl. No. 16/275,559 mailed May 26, 2021.
Non-Final Office Action for U.S. Appl. No. 16/275,559 mailed Sep. 4, 2020.
Non-Final Office Action for U.S. Appl. No. 16/276,965 mailed Jul. 26, 2021.
Non-Final Office Action for U.S. Appl. No. 16/276,965 mailed Jun. 19, 2020.
Non-Final Office Action for U.S. Appl. No. 16/276,965 mailed Nov. 30, 2020.
Non-Final Office Action for U.S. Appl. No. 16/277,411 mailed Feb. 9, 2021.
Non-Final Office Action for U.S. Appl. No. 16/278,482 mailed Jun. 23, 2020.
Non-Final Office Action for U.S. Appl. No. 16/279,352 mailed Nov. 10, 2020.
Non-Final Office Action for U.S. Appl. No. 16/280,566 mailed Dec. 21, 2020.
Non-Final Office Action for U.S. Appl. No. 16/281,237 mailed Aug. 21, 2020.
Non-Final Office Action for U.S. Appl. No. 16/281,264 mailed Jun. 29, 2020.
Non-Final Office Action for U.S. Appl. No. 16/810,121 mailed Mar. 9, 2022.
Non-Final Office Action for U.S. Appl. No. 16/952,327 mailed Nov. 8, 2022.
Non-Final Office Action for U.S. Appl. No. 16/952,327 mailed Oct. 13, 2023.
Non-Final Office Action for U.S. Appl. No. 16/952,389 mailed Dec. 21, 2022.

(56) References Cited

OTHER PUBLICATIONS

Non-Final Office Action for U.S. Appl. No. 16/952,444 mailed Jan. 6, 2023.
Non-Final Office Action for U.S. Appl. No. 17/069,064 mailed Dec. 9, 2021.
Non-Final Office Action for U.S. Appl. No. 17/069,064 mailed Nov. 7, 2022.
Non-Final Office Action for U.S. Appl. No. 17/069,321 mailed Nov. 18, 2021.
Non-Final Office Action for U.S. Appl. No. 17/069,570 mailed Oct. 2, 2023.
Non-Final Office Action for U.S. Appl. No. 17/069,570 mailed Oct. 6, 2022.
Non-Final Office Action for U.S. Appl. No. 17/070,323 mailed Oct. 6, 2022.
Non-Final Office Action for U.S. Appl. No. 17/070,670 mailed Oct. 30, 2023.
Non-Final Office Action for U.S. Appl. No. 17/070,670 mailed Oct. 5, 2022.
Non-Final Office Action for U.S. Appl. No. 17/077,769 mailed Oct. 5, 2022.
Non-Final Office Action for U.S. Appl. No. 17/078,439 mailed Jun. 1, 2023.
Non-Final Office Action for U.S. Appl. No. 17/078,472 mailed Feb. 14, 2024.
Non-Final Office Action for U.S. Appl. No. 17/078,472 mailed May 4, 2023.
Non-Final Office Action for U.S. Appl. No. 17/176,344 mailed Apr. 20, 2022.
Non-Final Office Action for U.S. Appl. No. 17/176,344 mailed Oct. 31, 2023.
Non-Final Office Action for U.S. Appl. No. 17/180,041 mailed Jan. 31, 2023.
Non-Final Office Action for U.S. Appl. No. 17/528,807 mailed Jan. 12, 2024.
Non-Final Office Action for U.S. Appl. No. 17/574,701 mailed Sep. 27, 2023.
Notice of Allowance for U.S. Appl. No. 16/275,559 mailed Jul. 27, 2023.
Notice of Allowance for U.S. Appl. No. 16/275,559 mailed Oct. 4, 2023.
Notice of Allowance for U.S. Appl. No. 16/276,965 mailed Jan. 26, 2022.
Notice of Allowance for U.S. Appl. No. 16/277,411 mailed Dec. 8, 2021.
Notice of Allowance for U.S. Appl. No. 16/278,482 mailed Dec. 2, 2020.
Notice of Allowance for U.S. Appl. No. 16/279,352 mailed Oct. 1, 2021.
Notice of Allowance for U.S. Appl. No. 16/280,566 mailed Aug. 31, 2021.
Notice of Allowance for U.S. Appl. No. 16/281,237 mailed Feb. 1, 2021.
Notice of Allowance for U.S. Appl. No. 16/281,264 mailed Nov. 12, 2020.
Notice of Allowance for U.S. Appl. No. 16/750,354 mailed Oct. 18, 2021.
Notice of Allowance for U.S. Appl. No. 16/810,086 mailed Jan. 7, 2022.
Notice of Allowance for U.S. Appl. No. 16/810,116 mailed Mar. 13, 2023.
Notice of Allowance for U.S. Appl. No. 16/810,121 mailed Aug. 19, 2022.
Notice of Allowance for U.S. Appl. No. 16/810,121 mailed Jun. 1, 2022.
Notice of Allowance for U.S. Appl. No. 16/810,172 mailed Jan. 10, 2022.
Notice of Allowance for U.S. Appl. No. 16/810,270 mailed Apr. 14, 2022.
Notice of Allowance for U.S. Appl. No. 16/810,270 mailed Jul. 22, 2022.
Notice of Allowance for U.S. Appl. No. 16/952,389 mailed Feb. 7, 2024.
Notice of Allowance for U.S. Appl. No. 16/952,444 mailed Feb. 15, 2024.
Notice of Allowance for U.S. Appl. No. 17/069,064 mailed Mar. 8, 2023.
Notice of Allowance for U.S. Appl. No. 17/069,321 mailed Feb. 2, 2022.
Notice of Allowance for U.S. Appl. No. 17/069,570 mailed Mar. 13, 2024.
Notice of Allowance for U.S. Appl. No. 17/070,323 mailed Aug. 30, 2023.
Notice of Allowance for U.S. Appl. No. 17/070,323 mailed May 15, 2023.
Notice of Allowance for U.S. Appl. No. 17/077,769 mailed Sep. 27, 2023.
Notice of Allowance for U.S. Appl. No. 17/078,439 mailed Dec. 5, 2023.
Notice of Allowance for U.S. Appl. No. 17/078,439 mailed Feb. 27, 2024.
Notice of Allowance for U.S. Appl. No. 17/173,944 mailed Jul. 10, 2023.
Notice of Allowance for U.S. Appl. No. 17/173,944 mailed Mar. 6, 2024.
Notice of Allowance for U.S. Appl. No. 17/173,944 mailed Nov. 8, 2023.
Notice of Allowance for U.S. Appl. No. 17/177,296 mailed Feb. 14, 2024.
Notice of Allowance for U.S. Appl. No. 17/177,296 mailed Nov. 17, 2023.
Notice of Allowance for U.S. Appl. No. 17/180,041 mailed Jun. 13, 2023.
Notice of Allowance for U.S. Appl. No. 17/180,041 mailed Sep. 18, 2023.
Notice of Allowance for U.S. Appl. No. 17/182,482 mailed Apr. 21, 2023.
Notice of Allowance for U.S. Appl. No. 17/182,482 mailed Jan. 5, 2023.
Notice of Missing Requirements for U.S. Appl. No. 18/447,025 mailed Feb. 1, 2024.
Office Action for Canadian Application No. 3,039,285 mailed Mar. 24, 2023.
Office Action for Canadian Application No. 3,080,800 mailed Sep. 12, 2023.
Office Action for Canadian Application No. 3,122,415 mailed Mar. 31, 2023.
Office Action for Canadian Application No. 3,176,272 mailed Jan. 2, 2024.
Office Action for Chinese Application No. 201780066201.3 mailed Jun. 29, 2021.
Office Action for Chinese Application No. 201980007116.9 mailed Nov. 28, 2022.
Office Action for Chinese Application No. 202080017728.9 mailed Nov. 6, 2023.
Office Action for Japanese Application No. 2019-521643 mailed Apr. 11, 2023.
Office Action for Japanese Application No. 2019-521643 mailed May 10, 2022.
Office Action for Japanese Application No. 2019-521643 mailed Oct. 27, 2022.
Office Action for Japanese Application No. 2019-521643 mailed Sep. 28, 2021.
Office Action for Japanese Application No. 2020-537746 mailed Feb. 21, 2023.
Office Action for Japanese Application No. 2021-533242 mailed Nov. 8, 2023.
Restriction Requirement for U.S. Appl. No. 16/275,559 mailed Jun. 2, 2020.
Restriction Requirement for U.S. Appl. No. 16/279,352 mailed Aug. 11, 2020.

(56) References Cited

OTHER PUBLICATIONS

Restriction Requirement for U.S. Appl. No. 16/280,566 mailed Aug. 11, 2020.
Restriction Requirement for U.S. Appl. No. 16/810,116 mailed Jun. 29, 2022.
Supplemental Notice of Allowability for U.S. Appl. No. 16/276,965 mailed Mar. 10, 2022.
Supplemental Notice of Allowability for U.S. Appl. No. 16/276,965 mailed Mar. 2, 2022.
Supplemental Notice of Allowability for U.S. Appl. No. 16/278,482 mailed Dec. 24, 2020.
Supplemental Notice of Allowability for U.S. Appl. No. 16/279,352 mailed Oct. 21, 2021.
Third Party Submission received during the prosecution of U.S. Appl. No. 17/078,439 on Sep. 28, 2022.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 16/750,354, filed Jan. 23, 2020.
U.S. Appl. No. 16/810,086, filed Mar. 5, 2020.
U.S. Appl. No. 16/810,121, filed Mar. 5, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
U.S. Appl. No. 17/528,015, filed Nov. 16, 2021.
U.S. Appl. No. 17/528,807, filed Nov. 17, 2021.
U.S. Appl. No. 17/532,318, filed Nov. 22, 2021.
U.S. Appl. No. 17/574,701, filed Jan. 13, 2022.
U.S. Appl. No. 17/609,589, filed Nov. 8, 2021.
U.S. Appl. No. 17/677,571, filed Feb. 22, 2022.
U.S. Appl. No. 17/678,122, filed Feb. 23, 2022.
U.S. Appl. No. 17/857,402, filed Jul. 5, 2022.
U.S. Appl. No. 18/121,995, filed Mar. 15, 2023.
U.S. Appl. No. 18/122,456, filed Mar. 16, 2023.
U.S. Appl. No. 18/122,486, filed Mar. 16, 2023.
U.S. Appl. No. 18/122,504, filed Mar. 16, 2023.
U.S. Appl. No. 18/444,972, filed Feb. 19, 2024.
U.S. Appl. No. 18/447,025, filed Aug. 9, 2023.
U.S. Appl. No. 18/511,532, filed Nov. 16, 2023.
U.S. Appl. No. 18/632,533, filed Apr. 11, 2024.
U.S. Appl. No. 18/632,545, filed Apr. 11, 2024.
U.S. Appl. No. 18/632,557, filed Apr. 11, 2024.
U.S. Appl. No. 18/632,569, filed Apr. 11, 2024.
U.S. Appl. No. 18/635,275, filed Apr. 15, 2024.
U.S. Appl. No. 18/635,286, filed Apr. 15, 2024.
U.S. Appl. No. 18/635,292, filed Apr. 15, 2024.
U.S. Appl. No. 18/637,653, filed Apr. 17, 2024.
U.S. Appl. No. 18/637,655, filed Apr. 17, 2024.
U.S. Appl. No. 18/637,667, filed Apr. 17, 2024.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
U.S. Appl. No. 63/003,955, filed Apr. 2, 2020.
U.S. Appl. No. 63/006,122, filed Apr. 7, 2020.
U.S. Appl. No. 63/114,136, filed Nov. 16, 2020.
U.S. Appl. No. 63/129,983, filed Dec. 23, 2020.
U.S. Appl. No. 63/158,708, filed Mar. 9, 2021.
U.S. Appl. No. 63/254,321, filed Oct. 11, 2021.
U.S. Appl. No. 63/317,199, filed Mar. 7, 2022.
U.S. Appl. No. 63/406,427, filed Sep. 14, 2022.
U.S. Appl. No. 63/432,496, filed Dec. 14, 2022.
"Compendium of Technical and Scientific Information for the Hemopump Temporary Cardiac Assist System", Johnson & Johnson Interventional Systems, 1988, pp. 1-15.
"Tanslation of decision of Board 4 (Nullity Board) of the German Federal Patent Court re German patent 10336902", pronounced Nov. 15, 2016, and appendices to decision, 62 pages.
Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Agarwal, et al., "Newer-generation ventricular assist devices.", Best Practice & Research Clinical Anaesthesiology, 2012, pp. 117-130.
Alba, et al., "The future is here: ventricular assist devices for the failing heart", Expert review of cardiovascular therapy, 2009, pp. 1067-1077.
Bai, et al., "A Split-Array, C-2C Switched-Capacitor Power Amplifier in 65 nm CMOS", IEEE Radio Frequency Integrated Circuits Symposium, 2017, pp. 336-339.
Burnett, et al., "Renal Interstitial Pressure and Sodium Excretion During Renal Vein Constriction", American Physiological Society, 1980, pp. F279-F282.
Butler, et al., "The Hemopump—A New Cardiac Prothesis Device", Reprinted from IEEE Transactions on Biomedical Engineering, vol. 37, No. 2, Feb. 1990, pp. 192-195.
Cassidy, et al., "The Conductance Volume Catheter Technique for Measurement of Left Ventricular Volume in Young Piglets", Pediatric Research, 1992, pp. 85-90.
Chan, et al., "Rapid manufacturing techniques in the development of an axial blood pump impeller", Proc. Instn Mech. Engrs vol. 217 Part H: J. Engineering in Medicine, 2003, pp. 469-475.
Chang, et al., "Leveraging Device-Arterial Coupling to Determine Cardiac and Vascular State", IEEE Transactions on Biomedical Engineering, vol. 66, No. 10, Oct. 2019, pp. 2800-2808.
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, 2007, pp. 872-878.
Damman, et al., "Increased Central Venous Pressure Is Associated With Impaired Renal Function and Mortality in a Broad Spectrum of Patients With Cardiovascular Disease", Journal of American College of Cardiology, 2009, pp. 582-588.
Dekker, et al., "Efficacy of a New Intraaortic Propeller Pump vs the Intraaortic Balloon Pump", CHEST, vol. 123, Issue 6, Jun. 2003, pp. 2089-2095.

(56) References Cited

OTHER PUBLICATIONS

Doty, et al., "The Effect of Increased Renal Venous Pressure on Renal Function", The Journal of Trauma,, Dec. 1999, pp. 1000-1003.
Felker, et al., "Anemia as a Risk Factor and Therapeutic Target in Heart Failure", Journal of the American College of Cardiology, 2004, pp. 959-966.
Firth, et al., "Raised Venous Pressure: A Direct Cause of Sodium Retention in Oedema?", The Lancet, May 7, 1988, pp. 1033-1036.
Flameng, "Temporary Cardiac Assist with an Axial Pump System", Steinkopff Verlag Darmstadt, 1991, 79 pages.
Forman, et al., "Incidence, Predictors at Admission, and Impact of Worsening Renal Function Among Patients Hospitalized With Heart Failure", Journal of American College of Cardiology, 2004, pp. 61-67.
Fraser, et al., "The use of computational fluid dynamics in the development of ventricular assist devices", Medical engineering & physics, 2011, pp. 263-280.
Frazier, et al., "First Human Use of the Hemopump, a CatheterMounted Ventricular Assist Device", Ann Thorac Surg, 1990, pp. 299-304.
Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gomes, et al., "Heterologous Valve Implantation in the Infra-Renal Vena Cava for Treatment of the Iliac Venous Valve Regurgitation Disease: Experimental Study", Rev Bras Cir Cardiovasc, 2002, pp. 367-369.
Gunther, et al., "Experimentelle Radiologie", Life Sciences, Berichte Aus Der Rheinischwestfälischen Technischen Hochschule Aachen Ausgabe Feb. 2002.
Haddy, et al., "Effect of Elevation of Intraluminal Pressure on Renal Vascular Resistance", Circulation Research Journal of the American Heart Association, 1956, pp. 659-663.
Heywood, et al., "High Prevalence of Renal Dysfunction and Its Impact on Outcome in 118,465 Patients Hospitalized With Acute Decompensated Heart Failure: A Report From the ADHERE Database", Journal of Cardiac Failure, 2007, pp. 422-430.
Hillege, et al., "Renal Function as a Predictor of Outcome in a Broad Spectrum of Patients With Heart Failure", Circulation Journal of the American Heart Association, 2006, pp. 671-678.
Hillege, et al., "Renal Function, Neurohormonal Activation, and Survival in Patients With Chronic Heart Failure", Circulation Journal of the American Heart Association, 2000, pp. 203-210.
Hsu, et al., "Review of recent patents on foldable ventricular assist devices", Recent Patents on Biomedical Engineering, 2012, pp. 208-222.
Ikari, "The Physics of Guiding Catheter; The IKARI Guiding Catheter in TRI", available at httu:i /www.docstoc.com/docs/148136553/The-[KARI-catheter---anovel-guide-for-TRI--.
Kafagy, et al., "Design of axial blood pumps for patients with dysfunctional fontan physiology: computational studies and performance testing", Artificial organs, 2015, pp. 34-42.
Kang, et al., "Fluid dynamics aspects of miniaturized axial-flow blood pump", Bio-medical materials and engineering, 2014, pp. 723-729.
Keller, et al., "Dynamic Modulation of Device-Arterial Coupling to Determine Cardiac Output and Vascular Resistance", Annals of Biomedical Engineering, vol. 48, No. 9, Sep. 2020, pp. 2333-2342.
Koochaki, et al., "A new design and computational fluid dynamics study of an implantable axial blood pump", Australasian Physical & Engineering Sciences in Medicine, 2013, pp. 417-422.
Lauten, et al., "Heterotopic Transcatheter Tricuspid Valve Implantation: First-In-Man Application of a Novel Approach to Tricuspid Regurgitation", European Heart Journal, Feb. 15, 2011, pp. 1207-1213.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
Mcalister, et al., "Renal Insufficiency and Heart Failure: Prognostic and Therapeutic Implications From a Prospective Cohort Study", Circulation Journal of the American Heart Association, 2004, pp. 1004-1009.
Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.
Meyns, et al., "The Heart-Hemopump Interaction: A Study of Hemopump Flow as a Function of Cardiac Activity", Artificial Organs, 1996, pp. 641-649.
Mullens, et al., "Elevated Intra-Abdominal Pressure in Acute Decompensated Heart Failure. A Potential Contributor to Worsening Renal Function", Journal of the American College of Cardiology, 2008, pp. 300-306.
Mullens, et al., "Importance of Venous Congestion for Worsening of Renal Function in Advanced Decompensated Heart Failure", Journal of American College of Cardiology, 2009, pp. 589-596.
Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, 2008, pp. 508-514.
Notarius, et al., "Central Venous Pressure During Exercise: Role of Muscle Pump", Canadian Journal of Physiology and Pharmacology, 1996, pp. 647-651.
Park, et al., "Nutcracker Syndrome: Intravascular Stenting Approach", Nephrol Dial Transplant, 2000, pp. 99-101.
Reul, et al., "Blood pumps for circulatory support", Perfusion—Sevenoaks, 2000, pp. 295-312.
Reul, et al., "Rotary blood pumps in circulatory assist", Perfusion, May 1995, pp. 153-158.
Rodefeld, "Cavopulmonary assist for the univentricular Fontan circulation: von Karman viscous impeller pump", The Journal of Thoracic and Cardiovascular Surgery, 2010, pp. 529-536.
Roundtree, et al., "The Hemopump Cardiac Assist System: Nursing Care of the Patient", Reprinted from Critical Care Nurse, Apr. 1991.
Schmitz-Rode, et al., "An Expandable Percutaneous Catheter Pump for Left Ventricular Support", Journal of the American College of Cardiology, vol. 45, No. 11, 2005, pp. 1856-1861.
Schmitz-Rode, et al., "Axial flow catheter pump for circulatory support", Biomed Tech (Berl), 2002, pp. 142-143.
Scholz, et al., "MechanicaL left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.
Semple, et al., "Effect of Increased Renal Venous Pressure on Circulatory "Autoregulation" of Isolated Dog Kidneys", Circulation Research Journal of the American Heart Association, 1959, pp. 643-648.
Sianos, et al., "The Recover® LP 2.5 catheter-mounted left ventricular assist device", EuroIntervention, 2006, pp. 116-119.
Siess, et al., "Concept, realization, and first in vitro testing of an intraarterial microaxial blood pump", Artificial Organs, 1995, pp. 644-652.
Siess, et al., "Hemodynamic system analysis of intraarterial microaxial pumps in vitro and in vivo", Artificial Organs, Jun. 1996, pp. 650-661.
Siess, "PhD Chapter 3—English translation", https://www.shaker.eu/en/content/catalogue/index.asp?lang=en&ID=8&ISBN=978-3-8265-6150-4&search=yes.
Siess, "System Analysis and Development of Intravascular Rotation Pumps for Cardiac Assist", Helmholtz-Institute—Chapter 3, Jun. 1998, 17 pages.
Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.

(56) References Cited

OTHER PUBLICATIONS

Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.
Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.
Song, et al., "Axial flow blood pumps", ASAIO journal, 2003, pp. 355-364.
Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.
Tang, et al., "Anemia in Chronic Heart Failure: Prevalence, Etiology, Clinical Correlates, and Treatment Options", Circulation Journal of the American Heart Association, 2006, pp. 2454-2461.
Throckmorton, et al., "Design of a protective cage for an intra vascular axial flow blood pump to mechanically assist the failing Fontan", Artificial organs, 2009, pp. 611-621.
Throckmorton, et al., "Mechanical Cavopulmonary Assist for the Univentricular Fontan Circulation Using a Novel Folding Propeller Blood Pump", ASAIO Journal, 2007, pp. 734-741.
Thunberg, et al., "Ventricular assist devices today and tomorrow", Journal of cardiothoracic and vascular anesthesia, 2010, pp. 656-680.
Timms, "A review of clinical ventricular assist devices", Medical engineering & physics, 2011, pp. 1041-1047.
Triep, et al., "Computational Fluid Dynamics and Digital Particle Image Velocimetry Study of the Flow Through an Optimized Micro-axial Blood Pump", Artificial Organs, May 2006, pp. 384-391.
Uthoff, et al., "Central venous pressure at emergency room presentation predicts cardiac rehospitalization in patients with decompensated heart failure", European Journal of Heart Failure, 2010, pp. 469-476.
Van Mieghem, et al., "Design and Principle of Operation of the HeartMate PHPTM (Percutaneous Heart Pump)", EuroIntervention, 2016.
Vercaemst, et al., "Impella: A Miniaturized Cardiac Support System in an Era of Minimal Invasive Cardiac Surgery", Presented at the 39th International Conference of the American Society of Extra-Corporeal Technology, Mar. 22-25, 2001.
Wampler, "Newspaper Articles", Captain Hemo, 1988, 6 pages.
Wampler, "Newsweek", Captain Hemo, May 16, 1988, 3 pages.
Wampler, "The first co-axial flow pump for human use: the Hemopump", Flameng W. (eds) Temporary Cardiac Assist with an Axial Pump System, 1991.
Wampler, "THI Today", Captain Hemo, Summer 1988, 2 pages.
Wampler, "Time Magazine", Captain Hemo, May 1988, 2 pages.
Wampler, et al., "Treatment of Cardiogenic Shock With the Hemopump Left Ventricular Assist Device", Annual of Thoracic Surgery, vol. 52, pp. 560-513, 1991.
Wampler, "U.S. News & World Report", Captain Hemo, pp. 1-2, May 16, 1988.
Wencker, "Acute Cardio-Renal Syndrome: Progression From Congestive Heart Failure to Congestive Kidney Failure", Current Heart Failure Reports, 2007, pp. 134-138.
Winton, "The Control of Glomerular Pressure by Vascular Changes Within the Mammalian Kidney, Demonstrated by the Actions of Adrenaline", Journal of Physiology, Nov. 1931, pp. 151-162.
Winton, "The Influence of Venous Pressure on the Isolated Mammalian Kidney", Journal of Physiology, Jun. 6, 1931, pp. 49-61.
Wood, "The Mechanism of the Increased Venous Pressure With Exercise in Congestive Heart Failure", Journal of Clinical Investigation, 1962, pp. 2020-2024.
Wu, et al., "Design and simulation of axial flow maglev blood pump", International Journal of Information Engineering and Electronic Business, 2011, p. 42.
Yancy, et al., "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, 2006, pp. 76-84.
Corrected Notice of Allowance for U.S. Appl. No. 17/528,015 mailed Apr. 11, 2025.
Corrected Notice of Allowance for U.S. Appl. No. 17/528,015 mailed May 13, 2025.
Corrected Notice of Allowance for U.S. Appl. No. 17/609,589 mailed Feb. 24, 2026.
Corrected Notice of Allowance for U.S. Appl. No. 17/678,122 mailed May 27, 2025.
Corrected Notice of Allowance for U.S. Appl. No. 17/722,752 mailed Jul. 25, 2025.
Corrected Notice of Allowance for U.S. Appl. No. 17/723,150 mailed Apr. 24, 2025.
Corrected Notice of Allowance for U.S. Appl. No. 17/857,402 mailed Oct. 30, 2024.
Corrected Notice of Allowance for U.S. Appl. No. 17/907,618 mailed Apr. 27, 2026.
Corrected Notice of Allowance for U.S. Appl. No. 18/122,456 mailed Feb. 19, 2026.
Corrected Notice of Allowance for U.S. Appl. No. 18/122,486 mailed Dec. 17, 2025.
Corrected Notice of Allowance for U.S. Appl. No. 18/511,532 mailed May 5, 2026.
Corrected Notice of Allowance for U.S. Appl. No. 18/933,729 mailed Jul. 2, 2025.
Corrected Notice of Allowance for U.S. Appl. No. 18/933,729 mailed Jul. 23, 2025.
Examination Report for Australian Application No. 2021253815 mailed Apr. 15, 2026.
Examination Report for Australian Application No. 2021253815 mailed Dec. 19, 2025.
Examination Report for Australian Application No. 2024203274 mailed May 1, 2025.
Examination Report for Australian Application No. 2025200291 mailed Sep. 16, 2025.
Examination Report for Indian Application No. 202247058135 mailed Jan. 27, 2026.
Examination Report for Indian Application No. 202417030022 mailed May 4, 2026.
Extended Search Report for European Application No. 24200871.2 mailed Jan. 30, 2025.
Extended Search Report for European Application No. 24200875.3 mailed Jan. 13, 2025.
Extended Search Report for European Application No. 24206716.3 mailed Nov. 21, 2024.
Extended Search Report for European Application No. 24209593.3 mailed Dec. 4, 2024.
Extended Search Report for European Application No. 24209594.1 mailed Dec. 4, 2024.
Extended Search Report for European Application No. 24211523.6 mailed Feb. 7, 2025.
Extended Search Report for European Application No. 24211525.1 mailed Feb. 20, 2025.
Extended Search Report for European Application No. 25151821.3 mailed Apr. 14, 2025.
Extended Search Report for European Application No. 25163036.4 mailed Jul. 25, 2025.
Extended Search Report for European Application No. 25163043.0 mailed Jul. 28, 2025.
Extended Search Report for European Application No. 25204084.5 mailed Feb. 2, 2026.
Extended Search Report for European Application No. 26152673.5 mailed Jun. 24, 2026.
Extended Search Report for European Application No. 26153273.3 mailed Jun. 24, 2026.

(56) References Cited

OTHER PUBLICATIONS

Final Office Action for U.S. Appl. No. 17/078,472 mailed Mar. 12, 2025.
Final Office Action for U.S. Appl. No. 17/176,344 mailed Oct. 7, 2025.
Final Office Action for U.S. Appl. No. 17/677,571 mailed Apr. 15, 2026.
Final Office Action for U.S. Appl. No. 17/678,812 mailed May 28, 2025.
Final Office Action for U.S. Appl. No. 17/682,073 mailed Feb. 23, 2026.
Final Office Action for U.S. Appl. No. 17/723,656 mailed Apr. 8, 2025.
Final Office Action for U.S. Appl. No. 17/723,656 mailed Jun. 2, 2026.
Final Office Action for U.S. Appl. No. 17/907,618 mailed Nov. 24, 2025.
Final Office Action for U.S. Appl. No. 18/001,680 mailed Dec. 23, 2025.
Final Office Action for U.S. Appl. No. 18/121,995 mailed Dec. 19, 2025.
Final Office Action for U.S. Appl. No. 18/122,504 mailed May 5, 2026.
Final Office Action for U.S. Appl. No. 18/122,504 mailed Oct. 23, 2025.
Final Office Action for U.S. Appl. No. 18/511,532 mailed Apr. 11, 2025.
Final Office Action for U.S. Appl. No. 18/632,533 mailed Jun. 15, 2026.
Final Office Action for U.S. Appl. No. 18/652,959 mailed Jul. 1, 2026.
International Search Report and Written Opinion from International Application No. PCT/IB2024/063109 mailed Jun. 2, 2025.
International Search Report and Written Opinion from International Application No. PCT/IB2024/063110 mailed Jun. 2, 2025.
International Search Report and Written Opinion from International Application No. PCT/IB2024/063113 mailed Jun. 11, 2025.
International Search Report and Written Opinion from International Application No. PCT/IB2024/063115 mailed Jun. 19, 2025.
International Search Report and Written Opinion from International Application No. PCT/IB2025/056384 mailed Dec. 16, 2025.
International Search Report and Written Opinion from International Application No. PCT/IB2025/056385 mailed Jan. 16, 2026.
International Search Report and Written Opinion from International Application No. PCT/IB2025/059116 mailed Jan. 2, 2026.
Invitation to Pay Additional Fees for International Application No. PCT/IB2024/063113 mailed Apr. 17, 2025.
Invitation to Pay Additional Fees for International Application No. PCT/IB2024/063115 mailed Apr. 15, 2025.
Invitation to Pay Additional Fees for International Application No. PCT/IB2025/056384 mailed Oct. 9, 2025.
Invitation to Pay Additional Fees for International Application No. PCT/IB2025/056385 mailed Oct. 1, 2025.
Invitation to Pay Additional Fees for International Application No. PCT/IB2025/059116 mailed Nov. 4, 2025.
Invitation to Pay Additional Fees for International Application No. PCT/IB2026/053511 mailed Jul. 8, 2026.
Issue Notification for U.S. Appl. No. 17/070,670 mailed Jan. 8, 2025.
Issue Notification for U.S. Appl. No. 17/528,015 mailed Jun. 18, 2025.
Issue Notification for U.S. Appl. No. 17/532,318 mailed Oct. 1, 2025.
Issue Notification for U.S. Appl. No. 17/609,589 mailed May 6, 2026.
Issue Notification for U.S. Appl. No. 17/678,122 mailed Jun. 4, 2025.
Issue Notification for U.S. Appl. No. 17/722,752 mailed Oct. 15, 2025.
Issue Notification for U.S. Appl. No. 17/723,150 mailed Oct. 1, 2025.
Issue Notification for U.S. Appl. No. 17/857,402 mailed Dec. 18, 2024.
Issue Notification for U.S. Appl. No. 18/122,456 mailed Feb. 25, 2026.
Issue Notification for U.S. Appl. No. 18/122,486 mailed Jan. 28, 2026.
Issue Notification for U.S. Appl. No. 18/511,532 mailed May 20, 2026.
Issue Notification for U.S. Appl. No. 18/933,729 mailed Jan. 28, 2026.
Liu, et al., "Crystallinity and Oxygen Transport Properties of PET Bottle Walls" Journal of Applied Polymer Science, vol. 94, pp. 671-677, 2004.
Non-Final Office Action for U.S. Appl. No. 17/078,472 mailed Aug. 12, 2025.
Non-Final Office Action for U.S. Appl. No. 17/078,472 mailed Nov. 19, 2024.
Non-Final Office Action for U.S. Appl. No. 17/176,344 mailed Feb. 20, 2025.
Non-Final Office Action for U.S. Appl. No. 17/609,589 mailed Jan. 30, 2025.
Non-Final Office Action for U.S. Appl. No. 17/609,589 mailed Sep. 5, 2025.
Non-Final Office Action for U.S. Appl. No. 17/677,571 mailed Aug. 20, 2025.
Non-Final Office Action for U.S. Appl. No. 17/677,571 mailed Feb. 20, 2025.
Non-Final Office Action for U.S. Appl. No. 17/678,122 mailed Dec. 5, 2024.
Non-Final Office Action for U.S. Appl. No. 17/678,812 mailed Dec. 3, 2025.
Non-Final Office Action for U.S. Appl. No. 17/682,073 mailed May 28, 2025.
Non-Final Office Action for U.S. Appl. No. 17/682,104 mailed Jan. 16, 2026.
Non-Final Office Action for U.S. Appl. No. 17/682,104 mailed May 28, 2025.
Non-Final Office Action for U.S. Appl. No. 17/722,752 mailed Mar. 17, 2025.
Non-Final Office Action for U.S. Appl. No. 17/723,150 mailed Dec. 19, 2024.
Non-Final Office Action for U.S. Appl. No. 17/723,656 mailed Dec. 5, 2024.
Non-Final Office Action for U.S. Appl. No. 17/723,656 mailed Nov. 3, 2025.
Non-Final Office Action for U.S. Appl. No. 17/907,618 mailed May 2, 2025.
Non-Final Office Action for U.S. Appl. No. 18/001,680 mailed Jun. 20, 2025.
Non-Final Office Action for U.S. Appl. No. 18/121,995 mailed Mar. 27, 2025.
Non-Final Office Action for U.S. Appl. No. 18/122,504 mailed Mar. 5, 2025.
Non-Final Office Action for U.S. Appl. No. 18/444,972 mailed Dec. 9, 2025.
Non-Final Office Action for U.S. Appl. No. 18/444,972 mailed Jun. 11, 2026.
Non-Final Office Action for U.S. Appl. No. 18/447,025 mailed Nov. 5, 2025.
Non-Final Office Action for U.S. Appl. No. 18/511,532 mailed Aug. 18, 2025.
Non-Final Office Action for U.S. Appl. No. 18/632,533 mailed Jan. 30, 2026.
Non-Final Office Action for U.S. Appl. No. 18/632,545 mailed Jan. 13, 2026.
Non-Final Office Action for U.S. Appl. No. 18/632,557 mailed Feb. 24, 2026.
Non-Final Office Action for U.S. Appl. No. 18/637,667 mailed Feb. 17, 2026.
Non-Final Office Action for U.S. Appl. No. 18/639,079 mailed Apr. 7, 2026.

(56) References Cited

OTHER PUBLICATIONS

Non-Final Office Action for U.S. Appl. No. 18/639,098 mailed Mar. 6, 2026.
Non-Final Office Action for U.S. Appl. No. 18/640,222 mailed Apr. 15, 2026.
Non-Final Office Action for U.S. Appl. No. 18/640,260 mailed Feb. 17, 2026.
Non-Final Office Action for U.S. Appl. No. 18/640,285 mailed Jan. 26, 2026.
Non-Final Office Action for U.S. Appl. No. 18/640,303 mailed Apr. 1, 2026.
Non-Final Office Action for U.S. Appl. No. 18/652,930 mailed Dec. 31, 2025.
Non-Final Office Action for U.S. Appl. No. 18/652,956 mailed Apr. 10, 2026.
Non-Final Office Action for U.S. Appl. No. 18/652,959 mailed Oct. 1, 2025.
Non-Final Office Action for U.S. Appl. No. 18/652,962 mailed Apr. 17, 2026.
Non-Final Office Action for U.S. Appl. No. 18/654,336 mailed Apr. 30, 2026.
Non-Final Office Action for U.S. Appl. No. 18/764,668 mailed May 12, 2026.
Non-Final Office Action for U.S. Appl. No. 18/882,984 mailed Apr. 24, 2026.
Non-Final Office Action for U.S. Appl. No. 18/933,745 mailed Jun. 16, 2026.
Non-Final Office Action for U.S. Appl. No. 18/933,759 mailed Jun. 23, 2026.
Non-Final Office Action for U.S. Appl. No. 19/013,744 mailed Jun. 15, 2026.
Non-Final Office Action for U.S. Appl. No. 19/576,211 mailed Jun. 25, 2026.
Non-Final Office Action for U.S. Appl. No. 19/631,329 mailed Jul. 1, 2026.
Non-Final Office Action for U.S. Appl. No. 19/631,338 mailed Jun. 25, 2026.
Non-Final Office Action for U.S. Appl. No. 19/636,115 mailed Jun. 17, 2026.
Notice of Allowance for U.S. Appl. No. 17/078,472 mailed Apr. 22, 2026.
Notice of Allowance for U.S. Appl. No. 17/078,472 mailed Dec. 17, 2025.
Notice of Allowance for U.S. Appl. No. 17/528,015 mailed Mar. 25, 2025.
Notice of Allowance for U.S. Appl. No. 17/532,318 mailed Feb. 25, 2025.
Notice of Allowance for U.S. Appl. No. 17/609,589 mailed Feb. 4, 2026.
Notice of Allowance for U.S. Appl. No. 17/678,122 mailed Apr. 30, 2025.
Notice of Allowance for U.S. Appl. No. 17/678,812 mailed Apr. 21, 2026.
Notice of Allowance for U.S. Appl. No. 17/722,752 mailed Jul. 7, 2025.
Notice of Allowance for U.S. Appl. No. 17/723,150 mailed Apr. 7, 2025.
Notice of Allowance for U.S. Appl. No. 17/907,618 mailed Apr. 9, 2026.
Notice of Allowance for U.S. Appl. No. 18/122,456 mailed Aug. 14, 2025.
Notice of Allowance for U.S. Appl. No. 18/122,456 mailed Jan. 12, 2026.
Notice of Allowance for U.S. Appl. No. 18/122,486 mailed Dec. 9, 2025.
Notice of Allowance for U.S. Appl. No. 18/511,532 mailed Apr. 1, 2026.
Notice of Allowance for U.S. Appl. No. 18/632,545 mailed May 8, 2026.
Notice of Allowance for U.S. Appl. No. 18/933,729 mailed Jul. 1, 2025.
Notice of Allowance for U.S. Appl. No. 18/933,729 mailed Nov. 18, 2025.
Office Action for Canadian Application No. 3,246,015 mailed Apr. 1, 2026.
Office Action for Chinese Application No. 202180006817.8 mailed Jun. 13, 2025.
Office Action for Chinese Application No. 202210520564.2 mailed May 23, 2025.
Office Action for Chinese Application No. 202210540435.X mailed May 22, 2025.
Office Action for Chinese Application No. 202210580274.7 mailed May 22, 2025.
Office Action for Chinese Application No. 202210583463.X mailed Jun. 13, 2025.
Office Action for Chinese Application No. 202210583463.X mailed Nov. 17, 2025.
Office Action for Chinese Application No. 202210587585.6 mailed Jun. 13, 2025.
Office Action for Chinese Application No. 202210587598.3 mailed Jun. 6, 2025.
Office Action for Chinese Application No. 202210791551.9 mailed May 16, 2025.
Office Action for Chinese Application No. 202210802982.0 mailed May 16, 2025.
Office Action for Chinese Application No. 202210802982.0 mailed Oct. 24, 2025.
Office Action for Chinese Application No. 202210847103.6 mailed May 16, 2025.
Office Action for Chinese Application No. 202280006309.4 mailed Dec. 4, 2025.
Office Action for Chinese Application No. 202280015894.4 mailed Aug. 1, 2025.
Office Action for Chinese Application No. 202310541980.5 mailed Apr. 28, 2026.
Office Action for Chinese Application No. 202310541980.5 mailed Jun. 16, 2025.
Office Action for Chinese Application No. 202310542349.7 mailed Jun. 4, 2025.
Office Action for Chinese Application No. 202310542349.7 mailed Mar. 28, 2026.
Office Action for Chinese Application No. 202310542349.7 mailed Nov. 28, 2025.
Office Action for Chinese Application No. 202311574718.7 mailed Feb. 11, 2026.
Office Action for Chinese Application No. 202311574730.8 mailed Apr. 2, 2026.
Office Action for Chinese Application No. 202311574758.1 mailed Jan. 28, 2026.
Office Action for Japanese Application No. 2022-559757 mailed Dec. 23, 2024.
Office Action for Japanese Application No. 2023-191120 mailed Mar. 17, 2025.
Office Action for Japanese Application No. 2023-547155 mailed Jan. 30, 2026.
Office Action for Japanese Application No. 2024-066507 mailed Feb. 19, 2026.
Office Action for Japanese Application No. 2024-066507 mailed Jun. 11, 2025.
Office Action for Japanese Application No. 2024-196041 mailed Feb. 18, 2026.
Office Action for Japanese Application No. 2024-519263 mailed Jun. 23, 2026.
Office Action for Japanese Application No. 2025-061899 mailed May 27, 2026.
Restriction Requirement for U.S. Appl. No. 17/907,618 mailed Feb. 13, 2025.
Restriction Requirement for U.S. Appl. No. 18/001,680 mailed Mar. 28, 2025.
Restriction Requirement for U.S. Appl. No. 18/122,486 mailed Apr. 14, 2025.

(56) References Cited

OTHER PUBLICATIONS

Restriction Requirement for U.S. Appl. No. 18/635,275 mailed Mar. 27, 2026.
Restriction Requirement for U.S. Appl. No. 18/635,286 mailed Jan. 28, 2026.
Restriction Requirement for U.S. Appl. No. 18/635,292 mailed Jan. 15, 2026.
Restriction Requirement for U.S. Appl. No. 18/637,653 mailed Mar. 4, 2026.
Restriction Requirement for U.S. Appl. No. 18/639,094 mailed Mar. 9, 2026.
Restriction Requirement for U.S. Appl. No. 18/889,744 mailed May 19, 2026.
Restriction Requirement for U.S. Appl. No. 18/947,762 mailed Apr. 27, 2026.
Restriction Requirement for U.S. Appl. No. 18/949,258 mailed Jun. 12, 2026.
Suriano, et al., "Styrene-Free Liquid Resins for Composite Reformulation", Systemic Circular Economy Solutions for Fiber Reinforced Composites, Digital Innovations in Architecture, Engineering and Construction, pp. 99-123, 2022.
U.S. Appl. No. 18/947,762, filed Nov. 14, 2024.
U.S. Appl. No. 18/949,258, filed Nov. 15, 2024.
U.S. Appl. No. 18/955,121, filed Nov. 21, 2024.
U.S. Appl. No. 18/958,181, filed Nov. 25, 2024.
U.S. Appl. No. 18/958,189, filed Nov. 25, 2024.
U.S. Appl. No. 18/958,196, filed Nov. 25, 2024.
U.S. Appl. No. 18/958,200, filed Nov. 25, 2024.
U.S. Appl. No. 19/011,892, filed Jan. 7, 2025.
U.S. Appl. No. 19/013,727, filed Jan. 8, 2025.
U.S. Appl. No. 19/013,744, filed Jan. 8, 2025.
U.S. Appl. No. 19/014,336, filed Jan. 9, 2025.
U.S. Appl. No. 19/014,344, filed Jan. 9, 2025.
U.S. Appl. No. 19/459,719, filed Jan. 26, 2026.
U.S. Appl. No. 19/460,541, filed Jan. 27, 2026.
U.S. Appl. No. 19/463,581, filed Jan. 29, 2026.
U.S. Appl. No. 19/466,779, filed Feb. 2, 2026.
U.S. Appl. No. 19/550,456, filed Feb. 26, 2026.
U.S. Appl. No. 19/550,462, filed Feb. 26, 2026.
U.S. Appl. No. 19/565,891, filed Mar. 13, 2026.
U.S. Appl. No. 19/573,404, filed Mar. 20, 2026.
U.S. Appl. No. 19/576,211, filed Mar. 24, 2026.
U.S. Appl. No. 19/631,329, filed Mar. 27, 2026.
U.S. Appl. No. 19/631,338, filed Mar. 27, 2026.
U.S. Appl. No. 19/636,115, filed Apr. 1, 2026.
U.S. Appl. No. 19/636,154, filed Apr. 1, 2026.
U.S. Appl. No. 63/566,681, filed Mar. 18, 2024.
U.S. Appl. No. 63/615,377, filed Dec. 28, 2023.
U.S. Appl. No. 63/692,734, filed Sep. 10, 2024.
Examination Report for Indian Application No. 202517007400 mailed Aug. 4, 2026.
Non-Final Office Action for U.S. Appl. No. 18/632,569 mailed Aug. 21, 2026.
Office Action for Chinese Application No. 202380014754.X mailed Jul. 22, 2026.
Office Action for Japanese Application No. 2023-547155 mailed Jul. 27, 2026.
Examination Report for Indian Application No. 202517007844 mailed Jul. 10, 2026.
Final Office Action for U.S. Appl. No. 18/632,557 mailed Jul. 13, 2026.
Final Office Action for U.S. Appl. No. 18/640,260 mailed Jul. 30, 2026.
Invitation to Pay Additional Fees for International Application No. PCT/IB2026/053512 mailed Jul. 17, 2026.
Issue Notification for U.S. Appl. No. 17/907,618 mailed Jul. 22, 2026.
Non-Final Office Action for U.S. Appl. No. 18/635,275 mailed Jul. 28, 2026.
Non-Final Office Action for U.S. Appl. No. 18/635,292 mailed Jul. 23, 2026.
Non-Final Office Action for U.S. Appl. No. 18/637,667 mailed Jul. 14, 2026.
Non-Final Office Action for U.S. Application No. 18/955, 121 mailed Aug. 13, 2026.
Non-Final Office Action for U.S. Application No. 18/958, 181 mailed Aug. 24, 2026.
Non-Final Office Action for U.S. Appl. No. 19/011,892 mailed Jul. 7, 2026.
Non-Final Office Action for U.S. Appl. No. 19/013,727 mailed Aug. 18, 2026.
Non-Final Office Action for U.S. Appl. No. 19/014,344 mailed Jul. 21, 2026.
Notice of Allowance for U.S. Appl. No. 17/078,472 mailed Aug. 12, 2026.
Notice of Allowance for U.S. Appl. No. 17/532,318 mailed Jun. 24, 2025.
Notice of Allowance for U.S. Appl. No. 17/682,073 mailed Jul. 29, 2026.
Notice of Allowance for U.S. Application No. 17/723, 150 mailed Jun. 17, 2025.
Notice of Allowance for U.S. Appl. No. 18/639,094 mailed Jul. 28, 2026.
Notice of Allowance for U.S. Application No. 18/654, 336 mailed Aug. 13, 2026.
U.S. Appl. No. 18/447,050, filed Aug. 9, 2023.
U.S. Appl. No. 18/447,064, filed Aug. 9, 2023.
U.S. Appl. No. 18/447,074, filed Aug. 9, 2023.
U.S. Appl. No. 18/447,086, filed Aug. 9, 2023.
U.S. Appl. No. 63/443,519, filed Feb. 6, 2023.
U.S. Appl. No. 63/470,259, filed Jun. 1, 2023.

* cited by examiner

THRUST BEARING FOR BLOOD PUMPS

CROSS-REFERENCES TO RELATED APPLICATIONS

The present application is a continuation of International Application PCT/IB2023/059141 to Tuval (published as WO 24/057255), entitled "Inlet guard and thrust bearing for blood pumps," filed Sep. 14, 2023, which claims priority from:

U.S. Provisional Patent Application 63/406,427 to Tuval, entitled "Ventricular assist device," filed Sep. 14, 2022;

U.S. Provisional Patent Application 63/432,496 to Tuval, entitled "Ventricular assist device," filed Dec. 14, 2022;

U.S. Provisional Patent Application 63/443,519 to Tuval, entitled "Ventricular assist device," filed Feb. 6, 2023; and U.S. Provisional Patent Application 63/470,259 to Tuval, entitled "Ventricular assist device," filed Jun. 1, 2023.

All of the above-referenced US Provisional applications are incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are mechanical circulatory support devices designed to assist and unload cardiac chambers in order to maintain or augment cardiac output. They are used in patients suffering from a failing heart and in patients at risk for deterioration of cardiac function during percutaneous coronary interventions. Most commonly, a left-ventricular assist device is applied to a defective heart in order to assist left-ventricular functioning. In some cases, a right-ventricular assist device is used in order to assist right-ventricular functioning. Such ventricular assist devices are either designed to be permanently implanted or mounted on a catheter for temporary placement.

SUMMARY OF EMBODIMENTS

In accordance with some applications of the present invention, a ventricular assist device includes an axial shaft configured for insertion into, and rotation within, a ventricle of a heart of a subject, an impeller coupled to the axial shaft, and a frame surrounding the impeller. A pump-outlet tube surrounding the frame such that, as the axial shaft rotates, the impeller pumps blood proximally, from the ventricle, through the pump-outlet tube. An inlet guard, which is shaped to define one or more holes, is disposed around the axial shaft and within the frame distally to the impeller, such that the blood flows to the impeller via the holes.

For some applications, the inlet guard is flat and/or is disposed such that it is perpendicular to the axial shaft (i.e., to the longitudinal axis of the frame). Thus, advantageously, the inlet guard may occupy relatively little space, and/or may provide an advantageous flow direction for the blood. Typically, the inlet guard is toric.

For some applications, the frame is assembled with the inlet guard inside in the following manner. During assembly of the pump-head portion, the proximal end of the frame is typically open. For some applications, the inlet guard is placed through the open proximal end of the frame while being supported upon a rod (e.g., a mandrel). The inlet guard typically has an overall torus shape, with the edges of the shape defining inner and outer circles. The inner circle defined by the inlet guard is typically coupled to the axial shaft (or to the distal bearing housing) and the outer circle is coupled to struts of the frame, to the pump-outlet tube and/or to an inner lining of the frame. For some applications, the aforementioned coupling of the inlet guard to other portions of the device is performed via suturing, via hooks, via adhesive, and/or via heat fusion.

As noted above, in some embodiments, the inlet guard is coupled to the distal bearing housing, which may house a radial and/or thrust bearing. In such embodiments, typically, the distal bearing housing is partly or entirely disposed within the frame. For example, at least 10%, 50%, or 80% of the length of the bearing housing may be disposed within the frame. Moreover, the distal bearing housing may extend into the frame even for applications in which the blood pump does not comprise inlet guard.

For some applications, the ventricular assist device includes a thrust bearing that is configured to reduce or prevent axial motion of axial shaft in response to variations in the pressure gradient against which the impeller is pumping (and, typically, to thereby prevent the impeller from undergoing axial motion in response to variations in the pressure gradient against which the impeller is pumping).

For some applications, a thrust bearing is disposed within the distal bearing housing, adjacent to the distal end of the axial shaft. Typically, the distal end of the axial shaft is configured to be in contact with the distal thrust bearing. When the impeller pumps blood in the proximal direction, this causes the axial shaft to be biased in the distal direction. The thrust bearing prevents distal movement of the axial shaft, such that the axial shaft and the impeller typically remain in axially fixed positions within frame.

In some embodiments, the thrust bearing includes a proximally-facing ceramic surface including, for example, zirconia. A distally-facing ceramic cover, comprising zirconia for example, covers the distal end of axial shaft, such that ceramic cover contacts ceramic surface as the axial shaft rotates. Thus, advantageously, there is a low-friction interface between the axial shaft and the thrust bearing.

In some embodiments, the axial shaft is shaped to define a shaft lumen. For some applications, the thrust bearing defines a bearing lumen therethrough. Typically, the bearing lumen functions as a portion of a continuous lumen through the device that is used for guidewire insertion and/or as a purging fluid channel. In other words, the bearing lumen is continuous with the shaft lumen.

For some applications, at least part of the bearing lumen is frustoconically-shaped, with a wider end of the bearing lumen facing distally. In other words, at its distal end, the lumen defines a portion of a cone, with a wide end of the cone-portion facing the distal direction. Typically, the frustoconical portion of the lumen facilitates the advancement of the guidewire through the thrust bearing in the distal-to-proximal direction.

For some applications, a drive cable of the ventricular assist device is coupled to the axial shaft within a proximal bearing housing that is disposed within the frame. In other words, the interface between the distal end of drive cable and the proximal end of axial shaft (i.e., the location at which the drive cable and the axial shaft are coupled to each other) is within the proximal bearing housing. Typically, the proximal bearing housing is rigid, such that the proximal bearing housing protects the location at which the drive cable and the axial shaft are coupled to each other from being exposed to forces, such as bending forces, that could weaken the coupling and thereby damage the ventricular assist device. For example, the proximal bearing housing may inhibit bending of the drive cable within the bearing housing.

Typically, in such embodiments, the radial separation between the proximal bearing housing and the distal end of the drive cable, which is within the proximal bearing housing, is less than 2 mm, e.g., less than 1 mm. Advantageously, this small radial separation may help inhibit bending of the drive cable.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

There is therefore provided, in accordance with some embodiments of the present invention, an apparatus, including:

- an axial shaft configured for insertion into, and rotation within, a ventricle of a heart of a subject;
- an impeller coupled to the axial shaft;
- a frame surrounding the impeller;
- a pump-outlet tube surrounding the frame such that, as the axial shaft rotates, the impeller pumps blood proximally, from the ventricle, through the pump-outlet tube; and
- an inlet guard, which is shaped to define one or more holes, disposed around the axial shaft and within the frame distally to the impeller, such that the blood flows to the impeller via the holes.

In some embodiments, the pump-outlet tube has an open distal end.

In some embodiments, the apparatus further includes a drive cable, and the axial shaft is coupled to the drive cable such that the axial shaft rotates with the drive cable.

In some embodiments, including a drive cable, the axial shaft is a distal portion of the drive cable.

In some embodiments, the inlet guard is perpendicular to the axial shaft.

In some embodiments, the inlet guard is flat.

In some embodiments, the inlet guard is toric.

In some embodiments, the frame includes multiple struts, and the inlet guard is coupled to the struts.

In some embodiments, the inlet guard is coupled to an inner wall of the pump-outlet tube.

In some embodiments, the apparatus further includes a lining that lines an inside of the frame, and the inlet guard is coupled to the lining.

In some embodiments, the inlet guard is polymeric.

In some embodiments, a thickness of the inlet guard is 40-100 microns.

In some embodiments, the apparatus further includes a thrust bearing disposed distally from the axial shaft so as to inhibit distal movement of the axial shaft beyond the thrust bearing.

In some embodiments, the holes are shaped such that, for each of the holes, a span of the hole in at least one direction is less than 1 mm.

In some embodiments, an area of each of the holes is 0.05-5 $mm^2$.

In some embodiments, a porosity of the inlet guard is at least 40%.

In some embodiments, each of the holes is hexagonal.

In some embodiments, a distance between each pair of adjacent ones of the holes is 0.01-0.1 mm.

In some embodiments, the apparatus further includes:

- a bearing configured to stabilize the axial shaft while the axial shaft rotates; and
- a bearing housing that houses the bearing and is coupled to the inlet guard.

In some embodiments, at least 10% of a length of the bearing housing is disposed within the frame.

In some embodiments, at least 50% of the length of the bearing housing is disposed within the frame.

In some embodiments, at least 80% of the length of the bearing housing is disposed within the frame.

In some embodiments, the bearing housing is disposed entirely within the frame.

In some embodiments, the bearing includes a thrust bearing disposed distally from the axial shaft so as to inhibit distal movement of the axial shaft beyond the thrust bearing.

In some embodiments, the frame includes a central cylindrical portion and a distal conical portion, and the inlet guard is disposed within 1 mm of a distal end of the central cylindrical portion.

In some embodiments, the distal end of the pump-outlet tube is proximal to a distal end of the distal conical portion.

In some embodiments, the distal end of the pump-outlet tube is within 1 mm of a distal end of the central cylindrical portion.

There is further provided, in accordance with some embodiments of the present invention, an apparatus, including:

- a blood pump, including:
  - an axial shaft configured for insertion into, and rotation within, a body of a subject;
  - an impeller coupled to the axial shaft such that, as the axial shaft rotates, the impeller pumps blood of the subject;
  - a thrust bearing including a proximally-facing ceramic surface and disposed distally from the axial shaft so as to inhibit distal movement of the axial shaft beyond the thrust bearing; and
  - a distally-facing ceramic cover that covers a distal end of the axial shaft, such that the ceramic cover contacts the ceramic surface as the axial shaft rotates.

In some embodiments, the apparatus further includes a drive cable, the axial shaft is coupled to the drive cable such that the axial shaft rotates with the drive cable.

In some embodiments, the apparatus further includes a drive cable, the axial shaft is a distal portion of the drive cable.

In some embodiments, the thrust bearing includes a piece of ceramic including the proximally-facing ceramic surface.

In some embodiments, the thrust bearing includes the proximally-facing ceramic surface by virtue of being coated with a ceramic coating.

In some embodiments, the proximally-facing ceramic surface includes zirconia.

In some embodiments, the distally-facing ceramic cover includes zirconia.

In some embodiments, the blood pump further includes a distal bearing housing that houses the distal thrust bearing and a distal radial bearing that is housed within the distal bearing housing and is configured to radially stabilize the axial shaft while the axial shaft rotates.

In some embodiments, the axial shaft is configured for insertion, over a guidewire, and is shaped to define a shaft lumen for passage of the guidewire therethrough, and the thrust bearing is shaped to define a bearing lumen that is configured to be continuous with the shaft lumen.

In some embodiments, at least a portion of the bearing lumen is frustoconically-shaped, a wider end of the bearing lumen facing distally.

In some embodiments, the bearing lumen is a first bearing lumen, and the thrust bearing is further shaped to define at least one second bearing lumen configured for proximal flow of a purging fluid, through the second bearing lumen, into an interface between the axial shaft and the thrust bearing.

In some embodiments, the blood pump includes a ceramic cap that includes the ceramic cover and fits around the distal end of the axial shaft.

In some embodiments, the blood pump includes a distal radial bearing configured to radially stabilize the axial shaft while the axial shaft rotates and the ceramic cap includes a ceramic sleeve that is configured to cover a distal portion of the axial shaft that rotates within the distal radial bearing as the axial shaft rotates.

There is further provided, in accordance with some embodiments of the present invention, an apparatus, including:

- a blood pump, including:
  - an axial shaft configured for insertion, over a guidewire, into a body of a subject, and for rotation within the body,
    - the axial shaft being shaped to define a shaft lumen for passage of the guidewire therethrough;
  - an impeller coupled to the axial shaft such that, as the axial shaft rotates, the impeller pumps blood of the subject; and
    - a thrust bearing disposed distally from the axial shaft so as to inhibit distal movement of the axial shaft beyond the thrust bearing, and shaped to define a bearing lumen that is configured to be continuous with the shaft lumen.

In some embodiments, the apparatus further includes a drive cable, and the axial shaft is coupled to the drive cable such that the axial shaft rotates with the drive cable.

In some embodiments, the apparatus further includes a drive cable, and the axial shaft is a distal portion of the drive cable.

In some embodiments, at least a portion of the bearing lumen is frustoconically-shaped, a wider end of the bearing lumen facing distally.

In some embodiments, the bearing lumen is a first bearing lumen, and the thrust bearing is further shaped to define at least one second bearing lumen configured for proximal flow of a purging fluid, through the second bearing lumen, into an interface between the axial shaft and the thrust bearing.

In some embodiments, the thrust bearing includes a proximally-facing ceramic surface, and the blood pump includes a distally-facing ceramic cover that covers a distal end of the axial shaft, such that the ceramic cover contacts the ceramic surface as the axial shaft rotates.

In some embodiments, the thrust bearing includes a piece of ceramic including the proximally-facing ceramic surface.

In some embodiments, the thrust bearing includes the proximally-facing ceramic surface by virtue of being coated with a ceramic coating.

In some embodiments, the proximally-facing ceramic surface includes zirconia.

In some embodiments, the distally-facing ceramic cover includes zirconia.

In some embodiments, the blood pump further includes a distal bearing housing that houses the distal thrust bearing and a distal radial bearing that is housed within the distal bearing housing and is configured to radially stabilize the axial shaft while the axial shaft rotates.

In some embodiments, the blood pump further includes a ceramic cap that fits around the distal end of the axial shaft and includes the ceramic cover.

In some embodiments, the blood pump includes a distal radial bearing that is configured to radially stabilize the axial shaft while the axial shaft rotates and the ceramic cap includes a ceramic sleeve that is configured to cover a distal portion of the axial shaft that rotates within the distal radial bearing as the axial shaft rotates.

There is further provided, in accordance with some embodiments of the present invention, an apparatus, including:

- a blood pump, including:
  - an axial shaft configured for insertion into, and rotation within, a body of a subject;
  - an impeller coupled to the axial shaft such that, as the axial shaft rotates, the impeller pumps blood of the subject;
  - a frame surrounding the impeller and including a distal conical portion;
  - a bearing adjacent to the axial shaft and configured to stabilize the axial shaft while the axial shaft rotates; and
  - a bearing housing that houses the bearing and is disposed at least partly within the distal conical portion of the frame.

In some embodiments, the apparatus further includes a drive cable, and the axial shaft is coupled to the drive cable such that the axial shaft rotates with the drive cable.

In some embodiments, the apparatus further includes a drive cable, and the axial shaft is a distal portion of the drive cable.

In some embodiments, the bearing housing occupies at least 10% of a length of the distal conical portion of the frame.

In some embodiments, the bearing includes a radial bearing configured to radially stabilize the axial shaft while the axial shaft rotates.

In some embodiments, the bearing includes a thrust bearing configured to axially stabilize the axial shaft while the axial shaft rotates.

In some embodiments, the frame further includes a cylindrical portion proximal to the distal conical portion, and the bearing housing is disposed at least partly within the cylindrical portion.

In some embodiments, at least 10% of a length of the bearing housing is disposed within the frame.

In some embodiments, at least 50% of the length of the bearing housing is disposed within the frame.

In some embodiments, at least 80% of the length of the bearing housing is disposed within the frame.

In some embodiments, the bearing housing is disposed entirely within the frame.

In some embodiments, the bearing is a distal bearing and the bearing housing is a distal bearing housing, the frame further includes a proximal conical portion, and the blood pump further includes:

a proximal bearing adjacent to the axial shaft proximally to the distal bearing, and configured to stabilize the axial shaft while the axial shaft rotates; and a proximal bearing housing that houses the proximal bearing and is disposed at least partly within the proximal conical portion of the frame.

In some embodiments, at least 10% of a length of the proximal bearing housing is disposed within the frame.

In some embodiments, at least 50% of the length of the proximal bearing housing is disposed within the frame.

In some embodiments, at least 80% of the length of the proximal bearing housing is disposed within the frame.

In some embodiments, the proximal bearing housing is disposed entirely within the frame.

In some embodiments, the proximal bearing includes a proximal radial bearing configured to radially stabilize the axial shaft while the axial shaft rotates.

In some embodiments, the proximal bearing includes a proximal thrust bearing configured to axially stabilize the axial shaft while the axial shaft rotates.

In some embodiments, the frame further includes a cylindrical portion between the proximal conical portion and the distal conical portion, and the proximal bearing housing is disposed at least partly within the cylindrical portion.

In some embodiments, a distance between a proximal end of the proximal bearing housing and a distal end of the distal bearing housing is less than 10% greater than a length of the frame.

DETAILED DESCRIPTION OF EMBODIMENTS

Figure 1A:
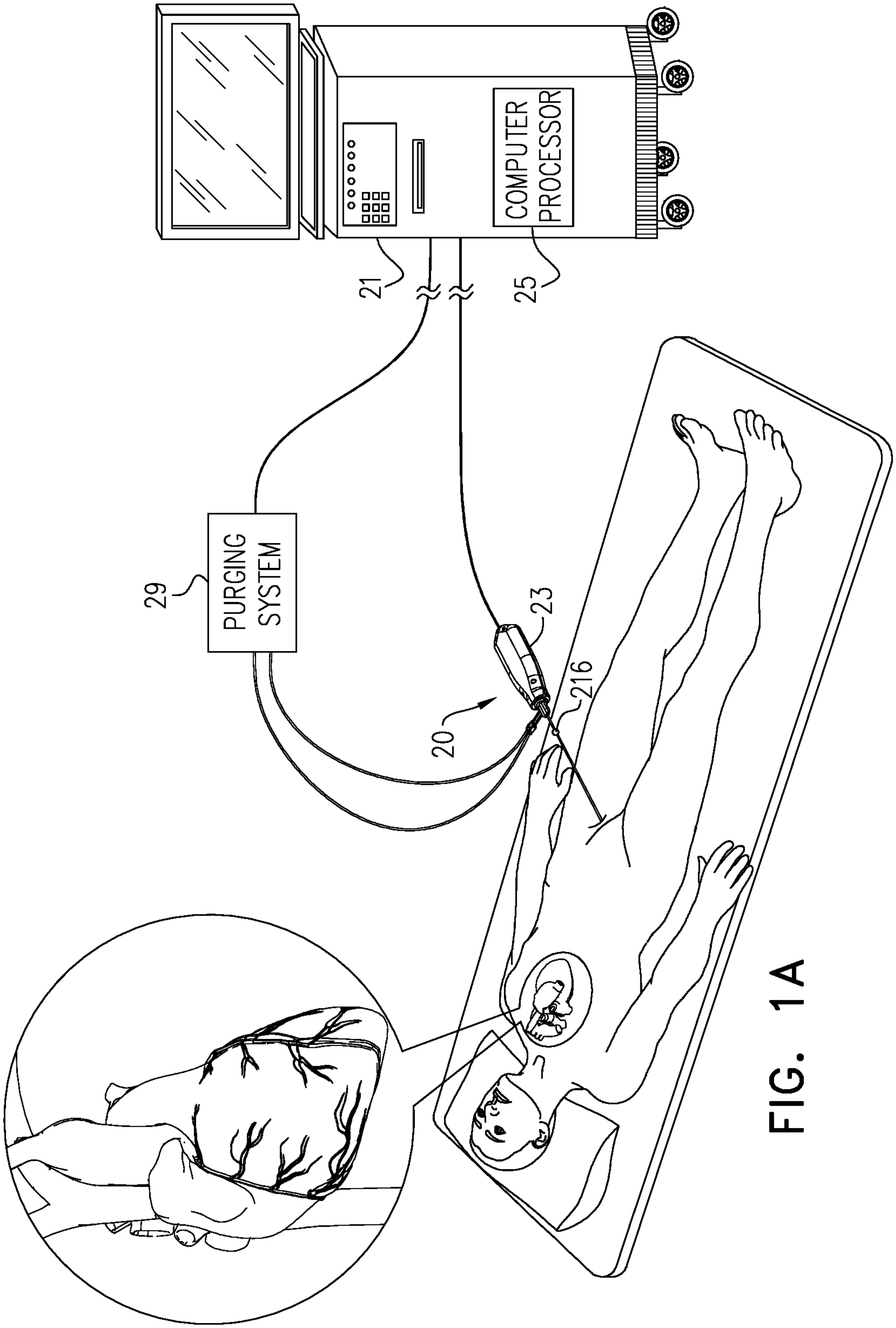
FIGS. 1A, 1B, and 1C are schematic illustrations of a ventricular assist device, a distal end of which is configured to be placed in a subject's left ventricle, in accordance with some applications of the present invention.
Figure 1B:
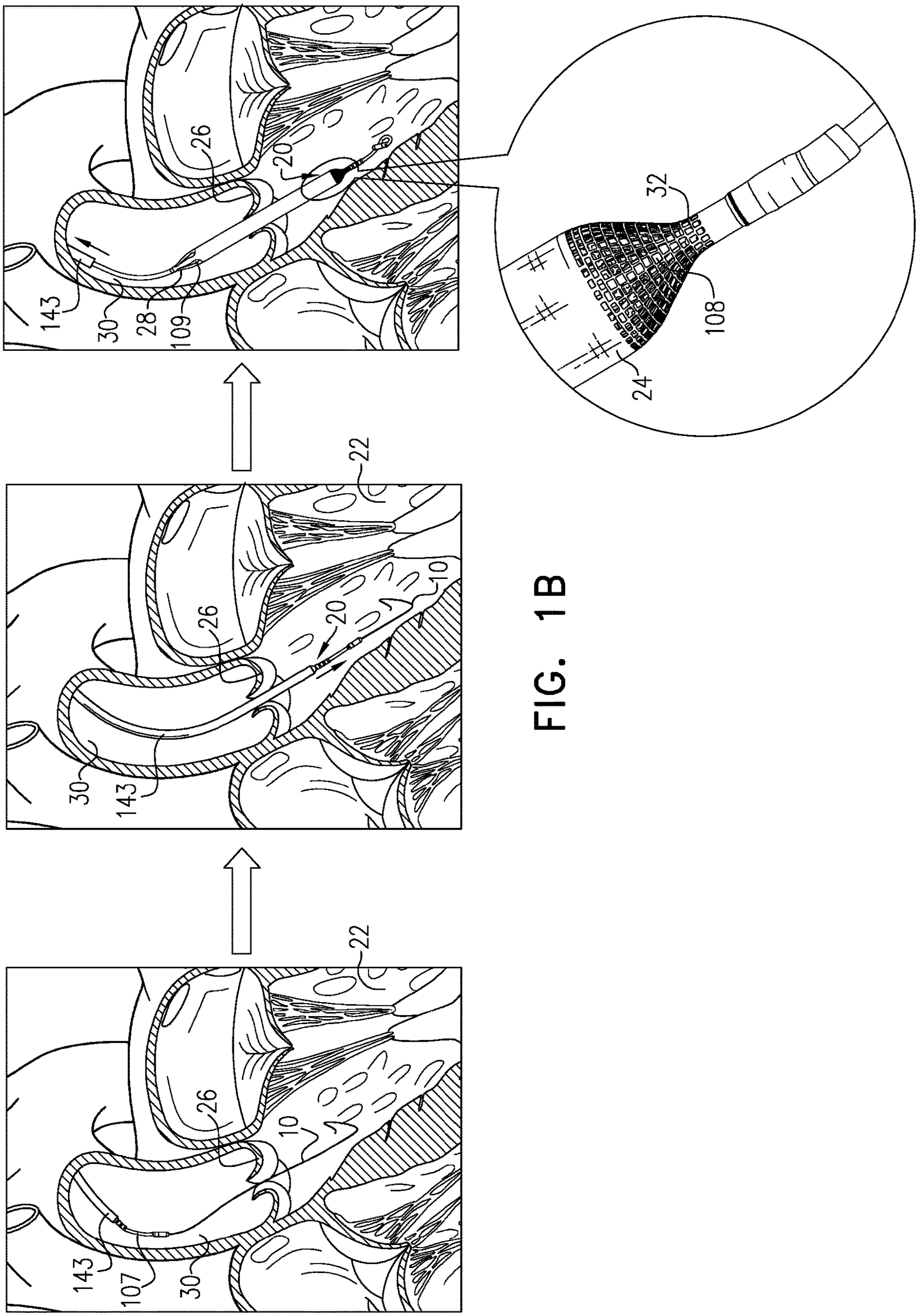
Figure 1C:
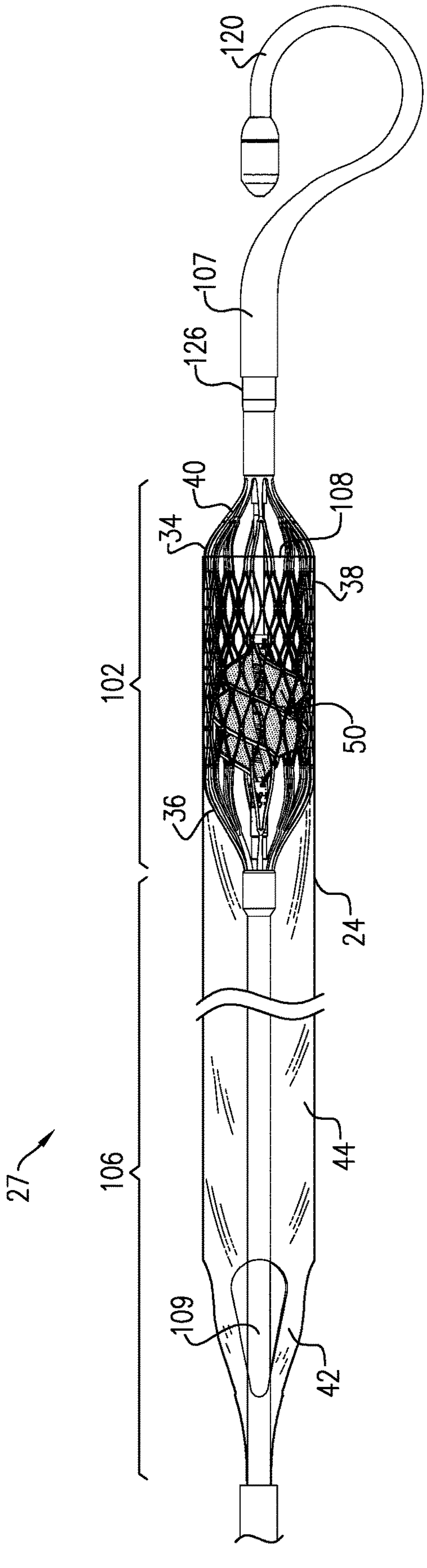

Reference is now made to FIGS. 1A, 1B, and 1C, which are schematic illustrations of a ventricular assist device 20, a distal end of which is configured to be disposed in a subject's left ventricle 22, in accordance with some applications of the present invention. FIG. 1A shows an overview of the ventricular assist device system including a control console 21 and a motor unit 23. FIG. 1B shows the ventricular assist device being inserted into the subject's left ventricle, and FIG. 1C shows a pump-head portion 27 of the ventricular assist device in greater detail.

As shown in FIG. 1B, the ventricular assist device includes a pump-outlet tube 24, which traverses an aortic valve 26 of the subject, such that a proximal end 28 of the pump-outlet tube is disposed in an aorta 30 of the subject and a distal end 32 of the pump-outlet tube is disposed within left ventricle 22. Pump-outlet tube 24 (which may also be referred to as a "blood-pump tube") is typically an elongate tube, an axial length of the pump-outlet tube typically being substantially larger than its diameter. The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

For some applications, the ventricular assist device is used to assist the functioning of a subject's left ventricle during a percutaneous coronary intervention. In such cases, the ventricular assist device is typically used for a period of up to six hours (e.g., up to ten hours), during a period in which there is risk of developing hemodynamic instability (e.g., during or immediately following the percutaneous coronary intervention). Alternatively or additionally, the ventricular assist device is used to assist the functioning of a subject's left ventricle for a longer period (e.g., 2-20 days, e.g., 4-14 days) upon a patient suffering from cardiogenic shock, which may include any low-cardiac-output state (e.g., acute myocardial infarction, myocarditis, cardiomyopathy, post-partum, etc.). For some applications, the ventricular assist device is used to assist the functioning of a subject's left ventricle for yet a longer period (e.g., several weeks or months), e.g., in a "bridge to recovery" treatment. For some such applications, the ventricular assist device is permanently or semi-permanently implanted, and the impeller of the ventricular assist device is powered transcutaneously, e.g., using an external antenna that is magnetically coupled to the impeller.

As shown in FIG. 1B, which shows steps in the deployment of the ventricular assist device in the left ventricle, typically the distal end of the ventricular assist device is guided to the left ventricle over a guidewire 10. During the insertion of the distal end of the device into the left ventricle, a delivery catheter 143 is disposed over the distal end of the device. Once the distal end of the device is disposed in the left ventricle, the delivery catheter is typically retracted to the aorta, and the guidewire is withdrawn from the subject's body. The retraction of the delivery catheter typically causes self-expandable components of the distal end of the device to assume non-radially-constrained configurations, as described in further detail hereinbelow. Typically, the ventricular assist device is inserted into the subject's body in order to provide an acute treatment to the subject. For some applications, in order to withdraw the left ventricular device from the subject's body at the end of the treatment, the delivery catheter is advanced over the distal end of the device, which causes the self-expandable components of the distal end of the device to assume radially-constrained configurations. Alternatively or additionally, the distal end of the device is retracted into the delivery catheter which causes the self-expandable components of the distal end of the device to assume radially-constrained configurations.

For some applications (not shown), the ventricular assist device and/or delivery catheter 143 includes an ultrasound transducer at its distal end and the ventricular assist device is advanced toward the subject's ventricle under ultrasound guidance.

Reference is made to FIG. 1C, which shows pump-head portion 27 of ventricular assist device 20, in accordance with some applications of the present invention, in greater detail. Typically, an impeller 50 is disposed within a distal portion 102 of pump-outlet tube 24 and is configured to pump blood from the left ventricle into the aorta by rotating. The pump-outlet tube typically defines one or more blood-inlet openings 108 at the distal end of the pump-outlet tube, via which blood flows into the pump-outlet tube from the left ventricle, during operation of the impeller. As shown in FIG. 1C, for some applications, the pump-outlet tube defines a single axially-facing blood-inlet opening. Alternatively, the pump-outlet tube defines a plurality of lateral blood-inlet openings (e.g., as shown in FIG. 1B), as described in further detail hereinbelow. For some applications, proximal portion 106 of the pump-outlet tube defines one or more blood-outlet openings 109, via which blood flows from the pump-outlet tube into the ascending aorta, during operation of the impeller.

For some applications, control console 21 (shown in FIG. 1A), which typically includes a computer processor 25, drives the impeller to rotate. For example, the computer processor may control a motor 74 (shown in FIG. 7B), which is disposed within motor unit 23 (shown in FIG. 1A) and which drives the impeller to rotate via a drive cable 130 (shown in FIG. 12A). For some applications, the computer processor is configured to detect a physiological parameter of the subject (such as left-ventricular pressure, cardiac afterload, rate of change of left-ventricular pressure, etc.) and to control rotation of the impeller in response thereto, as described in further detail hereinbelow. Typically, the operations described herein that are performed by the computer processor, transform the physical state of a memory, which is a real physical article that is in communication with the computer processor, to have a different magnetic polarity, electrical charge, or the like, depending on the technology of the memory that is used. Computer processor 25 is typically a hardware device programmed with computer program instructions to produce a special-purpose computer. For example, when programmed to perform the techniques described herein, computer processor 25 typically acts as a special-purpose, ventricular-assist computer processor and/or a special-purpose, blood-pump computer processor.

For some applications, a purging system 29 (shown in FIG. 1A) drives a fluid (e.g., a glucose solution) to pass through portions of ventricular assist device 20, for example, in order to cool portions of the device, to purge and/or lubricate interfaces between rotating parts and stationary bearings, and/or in order to wash debris from portions of the device.

Typically, along distal portion 102 of pump-outlet tube 24, a frame 34 is disposed within the pump-outlet tube around impeller 50. The frame is typically made of a shape-memory alloy, such as nitinol. For some applications, the shape-memory alloy of the frame is shape set such that at least a portion of the frame (and thereby distal portion 102 of tube 24) assumes a generally circular, elliptical, or polygonal cross-sectional shape in the absence of any forces being applied to distal portion 102 of tube 24. By assuming its generally circular, elliptical, or polygonal cross-sectional shape, the frame is configured to hold the distal portion of the pump-outlet tube in an open state. Typically, during operation of the ventricular assist device, the distal portion of the pump-outlet tube is configured to be placed within the subject's body, such that the distal portion of the pump-outlet tube is disposed at least partially within the left ventricle.

For some applications, along proximal portion 106 of pump-outlet tube 24, the frame is not disposed within the pump-outlet tube, and the pump-outlet tube is therefore not supported in an open state by frame 34. Pump-outlet tube 24 is typically made of a blood-impermeable collapsible material, such that the pump-outlet tube is collapsible. For example, pump-outlet tube 24 may include polyurethane, polyester, and/or silicone. Alternatively or additionally, the pump-outlet tube is made of polyethylene terephthalate (PET) and/or polyether block amide (e.g., PEBAX®). For some applications (not shown), the pump-outlet tube is reinforced with a reinforcement structure, e.g., a braided reinforcement structure, such as a braided nitinol tube. Typically, the proximal portion of the pump-outlet tube is configured to be placed such that it is at least partially disposed within the subject's ascending aorta. For some applications, the proximal portion of the pump-outlet tube traverses the subject's aortic valve, passing from the subject's left ventricle into the subject's ascending aorta, as shown in FIG. 1B.

As described hereinabove, the pump-outlet tube typically defines one or more blood-inlet openings 108 at the distal end of the pump-outlet tube, via which blood flows into the pump-outlet tube from the left ventricle, during operation of the impeller. For some applications, the proximal portion of the pump-outlet tube defines one or more blood-outlet openings 109, via which blood flows from the pump-outlet tube into the ascending aorta, during operation of the impeller. Typically, the pump-outlet tube defines a plurality of blood-outlet openings 109, for example, between two and eight blood-outlet openings (e.g., between two and four blood-outlet openings). During operation of the impeller, the pressure of the blood flow through the pump-outlet tube typically maintains the proximal portion of the tube in an open state. For some applications, in the event that, for example, the impeller malfunctions, the proximal portion of the pump-outlet tube is configured to collapse inwardly, in response to pressure outside of the proximal portion of the pump-outlet tube exceeding pressure inside the proximal portion of the pump-outlet tube. In this manner, the proximal portion of the pump-outlet tube acts as a safety valve, preventing retrograde blood flow into the left ventricle from the aorta.

Referring again to FIG. 1C, for some applications, frame 34 is shaped such that the frame defines a proximal conical portion 36, a central cylindrical portion 38, and a distal conical portion 40. Typically, the proximal conical portion is proximally-facing, i.e., facing such that the narrow end of the cone is proximal with respect to the wide end of the cone. Further typically, the distal conical portion is distally-facing, i.e., facing such that the narrow end of the cone is distal with respect to the wide end of the cone.

Figure 4:
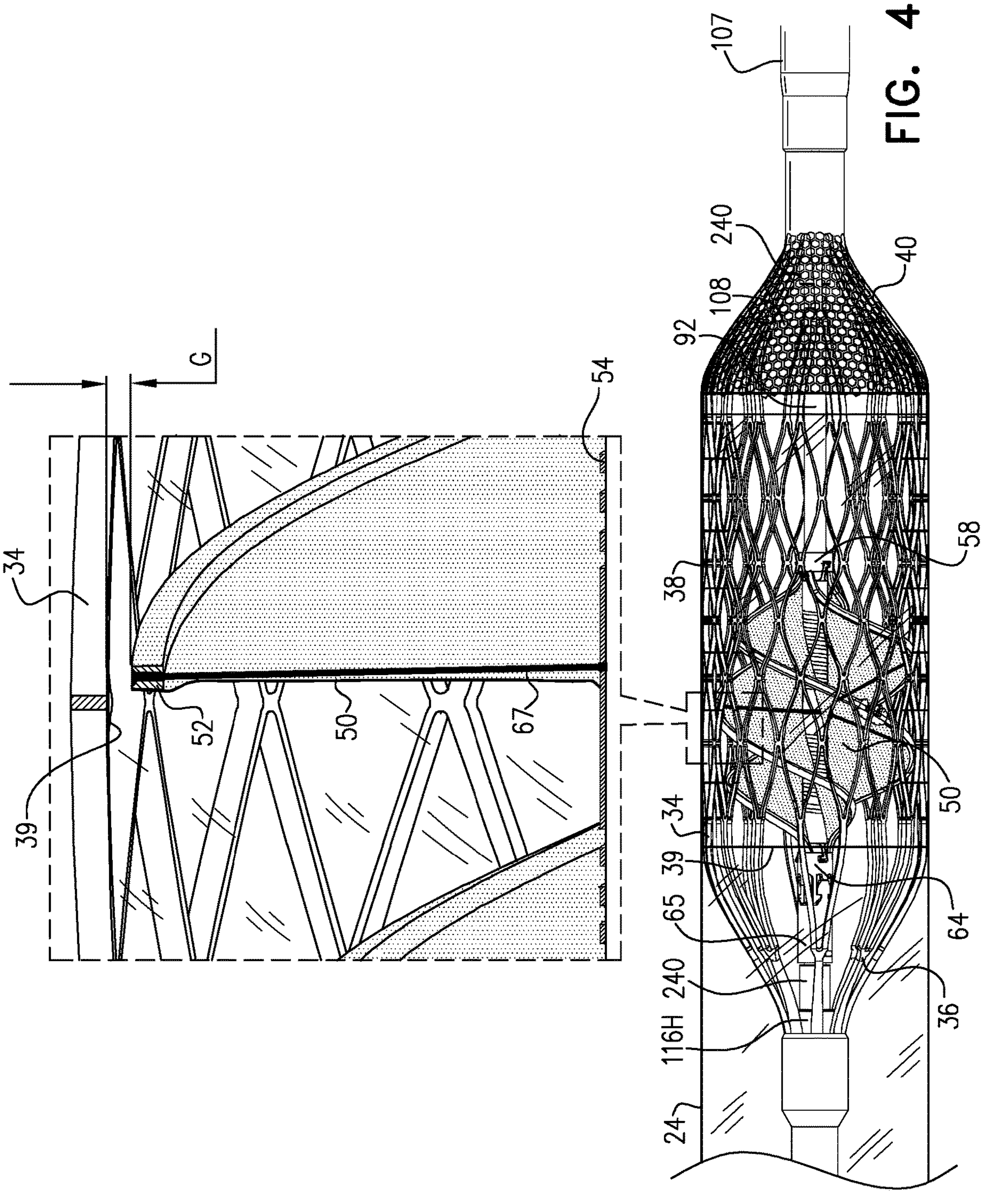
FIG. 4 is a schematic illustration of an impeller disposed inside a frame of a ventricular assist device, in accordance with some applications of the present invention.

For some applications, within at least a portion of frame 34 (e.g., along all of, or a portion of, the central cylindrical portion of the frame), an inner lining 39, shown in FIG. 4 for example, lines the frame. In accordance with respective applications, the inner lining partially overlaps or fully overlaps with pump-outlet tube 24 over the portion of the frame that the inner lining lines, as described in further detail hereinbelow with reference to FIGS. 10A-B. For other applications, as shown in FIG. 1C, the pump-head portion does not comprise inner lining 39.

Typically, pump-outlet tube 24 includes a conical proximal portion 42 and a cylindrical central portion 44. The proximal conical portion is typically proximally-facing, i.e., facing such that the narrow end of the cone is proximal with respect to the wide end of the cone. Typically, blood-outlet openings 109 are defined by pump-outlet tube 24, such that the openings extend at least partially along the proximal conical portion of tube 24. For some such applications, the blood-outlet openings are teardrop-shaped, as shown in FIG. 1C. Typically, the teardrop-shaped nature of the blood-outlet openings in combination with the openings extending at least partially along the proximal conical portion of tube 24 causes blood to flow out of the blood-outlet openings along flow lines that are substantially parallel with the longitudinal axis of tube 24 at the location of the blood-outlet openings.

For some applications (not shown), the diameter of pump-outlet tube 24 changes along the length of the central portion of the pump-outlet tube, such that the central portion of the pump-outlet tube has a frustoconical shape. For example, the central portion of the pump-outlet tube may widen from its proximal end to its distal end, or may narrow from its proximal end to its distal end. For some applications, at its proximal end, the central portion of the pump-outlet tube has a diameter of between 5 and 7 mm, and at its distal end, the central portion of the pump-outlet tube has a diameter of between 8 and 12 mm.

Again referring to FIG. 1C, the ventricular assist device typically includes a distal-tip element 107 that is disposed distally with respect to frame 34 and that includes an axial-shaft-receiving tube 126 and a distal-tip portion 120. Typically, the axial-shaft-receiving tube is configured to receive a distal portion of an axial shaft 92 (FIG. 4) of the pump-head portion during axial back-and-forth motion of the axial shaft (as described in further detail hereinbelow), and/or during delivery of the ventricular assist device. (Typically, during delivery of the ventricular assist device, the frame is maintained in a radially-constrained configuration, which typically causes the axial shaft to be disposed in a different position with respect to the frame relative to its disposition with respect to the frame during operation of the ventricular assist device). Typically, distal-tip portion 120 is configured to assume a curved shape upon being deployed within the subject's left ventricle, e.g., as shown in FIG. 1C. For some applications, the curvature of the distal-tip portion is configured to provide an atraumatic tip to ventricular assist device 20. Alternatively or additionally, the distal-tip portion is configured to space blood-inlet openings 108 of the ventricular assist device from walls of the left ventricle.

As shown in the enlarged portion of FIG. 1B, for some applications, pump-outlet tube 24 extends to the end of distal conical portion 40 of the frame, and the pump-outlet tube defines a plurality of lateral blood-inlet openings 108, as described in further detail hereinbelow. For such applications, the pump-outlet tube typically defines a distal conical portion that is distally facing, i.e., such that the narrow end of the cone is distal with respect to the wide end of the conc. For some such applications (not shown), the pump-outlet tube defines two to four lateral blood-inlet openings (e.g., four lateral blood-inlet openings). Typically, for such applications, each of the blood-inlet openings defines an area of more than 20 square mm (e.g., more than 30 square mm), and/or less than 60 square mm (e.g., less than 50 square mm), e.g., 20-60 square mm, or 30-50 square mm. Alternatively or additionally, the outlet tube defines a greater number of smaller lateral blood-inlet openings, e.g., more than 10 blood-inlet openings, more than 50 blood-inlet openings, more than 200 blood-inlet openings, or more than 400 blood-inlet openings, e.g., 50-100 blood-inlet openings, 100-400 blood-inlet openings, or 400-600 blood-inlet openings. For some such applications, each of the blood-inlet openings defines an area of more than 0.05 square mm (e.g., more than 0.1 square mm), and/or less than 3 square mm (e.g., less than 1 square mm), e.g., 0.05-3 square mm, or 0.1-1 square mm. Alternatively, each of the blood-inlet openings defines an area of more than 0.1 square mm (e.g., more than 0.3 square mm), and/or less than 5 square mm (e.g., less than 1 square mm), e.g., 0.1-5 square mm, or 0.3-1 square mm. Such applications are described in further detail hereinbelow, for example, with reference to FIGS. 11A-E.

It is noted that the lateral blood-inlet openings are typically defined by the distal conical portion of the pump-outlet tube. As such, even the blood-inlet openings that are described as "lateral blood-inlet openings" are typically not oriented entirely laterally with respect to the longitudinal axis of the pump-outlet tube. Rather, they are obliquely disposed with respect to the longitudinal axis of the pump-outlet tube. By contrast, in some embodiments, the blood-outlet openings are described as "laterally-facing blood-outlet openings" because in such embodiments the blood-outlet openings are disposed laterally with respect to the longitudinal axis of the pump-outlet tube, by virtue of being defined by the central cylindrical portion of the pump-outlet tube. It is noted that in other embodiments, the blood-outlet openings are disposed obliquely with respect to the longitudinal axis of the pump-outlet tube, by virtue of being defined at least partially by the proximal conical portion of the pump-outlet tube.

In general, the scope of the present disclosure includes combining a pump-outlet-tube that defines a single axially-facing blood-inlet opening 108 as shown in FIG. 1C, or a pump-outlet-tube that defines a plurality of lateral blood-inlet openings 108 as shown in FIG. 1B in combination with other features of the ventricular assist device that are described herein, mutatis mutandis.

Figure 2:
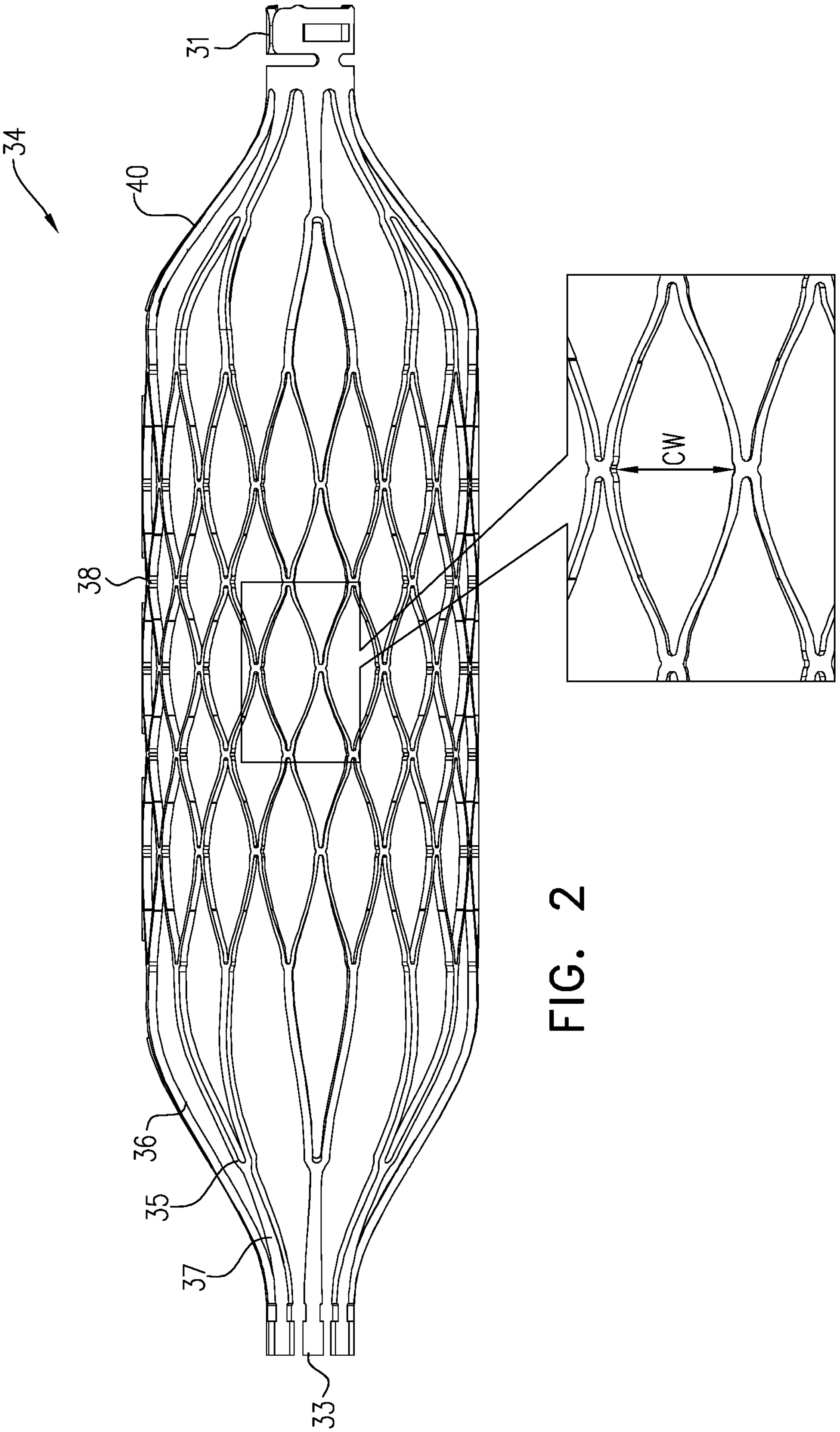
FIG. 2 is a schematic illustration of a frame that houses an impeller of a ventricular assist device, in accordance with some applications of the present invention.

Reference is now made to FIG. 2, which is schematic illustration of frame 34 that houses an impeller of ventricular assist device 20, in accordance with some applications of the present invention. Frame 34 is typically made of a shape-memory alloy, such as nitinol, and the shape-memory alloy of the frame is shape set such that the central portion 38 of the frame (and thereby tube 24) assumes a generally circular, elliptical, or polygonal cross-sectional shape in the absence of any forces being applied to pump-outlet tube 24. By assuming its generally circular, elliptical, or polygonal cross-sectional shape, the frame is configured to hold the distal portion of the tube in an open state. (Given that, typically, central portion 38 of the frame has a circular cross-section, the central portion of the frame is also referred to herein as the "cylindrical portion" of the frame.)

Typically, the frame is a stent-like frame, in that it comprises struts that, in turn, define cells. Further typically, the frame is covered with pump-outlet tube 24, and/or covered with an inner lining 39, described hereinbelow with reference to FIGS. 10A-B. As described hereinbelow, for some applications, impeller 50 undergoes axial back-and-forth motion with respect to frame 34. Typically, over the course of the motion of the impeller with respect to the frame, the location of the portion of the impeller that defines the maximum span of the impeller is disposed within central cylindrical portion 38 of frame 34. In some cases, if the cells of the central cylindrical portion 38 of frame 34 are too large, then pump-outlet tube 24, and/or inner lining 39, gets stretched between edges of the cells, such that the pump-outlet tube 24, and/or inner lining 39, does not define a circular cross-section. For some applications, if this occurs in the region in which the portion of the impeller that defines the maximum span of the impeller is disposed, this results in a substantially non-constant gap between the edges of the impeller blades and tube 24 (and/or inner lining) at that location, over the course of a rotation cycle of the impeller. For some applications, this may lead to increased hemolysis relative to if there were a substantially constant gap between the edges of the impeller blades and tube 24 (and/or inner lining) at that location, over the course of the rotation cycle of the impeller.

Referring to FIG. 2, at least partially in view of the issues described in the above paragraph, within central cylindrical portion 38 of frame 34, the frame defines a large number of relatively small cells. Typically, when the frame is disposed in its non-radially-constrained configuration, the maximum cell width CW of the each of the cells (i.e., the distance from the inner edge of the strut at the central junction on one side of the cell to the inner edge of the strut at the central junction on the other side of the cell, as measured around the circumference of cylindrical portion 38) within the cylindrical portion of the frame is less than 2 mm, e.g., between 1.4 mm and 1.6 mm, or between 1.6 and 1.8 mm. Since the cells are relatively small, inner lining 39 defines a substantially circular cross-section within the cylindrical portion of the frame.

Still referring to FIG. 2, and starting from the distal end of the frame (which is to the right of the figure), typically the frame defines the following portions: (a) coupling portion 31 via which the frame is coupled to a distal bearing housing 118H (shown in FIG. 5A) of the ventricular assist device, (b) distal conical portion 40, (c) central cylindrical portion 38, (d) proximal conical portion 36, and (e) proximal strut junctions 33. As illustrated, as the frame transitions from a proximal end of the frame toward the center of the frame (e.g., as the frame transitions from proximal strut junctions 33, through proximal conical portion 36, and to central cylindrical portion 38), struts 37 of the frame pass through junctions 35, at which the two struts branch from a single strut, in a Y-shape. As described in further detail hereinbelow, typically frame 34 is placed in a radially-constrained (i.e., crimped) configuration within delivery catheter 143 by the frame being axially elongated. Moreover, the frame typically transmits its radial narrowing to the impeller, and the impeller becomes radially constrained by becoming axially elongated within the frame. For some applications, the struts of the frame being configured in the manner described above facilitates transmission of axial elongation from the delivery catheter (or another device that is configured to crimp the frame) to the frame, which in turn facilitates transmission of axial elongation to the impeller. This is because the pairs of struts that branch from each of junctions 35 are configured to pivot about the junction and move closer to each other such as to close the space between them.

Still referring to FIG. 2, during the assembly of the ventricular assist device, initially, distal coupling portion 31 is coupled to a distal bearing housing 118H (shown in FIG. 5A), e.g., via a snap-fit mechanism. For some applications, proximal strut junctions 33 are still maintained in open states at this stage, in order for the impeller to be placed within the frame via the proximal end of the frame. Typically, the structure of frame 34 shown in FIG. 2 is used in applications in which pump-outlet tube extends to the distal end of frame 34 (e.g., as shown in FIG. 1B). In such cases, the impeller cannot be inserted via the distal end of the frame, since the distal end of the frame is covered by pump-outlet tube 24. During the assembly of the ventricular assist device, subsequently to the impeller being inserted via the proximal end of the frame, the proximal strut junctions are closed. For some applications, the proximal strut junctions are closed around the outside of a proximal bearing housing 116H (shown in FIG. 5A), as described in further detail hereinbelow with reference to FIGS. 5A-B. Typically, a securing element 117 (e.g., a ring shown in FIG. 5A) holds the strut junctions in their closed configurations around the outside of proximal bearing housing 116H.

Typically, when disposed in its non-radially constrained configuration, frame 34 has a total length of more than 25 mm (e.g., more than 30 mm), and/or less than 50 mm (e.g., less than 45 mm), e.g., 25-50 mm, or 30-45 mm. Typically, when disposed in its radially-constrained configuration (within delivery catheter 143), the length of the frame increases by between 2 and 5 mm. Typically, when disposed in its non-radially constrained configuration, the central cylindrical portion of frame 34 has a length of more than 10 mm (e.g., more than 12 mm), and/or less than 25 mm (e.g., less than 20 mm), e.g., 10-25 mm, or 12-20 mm. For some applications, a ratio of the length of the central cylindrical portion of the frame to the total length of the frame is more than 1:4 and/or less than 1:2, e.g., between 1:4 and 1:2.

Figure 3C:
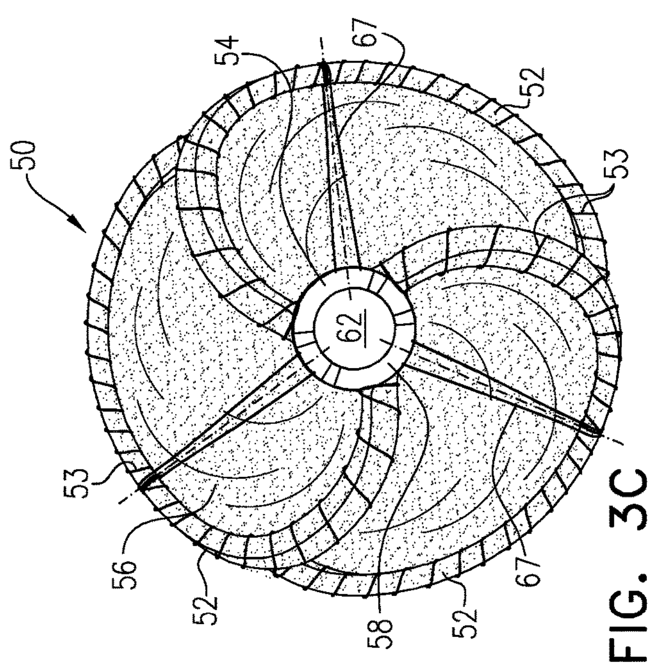
FIGS. 3A, 3B, 3C, 3D, 3E, 3F, and 3G are schematic illustrations of an impeller of a ventricular assist device or portions thereof, in accordance with some applications of the present invention.
Figure 3A:
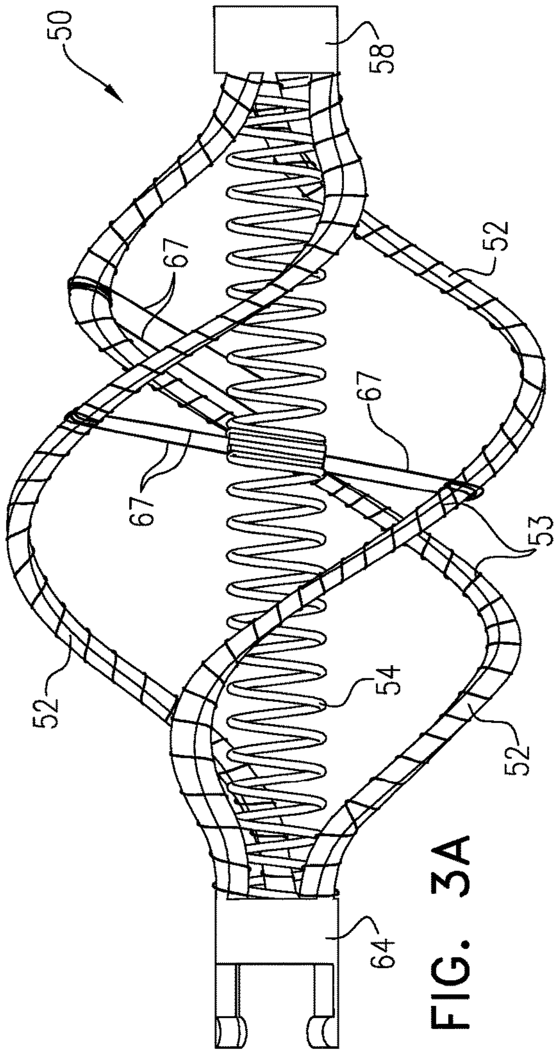
Figure 3B:
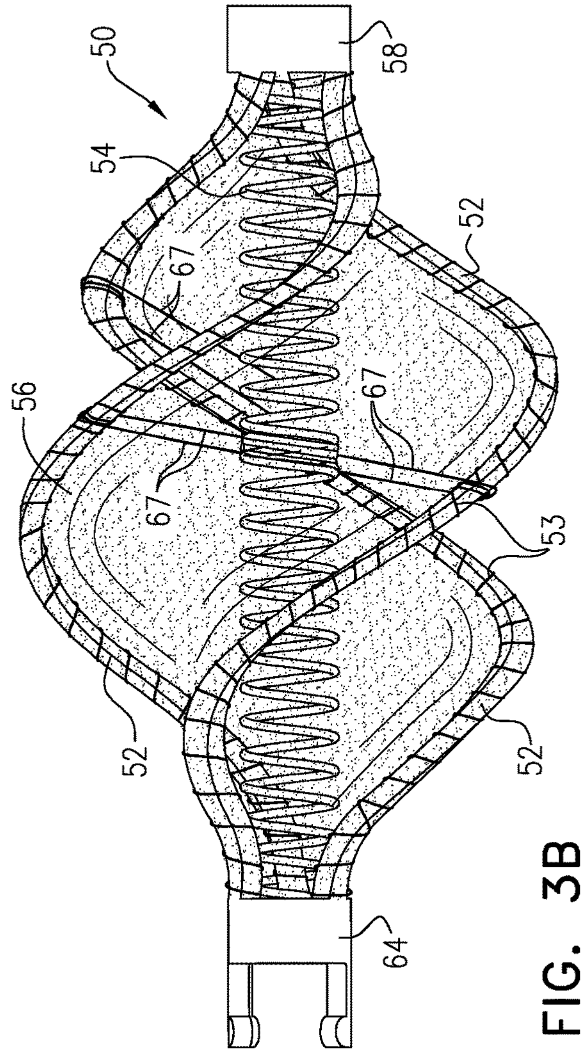
Figure 3E:
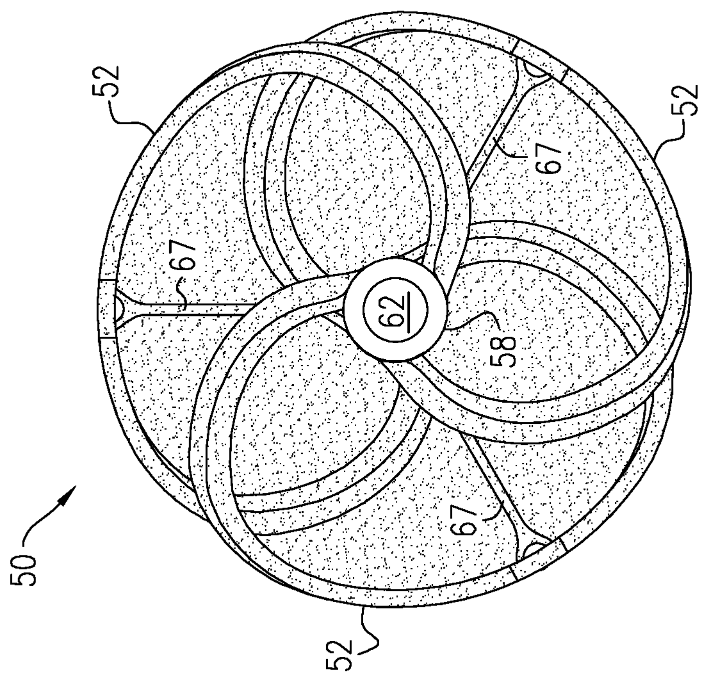
Figure 3D:
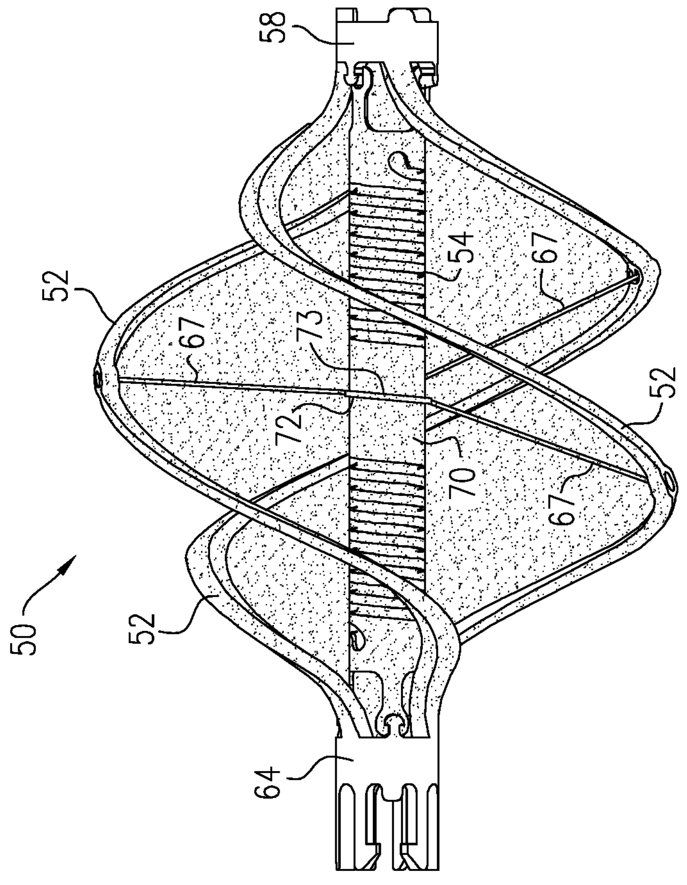

Reference is now made to FIGS. 3A-E, which are schematic illustrations of impeller 50 or portions thereof, in accordance with some applications of the present invention. Typically, the impeller includes at least one outer helical elongate element 52, which winds around a central axial spring 54, such that the helix defined by the helical elongate element is coaxial with the central axial spring. Typically, the impeller includes two or more helical elongate elements (e.g., three helical elongate elements, as shown in FIGS. 3A-C). For some applications, the helical elongate elements and the central axial spring are made of a shape-memory material, e.g., a shape-memory alloy, such as nitinol. Typically, each of the helical elongate elements and the central axial spring support a film 56 of a material (e.g., an elastomer, such as polyurethane, and/or silicone) therebetween. For some applications, the film of material includes pieces of nitinol embedded therein, for example in order to strengthen the film of material. For illustrative purposes, the impeller is shown in the absence of the material in FIG. 3A. FIGS. 3B and 3C show respective views of the impeller with the material supported between the helical elongate elements and the spring. FIGS. 3D and 3E show similar respective views of the impeller to those shown in FIGS. 3B and 3C, but with certain features of the impeller differing from those shown in FIGS. 3B and 3C, as elaborated upon hereinbelow.

Each of the helical elongate elements, together with the film extending from the helical elongate element to the spring, defines a respective impeller blade, with the helical elongate elements defining the outer edges of the blades, and the axial spring defining the axis of the impeller. Typically, the film of material extends along and coats the spring. For some applications, sutures 53 (e.g., polyester sutures, shown in FIGS. 3A-C) are wound around the helical elongate elements. Typically, the sutures are configured to facilitate bonding between the film of material (which is typically an elastomer, such as polyurethane, or silicone) and the helical elongate element (which is typically a shape-memory alloy, such as nitinol). For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol).

Typically, proximal ends of spring 54 and helical elongate elements 52 extend from a proximal bushing (i.e., sleeve bearing) 64 of the impeller, such that the proximal ends of spring 54 and helical elongate elements 52 are disposed at a similar radial distance from the longitudinal axis of the impeller, as each other. Similarly, typically, distal ends of spring 54 and helical elongate elements 52 extend from a distal bushing 58 of the impeller, such that the distal ends of spring 54 and helical elongate elements 52 are disposed at a similar radial distance from the longitudinal axis of the impeller, as each other. The helical elongate elements typically rise gradually from the proximal bushing before reaching a maximum span and then falling gradually toward the distal bushing. Typically, the helical elongate elements are symmetrical along their lengths, such that the rising portions of their lengths are symmetrical with respect to the falling portions of their lengths. Typically, the impeller defines a lumen 62 therethrough (shown in FIG. 3C), with the lumen typically extending through, and being defined by, spring 54, as well as proximal bushing 64 and distal bushing 58, of the impeller.

Reference is now made to FIG. 4, which is a schematic illustration of impeller 50 disposed inside frame 34 of ventricular assist device 20, in accordance with some applications of the present invention. For some applications, within at least a portion of frame 34 (e.g., along all of, or a portion of, central cylindrical portion 38 of the frame), inner lining 39 lines the frame. In accordance with respective applications, the inner lining partially overlaps or fully overlaps with pump-outlet tube 24 over the portion of the frame that the inner lining lines, as described in further detail hereinbelow with reference to FIGS. 9A-B.

As shown in FIG. 4, typically there is a gap G between the outer edge of impeller 50 and inner lining 39, even at a location at which the span of the impeller is at its maximum. For some applications, it is desirable that the gap between the outer edge of the blade of the impeller and inner lining 39 be relatively small, in order for the impeller to efficiently pump blood from the subject's left ventricle into the subject's aorta. (It is noted that, by virtue of the relatively small gap between the outer edge of impeller 50 and inner lining 39 even at a location at which the span of the impeller is at its maximum, as well as the shape of the impeller, the impeller functions as an axial-flow impeller, with the impeller pumping blood in the axial direction from a distal end of pump-outlet tube 24 to the proximal end of the pump-outlet tube.) It is also desirable that a gap between the outer edge of the blade of the impeller and the inner surface of frame 34 be maintained throughout the rotation of the impeller within frame 34, for example, in order to reduce the risk of hemolysis.

For some applications, when impeller 50 and frame 34 are both disposed in non-radially-constrained configurations and prior to operation of the impeller, gap G between the outer edge of the impeller and the inner lining 39, at the location at which the span of the impeller is at its maximum, is greater than 0.05 mm (e.g., greater than 0.1 mm), and/or less than 1 mm (e.g., less than 0.4 mm), e.g., 0.05-1 mm, or 0.1-0.4 mm. For some applications, when the impeller is disposed in its non-radially-constrained configurations and prior to operation of the impeller, the outer diameter of the impeller at the location at which the outer diameter of the impeller is at its maximum is more than 7 mm (e.g., more than 8 mm), and/or less than 10 mm (e.g., less than 9 mm), e.g., 7-10 mm, or 8-9 mm. For some applications, when frame 34 is disposed in its non-radially-constrained configuration, the inner diameter of frame 34 (as measured from the inside of inner lining 39 on one side of the frame to the inside of inner lining on the opposite side of the frame) is greater than 7.5 mm (e.g., greater than 8.5 mm), and/or less than 10.5 mm (e.g., less than 9.5 mm), e.g., 7.5-10.5 mm, or 8.5-9.5 mm. For some applications, when the frame is disposed in its non-radially-constrained configuration, the outer diameter of frame 34 is greater than 8 mm (e.g., greater than 9 mm), and/or less than 13 mm (e.g., less than 12 mm), e.g., 8-13 mm, or 9-12 mm.

Typically, an axial shaft 92 passes through the axis of impeller 50, via lumen 62 of the impeller. For some applications, the axial shaft is rigid, e.g., a rigid tube. For some applications, the axial shaft is made of a shape-memory material (e.g., a shape memory alloy, such as nitinol). Typically, such materials have some elasticity, such that in the event that the axial shaft becomes bent (e.g., during delivery of the pump head to the left ventricle), the axial shaft still assumes a straight shape, once deployed inside the subject's body.

Proximal bushing 64 is disposed over axial shaft 92, and distal bushing 58 is disposed over the axial shaft distally from the proximal bushing. For some applications, proximal bushing 64 of the impeller is coupled to the shaft such that the axial position of the proximal bushing with respect to the shaft is fixed, and distal bushing 58 of the impeller is slidable with respect to (i.e., is slidable along) the shaft. For example, the proximal bushing may be coupled to a coupling element 65 disposed on the axial shaft (shown in FIG. 4), for example via a snap-fit mechanism. Alternatively, distal bushing 58 of the impeller is coupled to the shaft such that the axial position of the distal bushing with respect to the shaft is fixed, and proximal bushing 64 of the impeller is slidable with respect to the shaft.

Figures 5A, 5B:
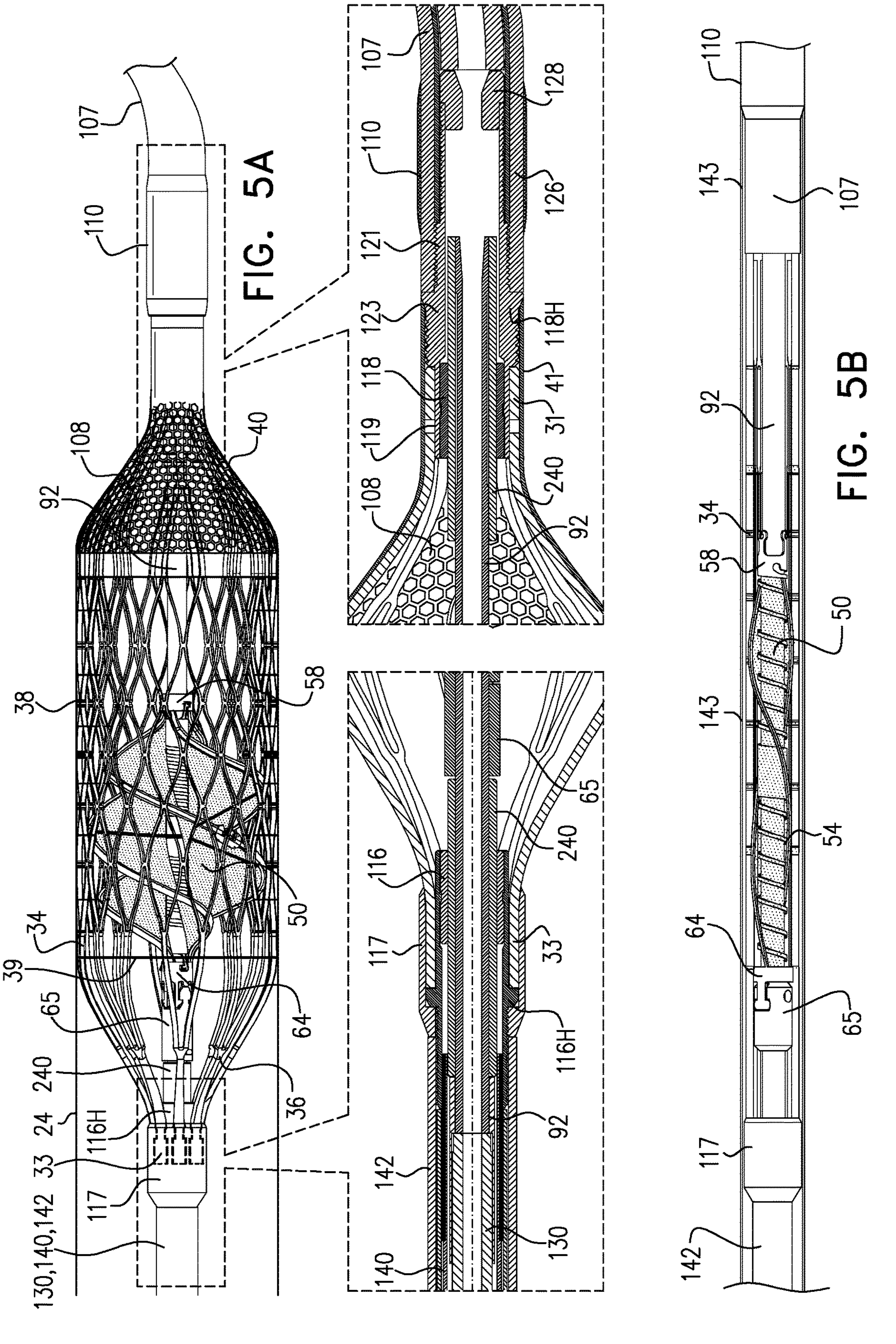
FIGS. 5A and 5B are schematic illustrations of the impeller and the frame of the ventricular assist device, respectively in non-radially-constrained and radially-constrained states thereof, in accordance with some applications of the present invention.

The axial shaft itself is radially stabilized via a proximal radial bearing 116 and a distal radial bearing 118 (FIG. 5A). In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller.

Referring again to FIGS. 3A-C, for some applications, the impeller includes a plurality of elongate elements 67 extending radially from central axial spring 54 to outer helical elongate elements 52. The elongate elements are typically flexible but are substantially non-stretchable along the axis defined by the elongate elements. Further typically, each of the elongate elements is configured not to exert force upon the helical elongate element, unless force is acting upon the impeller that is causing the helical elongate element to move radially outward, such that (in the absence of the elongate element) a separation between the helical elongate element and the central axial spring would be greater than a length of the elongate element. For example, the elongate elements may include strings (such as polyester, and/or another polymer or a natural material that contains fibers) and/or wires (such as nitinol wires, and/or wires made of a different alloy, or a metal).

For some applications, the elongate elements 67 maintain helical elongate element 52 (which defines the outer edge of the impeller blade) within a given distance with respect to the central axial spring. In this manner, the elongate elements are configured to prevent the outer edge of the impeller from being forced radially outward due to forces exerted upon the impeller during the rotation of the impeller. The elongate elements are thereby configured to maintain the gap between the outer edge of the blade of the impeller and the inner surface of frame 34, during rotation of the impeller. Typically, more than one (e.g., more than two) and/or fewer than eight (e.g., fewer than four) elongate elements 67 are used in the impeller, with each of the elongate elements typically being doubled (i.e., extending radially from central axial spring 54 to an outer helical elongate element 52, and then returning from the helical elongate element back to the central axial spring). For some applications, a plurality of elongate elements, each of which extends from the spring to a respective helical elongate element and back to the spring, are formed from a single piece of string or a single wire.

Reference is now made to FIGS. 3D and 3E, which are schematic illustrations of impeller 50, the impeller including a single integrated impeller-overexpansion-prevention element 72 that defines a plurality of elongate elements 67, in accordance with some applications of the present invention. For some applications, impeller-overexpansion-prevention element 72 (which defines a plurality of elongate elements 67) is used as an alternative to elongate elements 67 as shown in FIGS. 3A-C. For some applications, element 72 defines a ring 73 and the plurality of elongate elements 67 extending radially from the ring. For some applications, rather than threading strings and/or wire around spring 54, ring 73 of element 72 is placed around (and coupled to) the spring, e.g., by being placed around a tube 70, which is typically disposed at the longitudinally-central location of the spring. The ends of respective elongate elements 67 are then coupled to respective helical elongate elements 52. As described hereinabove, elongate elements 67 are typically flexible but are substantially non-stretchable along the axis defined by the elongate elements. Further typically, each of elongate elements 67 is configured to substantially not resist compression. Rather, each elongate element 67 is configured to exert a tensile force upon helical elongate element 52 that prevents helical elongate element 52 from moving radially outward, such that (in the absence of elongate element 67) a separation between helical elongate element 52 and central axial spring 54 would be greater than a length of elongate element 67. When a force is acting upon the impeller that would cause the helical elongate element 52 to move radially outward (in the absence of elongate element 67), the impeller-overexpansion-prevention element is configured to prevent radial expansion of the impeller. Typically, a respective elongate element 67 is disposed within each one of the impeller blades and is configured to prevent the impeller blade from radially expanding. For some applications, element 72 is made of polyester, and/or another polymer or a natural material that contains fibers, and/or nitinol (or a similar shape-memory alloy).

It is noted that the scope of the present application includes using single integrated impeller-overexpansion-prevention element 72 with an impeller having a different construction from that shown in FIGS. 3D-E. For example, the single integrated impeller-overexpansion-prevention element 72 could be used with an impeller having an axial structure constructed differently from spring 54 (but, typically nonetheless, defining a lumen therethrough, such that the impeller defines lumen 62 therethrough). Alternatively or additionally, the single integrated impeller-overexpansion-prevention element 72 could be used with the impeller described below with reference to FIGS. 3F-G.

For some applications, the following assembly technique is used to manufacture the impeller while enhancing bonding of an elastomeric material that is used to form film 56 to the at least one helical elongate element. Typically, bonding of the elastomeric material to the at least one helical elongate element is performed in a manner that does not cause a protrusion from the effective edge of the impeller blade. Further typically, bonding of the elastomeric material to the at least one helical elongate element is performed in a manner that provides the impeller blade with a rounded outer edge, by the elastomeric material rounding edges of the helical elongate element. Proximal bushing 64, distal bushing 58, and helical elongate elements 52 are cut from a tube of shape-memory material, such as nitinol. The cutting of the tube, as well as the shape setting of the shape-memory material, is typically performed such that the helical elongate elements and the bushings are defined by a tube of shape-memory material that is cut and shape set.

For some applications, prior to being coupled to spring 54, a plasma treatment is applied to the helical elongate elements. Alternatively or additionally, prior to being coupled to spring 54, the helical elongate elements are coated with a coupling agent. Typically, a coupling agent is selected that has at least two functional groups that are configured to bond respectively with the helical elongate elements and with the elastomeric material. For example, a silane compound, such as n-(2-aminoethyl)-3-aminopropyltrimethoxysilane, may be used, with the silane compound containing a first functional group (e.g., (OH)) which is configured to bond with the helical elongate elements (which are typically made of an alloy, such a nitinol), and the silane compound containing a second functional group (e.g., (NH2)) which is configured to bond with the elastomeric material. Typically, the functional groups in the coupling agent are active only for a given time period (e.g., approximately an hour or less). Therefore, during this time period, a coat of elastomeric material is applied around the helical elongate elements. Typically, the coat of elastomeric material is the same elastomeric material or a similar elastomeric material to that used in film 56. For example, a polycarbonate-based thermoplastic polyurethane, such as Aromatic Carbothane™ (e.g., Aromatic Carbothane™ 75A) may be used in film 56, and the coating may be the same polycarbonate-based thermoplastic polyurethane, or a similar polycarbonate-based thermoplastic polyurethane, such as Pellethane® (e.g., Pellethane® 90A).

As described hereinabove, proximal bushing 64, distal bushing 58, and helical elongate elements 52 are typically cut from a tube of shape-memory material, such as nitinol. For some applications, subsequently to the coating having been applied to the helical elongate elements 52, spring 54 is coupled to the helical elongate elements. Typically, spring 54 is inserted into the cut and shape-set tube, such that the spring extends along the length of the tube from at least the proximal bushing to the distal bushing. For some applications, the spring is inserted into the cut and shape-set tube while the spring is in an axially compressed state, and the spring is configured to be held in position with respect to the tube, by exerting a radial force upon the proximal and distal bushings. Alternatively or additionally, portions of the spring are welded to the proximal and distal bushings. For some applications, the spring is cut from a tube of a shape-memory material, such as nitinol. For some such applications, the spring is configured such that, when the spring is disposed in a non-radially-constrained configuration (in which the spring is typically disposed during operation of the impeller), there are substantially no gaps between windings of the spring and adjacent windings thereto.

Typically, at this stage, overexpansion-prevention element 72 is placed between the spring and the helical elongate elements, as described hereinabove, such that an assembly is formed that includes coated helical elongate elements 52, spring 54, and overexpansion-prevention element 72.

For some applications, at this stage, the assembly of coated helical elongate elements 52, spring 54, and overexpansion-prevention element 72 is sprayed with a further layer of an elastomeric material. Typically, the elastomeric material that is sprayed is the same elastomeric material or a similar elastomeric material to that used as film 56. For example, a polycarbonate-based thermoplastic polyurethane, such as Aromatic Carbothane™ (e.g., Aromatic Carbothanc™ 75A) may be used as film 56, and the sprayed material may be the same polycarbonate-based thermoplastic polyurethane, or a similar polycarbonate-based thermoplastic polyurethane, such as Pellethane® (e.g., Pellethane® 90A). For some applications, applying the spray to the helical elongate elements rounds the helical elongate elements. Typically, when the helical elongate element has a rounded cross section, the elastomeric material forms a layer having a substantially uniform thickness at the interface with the helical elongate element. For some applications, the step of applying the coat of elastomeric material to the helical elongate elements, as described above, at least partially rounds the helical elongate elements.

For some applications, subsequently to the spray having been applied, the assembly of coated helical elongate elements 52, spring 54, and overexpansion-prevention element 72 is dipped in the elastomer from which film 56 is made. For some applications, the material from which the film is made is an elastomer having an ultimate elongation of more than 300 percent, e.g., more than 400 percent. Typically, the material has a relatively low molecular weight. For some applications, the material has a melt flow index (which is an indirect measure of molecular weight) of at least 4, e.g., at least 4.3. For some applications, the material has an ultimate tensile strength of more than 6000 psi, e.g., more than 7000 psi, or more than 7500 psi. For some applications, the material is a polycarbonate-based thermoplastic polyurethane, e.g., a Carbothane™. For some applications, Aromatic Carbothane™ (e.g., Aromatic Carbothane™ 75A) is used. Typically, such materials combine one or more of the following properties: no outer diameter loss caused during the dip process, resistance to fatigue, resistance to becoming misshaped by being crimped, and low outer diameter loss during crimping. Subsequently, the material is cured such that it solidifies, e.g., by being left to dry. Typically, during this stage, the impeller is disposed on a mandrel, such that the mandrel passes through lumen 62 defined by the bushings and the spring, thereby maintaining the lumen during the drying. For some applications, while the material from which the film is made is drying, the impeller is rotated, which typically facilitates the formation of a film of material having a substantially uniform thickness within each of the impeller blades. Once the material has dried, the mandrel is typically removed from lumen 62.

In accordance with the above description of the application of film 56 to the helical elongate elements, the scope of the present disclosure includes any technique whereby, prior to the helical elongate elements being dipped into the elastomeric material from which film 56 is made, additional layers of the same elastomeric material, a different elastomeric material, and/or a mediating material are applied to the helical elongate elements, whether by spraying, dipping, or a different coating method. For some applications, additional layers of elastomeric material are configured to round the helical elongate elements, and/or to act as mediators to enhance bonding between the helical elongate elements and film 56 of material. For some applications, a mediating material (such as silane) is configured to act as a mediator to enhance bonding between the helical elongate elements and film 56 of material.

Typically, impeller 50 is inserted into the left ventricle transcatheterally, while impeller 50 is in a radially-constrained configuration. In the radially-constrained configuration, both helical elongate elements 52 and central axial spring 54 are axially elongated and radially constrained. Typically, film 56 of the material (e.g., silicone and/or polyurethane) changes shape to conform to the shape changes of the helical elongate elements and the axial support spring, both of which support the film of material. Typically, using a spring to support the inner edge of the film allows the film to change shape without the film becoming broken or collapsing, due to the spring providing a large surface area to which the inner edge of the film bonds. For some applications, using a spring to support the inner edge of the film reduces a diameter to which the impeller can be radially constrained, relative to if, for example, a rigid shaft were to be used to support the inner edge of the film, since the diameter of the spring itself can be reduced by axially elongating the spring.

As described hereinabove, for some applications, proximal bushing 64 of impeller 50 is coupled to axial shaft 92 such that the axial position of the proximal bushing with respect to the shaft is fixed, and distal bushing 58 of the impeller is slidable with respect to the shaft. For example, the proximal bushing may be coupled to coupling element 65 disposed on the axial shaft (shown in FIG. 4), for example via a snap-fit mechanism. For some applications, when the impeller is radially constrained for the purpose of inserting the impeller into the ventricle or for the purpose of withdrawing the impeller from the subject's body, the impeller axially elongates by the distal bushing sliding along the axial shaft distally. Alternatively (not shown), distal bushing 58 of the impeller is coupled to the shaft such that the axial position of the distal bushing with respect to the shaft is fixed, and proximal bushing 64 of the impeller is slidable with respect to the shaft. For some such applications, when the impeller is radially constrained for the purpose of inserting the impeller into the ventricle or for the purpose of withdrawing the impeller from the subject's body, the impeller axially elongates by the proximal bushing sliding along the axial shaft proximally. Subsequent to being released inside the subject's body, the impeller assumes its non-radially-constrained configuration (in which the impeller is typically disposed during operation of the impeller), which is as shown in FIGS. 3A-E.

Figure 3F:
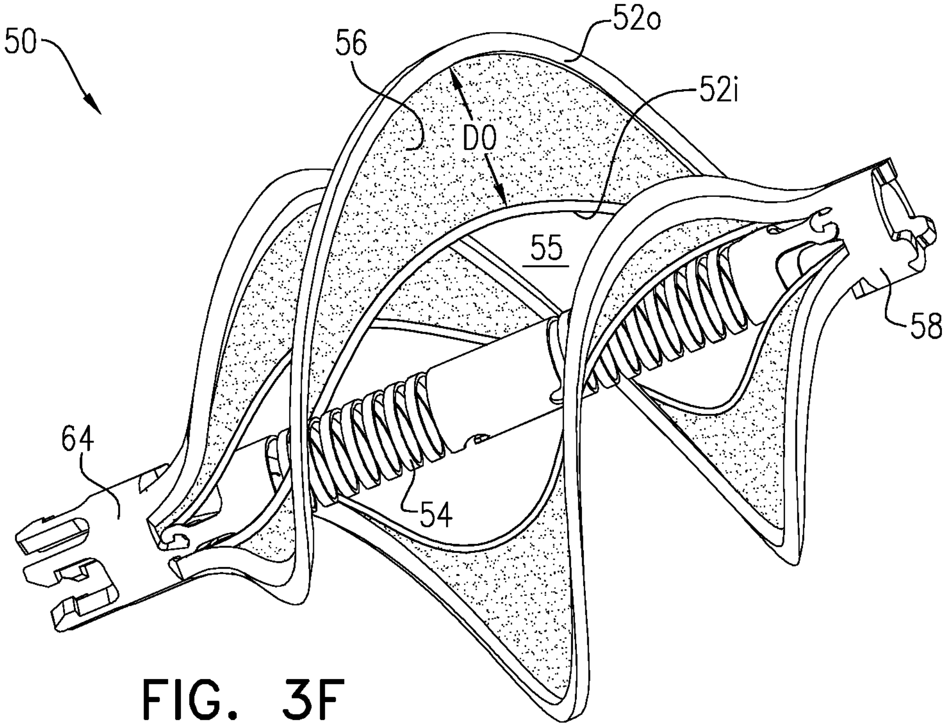
Figure 3G:
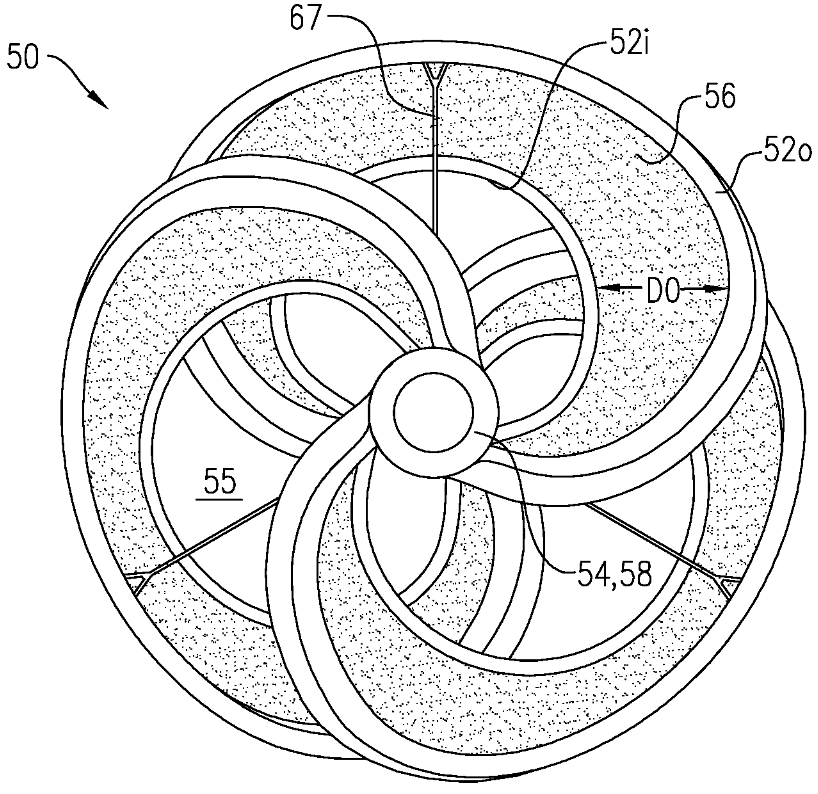

Reference is now made to FIGS. 3F and 3G, which are schematic illustrations of impeller 50, in accordance with some applications of the present invention. The impeller as shown in FIGS. 3F and 3G is generally similar to the impeller described hereinabove with reference to FIGS. 3A-E, except for the differences described below.

For some applications, each of the impeller blades comprises an inner helical elongate element **52*i*, an outer helical elongate element 520, and a film 56 of material extending between the inner helical elongate element and the outer helical elongate element. Each blade is proximally coupled to proximal bushing 64 and distally coupled to distal bushing 58 such that, as axial shaft 92 (FIG. 4) rotates, the blades rotate, thereby pumping blood of the subject. For example, as shown in FIG. 3F, each of the inner helical elongate elements and each of the outer helical elongate elements may be proximally coupled to the proximal bushing and distally coupled to the distal bushing. Alternatively, at the proximal and/or distal end of the blade, only one of the helical elongate elements may be coupled to the bushing, and the other helical elongate element may be coupled to the former helical elongate element. Typically, the inner helical elongate element extends between proximal bushing 64 and distal bushing 58 so as to define a radial gap 55 between the axial shaft (which, as noted above with reference to FIG. 4, may be surrounded by central axial spring 54) and the inner helical elongate element. Radial gap 55 is open, i.e., there is no film of material extending between the axial shaft (or central axial spring) and the inner helical elongate element. Thus, there is typically a radial gap 55** between the central axial spring and the impeller blade. For some applications, by defining the radial gap, the efficiency with which the impeller pumps blood is increased, and/or hemolysis that is generated by the impeller is reduced relative to a generally similar impeller that does not define such a gap.

Typically, the materials used for the blades in the impeller as shown in FIGS. 3F-G are generally similar to those described hereinabove, with reference to FIGS. 3A-E. For example, the films of material may be elastomeric, and/or pieces of nitinol may be embedded into the films of material. Further typically, the films of material are bonded to the helical elongate elements using generally similar techniques to those described hereinabove. For example, sutures 53 (FIGS. 3A-C) may couple the films of material to the inner helical elongate elements and to the outer helical elongate elements.

In some applications, proximal bushing 64, distal bushing 58, inner helical elongate elements **52*i*, and outer helical elongate elements 520** are cut from a tube of shape-memory material, such as nitinol. For some applications, the inner helical elongate elements, the outer helical elongate elements and the proximal and distal bushings are all formed from a single integral structure, for example, a single tube of a shape-memory alloy, such as nitinol. The structure is typically cut and shaped such as to define the aforementioned structures. Alternatively, the outer helical elongate elements and the proximal and distal bushings are formed from a first structure (which is a single integral structure) and the inner helical elongate elements are formed from one or more additional structures that are coupled to the first structure. For example, the outer helical elongate elements and the proximal and distal bushings may be formed from a first tube of a shape-memory alloy, such as nitinol, and the inner helical elongate elements may be cut and formed from a second tube of a shape-memory alloy, such as nitinol. Further alternatively, the inner helical elongate elements and the proximal and distal bushings are formed from a first structure (which is a single integral structure) and the outer helical elongate elements are formed from one or more additional structures that are coupled to the first structure. For example, the inner helical elongate elements and the proximal and distal bushings may be formed from a first tube of a shape-memory alloy, such as nitinol, and the outer helical elongate elements may be cut and formed from a second tube of a shape-memory alloy, such as nitinol.

As shown in FIG. 3G, for some applications, the impeller additionally comprises respective elongate elements 67 that couple the blades to spring 54 (which extends between the proximal bushing and the distal bushing) and are configured to inhibit radial expansion of the impeller by resisting tensile force. For example, elongate elements 67 may couple the blades directly to spring 54, as in FIGS. 3A-C. Alternatively, as shown in FIG. 3D, the impeller may comprise impeller-overexpansion-prevention element 72, which comprises elongate elements 67, such that the elongate elements couple the blades to the spring by virtue of being coupled to ring 73.

Typically, in such applications, as shown in FIG. 3G, elongate elements 67 are coupled to outer helical elongate elements 520. Optionally, the elongate elements may loop around outer helical elongate elements 520 and/or pass through inner helical elongate elements **52*i***.

Typically, for each of the blades, the distance DO between the inner helical elongate element and the outer helical elongate element increases moving, from the proximal or distal end of the blade, toward a middle portion of the blade. For example, DO may attain its maximum value midway between proximal bushing 64 and distal bushing 58 and/or at a maximal radial span of the outer helical elongate element. For some applications, the maximum value of DO is between 1 and 3.5 mm.

Figure 5C:
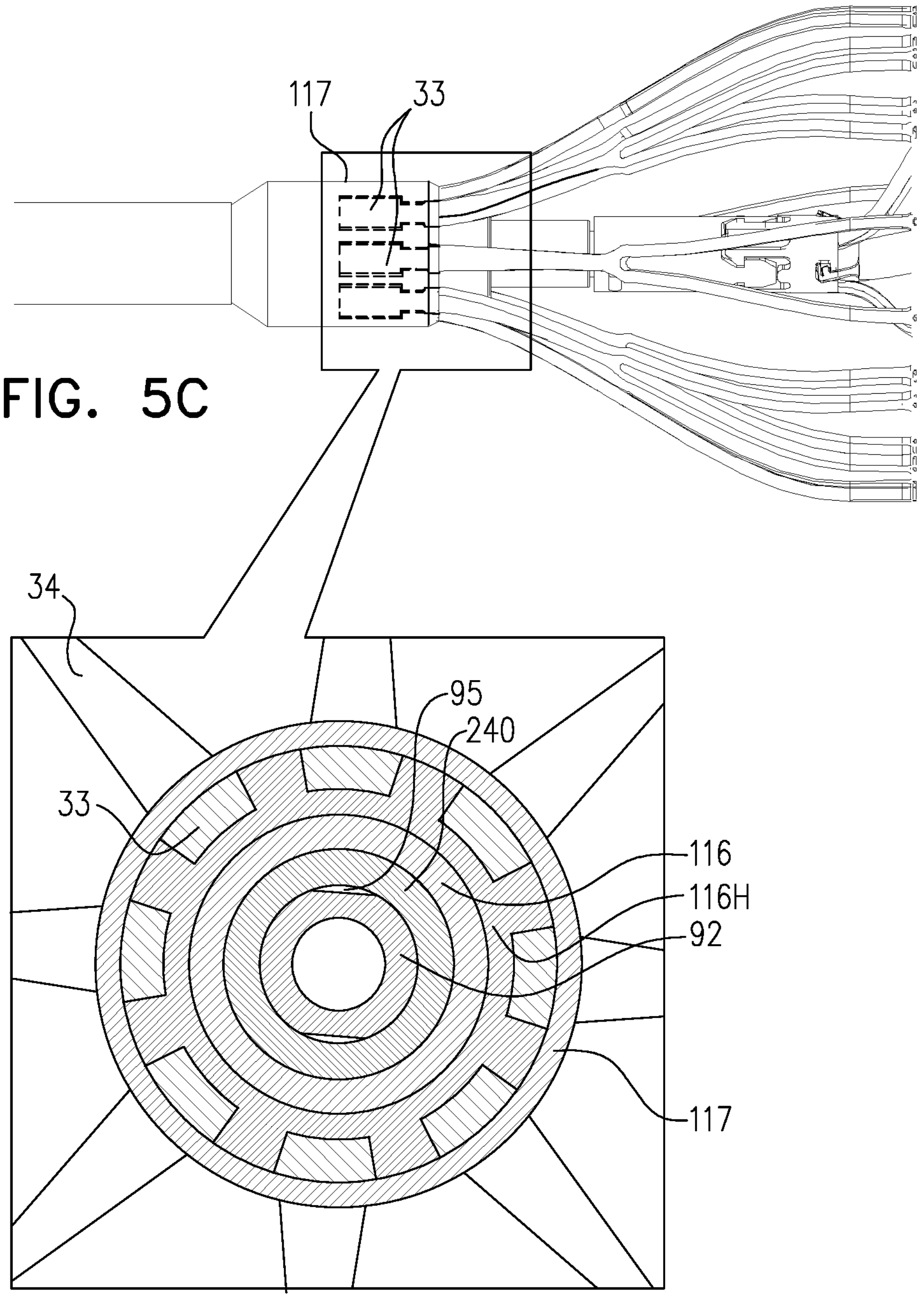
FIG. 5C is an enlarged schematic illustration of the proximal end of the frame of the ventricular assist device, in accordance with some applications of the present invention.

Reference is now made to FIGS. 5A and 5B, which are schematic illustrations of impeller 50 and frame 34 of ventricular assist device 20, respectively in non-radially-constrained and radially-constrained states thereof, in accordance with some applications of the present invention. The impeller and the frame are typically disposed in the radially-constrained states during the transcatheteral insertion of the impeller and the frame into the subject's body, and are disposed in the non-radially-constrained states during operation of the impeller inside the subject's left ventricle. Reference is also made to FIG. 5C, which is an enlarged schematic illustration of the proximal end of the frame of the ventricular assist device, in accordance with some applications of the present invention.

As indicated in FIG. 5B, the frame and the impeller are typically maintained in radially-constrained configurations by delivery catheter 143. Typically, in the radially-constrained configuration of the impeller, the impeller has a total length of more than 15 mm (e.g., more than 20 mm), and/or less than 30 mm (e.g., less than 25 mm), e.g., 15-30 mm, or 20-25 mm. Further typically, in the non-radially constrained configuration of the impeller, the impeller has a length of more than 8 mm (e.g., more than 10 mm), and/or less than 18 mm (e.g., less than 15 mm), e.g., 8-18 mm, or 10-15 mm. Still further typically, when the impeller and frame 34 are disposed in radially-constrained configurations (as shown in FIG. 5B), the impeller has an outer diameter of less than 2 mm (e.g., less than 1.6 mm) and the frame has an outer diameter of less than 2.5 mm (e.g., less than 2.1 mm).

As described hereinabove, typically, axial shaft 92 passes through the axis of impeller 50, via lumen 62 of the impeller. Typically, proximal bushing 64 of the impeller is coupled to the shaft via a coupling element 65 such that the axial position of the proximal bushing with respect to the shaft is fixed, and distal bushing 58 of the impeller is slidable with respect to the shaft. Alternatively, distal bushing 58 of the impeller is coupled to the shaft such that the axial position of the distal bushing with respect to the shaft is fixed, and proximal bushing 64 of the impeller is slidable with respect to the shaft.

The axial shaft itself is radially stabilized via a proximal radial bearing 116 and a distal radial bearing 118. Typically, proximal bearing housing 116H is disposed around, and houses, the proximal bearing, and distal bearing housing 118H is disposed around, and houses, the distal bearing. For some such applications, the radial bearings and the bearing housings are made of respective, different materials from each other. For example, the radial bearings may be made of a first material that has a relatively high hardness, such as ceramic (e.g., zirconia), and the bearing housings may be made of a second material that is moldable into a desired shape, such as a metal or an alloy (e.g., stainless steel, cobalt chromium, and/or nitinol).

For some applications, axial shaft 92 is made of a metal or an alloy, such as stainless steel. For some such applications, the axial shaft is covered with ceramic sleeves 240 (e.g., zirconia sleeves) along regions of the axial shaft that come into contact with either of the proximal and distal bearings 116, 118 during operation of the ventricular assist device. In this manner, the radial interfaces between the axial shaft and the proximal and distal bearings are ceramic-ceramic interfaces. As described in further detail herein, typically, the impeller and the axial shaft are configured to undergo axial back-and-forth motion during operation of the ventricular assist device. Therefore, for some applications, at locations along the axial shaft corresponding to each of the proximal and distal bearings, the axial shaft is covered with the ceramic sleeve along a length of more than 5 mm, e.g., more than 7 mm. In this manner, over the course of the axial back-and-forth motion of the axial shaft, the ceramic sleeves remain in contact with the radial bearings.

For some applications, along each portion of the axial shaft that is covered with a ceramic sleeve, the shaft is shaped (e.g., via milling, molding, or a different shaping process) to define one or more grooves or indents 95, as shown in the transverse cross-sectional view of FIG. 5C. Alternatively or additionally (not shown), the inner surface of the ceramic sleeve is shaped to define or more grooves or indents. For some such applications, in order to bond the sleeve to the axial shaft, an adhesive is injected into the groove or indent and the adhesive then spreads from the groove or indent across the interface between the axial shaft and the sleeve.

For some applications, the proximal bearing housing 116H and distal bearing housing 118H perform additional functions. Referring first to the proximal bearing housing, as described hereinabove, for some applications, proximal strut junctions 33 of frame 34 are closed around the outside of the proximal bearing housing. For some applications, the outer surface of the proximal bearing housing defines grooves that are shaped such as to receive the proximal strut junctions. For example, as shown, the proximal strut junctions have widened heads, and the outer surface of the proximal bearing housing defines grooves that are shaped to conform with the widened heads of the proximal strut junctions. Typically, securing element 117 (which typically includes a ring) holds the strut junctions in their closed configurations around the outside of proximal bearing housing 116H.

For some applications, additional portions of the ventricular assist device are coupled to the proximal bearing housing. For example, for some applications, a drive cable 130 extends from outside the subject's body to axial shaft 92, and is coupled to the axial shaft such that the axial shaft rotates with the drive cable. Typically, the drive cable rotates within a first outer tube 140, which functions as a drive-cable-bearing tube, and which extends from outside the subject's body to the proximal bearing housing. For some applications, the first outer tube is disposed within a second outer tube 142 (also referred to herein as a "delivery tube"), which also extends from outside the subject's body to the proximal bearing housing. For some applications, first outer tube 140 and/or second outer tube 142 is coupled to the proximal bearing housing (e.g., using an adhesive). For example, first outer tube 140 may be coupled to an inner surface of the proximal bearing housing, and second outer tube 142 may be coupled to an outer surface of the proximal bearing housing.

Referring now to distal bearing housing 118H, for some applications, distal coupling portion 31 of frame 34 is coupled to an outer surface of distal bearing housing 118H, e.g., via a snap-fit mechanism. For example, the outer surface of a proximal-most portion 119 of the distal bearing housing may include a snap-fit mechanism to which distal coupling portion 31 of frame 34 is coupled. For some applications, distal bearing 118 is disposed within the proximal-most portion 119 of the distal bearing housing, as shown in FIG. 5A. As described hereinabove, for some applications, pump-outlet tube 24 extends to the distal end of frame 34 and defines lateral blood-inlet openings 108. For some such applications, a coupling portion 41 (e.g., a tubular coupling portion) extends distally from the pump-outlet tube, and the coupling portion is coupled to the distal bearing housing in order to anchor the distal end of the pump-outlet tube. For some applications, an intermediate portion 123 of the distal bearing housing defines a ridged or a threaded outer surface, to which coupling portion 41 of the pump-outlet tube is coupled (e.g., via an adhesive). For some applications, the outer surface is ridged in order to enhance bonding between the distal bearing housing and coupling portion 41 of the pump-outlet tube. For some applications, the outer surface is threaded in order to enhance bonding between the distal bearing housing and coupling portion 41 of the pump-outlet tube and to facilitate the application of adhesive between the outer surface and coupling portion 41 of the pump-outlet tube, as described in further detail hereinbelow with reference to FIG. 12B. For some applications, a distal portion 121 of the distal bearing housing is configured to stiffen a region of distal-tip element 107 into which the distal end of shaft 92 moves (e.g., axial-shaft-receiving tube 126, or a portion thereof). Typically, distal-tip element 107 is coupled to an outer surface of distal portion 121 of the distal bearing housing (e.g., via adhesive). For some applications, at least a portion of the outer surface of distal portion 121 of the distal bearing housing is ridged and/or threaded in order to enhance bonding between distal-tip element 107 and the distal bearing housing.

As described above, axial shaft 92 is radially stabilized via proximal radial bearing 116 and distal radial bearing 118. In turn, the axial shaft, by passing through lumen 62 defined by the impeller, radially stabilizes the impeller with respect to the inner surface of frame 34 and inner lining 39, such that even a relatively small gap between the outer edge of the blade of the impeller and inner lining 39 (e.g., a gap that is as described above) is maintained, during rotation of the impeller, as described hereinabove. Typically, the impeller itself is not directly disposed within any radial bearings or thrust bearings. Rather, bearings 116 and 118 act as radial bearings with respect to the axial shaft.

In some embodiments, pump-head portion 27 (and more generally ventricular assist device 20) does not include any thrust bearing that is configured to be disposed within the subject's body and that is configured to oppose thrust generated by the rotation of the impeller. For some applications, one or more thrust bearings are disposed outside the subject's body (e.g., within motor unit 23, shown in FIGS. 1A and 7A-B), and opposition to thrust generated by the rotation of the impeller is provided solely by the one or more thrust bearings disposed outside the subject's body. For some applications, a mechanical element and/or a magnetic element is configured to maintain the impeller within a given range of axial positions. For example, a magnet (e.g., magnet 82, described hereinbelow with reference to FIG. 7B) that is disposed at the proximal end of the drive cable (e.g., outside the subject's body) may be configured to impart axial motion to the impeller, and/or to maintain the impeller within a given range of axial positions.

In alternate embodiments, axial shaft 92 is omitted, and the impeller is instead coupled to a distal portion of drive cable 130; for example, the drive cable may pass through lumen 62 (FIG. 3E) of the impeller. In other words, the distal portion of the drive cable may function as an axial shaft. It should thus be understood that throughout the present description, the distal portion of the drive cable, which may also be referred to as an "axial shaft," may substitute for axial shaft 92.

Figure 5D:
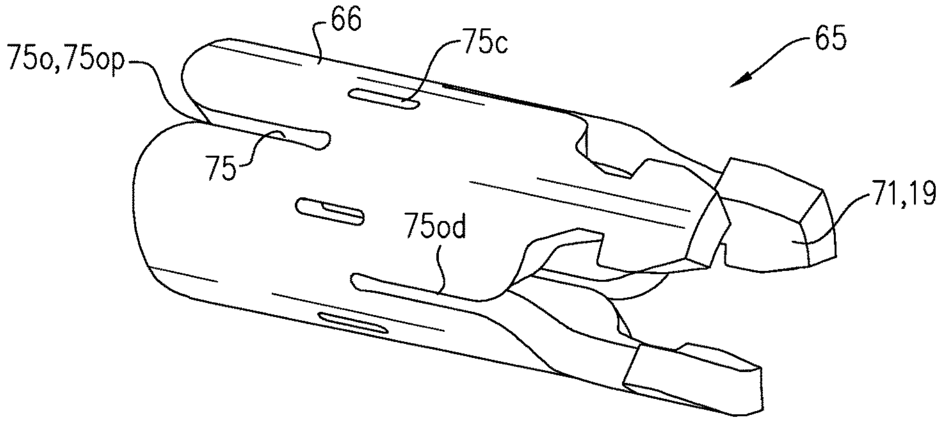
FIGS. 5D, 5E, and 5F are schematic illustrations of a coupling element, in accordance with some applications of the present invention.
Figure 5E:
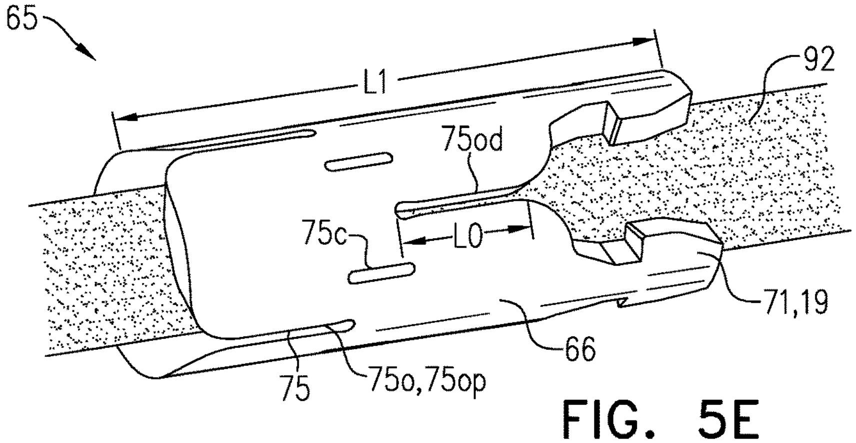
Figure 5F:
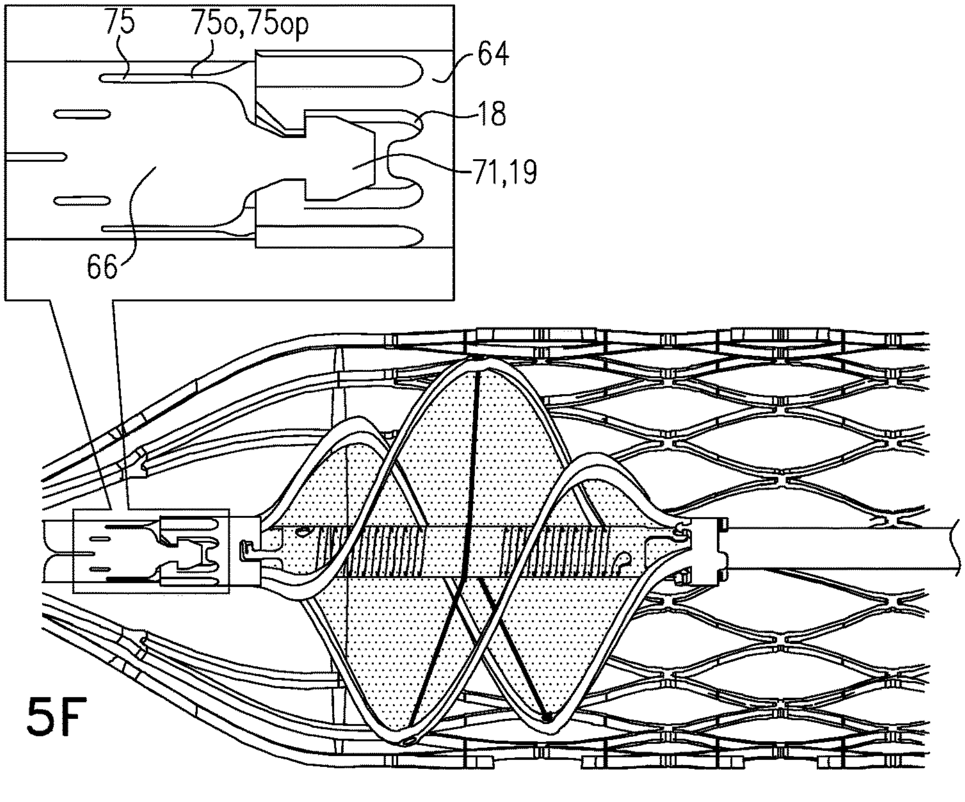

Reference is now made to FIGS. 5D, 5E, and 5F, which are schematic illustrations of coupling element 65, in accordance with some applications of the present invention. As described hereinabove, for some applications, proximal bushing 64 of impeller 50 is coupled to axial shaft 92 such that the axial position of the proximal bushing with respect to the shaft is fixed, and distal bushing 58 of the impeller is slidable with respect to the shaft. For some applications, the proximal bushing is coupled to the axial shaft via coupling element 65, for example via a snap-fit mechanism. Typically, the coupling element includes a first region (or "portion") 66 disposed around axial shaft 92, and a second region (or "portion") 71, which may also be disposed around the axial shaft.

The coupling element is coupled to proximal bushing 64 at second region 71. This coupling may be effected via a snap-fit mechanism, as noted above. For example, second region 71 may be shaped to define one or more protrusions 19, proximal bushing 64 may be shaped to define one or more indentations 18, and the proximal bushing may couple to second region 71 by virtue of protrusions 19 snapping into indentations 18. Alternatively, the proximal bushing may be shaped to define protrusions 19, second region 71 may be shaped to define indentations 18, and the proximal bushing may couple to second region 71 by virtue of the protrusions snapping into the indentations.

The coupling element is coupled to axial shaft 92 at first region 66. For example, for some applications, the first region of the coupling element is welded to the shaft. For other applications, the coupling element (or at least first region 66) is made of a shape-memory material (e.g., a shape-memory alloy, such as nitinol or cobalt chromium). For example, the coupling element may comprise a tube of the shape-memory material that is cut to define the first and second regions. For some such applications, at least the first region of the coupling element (or the entire coupling element) is shape set to have an inner diameter that is smaller (e.g., between 0.01 and 0.1 mm smaller) than the outer diameter of the axial shaft. For example, the axial shaft may have an outer diameter of 0.9 mm and the inner diameter of the first region of the coupling element may be between 0.85 and 0.89 mm (e.g., 0.87 mm). Thus, following the placement of the first region around the axial shaft, the first region becomes radially contracted around, and thus locked in place with respect to, the axial shaft. For some applications, coupling the coupling element to the axial shaft via this method, rather than via welding, is desirable, since the coupling element and/or the axial shaft can be weakened by being heated during the welding.

For some applications, the first region of the coupling element is shaped to define one or more slits 75, e.g., by virtue of comprising a tube that defines slits 75. Slits 75 facilitate a radial expansion of the first region such that the first region is placeable around the axial shaft. Following the placement around the axial shaft, the first region may radially contract around the axial shaft, as described above.

Slits 75 may incorporate various features for facilitating the expansion of first region 66. For example, in some embodiments, one or more of slits 75 are open-ended slits 75o, each of which has an open end. Open-ended slits 75o may include one or more proximally-open slits 75*op*, which are open at the proximal end of first region 66, and/or one or more distally-open slits 75*od*, which are open at the distal end of the first region. Optionally, the length L0 of each of the open-ended slits may be 5-40% of the length L1 of the coupling element. Alternatively or additionally to open-ended slits 75o, one or more of slits 75 may be closed-ended slits 75*c*, each of which does not have any open end. In some embodiments, as shown in FIGS. 5D-F, closed-ended slits 75*c* alternate with open-ended slits 75o around the circumference of first region 66.

During manufacture of the blood pump, first region 66 is placed around axial shaft 92 such that, as described above, the first region becomes radially contracted around the axial shaft. Typically, in addition to first region 66, second region 71 is placed around the axial shaft.

Typically, the coupling element is coupled to the axial shaft in the above-described manner without altering the temperature of the coupling element or of portions thereof. Alternatively, for some applications, the temperature of the coupling element is altered in order to facilitate the coupling of the coupling element to the axial shaft. For example, the first region may be radially expanded (with slits 75 facilitating the radial expansion) while the temperature of the first region is below the transformation temperature of the shape-memory material, and the first region may then be placed around the axial shaft while the first region is radially expanded. In other words, prior to the radial expansion, the coupling element may be cooled to below the transformation temperature of the shape-memory material, which is typically below ambient temperature, such as to increase the flexibility of the shape-memory material. The coupling element may then be placed around the axial shaft, while it is in its expanded configuration. Subsequently, the coupling element heats up to above its transformation temperature, causing it to radially contract towards the shape to which it was shape set. As described above, at least the first region of the coupling element (or the entire coupling element) is shape set to have an inner diameter that is smaller (e.g., between 0.01 and 0.1 mm smaller) than the outer diameter of the axial shaft. Therefore, as the coupling element radially contracts it exerts inward radial pressure on the axial shaft, causing it to become locked in place with respect to the axial shaft.

Subsequent to coupling the coupling element to the axial shaft, the impeller is coupled to the axial shaft, by coupling proximal bushing 64 to the second region of the coupling element.

As described above, this coupling may be performed via a snap-fit mechanism; for example, protrusions 19 may be snapped into indentations 18. Thus, as the axial shaft rotates, the blades of the impeller rotate, thereby pumping blood of the subject.

In alternate embodiments, second region 71 is coupled to distal bushing 58 (e.g., via a snap-fit mechanism, as described), such that the distal bushing is fixed in place with respect to the axial shaft, and proximal bushing 64 is slidable along the axial shaft.

Figure 6A:
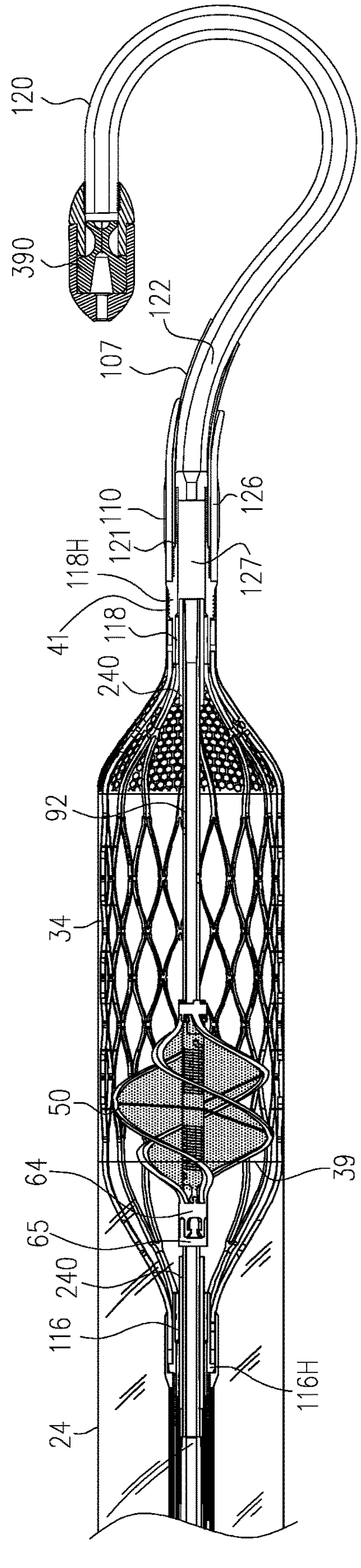
FIGS. 6A and 6B are schematic illustrations of a ventricular assist device at respective stages of a motion cycle of the impeller of the ventricular assist device with respect to the frame of the ventricular assist device, in accordance with some applications of the present invention.
Figure 6B:
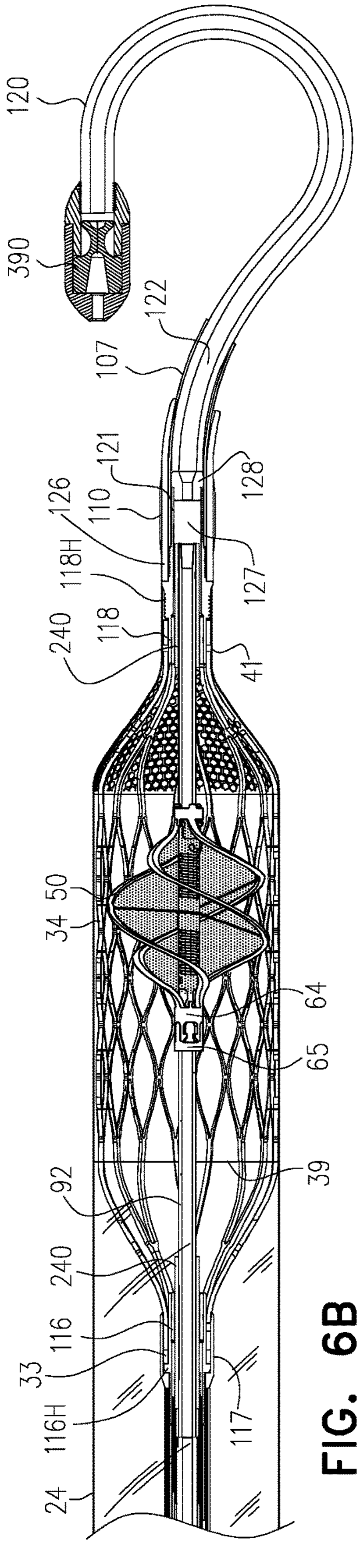

Reference is now made to FIGS. 6A and 6B, which are schematic illustrations of ventricular assist device 20 at respective stages of a motion cycle of impeller 50 of the ventricular assist device with respect to frame 34 of the ventricular assist device, in accordance with some applications of the present invention. For some applications, while the impeller is pumping blood through tube 24 by rotating, axial shaft 92 (to which the impeller is fixated) is driven to move the impeller axially back-and-forth within frame 34, by the axial shaft moving in an axial back-and-forth motion, as described in further detail hereinbelow with reference to FIG. 7A. Alternatively or additionally, the impeller and the axial shaft are configured to move axially back-and-forth within frame 34 in response to forces that are acting upon the impeller, and without requiring the axial shaft to be actively driven to move in the axial back-and-forth motion. Typically, over the course of the subject's cardiac cycle, the pressure difference between the left ventricle and the aorta varies from being approximately zero during ventricular systole (hereinafter "systole") to a relatively large pressure difference (e.g., 50-70 mmHg) during ventricular diastole (hereinafter "diastole"). For some applications, due to the increased pressure difference that the impeller is pumping against during diastole (and due to the fact that drive cable 130 is stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller to cause them to undergo this motion. FIGS. 6A and 6B show the impeller and axial shaft disposed at respective positions within frame 34 during the above-described axial back-and-forth motion cycle.

For some applications, by moving in the axial back-and-forth motion, the portions of the axial shaft that are in contact with proximal bearing 116 and distal bearing 118 are constantly changing. For some such applications, in this manner, the frictional force that is exerted upon the axial shaft by the bearings is spread over a larger area of the axial shaft than if the axial shaft were not to move relative to the bearings, thereby reducing wear upon the axial shaft, ceteris paribus. Alternatively or additionally, by moving in the back-and-forth motion with respect to the bearing, the axial shaft cleans the interface between the axial shaft and the bearings from any residues, such as blood residues.

For some applications, at the proximal-most position of the impeller during its motion cycle, the proximal end of the impeller is disposed within the proximal conical section of frame 34, as shown in FIG. 6A. For some applications, at the distal-most position of the impeller during its motion cycle, the distal end of the impeller is disposed at the distal end of the cylindrical section of frame 34. Alternatively, even at the distal-most position of the impeller during its motion cycle, the distal end of the impeller is disposed proximally to the distal end of the cylindrical section of frame 34, as shown in FIG. 6B. Typically, over the course of the entire cardiac cycle, the section of the impeller at which the span of the impeller is at its maximum is disposed within the cylindrical portion of the frame 34. However, a proximal portion of the impeller is typically disposed within the proximal conical section of the frame during at least a portion of the cardiac cycle.

Reference is again made to FIGS. 6A and 6B. Typically, distal-tip element 107 is a single integrated element that includes both axial-shaft-receiving tube 126 and distal-tip portion 120. Typically, the axial-shaft-receiving tube is configured to receive a distal portion of axial shaft 92 of the pump-head portion during axial back-and-forth motion of the axial shaft (as described in further detail hereinbelow), and/or during delivery of the ventricular assist device. (Typically, during delivery of the ventricular assist device, the frame is maintained in a radially-constrained configuration, which typically causes the axial shaft to be disposed in a different position with respect to the frame relative to its disposition with respect to the frame during operation of the ventricular assist device). For some applications, distal-tip portion 120 is configured to be soft, such that the distal-tip portion is configured not to injure tissue of the subject, even if the distal-tip portion comes into contact with the tissue (e.g., tissue of the left ventricle). For example, distal-tip portion 120 or the entire distal-tip element may be made of silicone, polyethylene terephthalate (PET) and/or polyether block amide (e.g., PEBAX®). For some applications, the distal-tip portion defines a lumen 122 therethrough. For some such applications, during insertion of the ventricular assist device into the left ventricle, guidewire 10 (FIG. 1B) is first inserted into the left ventricle, for example, in accordance with known techniques. The distal-tip portion of the ventricular assist device is then guided to the left ventricle by advancing the distal-tip portion over the guidewire, with the guidewire disposed inside lumen 122. For some applications, a duckbill valve 390 (or a different type of valve) is disposed at the distal end of lumen 122 of distal-tip portion 120.

Typically, during the insertion of the ventricular assist device into the subject's ventricle, delivery catheter 143 (FIG. 5B) is placed over impeller 50 and frame 34 and maintains the impeller and the frame in their radially-constrained configurations. For some applications, distal-tip element 107 extends distally from the delivery catheter during the insertion of the delivery catheter into the subject's ventricle, as shown in FIG. 1B. For some applications, toward the proximal end of the distal-tip element, the distal-tip element has a protrusion 110. Referring to FIG. 5B (which shows the pump-head portion disposed inside delivery catheter 143), for some applications, during the insertion of the ventricular assist device into the subject's ventricle, the delivery catheter extends until the proximal side of the protrusion, such that the delivery catheter and the protrusion form a smooth continuous surface. The distal side of protrusion 110 is tapered, such that the vasculature is exposed to a tapered diameter change, and is not exposed to any edges arising from a sharp change in diameter at the interface between the delivery catheter and the distal-tip element.

For some applications, distal-tip element 107 defines an overall curvature that is similar to that of a question mark or a tennis-racket, with the distal-tip element defining a straight proximal portion and a bulge on one side of the longitudinal axis of the straight proximal portion. Typically, the ventricular assist device is introduced into the subject's ventricle over a guidewire, as described hereinabove. Distal-tip portion 120 defines lumen 122, such that the distal-tip portion is held in a straightened configuration during the introduction of the ventricular assist device into the subject's ventricle (e.g., as shown in the left frame of FIG. 1B). For some applications, upon the guidewire being removed, distal-tip portion is configured to assume its curved shape.

Referring again to FIGS. 6A-B, for some applications, axial-shaft-receiving tube 126 extends proximally from distal-tip portion 120 of distal-tip element 107. As described hereinabove, typically, the axial shaft undergoes axial back-and-forth motion during the operation of impeller 50. Axial-shaft-receiving tube 126 defines lumen 127, which is configured to receive the axial shaft when the axial shaft extends beyond distal bearing 118. For some applications, the axial shaft-receiving tube defines a stopper 128 at its distal end, the stopper being configured to prevent advancement of the axial shaft beyond the stopper. For some applications, the stopper comprises a rigid component that is inserted (e.g., embedded) into the distal end of the shaft-receiving tube. Alternatively (not shown), the stopper comprises a shoulder between lumen 127 of the axial-shaft-receiving tube and lumen 122 of distal-tip portion 120.

Typically, during normal operation of the impeller, the axial shaft does not come into contact with stopper 128, even when drive cable 130 (shown in FIG. 5A) is maximally elongated (e.g., during diastole). However, stopper 128 is configured to prevent the axial shaft from protruding into the tip portion when the delivery catheter is advanced over impeller 50 and frame 34, during retraction of ventricular assist device 20 from the subject's ventricle. In some cases, during the advancement of the delivery catheter over the frame and the impeller, the drive cable is at risk of snapping. In the absence of stopper 128, in such cases, the axial shaft may protrude into the tip portion. Stopper 128 prevents this from happening, even in the event that the drive cable snaps.

It is noted that, at the proximal end of frame 34, proximal radial bearing 116 also functions as a stopper, by preventing coupling element 65 and/or proximal bushing 64 of impeller 50 from being able to move beyond the proximal radial bearing. Typically, during normal operation of the impeller, coupling element 65 and proximal bushing 64 do not come into contact with proximal radial bearing 116. However, proximal radial bearing 116 is configured to prevent coupling element 65 and/or proximal bushing 64 of impeller 50 from migrating proximally from inside the frame, for example, when the impeller and the frame are held in radially-constrained (i.e., crimped) configurations inside delivery catheter 143. Typically, the coupling element and/or the proximal bushing is proximally-extended such as to prevent a central region of the impeller (at which the span of the impeller is at its maximum) from sliding proximally into the proximal conical portion of frame 34. For example, in the systolic phase of the impeller's motion cycle (shown in FIG. 6A), if the impeller were to slide further proximally by more than a given amount, the coupling element would contact proximal radial bearing 116, thereby preventing further proximal motion of the impeller. For some applications, the coupling element and/or the proximal bushing is proximally extended such that it has a total length of more than 1.5 mm, e.g., more than 4 mm. For some applications (not shown), a separate stopper element is disposed upon the axial shaft proximally with respect to coupling element and/or proximal bushing 64. Typically, the stopper is configured as described with reference to the coupling element. Namely, if the impeller were to slide further proximally by more than a given amount, the stopper element would contact proximal radial bearing 116, thereby preventing further proximal motion of the impeller.

Typically, during operation of the ventricular assist device, and throughout the axial back-and-forth motion cycle of the impeller, the impeller is disposed relatively close to the distal-tip portion. For example, the distance of the impeller to the distal-tip portion may be within the distal-most 50 percent, e.g., the distal-most 30 percent (or the distal-most 20 percent) of tube 24, throughout the axial back-and-forth motion cycle of the impeller.

Figure 6C:
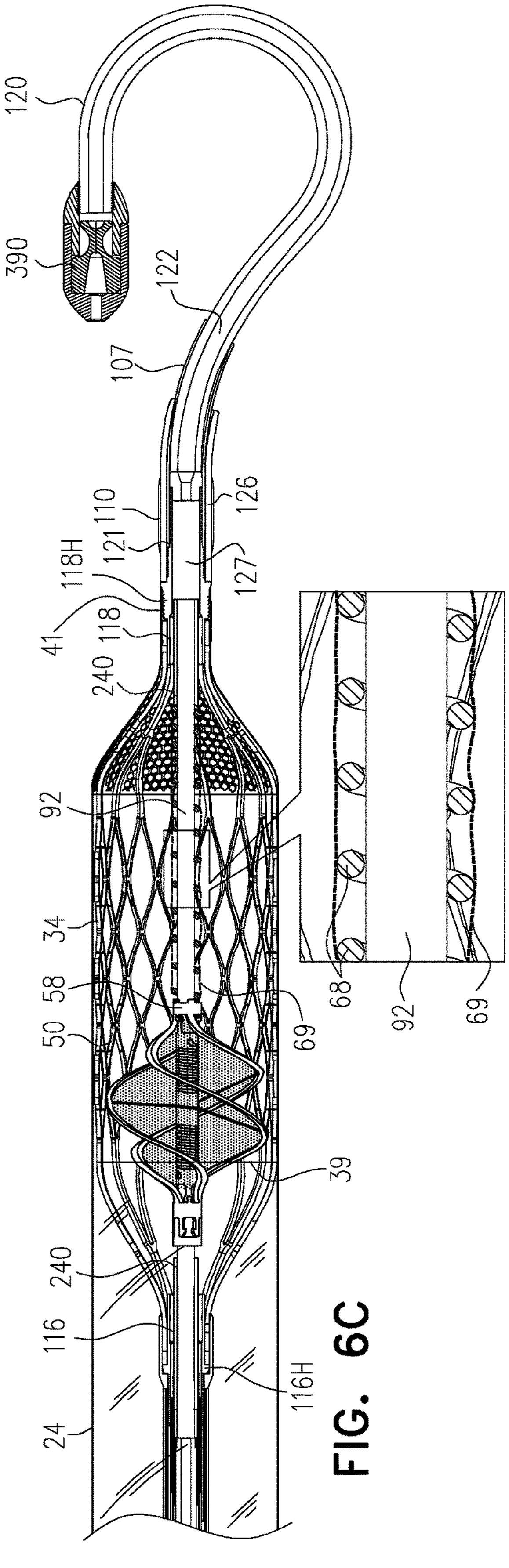
FIGS. 6C and 6D are schematic illustrations of a ventricular assist device that includes a motion-cushioning spring, in accordance with some applications of the present invention.
Figure 6D:
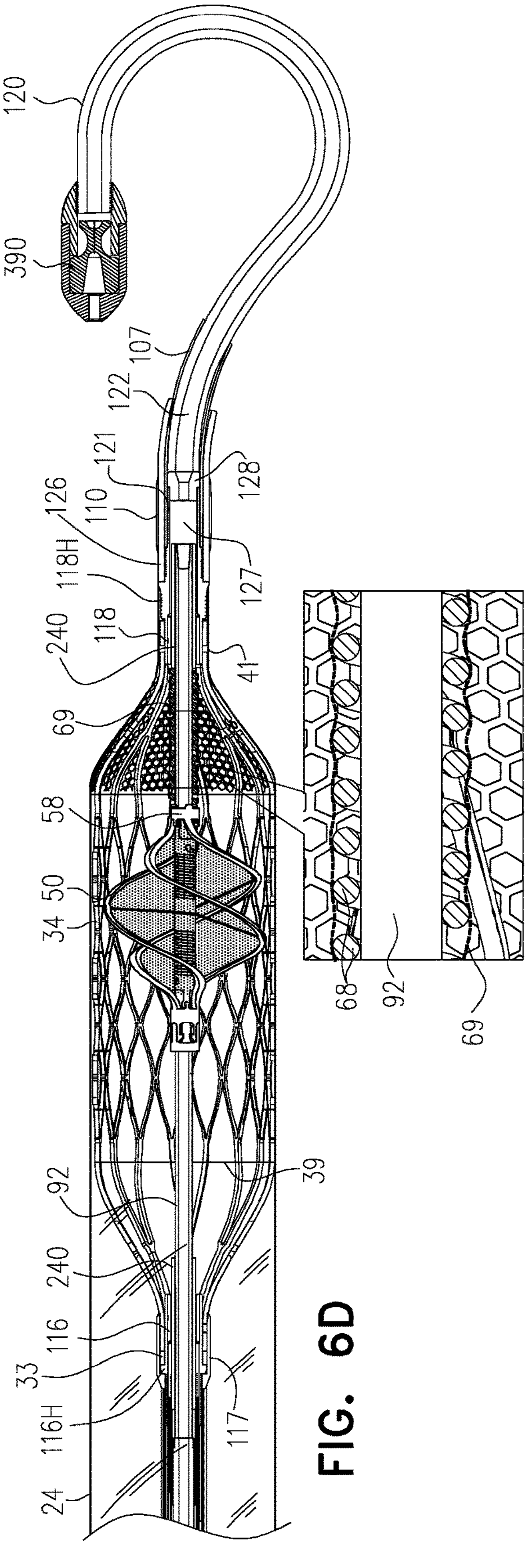

Reference is now made to FIGS. 6C and 6D, which are schematic illustrations of a ventricular assist device that includes a motion-cushioning spring 68, in accordance with some applications of the present invention. As described in further detail hereinbelow, typically, during operation of the ventricular assist device (i.e., as the impeller is rotating), the impeller undergoes axial back-and-forth motion. For some applications, as the impeller undergoes the axial back-and-forth motion, the motion-cushioning spring is configured to act as a shock absorber, to provide cushioning to the motion. FIG. 6C shows the impeller at the systolic phase of the motion cycle of the impeller and FIG. 6D shows the impeller at the diastolic phase of its motion cycle. As shown, as the impeller moves distally from its systolic position to its diastolic position, the motion-cushioning spring becomes more compressed. For some applications, the impeller is configured to be radially constrained (i.e., crimped) by becoming axially elongated, and the motion-cushioning spring is configured to become compressed such as to accommodate the axial elongation of the impeller. Typically, when the impeller is in a radially-constrained configuration, during insertion of the pump head into the left ventricle, the impeller is axially elongated such that the distal end of the impeller is disposed further distally within frame 34 and the spring is further compressed relative to the configurations of the impeller and the spring shown in FIG. 6D.

Typically, the motion-cushioning spring is disposed around axial shaft 92 between the distal end of the impeller (e.g., distal bushing 58 of the impeller) and distal bearing 118. For some applications, the motion-cushioning spring is coupled to distal bearing 118 or the distal bearing housing 118H and extends proximally over axial shaft 92 from the distal bearing or the distal bearing housing 118H. Typically, in such cases, the motion-cushioning spring remains rotationally stationary as the impeller rotates, and the impeller is configured to rotate with respect to the motion-cushioning spring. Alternatively or additionally, the motion-cushioning spring is coupled to the distal end of the impeller (e.g., distal bushing 58 of the impeller) and/or extends distally over axial shaft 92 from the distal end of the impeller (e.g., distal bushing 58 of the impeller). For some such applications, the motion-cushioning spring is configured to rotate together with the impeller. Alternatively, the motion-cushioning spring extends from a radial bearing that is disposed around the distal end of the impeller (e.g., distal bushing 58 of the impeller), such that motion-cushioning spring remains rotationally stationary as the impeller rotates, and the impeller is configured to rotate with respect to the motion-cushioning spring.

For some applications, the motion-cushioning spring is coupled to an elastomeric material 69 (such as polyurethane, and/or silicone), such that at least a portion of axial shaft 92 that is between the distal end of the impeller and the distal radial bearing is covered by the elastomeric material. For some applications, coupling the elastomeric material to the spring reduces a risk of the generation of thrombi and/or hemolysis by the spring, relative to if the spring were not coupled to the elastomeric material. It is noted that the scope of the present disclosure includes providing the motion-cushioning spring in the absence of elastomeric material, as may be desirable in some cases.

FIGS. 6C and 6D show the spring as being coated with the elastomeric material with the elastomeric material extending between adjacent windings of the spring. Alternatively, the spring is embedded within the elastomeric material. Typically, the elastomeric material is generally similar to the elastomeric material that is used for film 56 of material within impeller 50. Further typically, the elastomeric material is coupled to the motion-cushioning spring in a generally similar manner to that described hereinabove with reference to the coupling of the film of elastomeric material to the spring of the impeller. Typically, the elastomeric material is coupled to the motion-cushioning spring in such a manner that the elastomeric material changes shape (e.g., by stretching and compressing) to conform to shape changes that the motion-cushioning spring undergoes (e.g., when the motion-cushioning spring undergoes elongation and compression). Further typically, the elastomeric material is configured to undergo the above-described shape changes without the elastomeric material becoming broken or collapsing, and without the elastomeric material becoming creased when the spring is compressed.

Typically, purging fluid is pumped between first outer tube 140 and second outer tube 142. Typically, within the pump head, a portion of the purging fluid flows through the lumen defined by axial shaft 92 and then exits the axial shaft in the vicinity of distal bearing 118, in order to purge the interface between the axial shaft and the distal bearing. For some applications, the purging system is configured such that purging fluid flows proximally from the distal bearing along an interface between the axial shaft and the elastomeric material. In this manner, the interface between the axial shaft and the elastomeric material is purged and/or lubricated.

For some applications (not shown), a proximal motion-cushioning spring is disposed on the proximal side of the impeller. For some such applications, the proximal motion-cushioning spring is disposed around axial shaft 92 between the proximal end of the impeller (e.g., proximal bushing 64 of the impeller) and proximal bearing 116. For some applications, the proximal motion-cushioning spring is coupled to proximal bearing 116 or proximal bearing housing 116H and extends distally over axial shaft 92 from the proximal bearing or the proximal bearing housing. Typically, in such cases, the proximal motion-cushioning spring remains rotationally stationary as the impeller rotates, and the impeller is configured to rotate with respect to the motion-cushioning spring. Alternatively or additionally, the proximal motion-cushioning spring is coupled to the proximal end of the impeller (e.g., proximal bushing 64 of the impeller) and/or extends distally over axial shaft 92 from the proximal end of the impeller (e.g., proximal bushing 64 of the impeller). For some such applications, the motion-cushioning spring is configured to rotate together with the impeller. Alternatively, the proximal motion-cushioning spring extends from a radial bearing that is disposed around the proximal end of the impeller (e.g., proximal bushing 64 of the impeller), such that motion-cushioning spring remains rotationally stationary as the impeller rotates, and the impeller is configured to rotate with respect to the motion-cushioning spring.

For some applications, the pump head includes both a proximal motion-cushioning spring disposed on a proximal side of the impeller, and a distal motion-cushioning spring disposed on a distal side of the impeller, such that axial movement of the impeller in either the distal or the proximal direction is cushioned by the motion-cushioning springs.

Figure 7A:
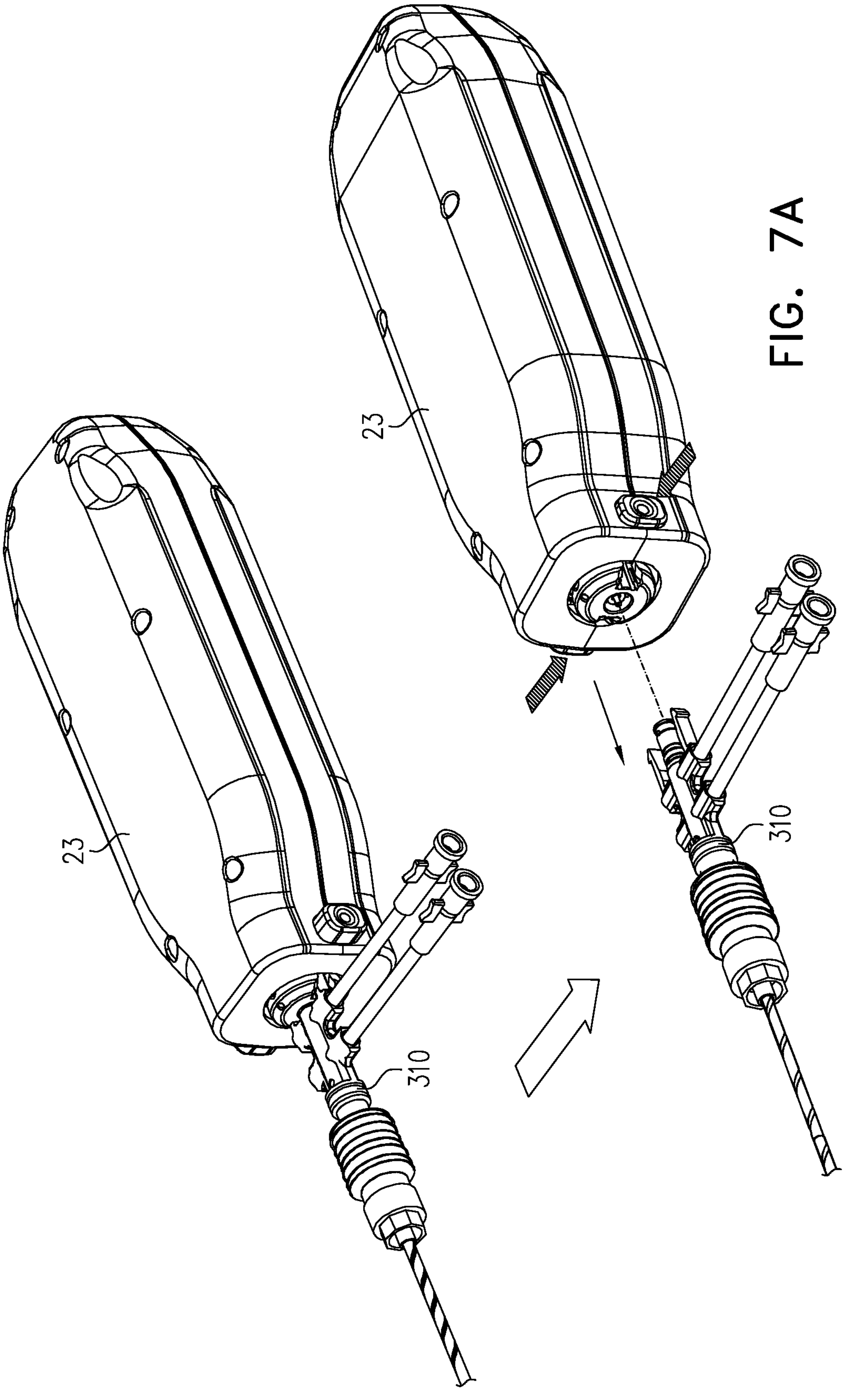
FIGS. 7A, 7B, 7C, and 7D are schematic illustration of a motor unit and/or a driven-magnet unit of a ventricular assist device, in accordance with some applications of the present invention.
Figure 7B:
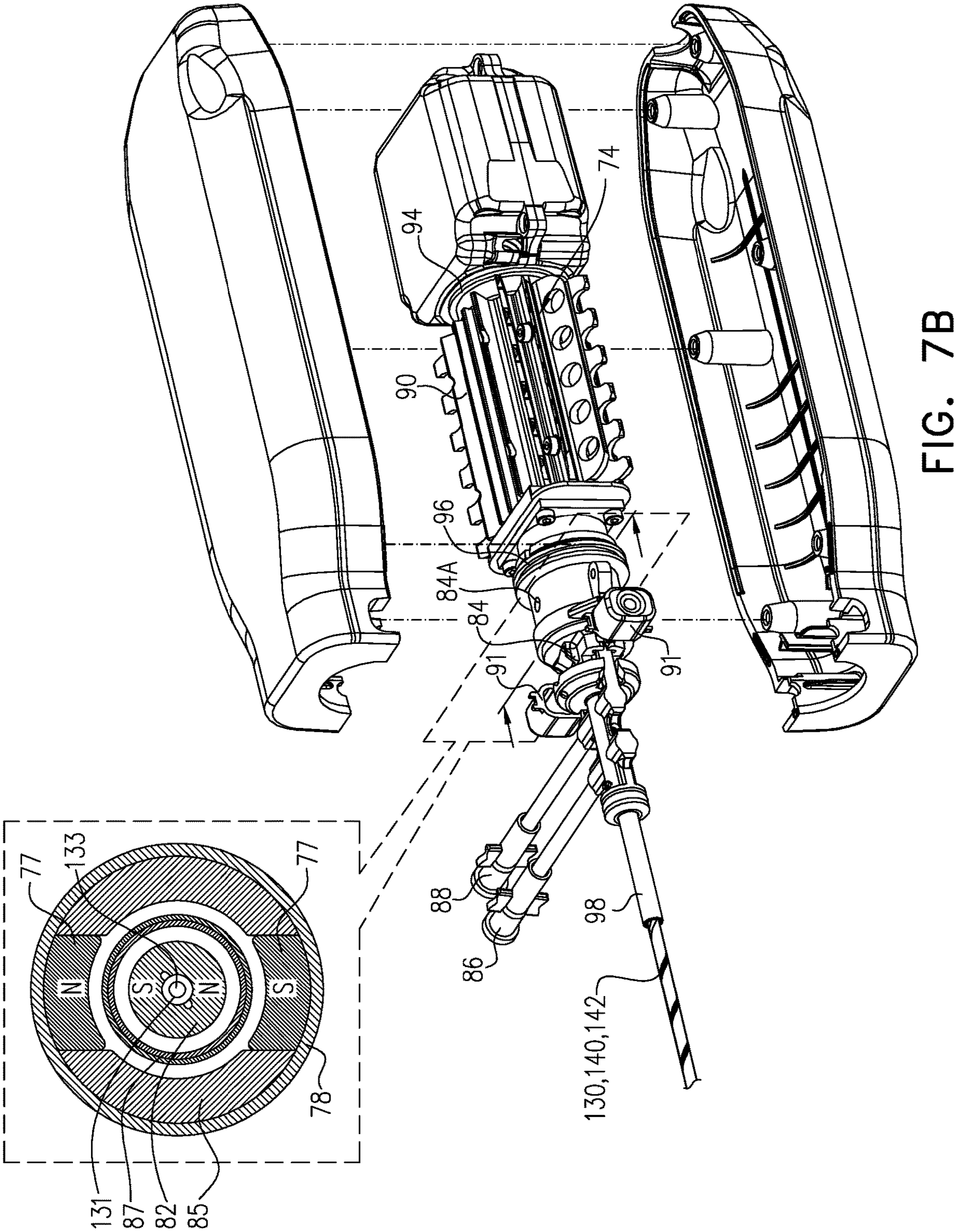
Figure 7C:
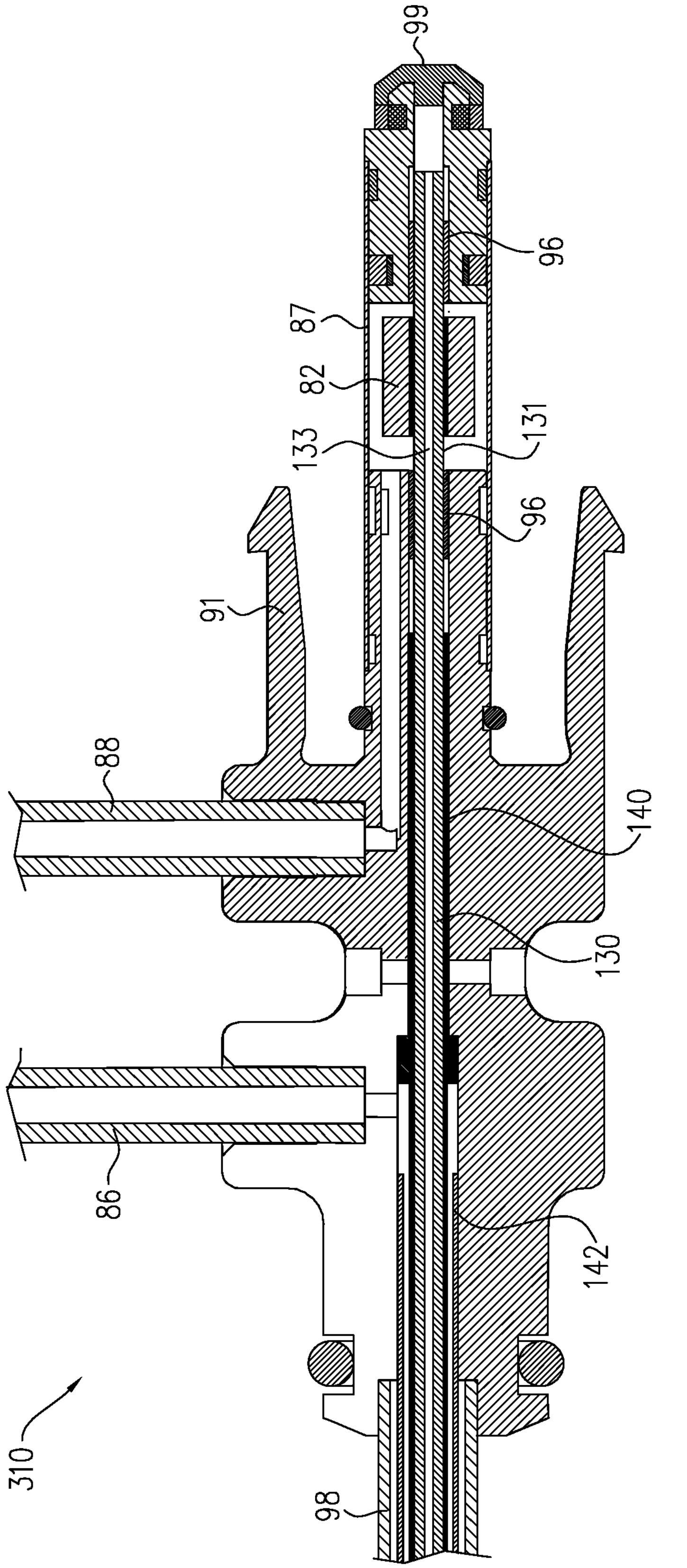
Figure 7D:
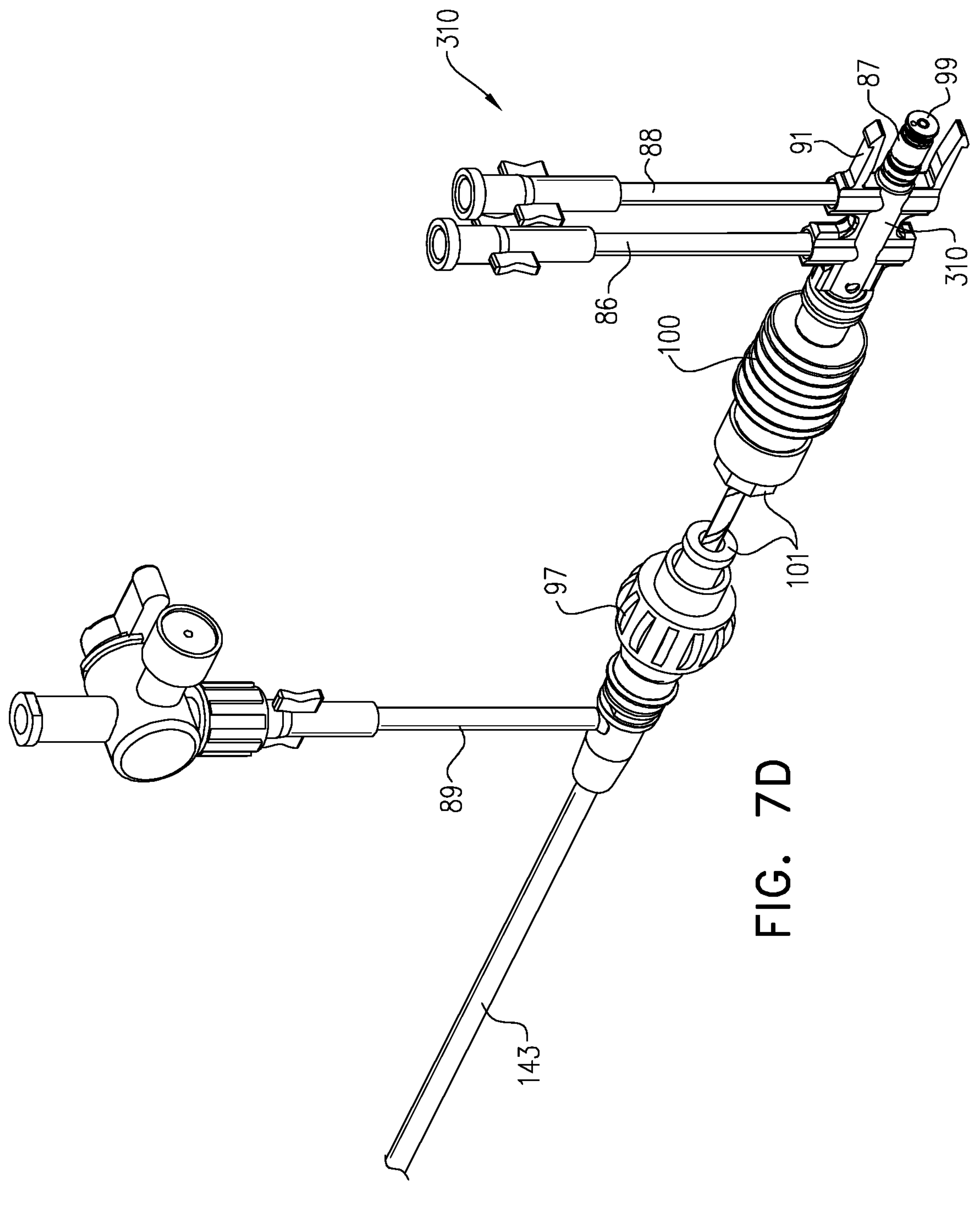

Reference is now made to FIGS. 7A-D, which are schematic illustrations of motor unit 23 and/or a driven-magnet unit 310 of ventricular assist device 20, in accordance with some applications of the present invention. FIG. 7A shows an oblique view of the motor unit and the driven-magnet unit, FIG. 7B shows an exploded view of the motor unit and the driven-magnet unit, FIG. 7C shows a cross-sectional view of the driven-magnet unit, and FIG. 7D shows an oblique view of the driven-magnet unit.

Referring to FIG. 7B, typically, motor unit 23 includes a motor 74 that is configured to impart rotational motion to impeller 50, via drive cable 130. For some applications, the motor unit includes ribs 90 that are configured to dissipate heat that is generated by the motor. For some applications, the motor unit includes vibration dampeners 94 and 96 that are configured to dampen vibration of the motor unit that is caused by rotational motion and/or axial back-and-forth motion of components of the ventricular assist device.

Typically, the motor is magnetically coupled to the drive cable. For some applications, the magnetic coupling of the motor to the drive cable is as shown in FIG. 7B. As shown in the cross-sectional frame of FIG. 7B, a set of driving magnets (or "drive magnets") 77 are coupled to the motor via a driving magnet housing 78. For some applications, the driving magnet housing includes a ring (as shown), and the driving magnets are adhered to an inner surface of the ring. For some applications, a spacer 85 is adhered to the inner surface of the driving magnet housing, between the two driving magnets, as shown. A driven magnet 82 is disposed between the driving magnets such that there is axial overlap between the driving magnets and the driven magnet. The driven magnet is coupled to a pin 131, which extends to beyond the distal end of driven magnet 82, where the pin is coupled to the proximal end of drive cable 130, as shown in FIG. 7C. For example, the driven magnet may be cylindrical and define a hole therethrough, and pin 131 may be adhered to an inner surface of the driven magnet that defines the hole. For some applications, the driven magnet is cylindrical, and the magnet includes a North pole and a South pole, which are divided from each other along the length of the cylinder, as shown. For some applications, the driven magnet is housed inside a cylindrical housing 87. Typically, pin 131 defines a lumen 133, which comprises a portion of a continuous lumen that extends through the ventricular assist device, as described in further detail hereinbelow.

It is noted that in the application shown in FIG. 7B, the driving magnets are disposed outside the driven magnet. However, the scope of the present application includes reversing the configurations of the driving magnets and the driven magnet, mutatis mutandis. For example, the proximal end of the drive cable may be coupled to two or more driven magnets, which are disposed around a driving magnet, such that there is axial overlap between the driven magnets and the driving magnet.

Typically, driven magnet 82 and pin 131 are held in axially fixed positions within motor unit 23. For some applications, driven-magnet unit 310 includes snap-fit prongs 91 (shown in FIG. 7C), via which the magnetic-coupling unit is reversibly coupled to motor unit 23. In addition, magnetic forces between the driving magnets and the driven magnet typically hold the driven magnet in a relatively fixed axial position.

Referring now to FIG. 7C, for some applications, pin 131 is disposed within radial bearings 96, which support the pin as the pin rotates. Typically, at its distal end, the pin is coupled to the proximal end of drive cable 130 (e.g., using coupling techniques described hereinbelow with reference to FIGS. 14A-H). Thus, the proximal end of the drive cable is typically held in an axially fixed position by the pin. Typically, drive cable 130 extends from pin 131 to axial shaft 92 (which is disposed within pump-head portion 27) and thereby at least partially fixes the axial position of the axial shaft, and in turn impeller 50. (Alternatively, as described above, the distal end of drive cable 130 may function as an axial shaft.) For some applications, the drive cable is somewhat stretchable. For example, the drive cable may be made of coiled wires that are stretchable. For some applications, the device does not include a thrust bearing in the pump-head portion or in the vicinity thereof. For such applications, the drive cable typically allows the axial shaft (and in turn the impeller) to assume a range of axial positions (by the drive cable becoming more or less stretched), but limits the axial motion of the axial shaft and the impeller to being within a certain range of motion (by virtue of the proximal end of the drive cable being held in an axially fixed position, and the stretchability of the drive cable being limited).

Still referring to FIG. 7C, typically, the drive cable rotates within a first outer tube 140, which functions as a drive-cable-bearing tube, and which extends from driven-magnet unit 310 (which is disposed outside the subject's body) to pump-head portion 27 (e.g., to proximal bearing housing 116H of the pump-head portion). For some applications, the first outer tube is disposed within a second outer tube 142, which also extends from driven-magnet unit 310 (which is disposed outside the subject's body) to pump-head portion 27 (e.g., to proximal bearing housing 116H of the pump-head portion).

Referring again to FIG. 7B, it is noted that, typically, motor 74 is mechanically coupled to, and configured to rotate, driving magnets 77. Driven magnet 82 axially overlaps driving magnets 77 such that, as the motor rotates the driving magnets, the driven magnet rotates. Drive cable 130 is coupled to driven magnet 82 (e.g., via pin 131) such that, as the driven magnet rotates, the impeller pumps blood of the subject within the body of the subject while the axial position of the impeller, and hence of the driven magnet, varies with the cardiac cycle of the subject.

For some applications, ventricular assist device 20 includes a magnetic sensor 84 configured to detect changes in the magnetic field caused by the variation in the axial position of the driven magnet. For example, sensor 84 may include a magnetometer (e.g., a Hall sensor) that is disposed within motor unit 23, as shown in FIG. 7B. (In some cases, sensor 84 is referred to herein as magnetometer 84.)

Figure 7E:
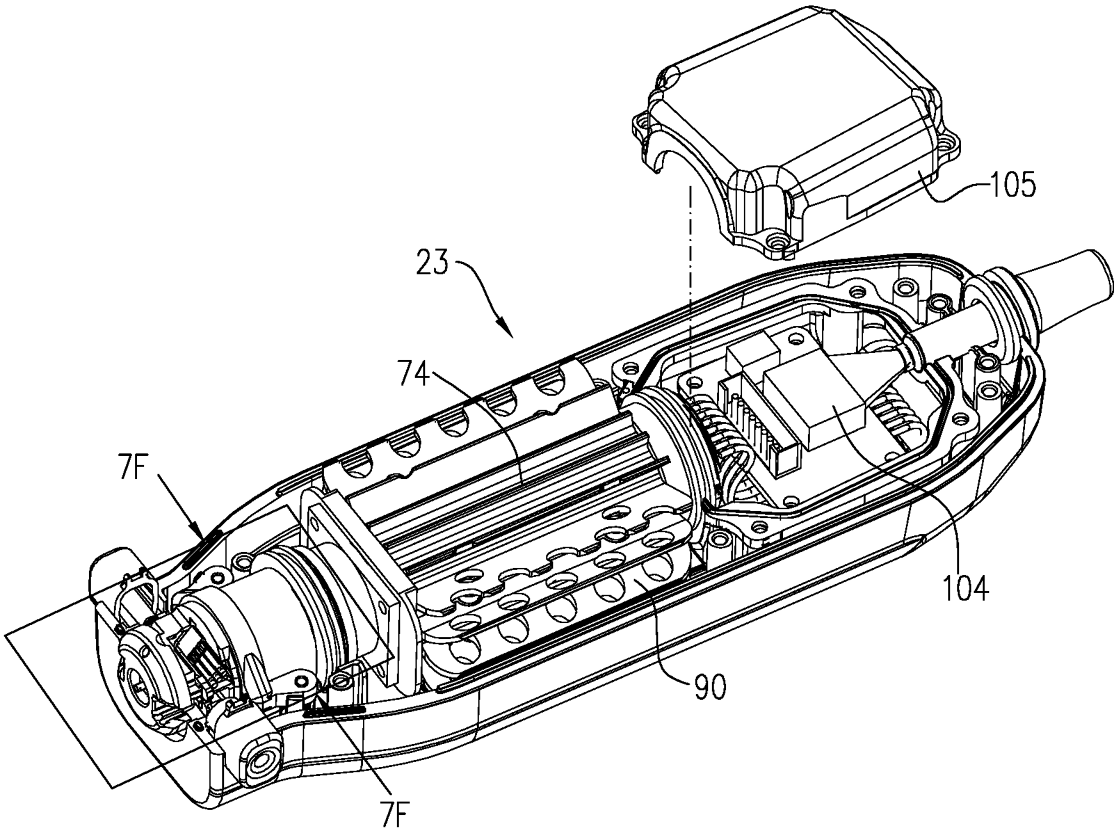
FIG. 7E is a schematic illustration of a motor unit, in accordance with some applications of the present invention.
Figure 7F:
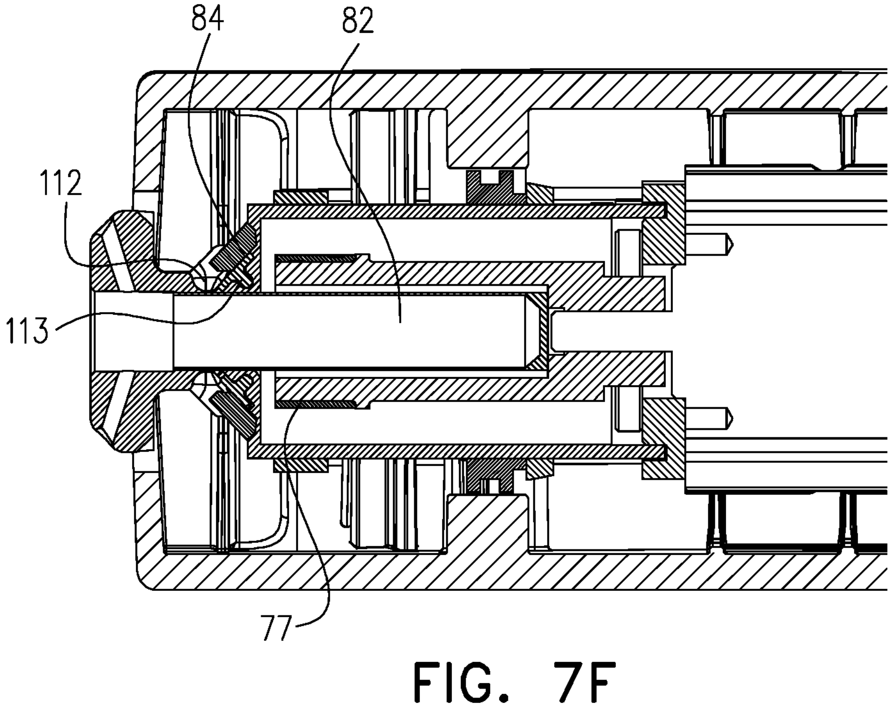
FIG. 7F shows a cross-sectional view of a portion of a motor unit, in accordance with some embodiments of the present invention.

Reference is now made to FIG. 7E, which is a schematic illustration of motor unit 23, in accordance with some applications of the present invention. Reference is also made to FIG. 7F, which shows a cross-sectional view of a portion of motor unit 23, in accordance with some embodiments of the present invention.

For some applications, a printed circuit board 104 is disposed inside a protective container 105. For some applications, magnetometer 84 is housed inside a magnetometer housing 112 that orients the magnetometer toward the interface between drive magnets 77 and driven magnet 82, such as to facilitate the detection of changes in magnetic flux density and/or magnetic phase by the magnetometer. For some applications, the magnetometer is disposed behind a metallic element 113 that is shaped to act as a passive magnetic lens, by directing the changes in magnetic flux and magnetic phase that are generated at the interface between the drive magnet and the driven magnet toward the magnetometer.

Referring now to FIG. 7D, typically the ventricular assist device is delivered to the subject's ventricle via delivery catheter 143. For some applications, the proximal end of the delivery catheter is sealingly coupled to driven-magnet unit 310 via a toric joint mechanism 101. Typically, a sterile sleeve 100 extends proximally from the toric joint mechanism, thereby allowing relative motion between the driven-magnet unit and the proximal end of the delivery catheter, while maintaining sterility. For some applications, a fixation unit 97 is configured to reversibly fix the position of the driven-magnet unit relative to the proximal end of the delivery catheter. For example, once the pump-head portion has been positioned within the patient's ventricle, the fixation unit may be used to fix the position of the driven-magnet unit relative to the proximal end of the delivery catheter. For some applications, the fixation unit is configured such that the position of the driven-magnet unit is fixed relative to the proximal end of the delivery catheter by screwing a portion of the fixation unit. For example, the fixation unit may include a Tuohy Borst adapter.

Referring again to FIG. 7C, for some applications, an additional sheath 98 covers second outer tube 142 within at least a portion of sterile sleeve 100. For some applications, driven magnet housing 87 defines a valve 99 at its proximal end. Typically, guidewire 10 (shown in FIG. 1B) passes out of the proximal end of the ventricular assist device via valve 99. Typically, the ventricular assist device is delivered to the subject's ventricle over the guidewire as described hereinabove. Further typically, once the pump-head portion has been deployed within the ventricle, the guidewire is retracted from the proximal end of the device via valve 99. Subsequently to the removal of the guidewire, the driven-magnet unit is typically coupled to motor unit 23.

As described hereinabove, typically purging system 29 (shown in FIG. 1A) is used with ventricular assist device 20. Typically, driven-magnet unit 310 includes an inlet port 86 and an outlet port 88, for use with the purging system. For some applications, a purging fluid is continuously or periodically pumped into the ventricular assist device via inlet port 86 and out of the ventricular assist device via outlet port 88. For some applications, an additional purging fluid inlet port 89 (FIG. 7D) is provided for pumping fluid between delivery catheter 143 and outer tube 142.

Figure 8A:
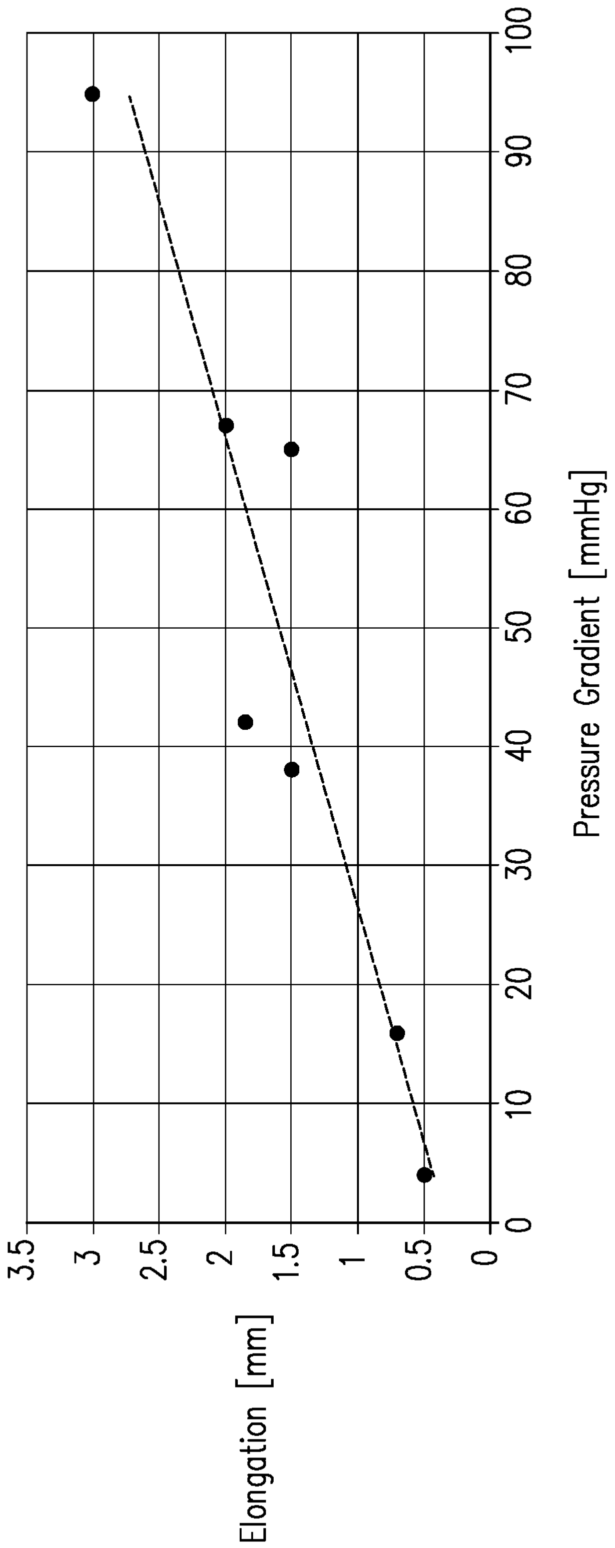
FIG. 8A is a graph indicating variations in the length of a drive cable of a ventricular assist device as a function of a varying pressure gradient against which the impeller of the blood pump pumps, as measured in experiments performed in accordance with some applications of the present invention.

Reference is now made to FIG. 8A, which is a graph indicating variations in the length of a drive cable of a ventricular assist device, as a function of a varying pressure gradient against which the impeller of the ventricular assist device pumps, as measured in experiments. An impeller and a drive cable as described herein were used to pump a glycerin-based solution through chambers, with the chambers set up to replicate the left ventricle and the aorta, and the solution having properties (such as, density and viscosity) similar to those of blood. The pressure gradient against which the impeller was pumping was varied in a pulsatile manner to represent the pulsatility of the pressure gradient against which the impeller typically pumps when it is pumping blood from the left ventricle to the aorta. At the same time, movement of the drive cable was imaged and changes in the length of the drive cable were determined via analysis of the images. The graph shown in FIG. 8A indicates the changes in the length of the drive cable that were measured, as a function of the pressure gradient. As shown in FIG. 8A, as the pressure gradient against which the impeller pumped increased, the drive cable became increasingly elongated. As indicated by the results shown in FIG. 8A and as described hereinabove, it is typically the case that, in response to variations in the pressure against which the impeller is pumping blood (e.g., the pressure difference between the left ventricle and the aorta), the impeller moves back and forth with respect to frame 34. In turn, the movement of the impeller causes drive cable 130 to become more or less elongated.

For some applications, during operation of the ventricular assist device, computer processor 25 of control console 21 (FIG. 1A) is configured to measure an indication of the pressure exerted upon the impeller (which is indicative of the pressure difference between the left ventricle and the aorta), by measuring an indication of tension in drive cable 130, and/or axial motion of the drive cable. For some applications, based upon the measured indication, the computer processor detects events in the subject's cardiac cycle, determines the subject's left-ventricular pressure, and/or determines the subject's cardiac afterload. For some applications, the computer processor controls the rotation of the impeller, and/or the axial back-and-forth motion of the axial shaft in response thereto.

For some applications, it is the case that the axial back-and-forth motion of the impeller gives rise to a measurable back-and-forth motion of the inner, driven magnet 82 relative to the outer, one or more drive magnets 77 (FIG. 7B), since the driven magnet is held in place with respect to the drive magnets via magnetic coupling, rather than rigid mechanical coupling. It is noted that typically the axial motion of the magnet is substantially less than that of the impeller, since the full range of motion of the impeller is not transmitted along the length of the drive cable (the drive cable typically being somewhat stretchable). For some applications, the magnetometer measures variations in the magnetic field that is generated by one of the magnets in order to measure the axial motion of drive cable 130, and, in turn, to determine the pressure against which the impeller is pumping. For example, the inner, driven magnet 82 may be axially longer than the outer, driving magnets 77. Due to the inner magnet being longer than the outer magnets, there are magnetic field lines that emanate from the inner magnet that do not pass to the outer magnets, and the magnetic flux generated by those field lines, as measured by the magnetometer, varies as the drive cable, and, in turn, the inner magnet moves axially. During operation, motor 74 rotates, creating an AC signal in the magnetometer, which typically has a frequency of between 200 Hz and 800 Hz. Typically, as the tension in the drive cable changes due to the subject's cardiac cycle, this gives rise to a low frequency envelope in the signal measured by the magnetometer, the low frequency envelope typically having a frequency of 0.5-2 Hz. For some applications, the computer processor measures the low frequency envelope, and derives the subject's cardiac cycle from the measured envelope.

For some applications, the magnetometer measurements are initially calibrated, such that the change in magnetic flux per unit change in pressure against which the impeller is pumping (i.e., per unit change in the pressure difference between the left ventricle and the aorta, or per unit change in the pressure gradient) is known. It is known that, in most subjects, at systole, the left-ventricular pressure is equal to the aortic pressure. Therefore, for some applications, the subject's aortic pressure is measured, and the subject's left-ventricular pressure at a given time is then calculated by the computer processor, based upon (a) the measured aortic pressure, and (b) the difference between the magnetic flux measured by the magnetometer at that time, and the magnetic flux measured by the magnetometer during systole (when the pressure in the left ventricle is assumed to be equal to that of the aorta). For example, the subject's aortic pressure may be measured by measuring pressure in a channel 224 defined by delivery catheter 143, as described in further detail hereinbelow with reference to FIG. 12A. For some applications, alternative or additional physiological parameters are determined using the above-described technique. For example, events in the subject's cardiac cycle and/or the subject's cardiac afterload may be determined.

For some applications, generally similar techniques to those described in the above paragraph are used, but as an alternative to or in addition to utilizing magnetometer measurements, a different parameter is measured in order to determine left ventricular blood pressure (and/or a different physiological parameter, e.g., events in the subject's cardiac cycle and/or the subject's cardiac afterload) at a given time. For example, it is typically the case that there is a relationship between the amount of power (and/or current) that is required to power the rotation of the impeller at a given rotation rate and the pressure difference that is generated by the impeller. (It is noted that some of the pressure difference that is generated by the impeller is used to overcome the pressure gradient against which the impeller is pumping, and some of the pressure difference that is generated by the impeller is used to actively pump the blood from the left ventricle to the aorta, by generating a positive pressure difference between the left ventricle and the aorta. Moreover, the relationship between the aforementioned components typically varies over the course of the cardiac cycle.) For some applications, calibration measurements are performed, such that the relationship between (a) power (and/or current) consumption by the motor that is required to rotate the impeller at a given rotation rate and (b) the pressure difference that is generated by the impeller, is known. For some applications, the subject's aortic pressure is measured, and the subject's left-ventricular pressure at a given time is then calculated by the computer processor, based upon (a) the measured aortic pressure, (b) the power (and/or current) consumption by the motor that is required to rotate the impeller at a given rotation rate at that time, and (c) the predetermined relationship between power (and/or current) consumption by the motor that is required to rotate the impeller at a given rotation rate and the pressure difference that is generated by the impeller. For some applications, the above-described technique is performed while maintaining the rotation rate of the impeller at a constant rate. Alternatively or additionally, the rotation rate of the impeller is varied, and the variation of the rotation rate of the impeller is accounted for in the above-described calculations. For some applications, alternative or additional physiological parameters are determined using the above-described technique. For example, events in the subject's cardiac cycle and/or the subject's cardiac afterload may be determined.

Typically, tube 24 has a known cross-sectional area (when the tube is in an open state due to blood flow through the tube). For some applications, the flow through tube 24 that is generated by the impeller is determined based on the determined pressure difference that is generated by the impeller, and the known cross-sectional area of the tube. For some applications, such flow calculations incorporate calibration parameters in order to account for factors such as flow resistance that are specific to the ventricular assist device (or type of ventricular assist device) upon which the calculations are performed. For some applications, the ventricular pressure-volume loop is derived, based upon the determined ventricular pressure.

For some applications, the computer processor determines one or more physiological parameters of the subject based upon data that are received via the ventricular assist device. Typically, the following parameters are detected via the ventricular assist device: arterial pressure (AP), electrical current consumption by the motor (I) and revolutions per minute (RPM) of the impeller. For some applications, the left ventricular pressure (LVP), the left ventricular end-diastolic pressure (LVEDP) and/or the pump flow rate are derived.

As described hereinabove, for some applications, the pressure difference between the left ventricle and the aorta (dP) is derived based upon electrical current consumption by the motor (I) and revolutions per minute (RPM) of the impeller. Left ventricular pressure (LVP) is derived by subtracting the pressure difference (dP) from the aortic pressure (AP). Left ventricular end-diastolic pressure (LVEDP) is then derived by analyzing the LVP curve, and pump flow rate is derived by integrating the pressure difference over time (along with empirically determined pumping performance parameters of the device).

For some applications, the dP curve is derived by determining (a) the maximum dP within a given first current time period (e.g., within the last second, within the last 0.5 seconds, or within a different time period that is typically between 0.1 seconds and 2 seconds, i.e., at a first frequency of between 0.5 Hz and 2 Hz), (b) the minimum dP within the given first current time period (e.g., within the last second, within the last 0.5 seconds, or within a different time period that is typically between 0.1 seconds and 2 seconds, i.e., at a first frequency of between 0.5 Hz and 2 Hz), and (c) the real-time value of the dP within a given second current time period (e.g., the current hundredth of second, or within a different time period that is typically between the current fiftieth of a second and the current two-hundredth of a second, i.e., at a second frequency that is typically between 50 Hz and 200 Hz). Typically, the second time period is smaller than the first time period, i.e., the second frequency is greater than the first frequency.

Typically, the value of each of (a), (b), and (c) is derived using a linear model. Further typically, within the first current time period, the real-time values of dP (which are detected at the second frequency) are corrected based upon the maximum dP and the minimum dP (which are detected at the first frequency), such as to generate a corrected dP curve. The LVP curve is then derived from the corrected dP curve. Typically, this results in more accurate values of LVP than if uncorrected real-time values of dP were to be used.

Referring again to FIG. 7B, for some applications, in addition to magnetometer 84, which is configured to measure the magnetic flux density generated by the driven magnet, a second magnetometer 84A (e.g., a second Hall sensor) measures an indication of the magnetic flux density generated by the driving magnet. For some applications, the second magnetometer measures magnetic flux density of the motor, which is indicative of the flux density cycle of the driving magnet, since the motor directly drives the driving magnet to rotate. Typically, as the impeller rotates such as to pump blood, torque is generated upon the impeller. Further typically, the strength of the torque is dependent upon various parameters, such as the flow that is generated by the impeller, the rotational speed of the impeller, and/or the pressure gradient against which the impeller is pumping. For some applications, it is the case that the torque generated upon the impeller gives rise to a measurable torque on the inner, driven magnet 82 relative to the outer, drive magnets 77, since the driven magnet is held in place with respect to the drive magnets via magnetic coupling, rather than rigid mechanical coupling. It is noted that typically the torque generated upon the driven magnet is substantially less than that generated upon the impeller, since the torque that is generated upon the impeller is not transmitted along the length of the drive cable. However, it is typically the case that the torque that is generated upon the impeller is at least partially transmitted to the driven magnet via the drive cable.

The torque that is transmitted to the driven magnet typically gives rise to a phase difference between the signal that is measured by magnetometer 84 (which measures magnetic flux density of the driven magnet) and the signal that is measured by second magnetometer 84A (which measures magnetic flux density of the motor and/or the driving magnet). For some applications, as the torque upon the impeller varies, this gives rise to a variation in the phase difference between the signal that is measured by magnetometer 84 and the signal that is measured by second magnetometer 84A. For some applications, the computer processor detects the variation in the aforementioned phase difference, and determines a physiological parameter of the subject, at least partially in response thereto. For example, at least partially based upon variations in the phase difference, the computer processor may determine the difference between the subject's left-ventricular pressure and the subject's aortic pressure, the subject's left ventricular pressure, an event in the subject's cardiac cycle, the subject's cardiac afterload, and/or a different physiological parameter. For some applications, the technique described in the present paragraph is used as an alternative to the above-described technique for using magnetic flux density measurements and/or power consumption measurements to determine physiological parameters. Alternatively, two or more of these techniques are used in combination with each other. For example, the subject's physiological parameters may be determined based upon a mathematical model that incorporates two or more measurements, and/or one of the techniques may be used to validate estimations of the subject's physiological parameters that are made using another one of the techniques.

Figure 8B:
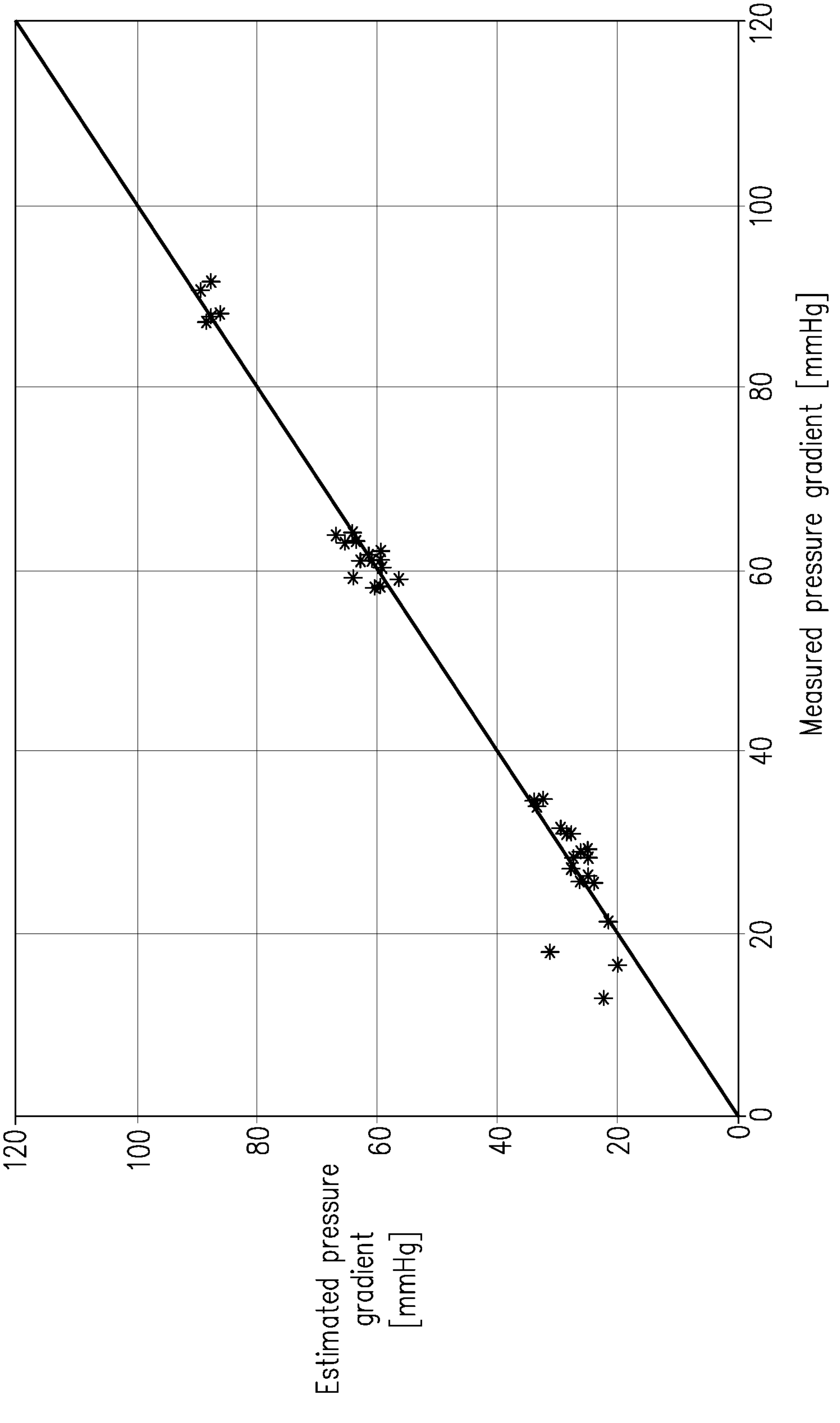
FIGS. 8B and 8C are graphs demonstrating a correlation between a phase difference signal and a pressure gradient against which the impeller of the blood pump pumps, in accordance with some applications of the present invention.
Figure 8C:
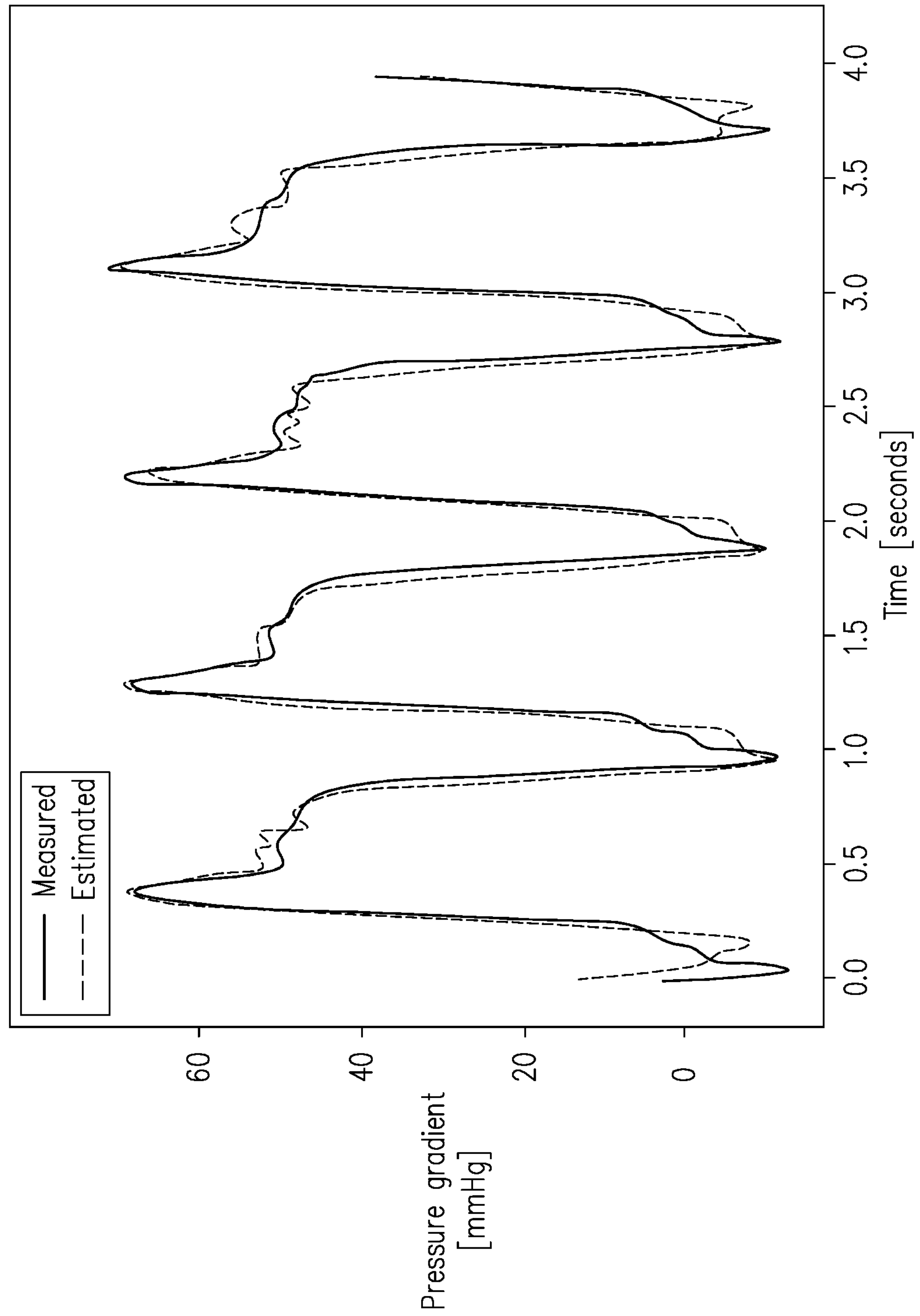

Reference is now made to FIGS. 8B and 8C, which are graphs that demonstrate the correlation between the phase difference signal and the pressure gradient against which impeller 50 pumps, in accordance with some applications of the present invention.

The graph shown in FIG. 8B shows the results of an experiment in which a ventricular assist device as described herein was used to pump blood against respective pressure gradients within a static in-vitro system (i.e., an in-vitro system in which when each measurement was taken, the pressure gradient was constant). A linear regression model was used to estimate the pressure gradient against which the impeller was pumping based upon a combination of the phase difference signal, the magnetic flux amplitude signal, and the current consumed by the motor. The graph shown in FIG. 8B shows the estimated pressure gradient versus the measured pressure gradient. As shown, the linear regression model which incorporates phase difference measurements provides a reliable method for estimating the pressure gradient against which the impeller is pumping.

The graph shown in FIG. 8C shows the results of an experiment in which a ventricular assist device as described herein was used to pump blood against respective pressure gradients within a pulsatile in-vitro system (i.e., an in-vitro system in which the pressure gradient was varied in a pulsatile manner). A space state model was used to estimate the pressure gradient against which the impeller was pumping based upon a combination of the phase difference signal, the magnetic flux amplitude signal, and the current consumed by the motor. The graph shown in FIG. 8C shows the estimated pressure gradient overlaid upon the measured pressure gradient. As shown, a space state model which incorporates phase difference measurements provides a reliable method for estimating the pressure gradient against which the impeller is pumping.

In accordance with the above, and in accordance with some applications of the invention, a magnetic phase difference between the one or more driven magnets and the one or more drive magnets is measured, and a physiological parameter of the subject is determined, at least partially in response thereto. For example, at least partially based upon variations in the phase difference, the computer processor may determine the difference between the subject's left-ventricular pressure and the subject's aortic pressure, the subject's left-ventricular pressure, an event in the subject's cardiac cycle, the subject's cardiac afterload, and/or a different physiological parameter. For some applications, the physiological parameter is determined based upon the phase difference measurements in combination with one or more additional measurements, such as magnetic flux amplitude measurements, power consumed by the motor, and/or current consumed by the motor. Typically, such measurements are combined into a mathematical model, such as a linear regression model, and/or a space state model.

Figure 9A:
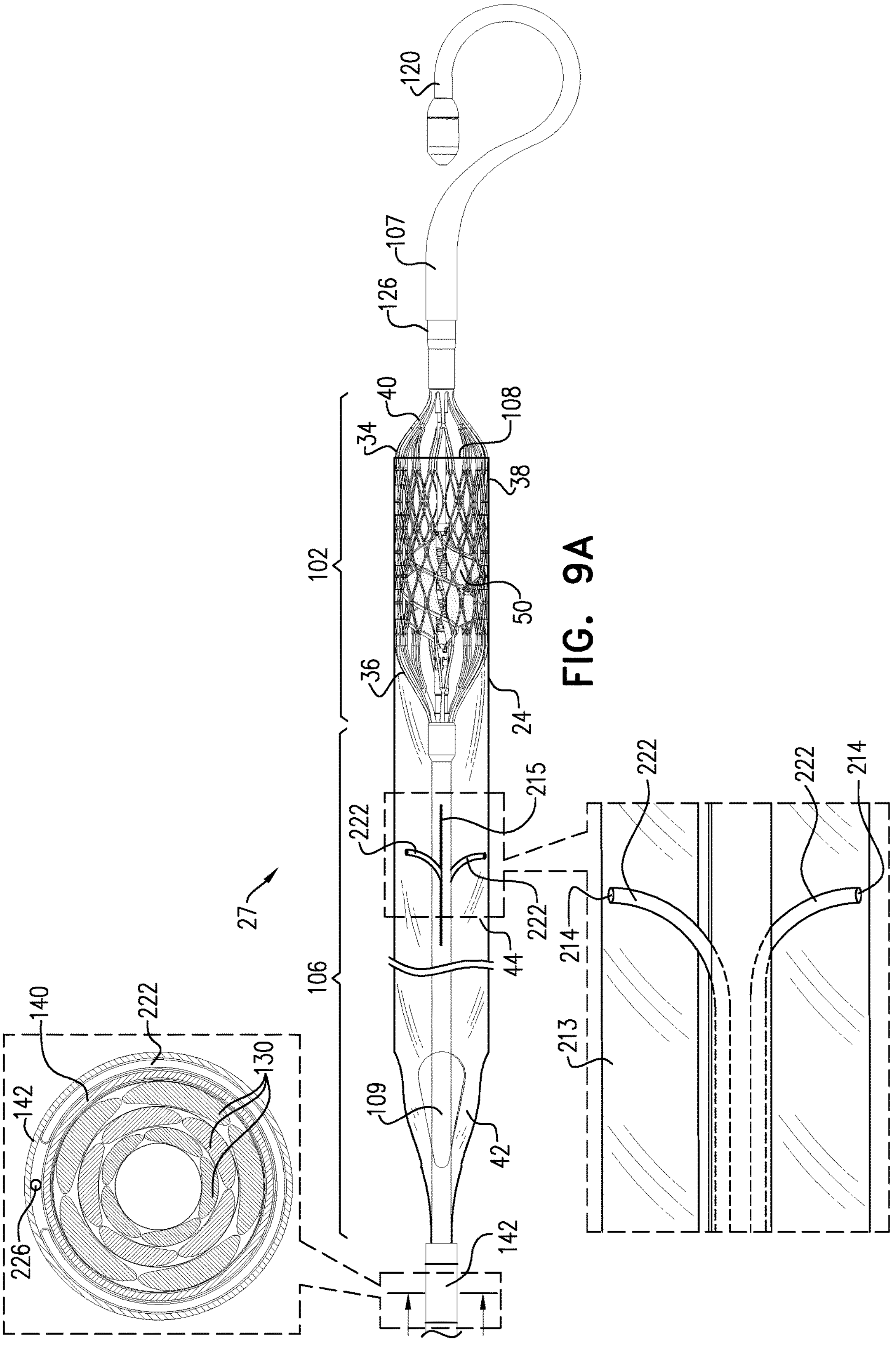
FIGS. 9A and 9B are schematic illustrations of a ventricular assist device that includes one or more blood-pressure-measurement tubes and/or fibers, in accordance with some applications of the present invention.
Figure 9B:
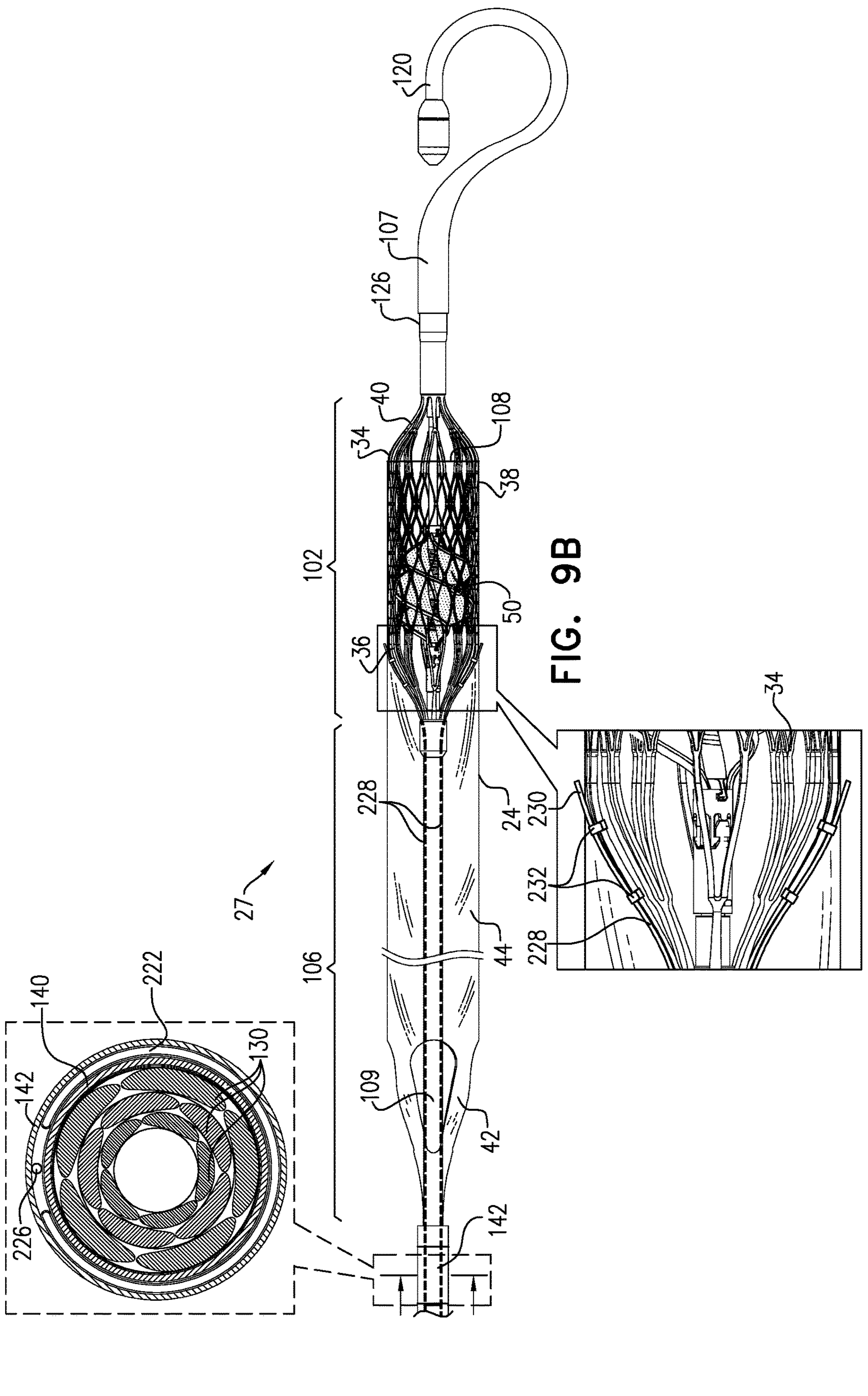

Reference is now made to FIGS. 9A and 9B, which are schematic illustrations of a ventricular assist device that includes one or more blood-pressure-measurement tubes 222 and/or fibers 228, in accordance with some applications of the present invention.

FIG. 9A is a schematic illustration of a ventricular assist device that includes one or more blood-pressure-measurement tubes 222, in accordance with some applications of the present invention. As described hereinabove, typically, the ventricular assist device includes pump-outlet tube 24, which traverses the subject's aortic valve, such that a proximal end of the tube is disposed within the subject's aorta and a distal end of the tube is disposed within the subject's left ventricle. Typically, a blood pump (which typically includes impeller 50) is disposed within the subject's left ventricle within tube 24, and is configured to pump blood through tube 24 from the left ventricle into the subject's aorta. For some applications, ventricular blood-pressure-measurement tube 222 is configured to extend at least to an outer surface 213 of tube 24, such that an opening 214 at the distal end of the blood-pressure-measurement tube is in direct fluid communication with the patient's bloodstream outside tube 24. Typically, opening 214 is configured to be within the subject's left ventricle proximally to the blood pump (e.g., proximally to impeller 50). A pressure sensor 216 (illustrated schematically in FIG. 1A) measures pressure of blood within the ventricular blood-pressure-measurement tube. Typically, by measuring pressure of blood within the left-ventricular blood-pressure-measurement tube, the pressure sensor measures the subject's blood pressure outside tube 24 (i.e., left-ventricular blood pressure). Typically, blood-pressure-measurement tube 222 extends from outside the subject's body to opening 214 at the distal end of tube 222, and pressure sensor 216 is disposed toward a proximal end of tube 222, e.g., outside the subject's body. For some applications, computer processor 25 (FIG. 1A) receives an indication of the measured blood pressure and controls the pumping of blood by the impeller, in response to the measured blood pressure.

For some applications, the ventricular assist device includes two or more such ventricular blood-pressure-measurement tubes 222, e.g., as shown in FIG. 9A. For some applications, based upon the blood pressure as measured within each of the left-ventricular blood-pressure-measurement tubes, computer processor 25 determines whether the opening of one of the two or more ventricular blood-pressure-measurement tubes is occluded. This may occur, for example, due to the opening coming into contact with the wall of the interventricular septum, and/or a different intraventricular portion. Typically, in response to determining that the opening of one of the two or more ventricular blood-pressure-measurement tubes is occluded, the computer processor determines the subject's left-ventricular pressure based upon the blood pressure measured within a different one of the two or more ventricular blood-pressure-measurement tubes.

For some applications, second outer tube 142 defines a groove 215 in a portion of the outer surface of the second outer tube that is configured to be disposed within tube 24. Typically, during insertion of the ventricular assist device into the subject's body, the portion of ventricular blood-pressure-measurement tube 222 that extends from within tube 24 at least to an outer surface of tube 24, is configured to be disposed within the groove, such that the portion of the ventricular blood-pressure-measurement tube does not protrude from the outer surface of the outer tube.

For some applications (not shown), distal portions of blood-pressure-measurement tubes 222 are disposed on the outside of pump-outlet tube 24. For example, blood-pressure-measurement tubes 222 may extend from outer tube 142 to the proximal end of pump-outlet tube 24, and thereafter the blood pressure measurement tubes may be built into the outer surface of tube pump-outlet tube 24, as shown in FIG. 16D of U.S. Pat. No. 10,881,770 to Tuval, which is incorporated herein by reference, for example.

As described hereinabove, for some applications, drive cable 130 extends from a motor outside the subject's body to axial shaft 92 upon which impeller 50 is disposed. Typically, the drive cable is disposed within first outer tube 140 and second outer tube 142, as described hereinabove. For some applications, a proximal portion of blood-pressure-measurement tube 222 comprises a channel between first outer tube 140 and second outer tube 142, as shown in the cross-section of FIG. 9A. In this regard, it is noted that blood-pressure-measurement tube should be understood to refer to a continuous lumen extending from pressure sensor 216 to the outside of pump-outlet tube 24 within the subject's left ventricle, regardless of whether there are changes in the structure of the lumen along the length of the lumen. As described hereinabove, typically purging fluid is also pumped between outer tube 140 and outer tube 142, and for some applications, the purging fluid is pumped via a purging-fluid channel 226. Typically, blood-pressure-measurement tube 222 occupies more of the cross-sectional area defined between first outer tube 140 and second outer tube 142 than purging-fluid channel 226, as shown in FIG. 9A. For example, the ratio of (a) the cross-sectional area defined between first outer tube 140 and second outer tube 142 that is occupied by blood-pressure-measurement tube 222 to (b) the cross-sectional area defined between first outer tube 140 and second outer tube 142 that is occupied by purging-fluid channel 226 is typically more than 3:2, more than 3:1, or more than 5:1. For some applications, pressure-measurement tube 222 occupies a relatively large proportion of the cross-sectional area defined between first outer tube 140 and second outer tube 142, in order for the blood pressure outside of pump-outlet tube 24 within the subject's left ventricle to be conveyed proximally to pressure sensor 216.

Referring to FIG. 9B, for some applications, an optical fiber 228 is configured to extend to at least an outer surface 213 (FIG. 9A) of tube 24, such that the distal end 230 of the optical fiber is directly exposed to the patient's bloodstream outside tube 24. Typically, the optical fiber extends from a proximal end of the fiber that is outside the subject's body (e.g., within motor unit 23) to distal end 230. Further typically, a light source and light detector (not shown) are disposed at the proximal end of the optical fiber and are configured to detect blood pressure at the distal end of the optical fiber by directing light via the optical fiber and detecting reflected light.

Typically, distal end 230 of optical fiber 228 is configured to be within the subject's left ventricle proximal to the blood pump (e.g., proximal to impeller 50). Typically, by measuring pressure of blood at distal end 230 of optical fiber 228, the pressure sensor thereby measures the subject's blood pressure outside tube 24 (i.e., left-ventricular blood pressure). For some applications, computer processor 25 (FIG. 1A) receives an indication of the measured blood pressure and controls the pumping of blood by the impeller, in response to the measured blood pressure.

For some applications, the ventricular assist device includes two or more such optical fibers 228, e.g., as shown in FIG. 9B. For some applications, based upon the blood pressure as measured using each of the optical fibers, computer processor 25 determines whether the distal end of one of the optical fibers is not exposed to the left ventricular bloodstream. This may occur, for example, due to the distal end of one of the optical fibers coming into contact with the wall of the interventricular septum, and/or a different intraventricular portion. Typically, in response to determining that the distal end of the one of the optical fibers is not exposed to the left ventricular bloodstream, the computer processor determines the subject's left-ventricular pressure based upon the blood pressure measured using a different one of the two or more optical fibers 228.

For some applications, along the length of second outer tube 142, the optical fibers are disposed within the second outer tube. Typically, at the distal end of second outer tube, the optical fibers are coupled to proximal conical portion 36 of frame 34, such that the optical fibers extend radially to the outer surface of pump-outlet tube 24. For example, as shown in FIG. 9B, the optical fibers may be sutured or tied to the proximal conical portion of frame 34, using coupling elements 232 (e.g., strings). For some applications (not shown), distal portions of optical fibers 228 are disposed on the outside of pump-outlet tube 24. For example (not shown), optical fibers 228 may extend from second outer tube 142 to the proximal end of pump-outlet tube 24, and thereafter the optical fibers may be coupled to the outer surface of pump-outlet tube 24.

Referring to both blood-pressure measurement tube 222 and optical fiber 228, it is noted that the distal end of the tube or the fiber is typically in direct fluid communication with the left-ventricular bloodstream of the subject at a location that is proximal to the proximal-most portion of blood-inlet opening(s) 108 (e.g., at least 1 cm, or at least 1.5 cm proximal to the proximal-most portion of blood-inlet opening(s) 108). Thus, the distal end of the tube or the fiber is typically exposed to blood that has a pressure that reflects the blood pressure of the left ventricle itself and that is not affected by any pressure variations that are generated in the vicinity of the blood-inlet openings as a result of fluid-flow dynamics generated at the blood-inlet openings.

Referring to both blood-pressure measurement tube 222 and optical fiber 228, for some applications, the tube or the fiber is coupled to the outer surface of second outer tube 142. For some applications, the tube or the fiber terminates within the aorta (e.g., on second outer tube 142 or at the proximal end of pump-outlet tube 24) in order to measure aortic pressure. For some applications, the tube or the fiber terminates at the outside of the pump-outlet tube, in the vicinity of frame 34, and is configured to measure left-ventricular pressure. For some such applications, the computer processor determines whether the frame is properly placed with reference to the aortic valve and the left ventricle based upon the blood pressure that is measured using the tube or the fiber. For some applications, the tube or the fiber terminates at the distal bearing housing 118H or at the distal-tip element 107, and is configured to measure pressure in the vicinity of the blood-inlet openings. For some applications, the tube or the fiber runs along the outside of at least a portion of the pump-outlet tube (e.g. from the proximal end of the pump-outlet tube until the vicinity of frame 34).

For some applications, the tube or the fiber is coupled to the outside of the pump-outlet tube by sandwiching the tube or the fiber between a polymeric membrane and the outer surface of the pump-outlet tube, using a bonding method, such as thermal boding, dipping, or gluing. For some applications, along the entire length of the overlap between the tube or the fiber and the pump-outlet tube, the tube or the fiber is bonded to the outside of the pump-outlet tube (e.g., using the aforementioned method(s)). Alternatively, the tube or the fiber is bonded to the outside of the pump-outlet tube (e.g., using the aforementioned method(s)) only at segmented locations along the length of the overlap between the tube or the fiber and the pump-outlet tube. For some applications, by bonding the tube or the fiber only at the segmented locations, the flexibility of the pump-outlet tube is greater than if the tube or the fiber were bonded to the pump-outlet tube along the entire length of the overlap between the tube or the fiber and the pump-outlet tube. As described above, for some applications, the tube or the fiber is coupled to the outside of the pump-outlet tube by sandwiching the tube or the fiber between a polymeric membrane and the outer surface of the pump-outlet tube. For some applications, the polymeric layer is applied at the segmented locations. For some such applications, a ring-shaped polymeric layer is applied around the full circumference of the pump-outlet tube at each of the segmented locations. Alternatively, as described below with reference to FIG. 31, at each of the segmented locations (or along the entire the entire length of the overlap between the tube or the fiber and the pump-outlet tube) one or more bands are applied only around part of the circumference of the pump-outlet tube. For some applications, the bands are bonded to the pump-outlet tube in such a manner that they cause the pump-outlet tube to assume a desired curvature upon being deployed inside the subject's body. For some applications, the bands are bonded to the pump-outlet tube in such a manner that they cause different regions of the pump-outlet tube to assume respective degrees of curvature and/or or such that they cause the pump-outlet tube to twist, upon blood being pumped through the pump-outlet tube.

Figure 10A:
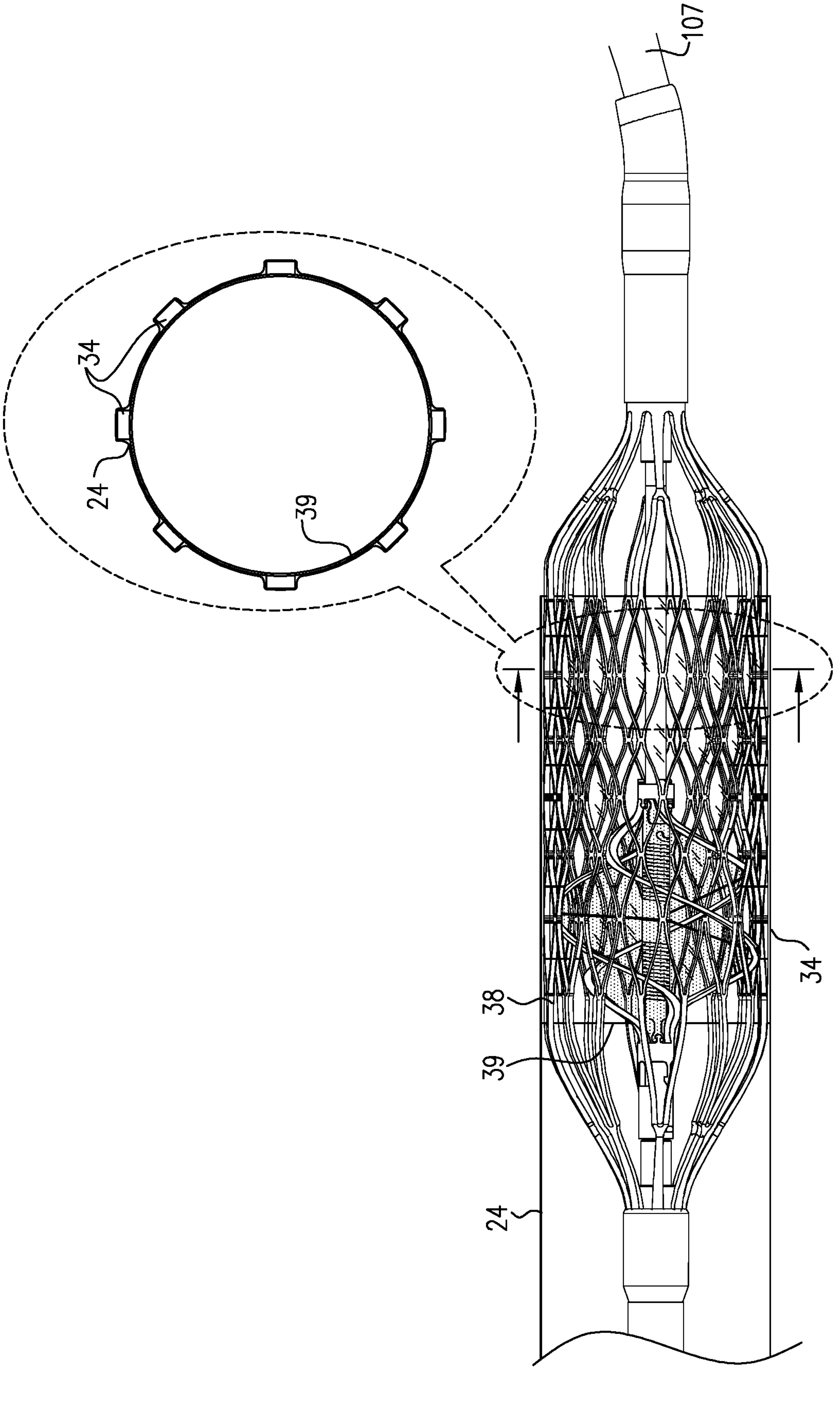
FIGS. 10A, 10B, and 10C are schematic illustrations of a ventricular assist device that includes an inner lining on the inside of the frame that houses the impeller, in accordance with some applications of the present invention.
Figure 10B:
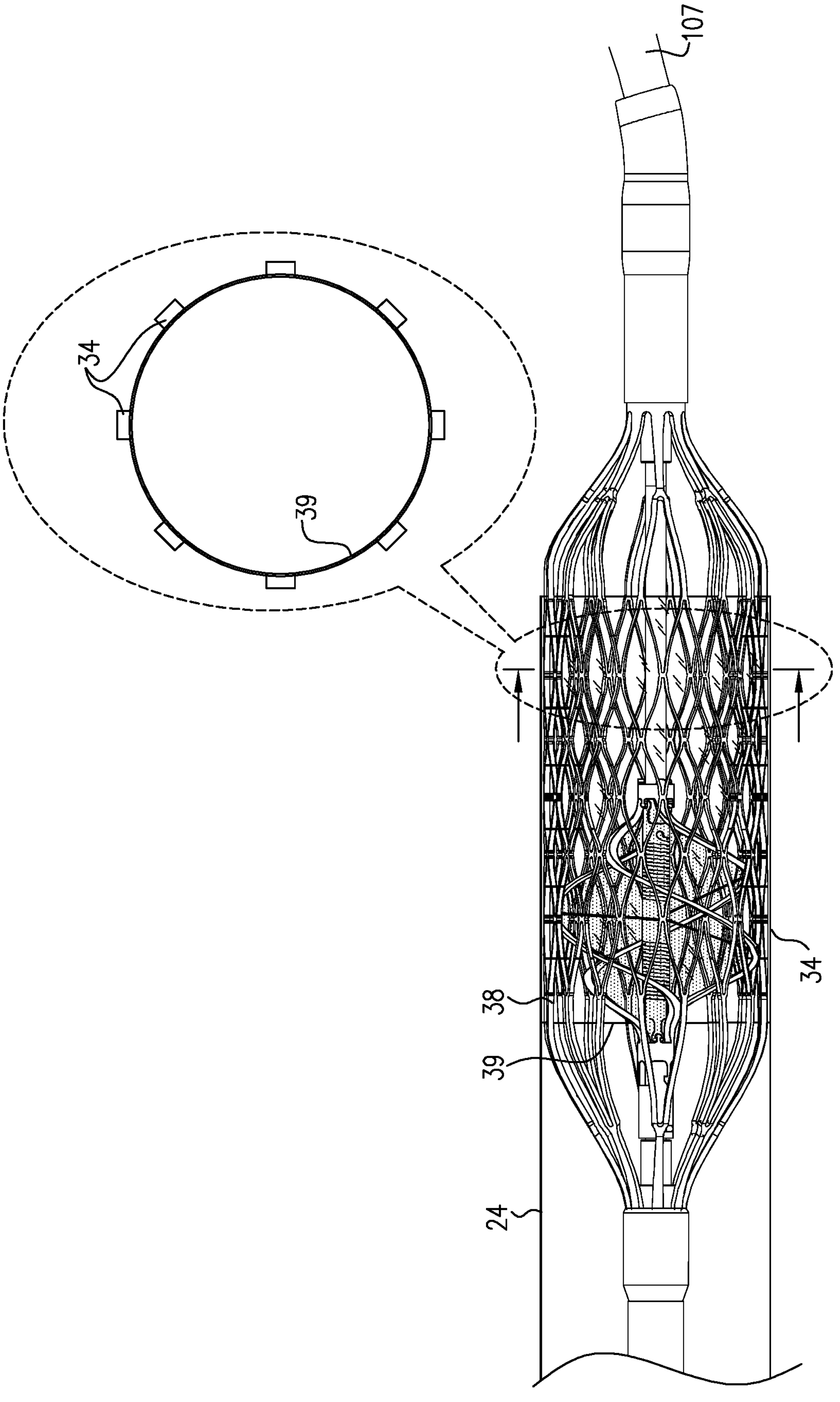

Reference is now made to FIGS. 10A and 10B, which are schematic illustrations of ventricular assist device 20, the device including inner lining 39 that lines the inside of frame 34 that houses impeller 50, in accordance with some applications of the present invention. For some applications, inner lining 39 is disposed inside frame 34, in order to provide a smooth inner surface (e.g., a smooth inner surface having a substantially circular cross-sectional shape) through which blood is pumped by impeller. Typically, by providing a smooth surface, the covering material reduces hemolysis that is caused by the pumping of blood by the impeller, relative to if the blood were pumped between the impeller and struts of frame 34. For some applications, inner lining 39 includes polyurethane, polyester, and/or silicone. Alternatively or additionally, the inner lining includes polyethylene terephthalate (PET) and/or polyether block amide (PEBAX®).

Typically, the inner lining is disposed over the inner surface of at least a portion of central cylindrical portion 38 of frame 34. For some applications, pump-outlet tube 24 also covers central cylindrical portion 38 of frame 34 around the outside of the frame, for example, such that pump-outlet tube 24 and inner lining 39 overlap over at least 50 percent of the length of the inner lining, for example, over the entire length of the cylindrical portion of frame 34, e.g., as shown in FIG. 10A. For some applications, there is only partial overlap between pump-outlet tube 24 and inner lining 39, e.g., as shown in FIG. 10B. For example, pump-outlet tube 24 may overlap with inner lining 39 along less than 50 percent (e.g., along less than 25 percent) of the length of the inner lining. For some such applications, during insertion of ventricular assist device 20 into the subject's body, the impeller is advanced distally within frame 34, such that the impeller is not disposed within the area of overlap between the pump-outlet tube and the inner lining, such that there is no longitudinal location at which the impeller, pump-outlet tube 24, frame 34, and inner lining 39 all overlap with each other. As shown in FIGS. 10A and 10B, for some applications, a single axially-facing blood inlet opening 108 is defined at the distal end of the pump-outlet tube and/or the inner lining. Alternatively, the inner lining is disposed over the inner surface of at least a portion of central cylindrical portion 38 of frame 34, and the pump-outlet tube extends to the distal end of the frame and defines a plurality of lateral blood-inlet openings 108. Such applications are described in further detail hereinbelow with reference to FIGS. 11A-E, for example.

Typically, over the area of overlap between inner lining 39 and pump-outlet tube 24, the inner lining is shaped to form a smooth surface (e.g., in order to reduce hemolysis, as described hereinabove), and pump-outlet tube 24 is shaped to conform with the struts of frame 34 (e.g., as shown in the cross-section in FIG. 10A). Further typically, the inner lining has a substantially circular cross-section (for example, due to the relatively small cell width within the central cylindrical portion of the frame, as described hereinabove with reference to FIG. 2). For some applications, over the area of overlap between inner lining 39 and pump-outlet tube 24, the pump-outlet tube and the inner lining are coupled to each other, e.g., via vacuum, via an adhesive, and/or using a thermoforming procedure.

For some applications, inner lining 39 and pump-outlet tube 24 are made of different materials from each other. For example, the inner lining may be made of polyurethane, and the pump-outlet tube may be made of polyether block amide (PEBAX®). Typically, for such applications, the material from which the inner lining is made has a higher thermoforming temperature than that of the material from which the pump-outlet tube is made. Alternatively, inner lining 39 and pump-outlet tube 24 are made of the same material as each other. For example, both the inner lining and the pump-outlet tube may be made of polyurethane or polyether block amide (PEBAX®).

For some applications, the pump-outlet tube and the inner lining are bonded to each other and/or the frame in the following manner. For some applications, the inner lining is directly bonded to the inner surface of the frame before the pump-outlet tube is bonded to the outside of the frame. It is noted that, by bonding the inner lining directly to the inner surface of the frame (rather than simply bonding the inner lining to the pump-outlet tube and thereby sandwiching the frame between the inner lining to the pump-outlet tube), any air bubbles, folds, and other discontinuities in the smoothness of the surface provided by the inner lining are typically avoided. For some applications, similar techniques to those described hereinabove for enhancing bonding between the elastomeric film and the helical elongate elements of the impeller, are used to enhance bonding between the inner lining and the inner surface of the frame. For some applications, initially, the frame is treated so as to enhance bonding between the inner lining and the inner surface of the frame. For some applications, the treatment of the frame includes applying a plasma treatment to the frame (e.g., to the inner surface of the frame), dipping the frame in a coupling agent that has at least two functional groups that are configured to bond respectively with the frame and with the material form which the inner lining is made (e.g., silane solution), and/or dipping the frame in a solution that contains the material from which the inner lining is made (e.g., polyurethane solution). For some applications, the inner lining is made of an elastomeric material (e.g., polyurethane) and the coupling agent is a silane solution, such as a solution of n-(2-aminoethyl)-3-aminopropyltrimethoxysilane, with the silane containing a first functional group (e.g., (OH)) which is configured to bond with the frame (which is typically made of an alloy, such a nitinol), and the silane containing a second functional group (e.g., (NH2)) which is configured to bond with the elastomeric material.

For some applications, subsequently, a solution that contains the material from which the inner lining is made (e.g., polyurethane solution) is sprayed over the central cylindrical portion of the frame. Once the inner surface of the frame has been treated, the inner lining is bonded to the inner surface of the central cylindrical portion of the frame (e.g., to the inner surface of a central cylindrical portion of the frame). Typically, the inner lining (which is shaped as a tube), is placed over a mandrel, the frame is placed over the inner lining, and pressure is applied by a heat shrinking process. Further typically, the assembly of the inner lining and the frame is heated in an oven.

Subsequently to the inner lining having been bonded to the frame, a portion of pump-outlet tube 24 is placed around the outside of the frame. As described above, for some applications, inner lining 39 and pump-outlet tube 24 are made of different materials from each other. For example, the inner lining may be made of polyurethane, and the pump-outlet tube may be made of polyether block amide (PEBAX®). Typically, for such applications, the material from which the inner lining is made has a higher thermoforming temperature than that of the material from which the pump-outlet tube is made. For some applications, in order to mold pump-outlet tube 24 to conform with the struts of frame 34, without causing the inner lining to deform, the frame is heated to a temperature that is above the thermoforming temperature of pump-outlet tube 24 but below the thermoforming temperature of inner lining 39.

Typically, the frame is heated from inside the frame, using the mandrel. Typically, while the frame is heated to the aforementioned temperature, an outer tube (which is typically made from silicone) applies pressure to pump-outlet tube 24 that causes pump-outlet tube 24 to be pushed radially inwardly, in order to cause the pump-outlet tube to conform with the shapes of the struts of the frame, as shown in the cross-section of FIG. 10A. For some applications, during this stage, the mandrel that is placed inside the inner lining and that heats the inner lining is shorter than the length of the inner lining. The mandrel is typically placed within the inner lining such that margins are left outside of the mandrel at each of the ends of the inner lining. Typically, the inner lining acts as a shield to protect the pump-outlet tube from being overheated and becoming damaged by the heating of the mandrel. Placing the inner lining on the mandrel in the aforementioned manner prevents the mandrel from coming into direct contact with the frame and/or the pump-outlet tube. For some applications, the combination of the frame, the inner lining, and the portion of pump-outlet tube 24 disposed around the frame is subsequently shape set to a desired shape and dimensions using shape setting techniques that are known in the art.

Figure 10C:
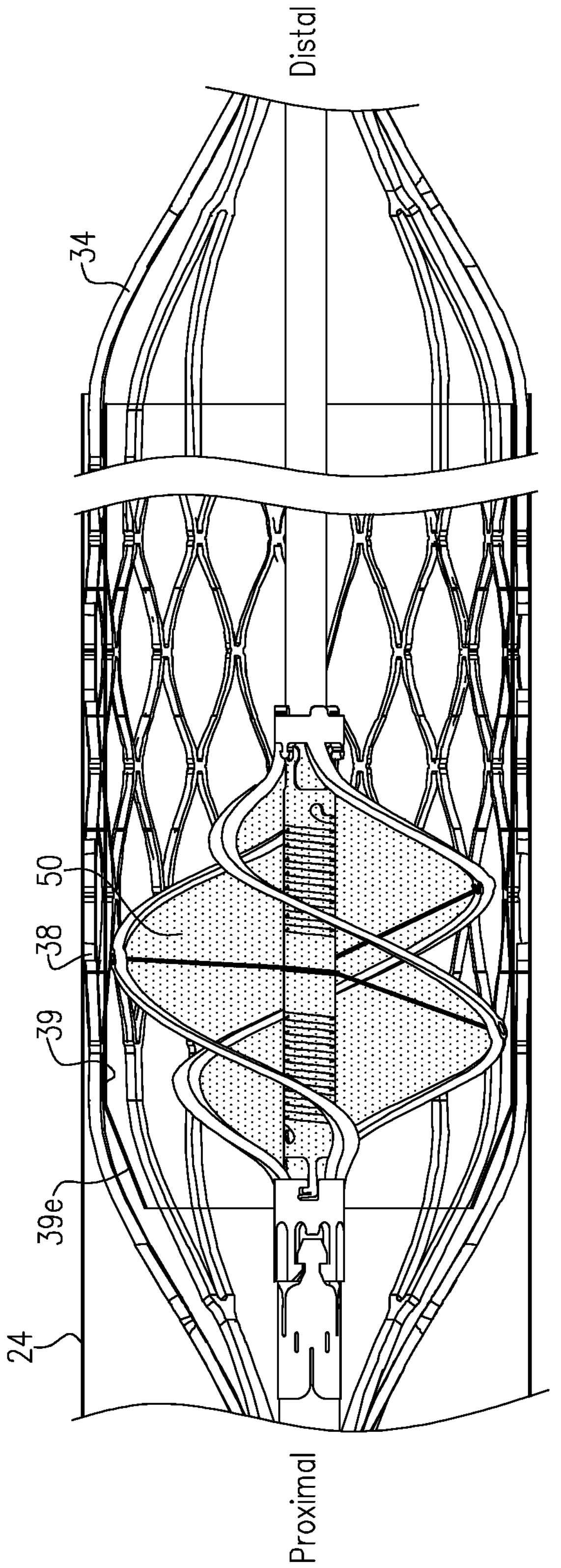

Reference is now made to FIG. 10C, which is a schematic illustration of an inner lining that includes an extension 39*e* extending proximally beyond cylindrical portion 38 of frame 34, in accordance with some applications of the present invention. For some applications, the inner lining extension 39*e* is not coupled to the inner surface of frame 34, but rather, the material that comprises the extension is free to flap within the blood flow that is generated by the impeller. In some cases, the inner lining extension increases the efficiency of pumping of the blood by the impeller, for example by rectifying non-linear flow paths of the blood that are generated by the pumping of the impeller.

Reference is now made to FIGS. 11A-E, which are schematic illustrations of pump-outlet tube 24 or a portion thereof, the pump-outlet tube being configured to define lateral blood-inlet openings 108 at a distal end thereof, in accordance with some applications of the present invention. For some applications, the pump-outlet tube extends substantially until the distal end of distal conical portion 40 of frame 34. For such applications, the pump-outlet tube typically defines a distal conical portion 46 which is distally facing, i.e., facing such that the narrow end of the cone is distal with respect to the wide end of the cone. Typically, the pump-outlet tube includes coupling portion 41 (e.g., a tubular coupling portion, as shown), which extends distally from the pump-outlet tube. As described hereinabove, the coupling portion is coupled to the distal bearing housing in order to anchor the distal end of the pump-outlet tube.

For some applications (not shown), the pump-outlet tube defines two to four lateral blood-inlet openings. Typically, for such applications, each of the blood-inlet openings defines an area of more than 20 square mm (e.g., more than 30 square mm), and/or less than 60 square mm (e.g., less than 50 square mm), e.g., 20-60 square mm, or 30-50 square mm. Alternatively or additionally, the outlet tube defines a greater number of smaller blood-inlet openings 108, e.g., more than 10 blood-inlet openings, more than 50 blood-inlet openings, more than 100 blood-inlet openings, or more than 150 blood-inlet openings, e.g., 50-100 blood-inlet openings, 100-150 blood-inlet openings, or 150-200 blood-inlet openings. For some applications, the blood-inlet openings are sized such as (a) to allow blood to flow from the subject's left ventricle into the tube and (b) to block structures from the subject's left ventricle from entering into the frame. Typically, for such applications, the distal conical portion 46 of pump-outlet tube 24 is configured to reduce a risk of structures from the left ventricle (such as chordae tendincae, trabeculae carneae, and/or papillary muscles) entering into frame 34 and potentially being damaged by the impeller and/or the axial shaft, and/or causing damage to the left ventricular assist device. Therefore, for some applications, the blood-inlet openings are shaped such that, in at least one direction, the widths (or spans) of the openings are less than 1 mm, e.g., 0.1-1 mm, or 0.3-0.8 mm. By defining such a small width (or span), it is typically the case that structures from the left ventricle (such as chordae tendincae, trabeculae carneae, and/or papillary muscles) are blocked from entering into frame 34. For some such applications, each of the blood-inlet openings defines an area of more than 0.05 square mm (e.g., more than 0.1 square mm), and/or less than 3 square mm (e.g., less than 1 square mm), e.g., 0.05-3 square mm, or 0.1-1 square mm. Alternatively, each of the blood-inlet openings defines an area of more than 0.1 square mm (e.g., more than 0.3 square mm), and/or less than 5 square mm (e.g., less than 1 square mm), e.g., 0.1-5 square mm, or 0.3-1 square mm.

Typically, the portion of the pump-outlet tube that defines the blood-inlet openings has a porosity of more than 40 percent, e.g., more than 50 percent, or more than 60 percent (where porosity is defined as the percentage of the area of this portion that is porous to blood flow). Thus, on the one hand, the blood-inlet openings are relatively small (in order to prevent structures of the left ventricular from entering the frame), but on the other hand, the porosity of the portion of the pump-outlet tube that defines the blood-inlet openings is relatively high, such as to allow sufficient blood flow into the pump-outlet tube.

Figure 11A:
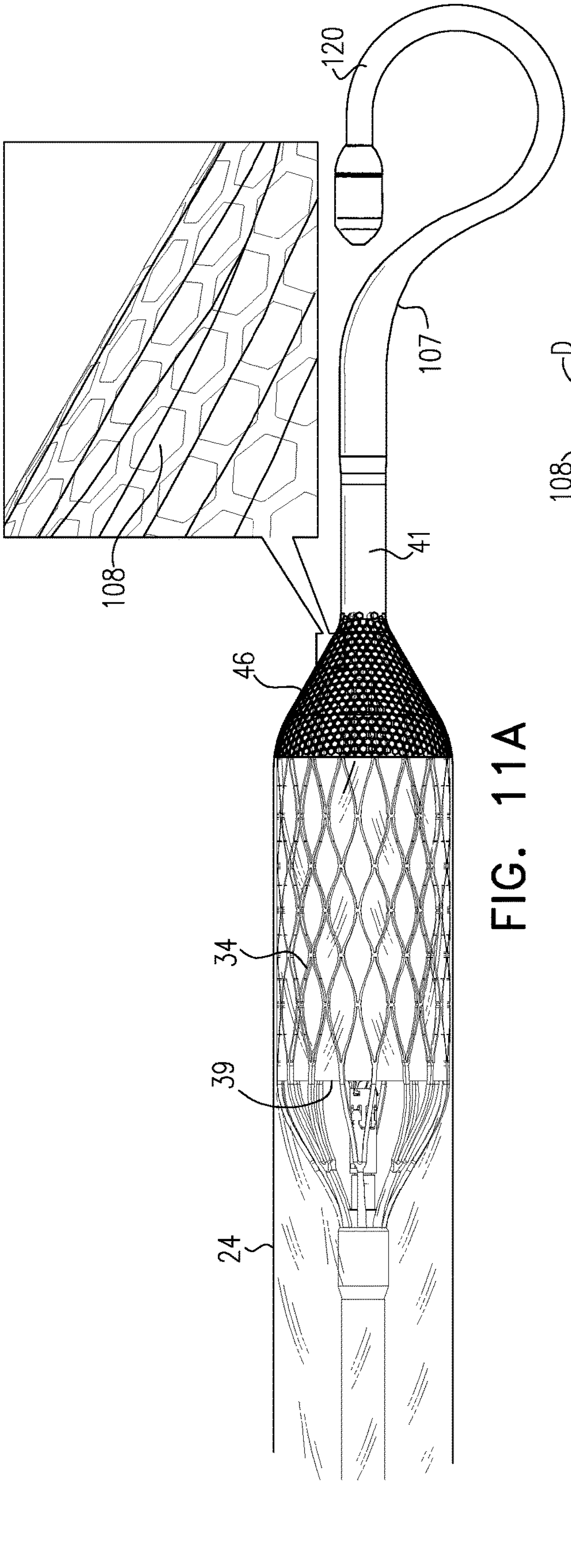
FIGS. 11A, 11B, 11C, 11D, and 11E are schematic illustrations of a pump-outlet tube that defines blood-inlet openings at a distal end thereof, in accordance with some applications of the present invention.
Figure 11B:
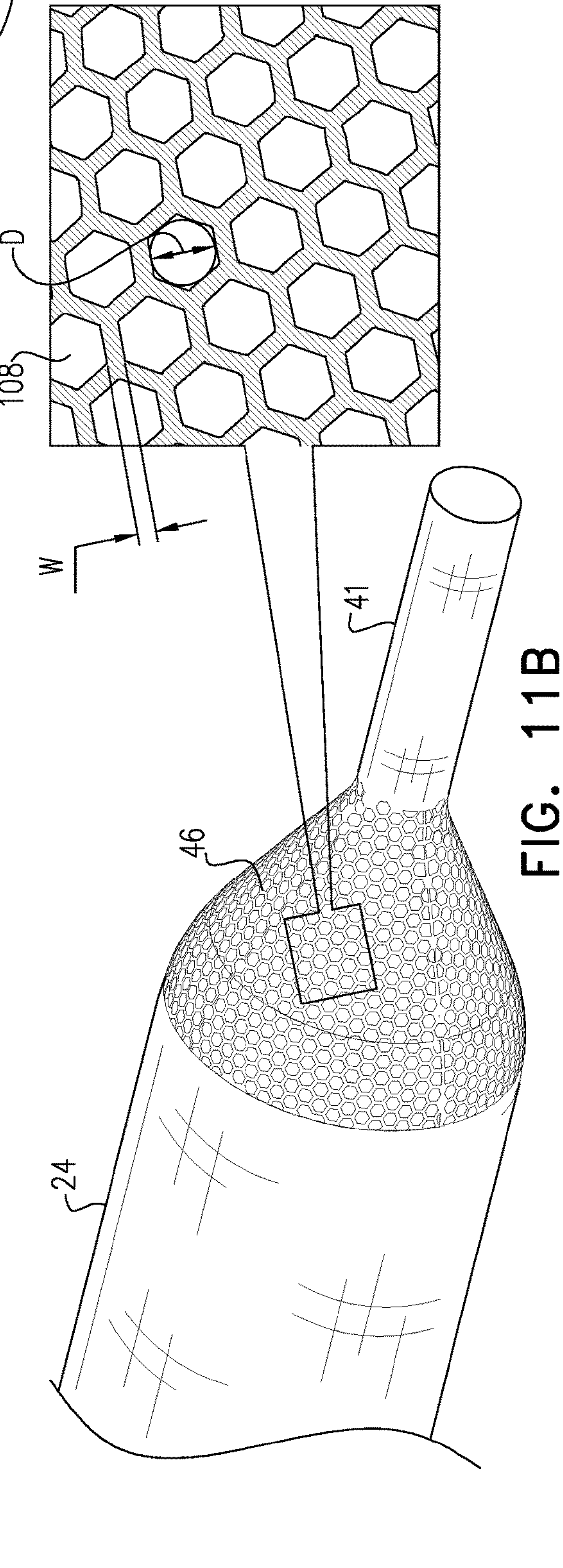
Figure 11C:
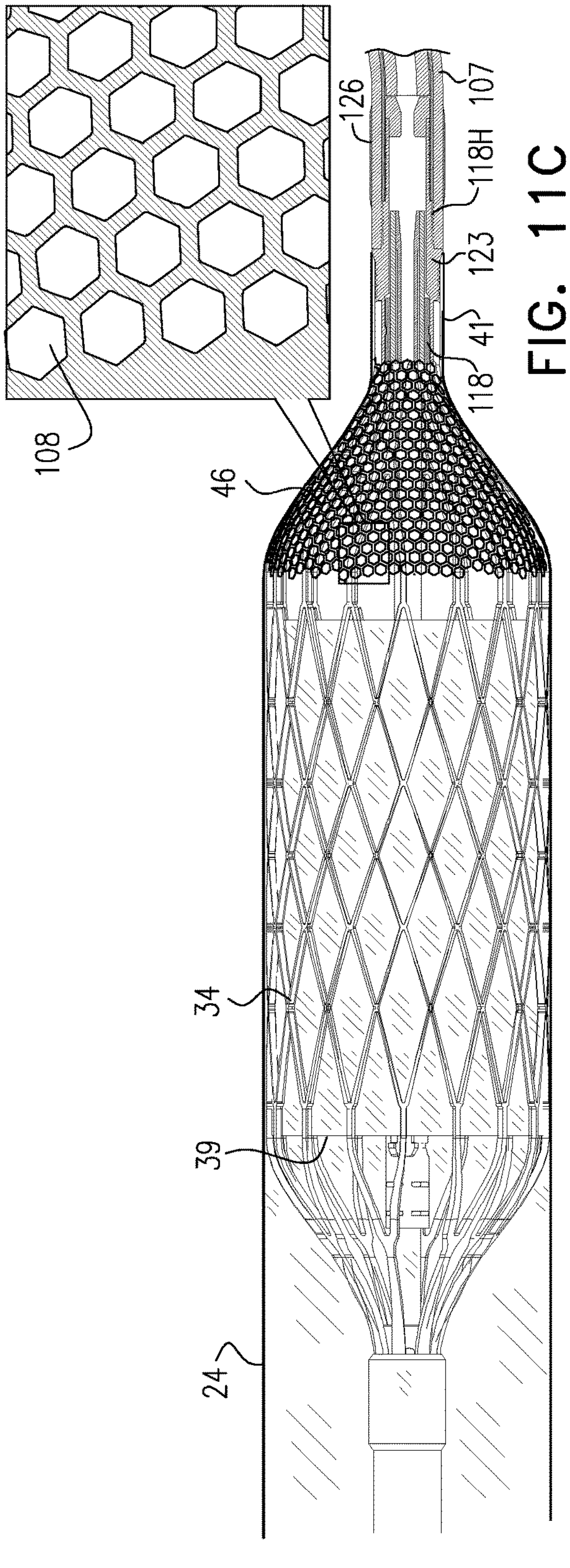

For some applications, each of the blood-inlet openings has a circular or a polygonal shape. For some applications, each of the blood-inlet openings has a hexagonal shape, as shown in FIGS. 11A-E. Typically, using openings having a hexagonal shape allows the portion of the pump-outlet tube that defines the blood-inlet openings to have a relatively high porosity (e.g., as described hereinabove), while providing the portion of the pump-outlet tube that defines the blood-inlet openings with sufficient material between the blood-inlet openings to prevent tearing and/or stretching of the material. As shown in FIG. 11B, for some applications, a width W of gaps between adjacent hexagonal (or other polygonal) holes is more than 0.01 mm (e.g., more than 0.04 mm), and/or less than 0.1 mm (e.g., less than 0.08 mm), for example, 0.01-0.1 mm, or 0.04-0.08 mm. For some applications, the distance D between opposing sides of each of the hexagons (or other types of polygons) is more than 0.2 mm (e.g., more than 0.4 mm) and/or less than 0.8 mm (e.g., less than 0.6 mm), e.g., 0.2-0.8 mm, or 0.4-0.6 mm. As indicated in FIG. 11B, typically each of the polygons encloses a circle (such that any structure that cannot pass through such a circle would be unable to pass through the polygon). Typically, the diameter of the circle enclosed by the polygon is the equivalent of distance D, e.g., more than 0.2 mm (e.g., more than 0.4 mm) and/or less than 0.8 mm (e.g., less than 0.6 mm), e.g., 0.2-0.8 mm, or 0.4-0.6 mm.

Figure 11D:
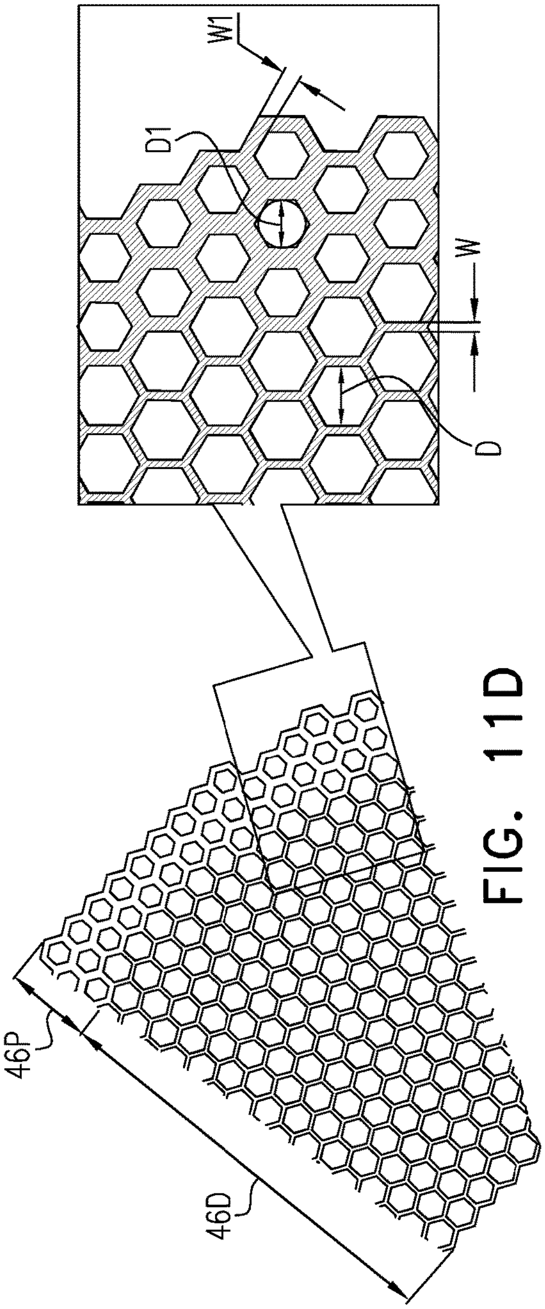

FIG. 11D shows a segment of distal conical portion 46 of pump-outlet tube 24, in accordance with some applications of the present invention. In the view shown in FIG. 11D, the segment is laid out flat for illustrative purposes. As shown in FIG. 11D, for some applications, within a proximal region 46P of distal conical portion 46 of pump-outlet tube 24, the widths W1 of the gaps between the hexagonal (or other type of polygonal) holes are larger than widths W of the gaps between the hexagonal (or other type of polygonal) holes within a distal region 46D of distal conical portion 46 of the pump-outlet tube. For some applications, the ratio of the widths of gaps between adjacent blood-inlet openings with the proximal region of the distal portion of the pump-outlet tube to the widths of gaps between adjacent blood-inlet openings within the distal region of the distal portion of the pump-outlet tube is greater than 3:2, e.g., between 3:2 and 5:2. Typically, for such applications, within proximal region 46P of distal conical portion 46 of pump-outlet tube 24, a distance D1 between opposing sides of each of the hexagons (or other type of polygons) is smaller than distance D between opposing sides of each of the hexagons (or other type of polygons) within distal region 46D of distal conical portion 46 of the pump-outlet tube. (As described hereinabove, typically, distances D and D1 also represent the diameter of a circle that is enclosed by the respectively sized polygons.) For some applications, the ratio of the diameter of a circle enclosed by each of the blood-inlet openings with the distal region of the distal portion of the pump-outlet tube to a diameter of a circle enclosed by each of the blood-inlet openings with the proximal region of the distal portion of the pump-outlet tube is greater than 7:6, e.g., between 7:6 and 4:3. Further typically, the distal conical portion of pump-outlet tube 24 has a higher porosity within distal region 46D than within proximal region 46P of the distal conical portion 46 of the pump-outlet tube. For example, the ratio of the porosity within distal region 46D to the porosity within proximal region 46P is more than 4:3, or more than 3:2. For some applications, the proximal region extends along a length of more than 0.5 mm, and/or less than 2 mm (e.g., less than 1.5 mm), for example, between 0.5 and 2 mm or 0.5-1.5 mm. For some applications, the total length of the distal conical portion is more than 6 mm and/or or less than 12 mm (e.g., less than 10 mm), for example, 6-12 mm, or 6-10 mm.

As described hereinabove with reference to FIGS. 10A-B, typically, the pump-outlet tube is coupled to frame 34 via heating. For some applications, within the proximal region 46P of distal conical portion 46 of pump-outlet tube 24, the gaps between the blood-inlet holes are wider and/or the blood-inlet holes are smaller than within distal region 46D, and/or the porosity is lower than within distal region 46D, in order to prevent and/or reduce damage (e.g., tearing, thinning, and/or stretching) that may be caused to the material that defines the blood-inlet holes during the above-described heating process. For some applications, as a result of the above-described heating process being applied, any difference between the sizes of the gaps between the blood-inlet holes and/or the sizes of the blood-inlet holes themselves and/or porosity between distal region 46D and proximal region 46P is reduced or even removed.

Typically, width W of the gaps between the hexagonal (or other type of polygonal) holes and distance D between opposing sides of each of the hexagons (or other type of polygons) within distal region 46D of distal conical portion 46 of the pump-outlet tube are as described hereinabove. For some applications, width W1 of gaps between adjacent hexagonal (or other polygonal) holes within proximal region 46P of distal conical portion 46 of pump-outlet tube 24 is more than 0.05 mm (e.g., more than 0.07 mm), and/or less than 0.2 mm (e.g., less than 0.15 mm), for example, 0.05-0.2 mm, or 0.07-0.15 mm. For some applications, distance D1 between opposing sides of each of the hexagons (or other types of polygons) within proximal region 46P of distal conical portion 46 of pump-outlet tube 24 is more than 0.1 mm (e.g., more than 0.3 mm) and/or less than 0.6 mm (e.g., less than 0.5 mm), e.g., 0.1-0.6 mm, or 0.3-0.5 mm.

The scope of the present disclosure includes having non-uniformly sized and/or shaped lateral blood-inlet openings (e.g., circular, rectangular, polygonal, and/or hexagonal lateral blood-inlet openings), disposed in any arrangement along the distal conical portion 46 of the pump-outlet tube. Similarly, the scope of the present disclosure includes a distal conical portion 46 of the pump-outlet tube that defines lateral blood-inlet openings being arranged such that the distal conical portion has a non-uniform porosity, with the porosity varying over different regions of the distal conical portion. For some applications, the shapes and/or sizes of the lateral blood-inlet openings, and/or the porosity of the distal conical portion, is varied such as to account for varying blood flow dynamics at different regions of the distal conical portion. Alternatively or additionally, the shapes and/or sizes of the lateral blood-inlet openings, and/or the porosity of the distal conical portion, is varied such as to account for changes in the shape of the distal conical portion along its length.

For some applications, along distal conical portion 46 of pump-outlet tube 24, the thickness of the polymeric material from which the pump-outlet tube is made is greater than the thickness in other regions of the pump-outlet tube (e.g., within the central cylindrical portion and/or the proximal conical portion of the pump-outlet tube). For some such applications, the tube is manufactured in this manner in order to prevent tearing of the tube within the distal conical portion 46, which defines blood-inlet openings 108, and may (in some cases) be at greater risk of tearing than other portions of the pump-outlet tube.

Figure 11E:
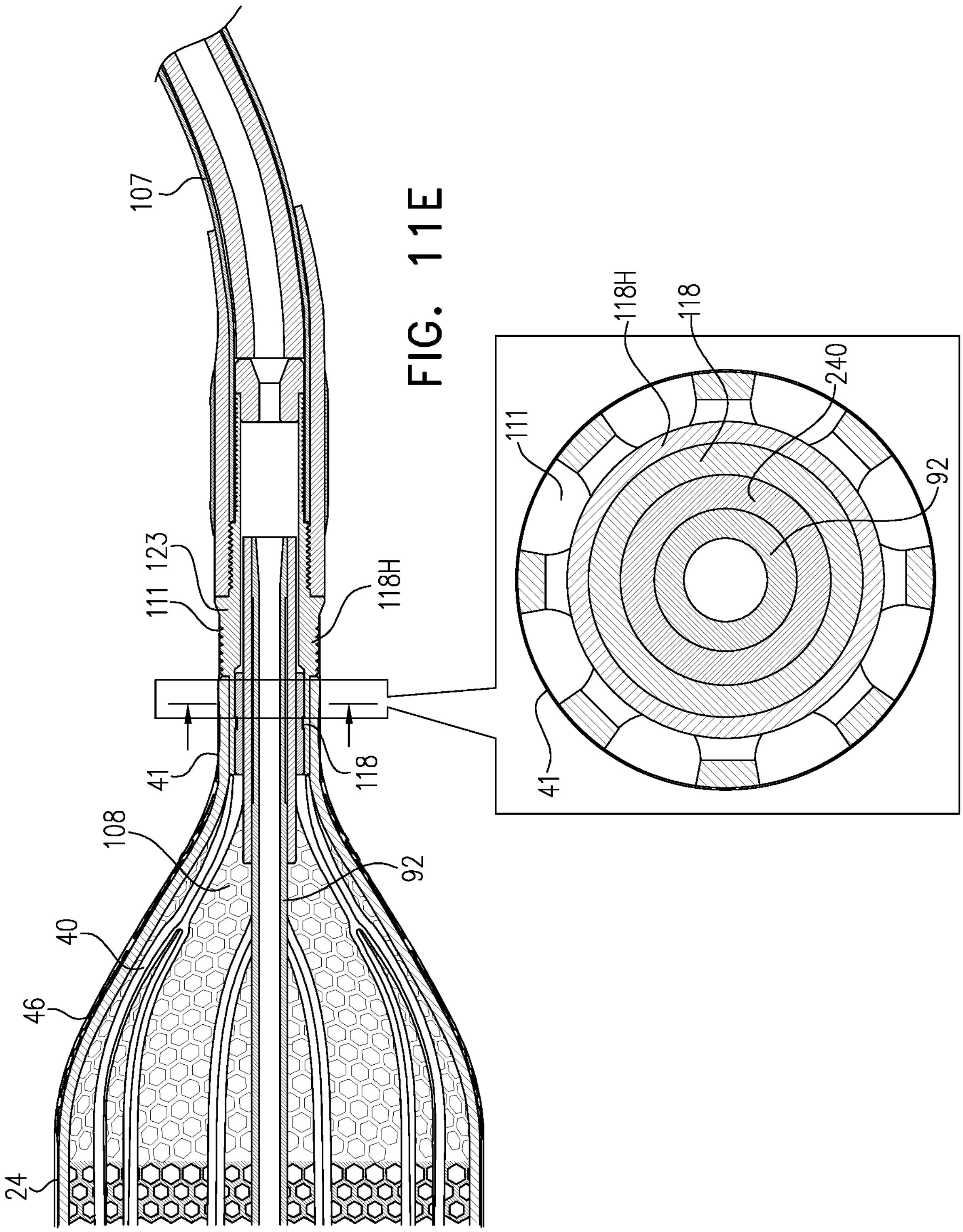

Reference is now made to FIG. 11E, which is an enlarged schematic illustration of the interface between the distal end of pump-outlet tube 24 and distal-tip element 107. Typically, the pump-outlet tube includes a coupling portion 41 (e.g., a tubular coupling portion, as shown), which extends distally from the pump-outlet tube. As described hereinabove, the coupling portion is coupled to distal bearing housing 118H in order to anchor the distal end of the pump-outlet tube. Also as described hereinabove, typically, the pump-outlet tube is coupled to the outside of the central cylindrical portion of the frame. For some applications, distal conical portion 46 of the pump-outlet tube is not itself bonded to distal conical portion 40 of the frame. Rather, distal conical portion 46 of the pump-outlet tube is held in place with respect to distal conical portion 40 of the frame, by virtue of coupling portion 41 being coupled to distal bearing housing 118H and the pump-outlet tube being coupled to the outside of the central cylindrical portion of the frame. Alternatively, the distal conical portion 46 of the pump-outlet tube is directly coupled to distal conical portion 40 of the frame (e.g., via heat shrinking).

As described hereinabove, for some applications, coupling portion 41 is coupled to the outer surface of portion 123 of distal bearing housing 118H. For some applications, coupling portion 41 defines a hole 111 (e.g., toward the distal end of the coupling portion), as shown in FIG. 11E. For some applications, an adhesive is applied between coupling portion 41 and the outer surface of portion 123 of distal bearing housing 118H, via the hole. For some applications, the outer surface of portion 123 of distal bearing housing 118H is threaded. Typically, the threaded outer surface allows the adhesive to gradually and uniformly spread between coupling portion 41 and the outer surface of portion 123 of distal bearing housing 118H. Further typically, the coupling portion is transparent, such that the spread of the adhesive is visible through the coupling portion. Therefore, for some applications, once the adhesive has sufficiently spread between coupling portion 41 and the outer surface of portion 123 of distal bearing housing 118H (e.g., once the outer surface of portion 123 has been covered with the adhesive), application of the adhesive is terminated.

Figure 12A:
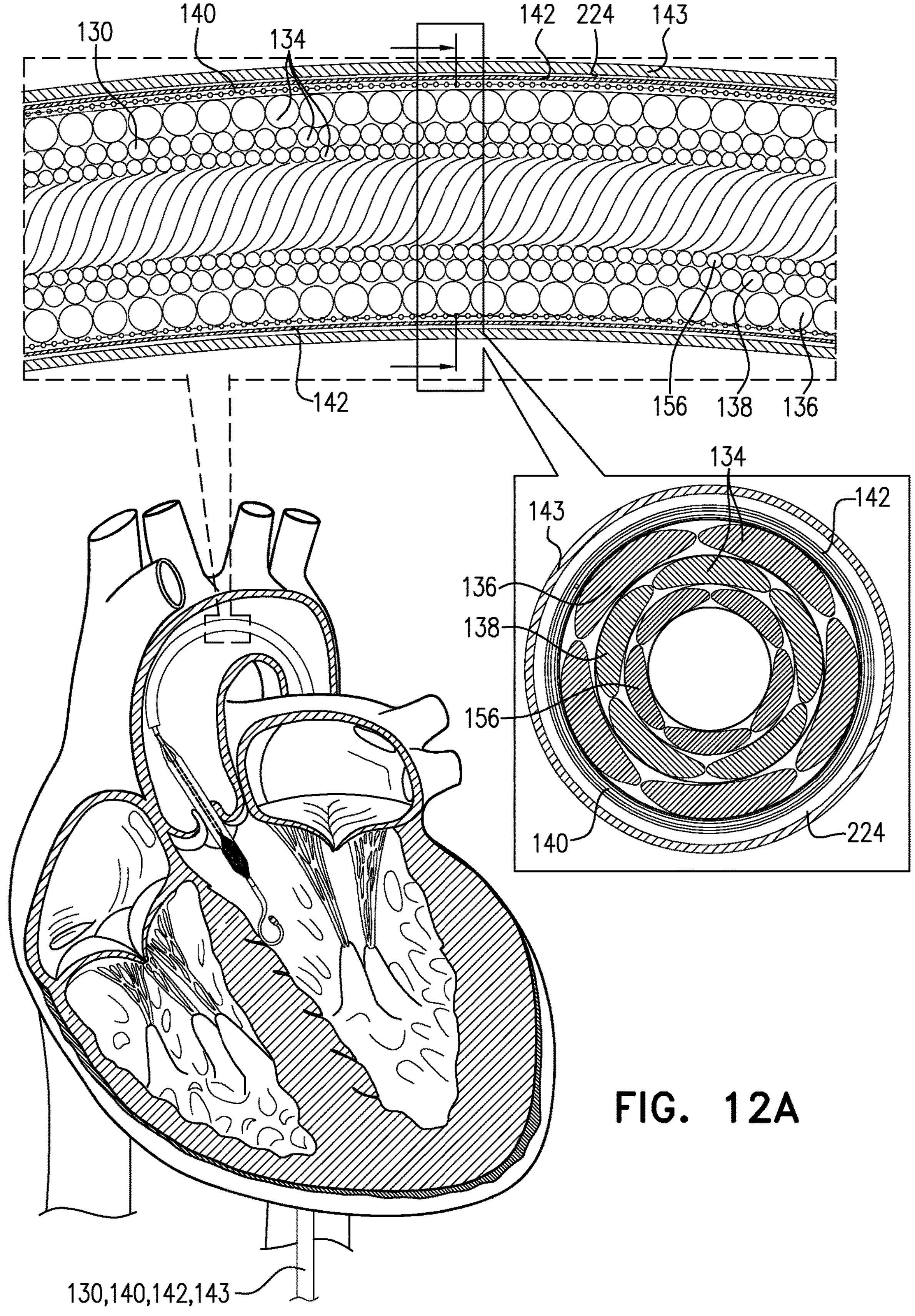
FIGS. 12A, 12B, and 12C are schematic illustrations of a drive cable of a ventricular assist device, in accordance with some applications of the present invention.
Figure 12B:
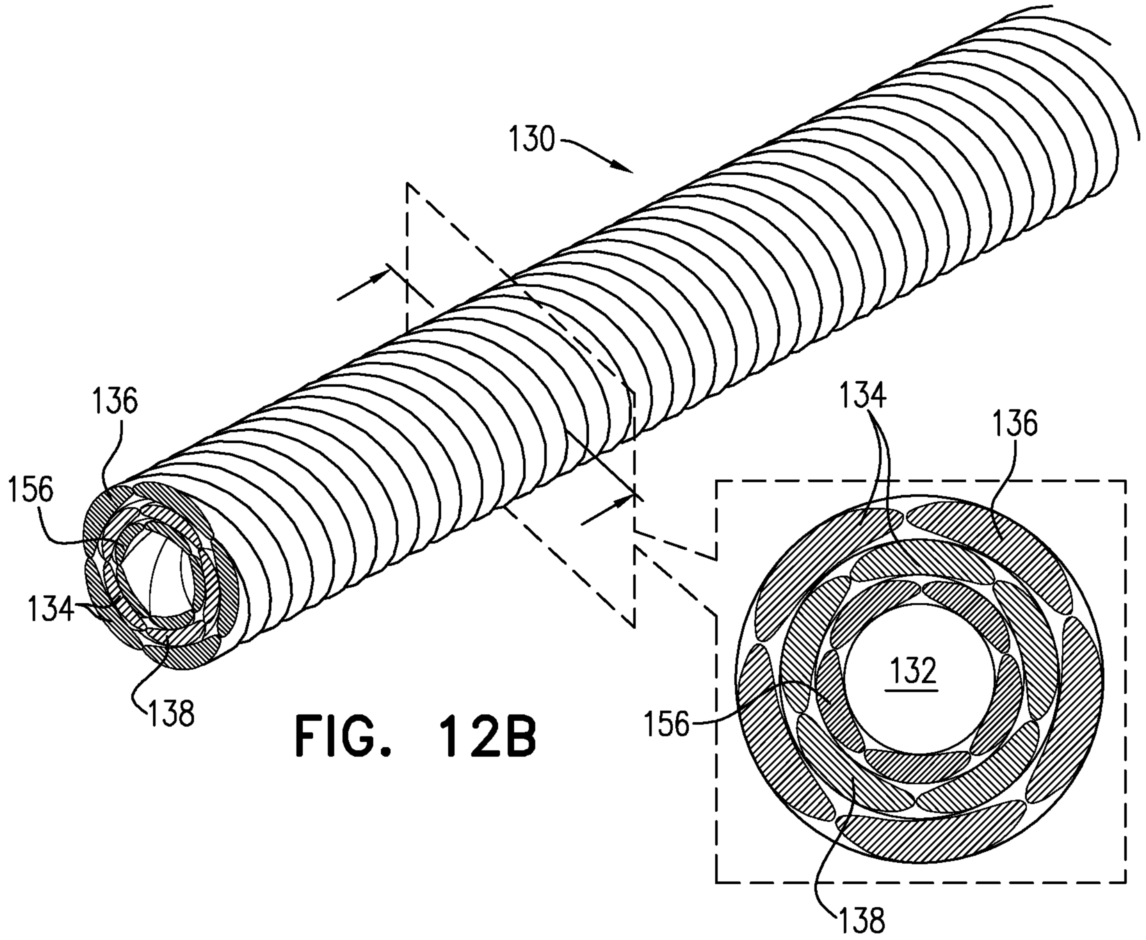
Figure 12C:
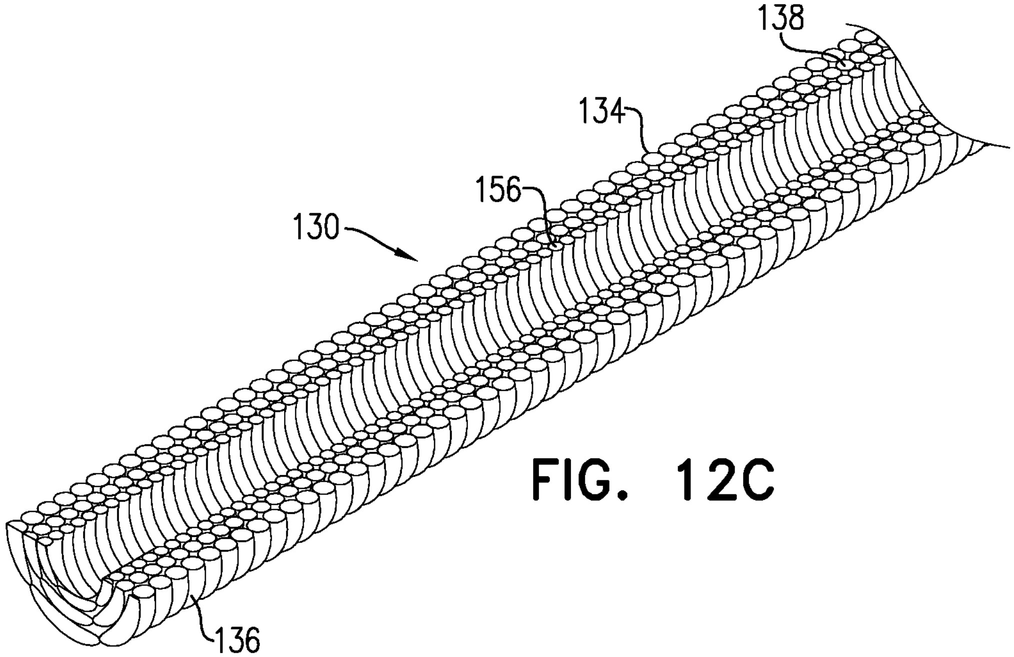

Reference is now made to FIGS. 12A, 12B, and 12C, which are schematic illustrations of drive cable 130 of ventricular assist device 20, in accordance with some applications of the present invention. Typically, the rotational motion of the of the motor is transmitted to the axial shaft via the drive cable. Typically, the drive cable extends from motor unit 23 (which is typically disposed outside the subject's body) to the proximal end of axial shaft 92 (with the connection between the distal end of the drive cable and the proximal end of the axial shaft being shown in one of the enlarged portions of FIG. 5A for example). For some applications, the drive cable includes a plurality of wires 134 that are disposed in a coiled configuration in order to impart sufficient strength and flexibility to the drive cable, such that a portion of the cable is able to be maintained within the aortic arch, while the cable is rotating and moving in the axial back-and-forth motion.

For some applications, the drive cable includes a plurality of coaxial layers of coiled wires. For example, as shown in FIGS. 12A-C, the drive cable may include an outer layer 136, an intermediate layer 138, and an inner layer 156, which are coaxial with each other and each of which comprises coiled wires. For some applications, the inner and outer layers are wound in a first direction (e.g., left hand wound) and the intermediate layer is wound in a different direction (e.g., right hand wound, or vice versa). For some applications, the drive cable includes a greater number or smaller number of layers of coiled wires (e.g., four layers or two layers). For some applications, each of the layers includes between 2 and 8, e.g., between 4 and 6, wires within the coil. For some such applications, a diameter of the drive cable is greater than 1.05 mm, e.g., between 1.1 and 1.4 mm, e.g., 1.1 mm, 1.2 mm, or 1.3 mm.

The drive cable is typically disposed within a first outer tube 140, which is configured to remain stationary while the drive cable undergoes rotational and/or axial back-and-forth motion. The first outer tube is configured to effectively act as a bearing tube for the drive cable, along the length of the drive cable. As such, first outer tube is also referred to herein as the drive-cable-bearing tube. The drive-cable-bearing tube is described in further detail hereinbelow with reference to FIGS. 12D-I. For some applications, the drive-cable-bearing tube is disposed within a second outer tube 142, which is typically made of a material having greater flexibility than that of the drive-cable-bearing tube (e.g., nylon, and/or polyether block amide), and typically has a thickness that is greater than that of the drive cable bearing tube. Second outer tube 142 may also be referred to herein as mechanical-property-providing tube 142 or as delivery tube 142. Second outer tube 142 is described in further detail hereinbelow, with reference to FIG. 13.

Typically, during insertion of the impeller and the frame into the left ventricle, impeller 50 and frame 34 are maintained in radially-constrained configurations by delivery catheter 143. As described hereinabove, in order for the impeller and the frame to assume non-radially-constrained configurations, the delivery catheter is retracted. For some applications, as shown in FIG. 12A, the delivery catheter remains in the subject's aorta during operation of the left ventricular device, and second outer tube 142 is disposed inside the delivery catheter. (Although FIG. 12A shows the distal end of the delivery catheter disposed within the aortic arch, for some application, the distal end of the delivery catheter is disposed within the descending aorta during operation of the left ventricular device.) For some applications, during operation of the left ventricular device, a channel 224 is defined between delivery catheter 143 and outer tube 142. (It is noted that the channel as shown in FIG. 12A is not to scale, for illustrative purposes.) For some such applications, the subject's aortic blood pressure is measured by measuring the pressure of blood within channel 224. For example, pressure sensor 216 (illustrated schematically in FIG. 1A) may be in fluid communication with channel 224, and may be configured to measure the subject's aortic pressure by measuring the pressure of blood within channel 224. Typically, in order to retract the left ventricular device from the subject's body, the delivery catheter is advanced over the impeller and the frame, such that the impeller and the frame assume their radially-constrained configurations. The catheter is then withdrawn from the subject's body.

Figure 12D:
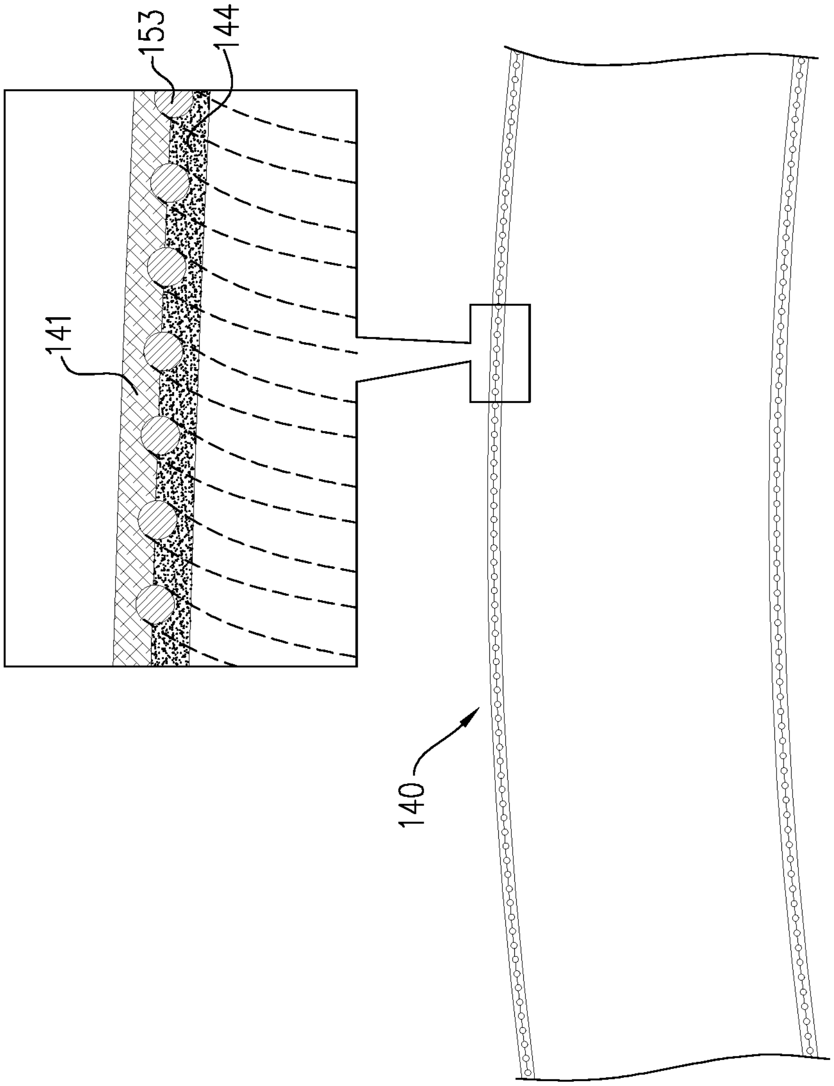
FIG. 12D is a schematic illustration of a drive cable bearing tube, in accordance with some applications of the present invention.
Figure 12E:
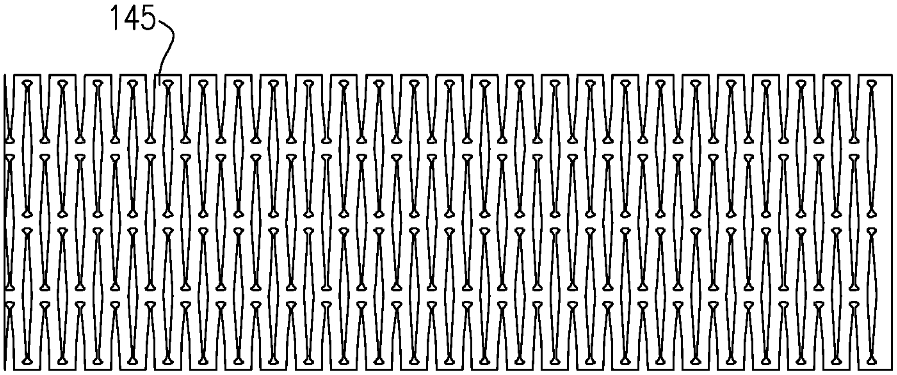
FIGS. 12E, 12F, 12G, and 12H are schematic illustrations of a laser-cut tube that is used in a drive-cable-bearing tube, in accordance with some applications of the present invention.
Figure 12F:
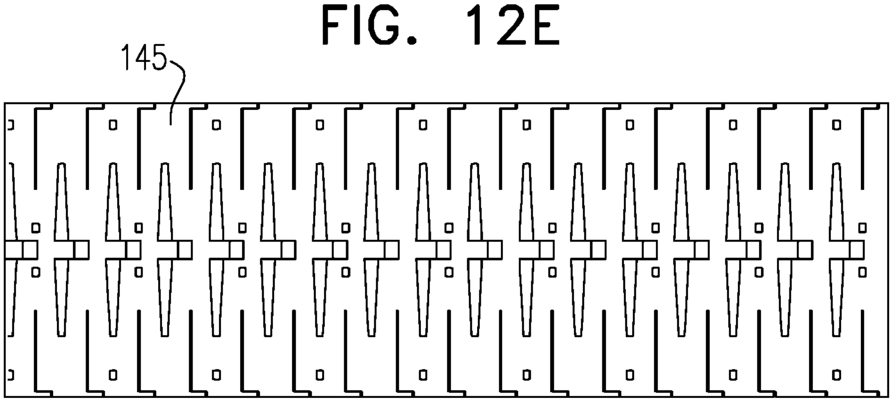
Figure 12G:
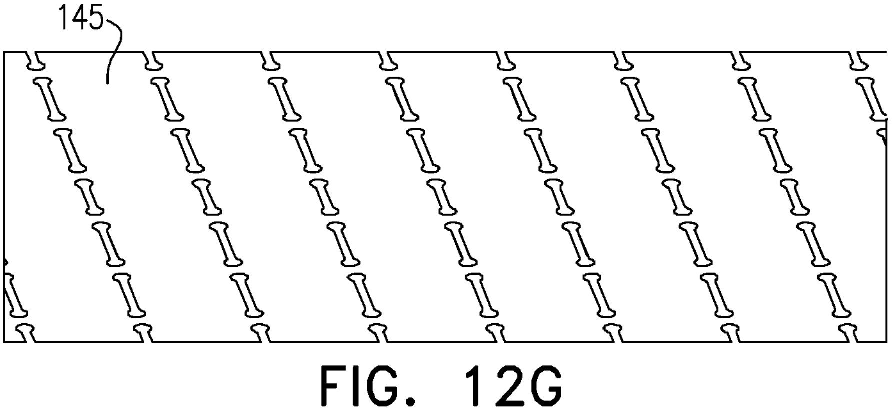
Figure 12H:
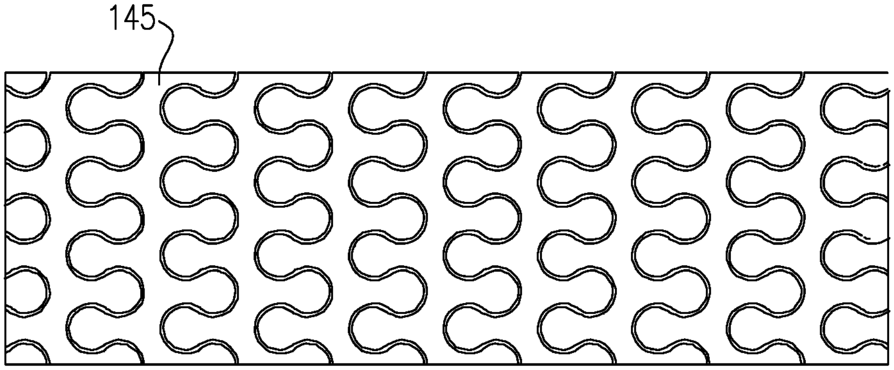

Reference is now made to FIG. 12D, which is a schematic illustration of first outer tube 140, which acts as a drive-cable-bearing tube, in accordance with some applications of the present invention. For some applications, the drive-cable-bearing tube includes an outer layer 141 and inner layer 144, each of which is typically made of a biocompatible polymeric material, and a coil 153 embedded between the outer and inner layers. For some applications, outer layer 141 is made of Pebax, inner layer 144 is made of PTFE and/or polyimide (e.g., a mixture of PTFE and/or polyimide), and the coil is made of an alloy, such as stainless steel. Typically, the inner layer includes materials that are configured to provide low levels of friction and high wear resistance. Further typically, the outer layer is configured to provide additional strength to the drive-cable-bearing tube, while still providing the drive-cable-bearing tube with sufficient flexibility that it is able to conform with the curvature of the aortic arch, for example. Typically, the coil is configured such as to maintain a substantially circular cross-section for the drive-cable-bearing tube, even within regions in which the drive-cable-bearing tube undergoes a substantial curve (e.g., within the aortic arch). Typically, in the absence of the coil, the drive-cable-bearing tube would have a tendency to flatten and form an elliptical cross-section within such regions.

For some applications, within at least some portions of the drive cable, the outer coiled wires of the drive cable are swaged such as to flatten the wires in the coil. For some applications, along a portion of the drive cable that is disposed within the aortic arch, the outer coiled wires of the drive cable are swaged in the above-described manner. Typically, if the outer coiled wires are rounded, then the outer coiled wires of the drive cable contact the inner surface of the drive-cable-bearing tube only at the outside of the circular cross-section of each of the wires, such that the frictional force that each wire exerts on the inner surface of the drive-cable-bearing tube is concentrated at that location. By contrast, if the wires are flattened, then the frictional force that each wire exerts on the inner surface of the drive-cable-bearing tube is evenly spread around the full circumference of the drive cable.

Reference is now made to FIGS. 12E, 12F, 12G, and 12H, which are schematic illustrations of a laser-cut tube 145 that comprises at least a portion of first outer tube (i.e., drive-cable-bearing tube) 140, in accordance with some applications of the present invention. For some applications, the first outer tube is made of a laser-cut shape memory material (e.g., a shape-memory alloy, such as nitinol or cobalt chromium) that is covered with and/or embedded within a polymeric material such as polyether block amide (e.g., PEBAX®) or thermoplastic polyurethane (e.g., Pellethane®). FIGS. 12E-H show the laser-cut tube as it would appear if it were cut longitudinally and laid flat. As shown, slits, openings, curves, and/or other shapes are typically cut into the tube in order to provide the tube with flexibility. For some applications, different regions of the tube are cut differently from each other, in order to provide different regions of the tube with different respective flexibilities. For example, a region of the tube that is configured to be positioned within the aortic arch, or within the ascending aorta, may be configured to have a greater flexibility than a portion that is configured to be positioned within the descending aorta.

For some applications (not shown), the bearing tube is made of one or more layers of coiled wires (e.g., as described hereinabove with reference to the drive cable). Typically the coiled wires are covered with and/or embedded within a polymeric material such as polyether block amide (e.g., PEBAX®) or thermoplastic polyurethane (e.g., Pellethane®). For some applications, the coiled wires are flattened, for example, using swaging. For some applications, different regions of the tube are formed using different numbers of layers of wires, and or different numbers of wires within each layer, in order to provide different regions of the tube with respective flexibilities. For example, a region of the tube that is configured to be positioned within the aortic arch, or within the ascending aorta, may be configured to have a greater flexibility than a portion that is configured to be positioned within the descending aorta.

For some applications, in order to reduce frictional forces between the drive cable and the drive-cable-bearing tube, beads are disposed between the drive cable and the drive-cable-bearing tube. Typically, the beads have diameters of between 0.05 mm and 0.15 mm. Further typically, the beads are not held in fixed positions within the space between the drive cable and the drive-cable-bearing tube, but rather are able to move within this space thereby facilitating movement of the drive cable relative to the drive-cable-bearing tube.

Figure 12I:
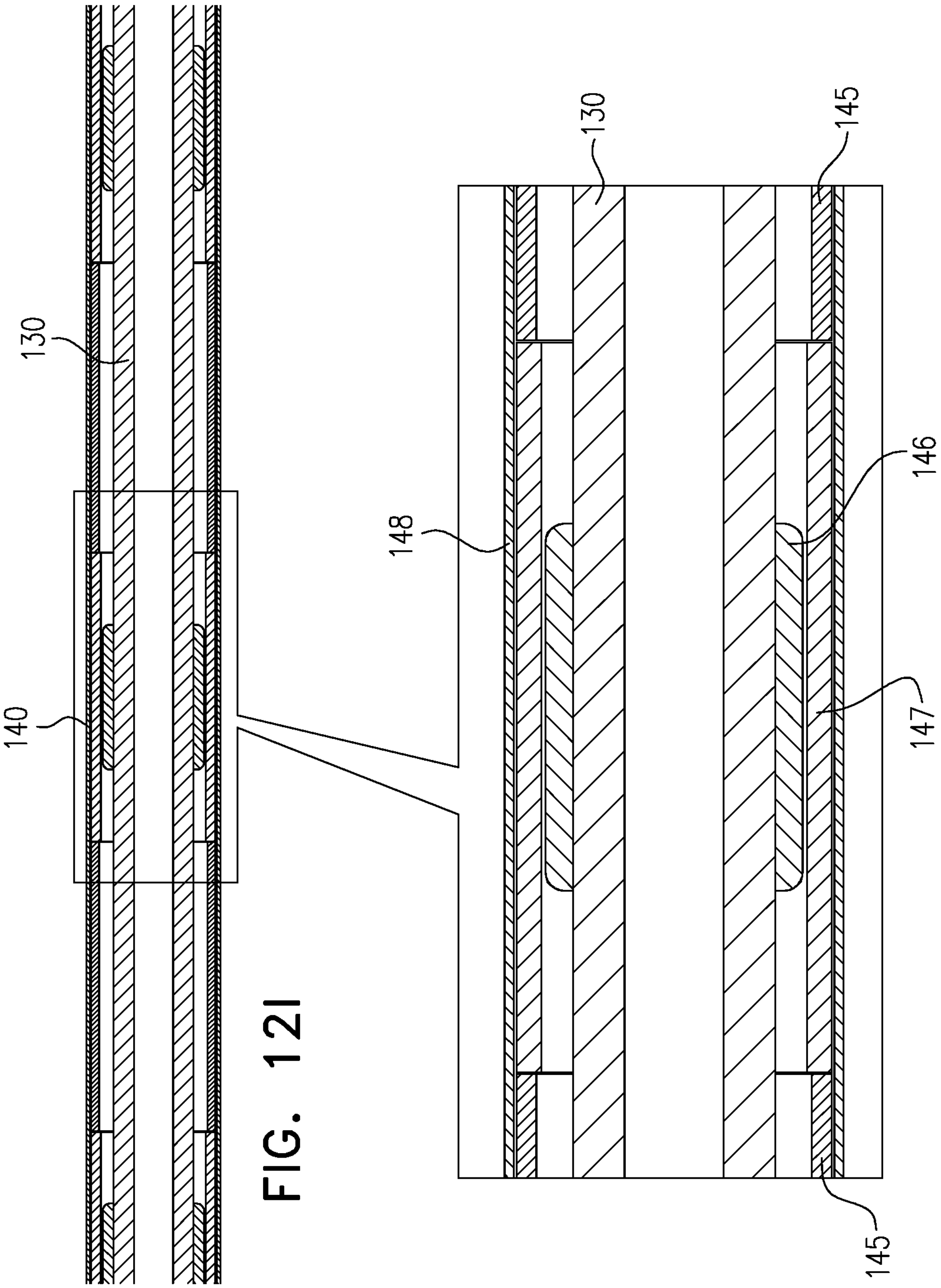
FIG. 12I is a schematic illustration of a portion of a drive cable and a drive-cable-bearing tube, in accordance with some applications of the present invention.

Reference is now made to FIG. 12I, which is a schematic illustration of a portion of drive cable 130 and drive-cable-bearing tube 140, in accordance with some applications of the present invention.

For some applications, drive-cable-bearing tube 140 comprises one or more inwardly-facing ceramic portions and drive cable 130 comprises one or more outwardly-facing ceramic portions. Drive cable 130 is configured to pass through the drive-cable-bearing tube such that the outwardly-facing ceramic portions are aligned with the inwardly-facing ceramic portions, i.e., such that, at one or more regions, the interface between the drive cable and the inner surface of the drive-cable-bearing tube is ceramic on ceramic. Drive cable 130 is further configured to couple to an intracorporeal device such as a blood pump (as described above), at the distal end of the drive-cable-bearing tube, and to rotate within the drive-cable-bearing tube, thereby rotating the intracorporeal device, while the outwardly-facing ceramic portions are aligned with the inwardly-facing ceramic portions. In some embodiments, the inwardly-facing ceramic portions and/or the outwardly-facing ceramic portions comprise zirconia.

In some embodiments, the inwardly-facing ceramic portions of the drive-cable-bearing tube comprise respective ceramic sleeves 147, which may line the inside of the main body of the drive-cable-bearing tube, or alternatively, may be integrated with the main body of the drive-cable-bearing tube. For example, the main body of the drive-cable-bearing tube may comprise a structure such as laser-cut tube 145 (or wires or a braid or a coil) that is covered with or embedded within a polymeric material 148. Ceramic sleeves 147 may line the structure, or alternatively, replace the structure, at certain locations, e.g., as shown in FIG. 12I.

Similarly, the outwardly-facing ceramic portions of the drive cable may comprise respective ceramic sleeves 146, which may cover the main body of the drive cable or alternatively, may be integrated with the main body of the drive cable.

Typically, regions of drive cable 130 and drive-cable-bearing tube 140 along which the drive cable exerts strong frictional forces on the inner surface of the drive-cable-bearing tube are configured in this manner, in order to prevent wear and heating along such regions. For example, for embodiments in which the drive-cable-bearing tube is configured to pass through the aorta of the subject, the drive-cable-bearing tube may comprise the inwardly-facing ceramic portions at a section of the drive-cable-bearing tube that is configured to sit (i.e., to be disposed) within the aortic arch of the subject, and/or a section of the drive-cable-bearing tube that is configured to sit within the ascending aorta of the subject. Thus, the drive-cable-bearing tube may be inserted through the aorta such that the inwardly-facing ceramic portions are within the aortic arch and/or the ascending aorta of the subject.

In some embodiments, each of the inwardly-facing ceramic portions is 10-200% longer than each of the outwardly-facing ceramic portions. Thus, even if the drive cable moves axially within the drive-cable-bearing tube, the outwardly-facing ceramic portions may remain aligned with the inwardly-facing ceramic portions.

Figure 13:
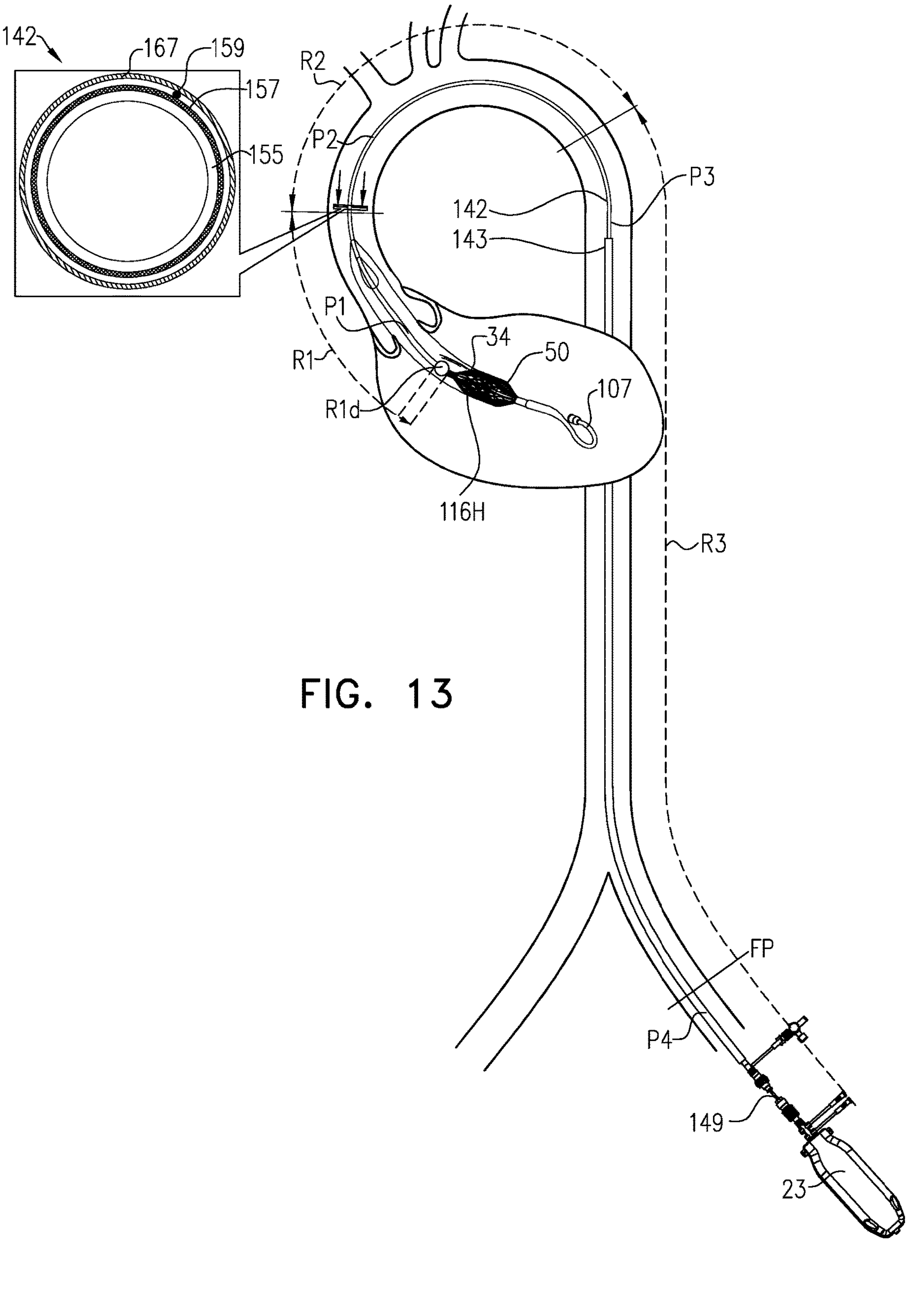
FIG. 13 is a schematic illustration of a delivery tube of a left-ventricular assist device, in accordance with some applications of the present invention.

Reference is now made to FIG. 13, which is a schematic illustration of delivery tube 142, in accordance with some applications of the present invention.

As described hereinabove, drive cable 130 passes through delivery tube 142, typically by virtue of passing through first outer tube 140, which functions as a drive-cable-bearing tube, which in turn passes through the delivery tube. Typically, both drive-cable-bearing tube 140 and the delivery tube extend from motor unit 23 until the proximal bearing housing 116H. Further typically, during delivery of pump-head portion 27 to the left ventricle, the pump-head portion, drive cable 130, drive-cable-bearing tube 140, and delivery tube 142 are disposed inside delivery catheter 143, with the delivery catheter maintaining the pump head in a radially constrained configuration. Once pump-head portion 27 has been delivered to the left ventricle, the delivery catheter is retracted (e.g., to the descending aorta, as shown in FIG. 13), which allows the pump-head portion to radially expand to the non-radially constrained configurations of the frame and impeller. Subsequently, drive cable 130 rotates the impeller so as to pump blood of the subject from the left ventricle into the aorta.

Typically, delivery tube 142 is configured to impart respective mechanical properties to respective portions of the length of the drive cable. Further typically, a purging fluid is pumped between drive-cable-bearing tube 140 and the delivery tube, such that the purging fluid flows to the pump head and purges interfaces between axial shaft 92 and the proximal and distal radial bearings 116 and 118, for example, as described with reference to FIGS. 11A-C of US 2022/0226632 to Tuval, which is incorporated herein by reference.

As shown in the enlarged cross-section through delivery tube 142, typically, the delivery tube comprises an outer layer 167, with an optional braid 157 (e.g., a metal or alloy (e.g., a stainless steel) braid) or coil disposed within outer layer 167.

For some applications, delivery tube 142 is configured to provide different mechanical properties to respective regions along the delivery tube. For example, outer layer 167 may vary along the length of the delivery tube, e.g., by virtue of having a variable composition and/or a variable thickness. Alternatively or additionally to outer layer 167 varying along the length of the delivery tube, braid 157 may have a pick density that varies along the length of the delivery tube, or the aforementioned coil (substituting for braid 157) may have a pitch that varies along the length of the delivery tube. Due to this variation in outer layer 167 and/or braid 157 (or the aforementioned coil), the flexural rigidity (or "stiffness") of the delivery tube at a first portion P1 of the delivery tube, which is configured to traverse the aortic valve of the subject, is less than the flexural rigidity at a second portion P2 of the delivery tube, which is configured to traverse at least a portion of the aortic arch of the subject, and the flexural rigidity at second portion P2 is less than the flexural rigidity at a third portion P3 of the delivery tube, which is configured to traverse the descending aorta of the subject. Advantageously, this variation in flexural rigidity facilitates the passage of the delivery tube through the aorta and into the left ventricle.

For example, outer layer 167 may comprise a (thermoplastic) polyurethane (e.g., Pellethane®) jacket (or "coating") at first portion P1, a polyether block amide (e.g. PEBAX®) jacket at second portion P2, and a polyamide (e.g. Grilamid®) jacket at third portion P3.

For some applications, the ratio between the pick density of the braid within first portion P1 of the delivery tube to pick density of the braid within third portion P3 of the delivery tube is between 3:2 and 5:2. For some applications, the pick density of the braid within the first portion of the delivery tube is between 30 and 50 picks per inch and the pick density of the braid within the third portion of the delivery tube is between 15 and 25 picks per inch.

In some embodiments, the flexural rigidity of delivery tube 142 monotonically increases between first portion P1 and third portion P3. For example, between a polyurethane jacket at first portion P1 and a polyamide jacket at third portion P3, outer layer 167 may comprise a single polyether block amide jacket, or multiple polyether block amide jackets having an increasing durometer moving proximally along the tube.

For some applications, the delivery tube defines a first region R1, a second region R2, and a third region R3. First region R1 comprises first portion P1, second region R2 comprises second portion P2, and third region R3 comprises third portion P3.

Typically, first region R1 is configured to extend proximally from the proximal end of the frame (e.g., from proximal bearing housing 116H) through the aortic valve and into the ascending aorta. For some applications, first region R1 has a length of between 70 mm and 100 mm, e.g., between 75 mm and 95 mm.

Typically, second region R2 extends proximally from the proximal end of first region R1 and around at least a portion of the aortic arch. For some applications, second region R2 has a length of between 40 mm and 80 mm (e.g., between 50 mm and 70 mm). Alternatively, second region R2 has a length of between 150 mm and 210 mm (e.g., between 160 mm and 200 mm). For some applications, along second region R2, there is a gradual decrease in the flexibility (i.e., a gradual increase in the flexural rigidity) of the delivery tube. For example, along second region R2, outer layer 167 may comprise multiple polyether block amide jackets having an increasing durometer moving proximally along the tube. Alternatively, the flexural rigidity of delivery tube 142 may be uniform along second region R2.

Typically, third region R3 extends from the proximal end of second region R2 along the descending aorta, out of the patient's vasculature (e.g., via a femoral puncture FP), and to motor unit 23. For some applications, third region R3 has a length of between 1200 mm and 1500 mm (e.g., between 1250 mm and 1450 mm). In some embodiments, there is a gradual decrease in flexibility from the distal end of region R3 to third portion P3. For example, along region R3 distally to third portion P3, outer layer 167 may comprise multiple polyether block amide jackets having an increasing durometer moving proximally along the tube.

In some embodiments, the flexural rigidity at the distal end of the delivery tube, which is identified in FIG. 13 as a distal region R1d of first region R1 and which couples to the pump head (e.g., to the proximal end of the proximal bearing housing), is greater than the flexural rigidity at first portion P1. Advantageously, this increased flexural rigidity may facilitate the coupling of the delivery tube to the pump head. Typically, in such embodiments, the flexural rigidity at the distal end of the delivery tube is between the flexural rigidity at first portion P1 and the flexural rigidity at third portion P3. For some applications, R1d has a length of between 5 mm and 15 mm (e.g., between 8 mm and 12 mm).

For example, outer layer 167 may comprise a polyurethane jacket at first portion P1 and a polyether block amide (e.g. PEBAX®) jacket at the distal end. The outer layer may further comprise a polyamide jacket at third portion P3, such that the flexural rigidity at the distal end is between that of first portion P1 and that of third portion P3.

In some such embodiments, the flexural rigidity monotonically increases between first portion P1 and the distal end of the delivery tube. (The flexural rigidity may thus increase monotonically moving both proximally and distally from first portion P1.) For example, distally to first portion P1, outer layer 167 may comprise multiple polyether block amide jackets having an increasing durometer moving distally along the tube.

In some embodiments, the flexural rigidity at a fourth portion P4 of the delivery tube, which is configured to span the point of insertion into the body of the subject (e.g., femoral puncture FP), is less than the flexural rigidity at third portion P3. Advantageously, this lesser flexural rigidity may facilitate the insertion into the body. Nonetheless, even in such embodiments, the flexural rigidity at the proximal end of the delivery tube—i.e., the flexural rigidity proximally to fourth portion P4, along the most proximal portion of third region R3, which may have a length of between 360 mm and 460 mm (e.g., between 380 mm and 440 mm)—is greater than the flexural rigidity at fourth portion P4 (and, optionally, greater than that of third portion P3), in order to facilitate advancing and retracting this portion of the delivery tube with respect to a handle 149, and/or in order to facilitate clamping of the delivery tube without causing the delivery tube to kink. For example, proximally to fourth portion P4, outer layer 167 may comprise a polyether block amide (e.g. PEBAX®) jacket with a high-performance polyamide (e.g., Grilamid®) outer coating. In some embodiments, along this most proximal portion of the delivery tube, the delivery tube comprises a coil or metal frame positioned between braid 157 and outer layer 167, e.g., between fiber 159, which is described immediately below, and outer layer 167. Advantageously, the coil or metal frame may further inhibit kinking of the delivery tube.

In some embodiments, the delivery tube further comprises at least one fiber 159 (e.g., an aromatic polyamide (i.e., aramid) fiber) that extends along the length of delivery tube 142 and increases the tensile rigidity (or "tensile strength") of the delivery tube, relative to if the delivery tube would not comprise fiber 159. In other words, fiber 159 resists elongation, thereby inhibiting elongation of the delivery tube. Thus, braid 157 resists bending (the degree of this resistance optionally varying along the length of the delivery tube) and elongation, while fiber 159 provides additional resistance to elongation (i.e., the fiber provides additional tensile strength). For some applications, a relatively high resistance to elongation (i.e., a relatively high tensile strength) is desirable along the full length of the delivery tube, in order to prevent elongation of the delivery tube when the delivery tube is disposed inside delivery catheter 143.

Typically, fiber 159 is disposed inside outer layer 167. For example, as shown in FIG. 13, fiber 159 may be disposed between braid 157 and outer layer 167. Alternatively, fiber 159 may be woven into braid 157.

Typically, the tensile rigidity of the delivery tube is more uniform than the flexural rigidity of the delivery tube.

For example, (a) the ratio between the tensile strength of third portion P3 and that of first portion P1 may be lower than (b) the ratio between the flexural rigidity of third portion P3 and that of first portion P1. For example, the ratio between the tensile strength of third portion P3 and that of first portion P1 is typically between 3:2 and 5:2 (e.g. 2:1), and the ratio between the flexural rigidity of third portion P3 and that of first portion P1 is typically between 5:2 and 7:2 (e.g., 3:1). Thus, for some applications, a ratio between the former ratio and the latter ratio is between 4:3 and 5:3, e.g., 3:2.

Alternatively or additionally, the ratio between the tensile rigidity at second portion P2 and the tensile rigidity at first portion P1 may be less than the ratio between the flexural rigidity at second portion P2 and the flexural rigidity at first portion P1. Alternatively or additionally, the ratio between the tensile rigidity at third portion P3 and the tensile rigidity at second portion P2 may be less than the ratio between the flexural rigidity at third portion P3 and the flexural rigidity at second portion P2. This latter ratio—or, for embodiments in which second region R2 has a variable flexural rigidity, the ratio between the flexural rigidity of third portion P3 and the mean flexural rigidity of second region R2—is typically between 3:2 and 5:2 (e.g. 2:1).

Typically, notwithstanding the nonuniformity of outer layer 167 and/or of braid 157, the delivery tube comprises a uniform inner surface. For example, braid 157 may be coated with a uniform polymeric inner lining 155 (e.g., a thermoplastic polyurethane (e.g., Pellethane®) inner lining) along the length of delivery tube 142. Thus, advantageously, outer tube 140 (or, in some embodiments, the drive cable itself) is exposed to the uniform inner surface.

In some embodiments, outer layer 167 becomes at least partly fused with the more inner portions of the delivery tube 142 during the manufacture thereof, e.g., via a reflow soldering process.

In the context of the above discussion regarding the flexural rigidity of respective portions of delivery tube 142, it is noted that a metric for quantifying flexural rigidity is Young's modulus multiplied by the second moment of area (which is also known as area moment of inertia).

Figure 14A:
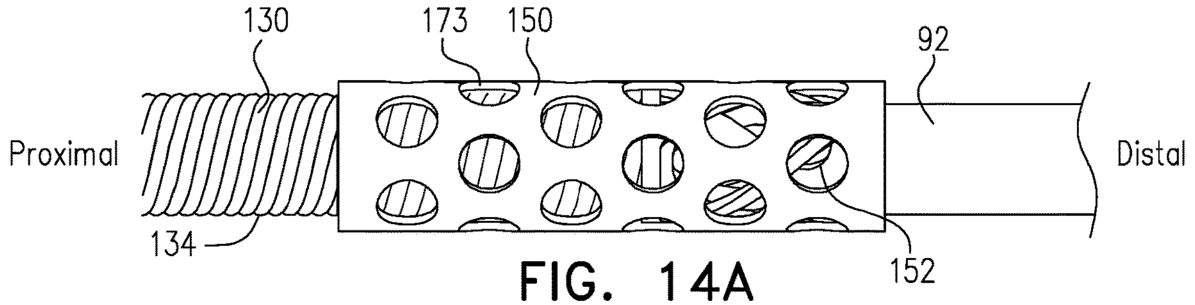
FIGS. 14A, 14B, 14C, 14D, 14E, 14F, 14G, and 14H are schematic illustrations of an interface between a drive cable and an axial shaft, in accordance with some applications of the present invention.
Figure 14B:
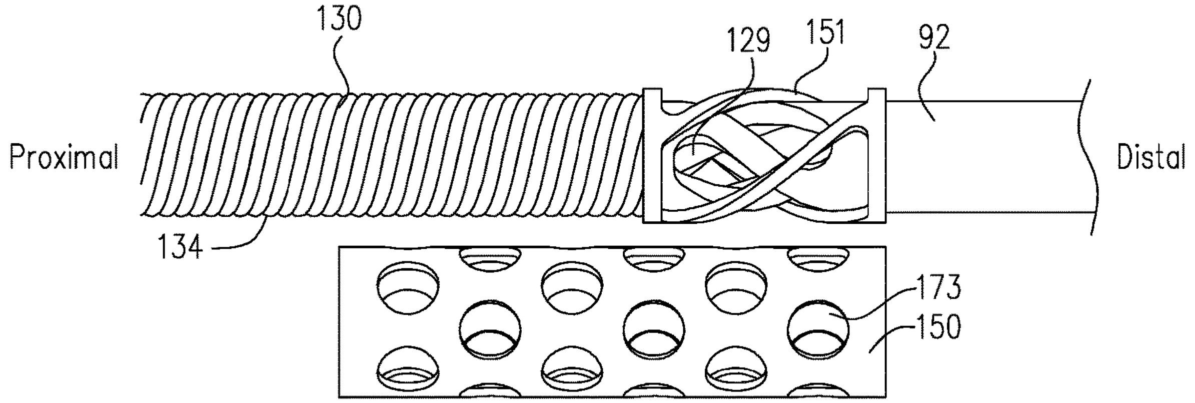

Reference is now made to FIGS. 14A and 14B, which are schematic illustrations of an interface between drive cable 130 and axial shaft 92, in accordance with some applications of the present invention.

As described hereinabove, typically, the drive cable, which comprises a plurality of (e.g., three layers of) coiled wires 134, extends from the motor unit 23 (which is disposed outside the subject's body) until the axial shaft 92, which is hollow. Rotational motion that is generated by the motor within the motor unit is typically transmitted to the axial shaft (and thereby transmitted to the impeller) via the drive cable.

For some applications, the drive cable is coupled to the axial shaft via welding. In some cases, however, the interface between the drive cable and the axial shaft can be weakened as a result of the heating that the drive cable and the axial shaft undergo during welding. Therefore, for some applications, the drive cable is coupled to the axial shaft via a coupling technique other than welding. To facilitate this coupling technique, the proximal end of the axial shaft may be shaped to define multiple shaft pores 152.

More specifically, for some applications, a porous coupling tube 150 (which may be polymeric) is placed around the distal end of drive cable and the proximal end of the axial shaft. In other words, the distal end of the drive cable and the proximal end of the axial shaft are inserted into opposing ends of coupling tube 150, which is shaped to define multiple coupling-tube pores 173. Subsequently, while the ends of the drive cable and axial shaft are inside the coupling tube, a molten bonding material is flowed between coiled wires 134 at the distal end of the drive cable via coupling-tube pores 173, and into the proximal end of the axial shaft via the coupling-tube pores and shaft pores 152, such that, upon solidifying, the material bonds the drive cable to the axial shaft. Typically, while the molten bonding material solidifies, the distal end of the drive cable, the proximal end of the axial shaft, and the coupling tube are compressed and heated.

Typically, the drive cable is also hollow, and it is desired that the drive cable and axial shaft be shaped to define a continuous lumen even after the bonding material solidifies. Hence, prior to the flowing of the molten bonding material, the drive cable and axial shaft are placed over a mandrel, such that the continuous lumen is maintained. (This continuous lumen is shown, for example, in FIG. 15B with reference number 132.)

Typically, the molten material includes a molten polymer including, for example, polyether ether ketone (PEEK). The polymer is heated such that it passes through the coupling-tube pores 173 and flows between the wires of the drive cable and into the shaft. Upon drying and solidifying, the polymeric material bonds the drive cable to the axial shaft. FIG. 14A shows the porous coupling tube disposed around the distal end of the drive cable and the proximal end of the axial shaft, whereas FIG. 14B shows an exploded view (for illustrative purposes) in which the porous coupling tube is shown separately from the distal end of the drive cable and the proximal end of the axial shaft.

In some embodiments, the molten material is flowed using a heat-shrinking process. In particular, a sleeve of the bonding material (e.g., a PEEK sleeve) is placed around the coupling tube, and an outer sleeve (made of polytetrafluoroethylene, for example) is placed around the sleeve of the material. Next, heat is applied to the sleeve of the material and to the outer sleeve. The applied heat melts the sleeve of the material, thereby forming the molten material, and shrinks the outer sleeve such that the outer sleeve forces the molten material between coiled wires 134 and into the proximal end of the axial shaft. Following the solidification of the molten material, the outer sleeve and any protruding pieces of the solidified material may be removed.

For some applications, the axial shaft (or at least the proximal end thereof) has a smaller outer diameter than the drive cable (or at least the distal end thereof). For example, the axial shaft may have a diameter of 0.9 mm and the drive cable may have a diameter of 1.1 mm, 1.2 mm, or 1.3 mm. For some such applications, prior to the insertion of the proximal end of the axial shaft into the coupling tube, a porous adaptor tube 151, which is shaped to define multiple adaptor-tube pores 129, is placed around the proximal end of the axial shaft so as to add to the outer diameter of the axial shaft, e.g., such that the outer diameter of the axial shaft with porous adaptor tube 151 disposed around it is approximately equal to the outer diameter of the distal end of the drive cable. Porous coupling tube 150 is then placed over the distal end of the drive cable and over the porous adaptor tube (which, in turn, is disposed over the proximal end of the axial shaft). The molten material is then flowed into the axial shaft via adaptor-tube pores 129.

In some embodiments, adaptor tube 151 is polymeric. In other embodiments, the adaptor tube comprises a metallic alloy.

For some applications, the distal end of the drive cable is coupled to the proximal end of the axial shaft using the following procedure. Porous adaptor tube 151 is placed over the proximal end of the axial shaft, and the porous coupling tube is then placed over the distal end of the drive cable and over the porous adaptor tube. The above-described assembly is then placed over a mandrel, which passes through the lumen defined by the axial shaft and the distal end of the drive cable. A polymeric material, such as polyether ether ketone, is heated such that it passes through the pores of the porous coupling tube, the porous adaptor tube, and into pores 152 of the axial shaft (e.g., using a heat-shrinking process). Typically, the mandrel prevents the polymeric material from entering the lumen defined by the axial shaft and the distal end of the drive cable. Upon drying and solidifying, the polymeric material bonds the drive cable to the axial shaft.

As described above, typically, delivery tube 142 is coupled to proximal bearing housing 116H (FIG. 5A). In some embodiments, after coupling the drive cable to the axial shaft, the drive cable (together with the axial shaft) is inserted through the delivery tube, such that the distal end of the drive cable is disposed within the proximal bearing housing proximally to proximal radial bearing 116. Thus, advantageously, the proximal bearing housing may help prevent any weakening in the coupling between the drive cable and the axial shaft.

With reference to FIG. 14B, it is noted that for some applications, prior to the insertion of the distal end of the drive cable into the coupling tube, wires 134 are merged together at the distal end of the drive cable so as to strengthen the distal end. For example, a molten material (e.g., PEEK) may be flowed between wires 134 at the distal end such that, upon solidification of the material, the distal end of the drive cable is shaped to define a tube.

Figure 14C:
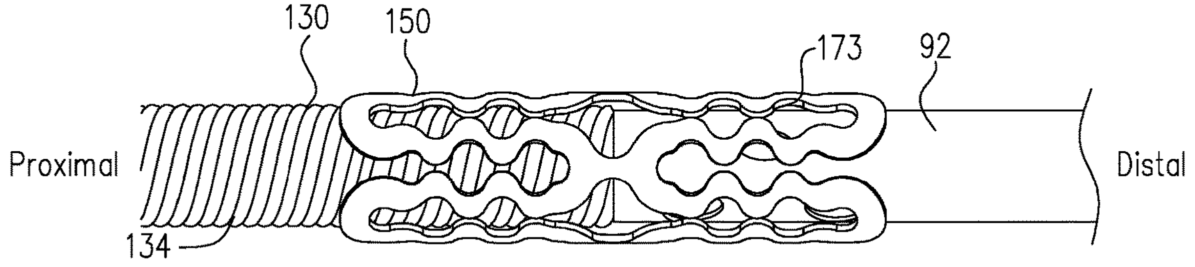
Figure 14D:
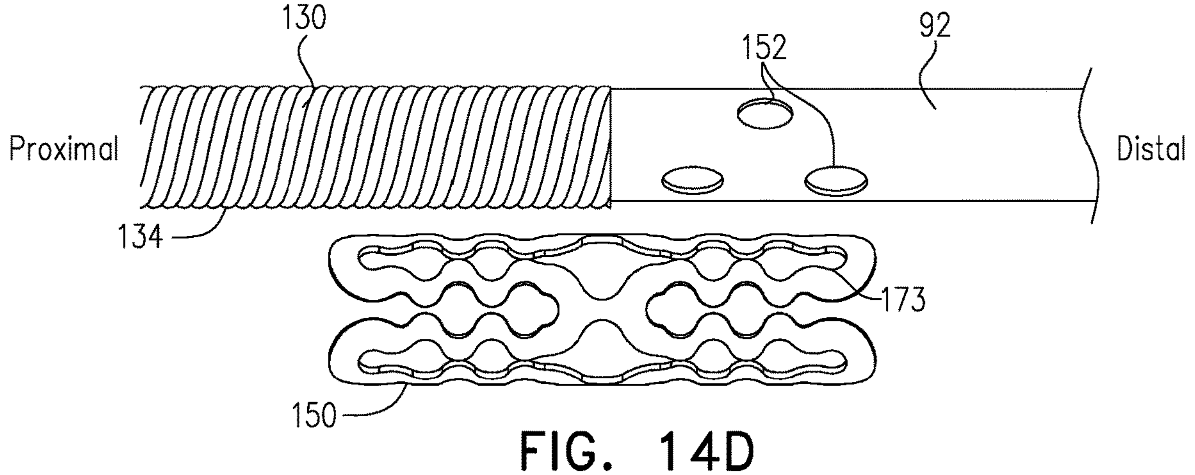

Reference is now made to FIGS. 14C-D, which are schematic illustrations of an interface between drive cable 130 and axial shaft 92, in accordance with some applications of the present invention. FIG. 14C shows the porous coupling tube disposed around the distal end of the drive cable and the proximal end of the axial shaft, whereas FIG. 14D shows an exploded view (for illustrative purposes) in which the porous coupling tube is shown separately from the distal end of the drive cable and the proximal end of the axial shaft.

In some embodiments, coupling tube 150 is compliant so as to conform both to the larger outer diameter of the drive cable and to the smaller outer diameter of the axial shaft, thus typically obviating the need for adaptor tube 151.

Figure 14E:
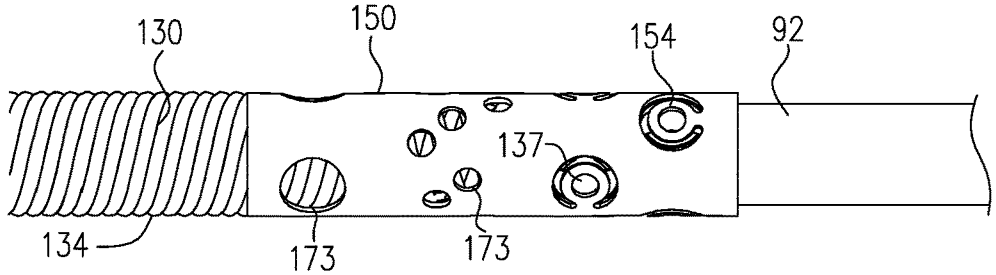
Figure 14F:
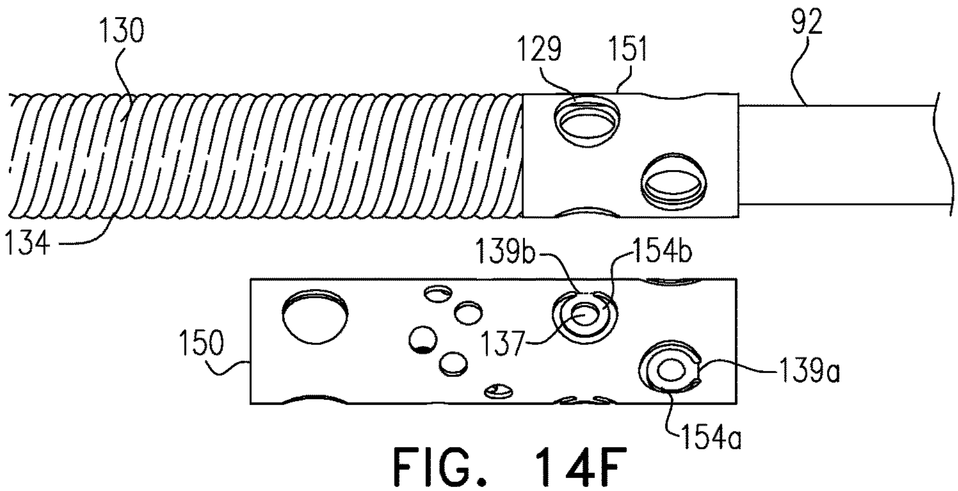

Reference is now made to FIGS. 14E-F, which are schematic illustrations of an interface between drive cable 130 and axial shaft 92, in accordance with some applications of the present invention. FIG. 14E shows the porous coupling tube disposed around the distal end of the drive cable and the proximal end of the axial shaft, whereas FIG. 14F shows an exploded view (for illustrative purposes) in which the porous coupling tube is shown separately from the distal end of the drive cable and the proximal end of the axial shaft.

In some embodiments, the wall of coupling tube 150 is shaped to define multiple tabs 154. Prior to the flowing of the molten material, at least some of tabs 154 are pushed into shaft pores 152 (FIG. 14D) such that these tabs protrude into the shaft pores, thereby strengthening the coupling of the drive cable to the axial shaft. For embodiments in which adaptor tube 151 is used, these tabs are typically pushed into the shaft pores via adaptor-tube pores 129, such that the tabs protrude into the shaft pores via the adaptor-tube pores.

In some embodiments, to strengthen the coupling even further, at least two of the tabs pushed into shaft pores 152 have different respective orientations with respect to the longitudinal axis of the coupling tube. In other words, at least two of these tabs are rotatable about rotation axes having different respective orientations with respect to the longitudinal axis. For example, in the embodiment shown in FIGS. 14E-F, one tab 154*a* is oriented parallelly to the longitudinal axis of the coupling tube, in that tab 154*a* is rotatable about a rotation axis 139*a* that is perpendicular to the longitudinal axis of the coupling tube, while another tab 154*b* is oriented perpendicularly to the longitudinal axis, in that tab 154*b* is rotatable about another rotation axis 139*b* that is parallel to the longitudinal axis. Together, tabs 154*a* and 154*b* help withstand both axial and rotational forces.

In some embodiments, the tabs pushed into shaft pores 152 are shaped to define respective holes 137, which allow the molten material to flow therethrough.

Figure 14G:
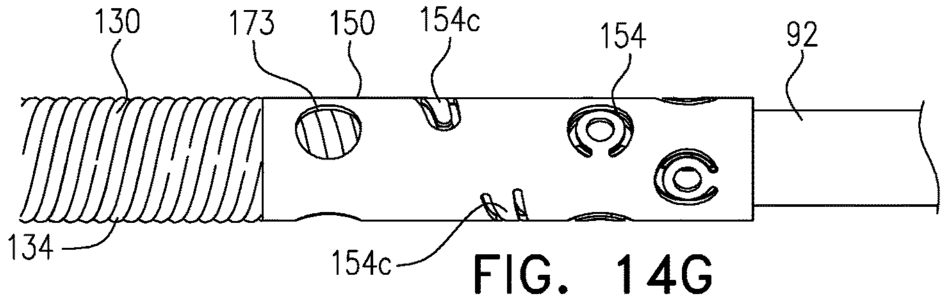
Figure 14H:
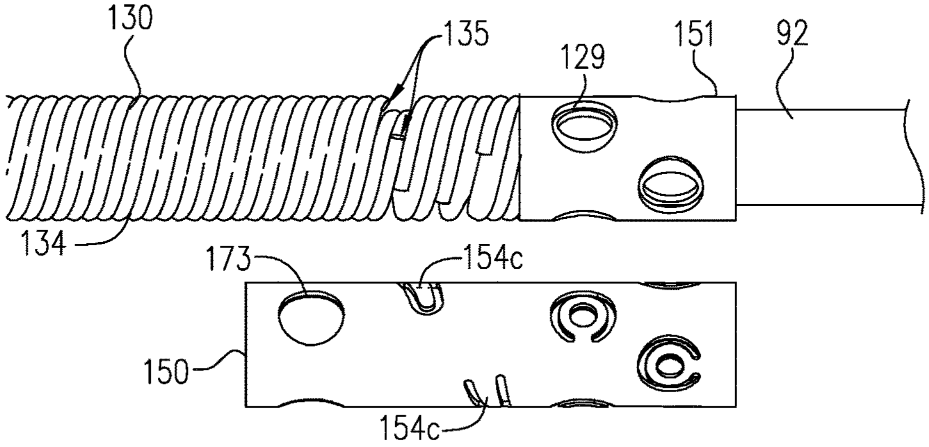

Reference is now made to FIGS. 14G-H, which are schematic illustrations of an interface between drive cable 130 and axial shaft 92, in accordance with some applications of the present invention. FIG. 14G shows the porous coupling tube disposed around the distal end of the drive cable and the proximal end of the axial shaft, whereas FIG. 14H shows an exploded view (for illustrative purposes) in which the porous coupling tube is shown separately from the distal end of the drive cable and the proximal end of the axial shaft.

In some embodiments, prior to flowing the molten material between coiled wires 134 at the distal end of the drive cable and into the proximal end of the axial shaft, some of tabs 154 are pushed between the coiled wires such that these tabs protrude between the coiled wires, thereby strengthening the coupling of the drive cable to the axial shaft. These tabs may have any shape that allows the tabs to fit between the coiled wires, which may be different from the shape of those of the tabs pushed into the shaft pores. For example, in some embodiments, U-shaped tabs 154*c* are pushed between the coiled wires.

In some embodiments, at least one of the coiled wires (in any one or more of the layers of the drive cable) is cut, at the distal end of the drive cable, so as to define one or more enlarged gaps between successive windings of the coiled wires, and some of the tabs (such as U-shaped tabs 154*c*) are pushed into the enlarged gaps. Such cuts 135 are shown in FIG. 14H.

It is noted that the scope of the present invention includes the use of tabs 154 to strengthen the coupling of the drive cable to the axial shaft even without the subsequent flowing of a molten material through coupling-tube pores 173.

In some embodiments, as shown in FIGS. 14E-H, coupling-tube pores 173 are preformed, and tabs 154 extend into the coupling-tube pores prior to being pushed into the shaft pores or between the coiled wires. (Thus, as the tabs are pushed, the coupling-tube pores are expanded.) In other embodiments, coupling-tube pores 173 are formed as the tabs are pushed, i.e., the pushing of the tabs forms coupling-tube pores 173 in the wall of the coupling tube.

Alternatively or additionally to coupling the distal end of the drive cable to the proximal end of the axial shaft, the techniques described above may be used to couple the proximal end of the drive cable to the distal end of another hollow shaft configured to couple the drive cable to a rotating element configured to rotate the drive cable. For example, as noted hereinabove with reference to FIG. 7A, for some applications, at the proximal end of the drive cable, the drive cable is coupled to driven magnet 82 (which is a rotating element configured to rotate the drive cable) via pin 131 (which is a hollow shaft). For some applications, the proximal end of the drive cable is coupled to the distal end of pin 131 using generally similar techniques to those described with reference to FIGS. 14A-H in relation to bonding the distal end of the drive cable to the proximal end of axial shaft 92. The scope of the present disclosure includes using the apparatus and techniques described with reference to FIGS. 14A-H to couple any two tubular and/or rod shaped components to each other, mutatis mutandis.

For some applications, the drive cable continues into the pump-head portion, rather than the drive cable ending at the coupling to the axial shaft. For some such applications, a reinforcing element is added inside the drive cable within the pump-head portion, in order to add to the rigidity of the drive cable within the pump-head portion. Typically, the reinforcing element defines a lumen therethrough, which functions as a portion of the continuous lumen described hereinbelow with reference to FIGS. 15A-C.

For some applications, the ventricular assist device does not define a lumen within the pump head, i.e., the axial shaft, which is coupled to the impeller, is solid. For some such applications, the axial shaft may have a relatively small diameter, such as a diameter less than 1 mm, e.g., less than 0.8 mm, 0.6 mm, or 0.4 mm. Thus, the axial shaft may have a smaller diameter than the drive cable (which, as noted above, is typically hollow, to facilitate the flow of purging fluid therethrough). For example, the drive cable may have an outer diameter greater than 1 mm (e.g., between 1 mm and 1.5 mm), and the axial shaft may have a diameter of less than 1 mm, e.g., less than 0.8 mm, 0.6 mm, or 0.4 mm. Advantageously, as a result of the axial shaft defining a smaller diameter, the pump-head portion can be radially constrained (i.e., crimped) to a smaller diameter.

Optionally, the drive cable may be coupled to the smaller-diameter axial shaft as described above with reference to FIGS. 14A-H. Alternatively or additionally, the drive cable may be coupled to the smaller-diameter axial shaft within the proximal bearing housing, such that the proximal bearing housing helps keep these two elements from separating from one another.

Figure 15A:
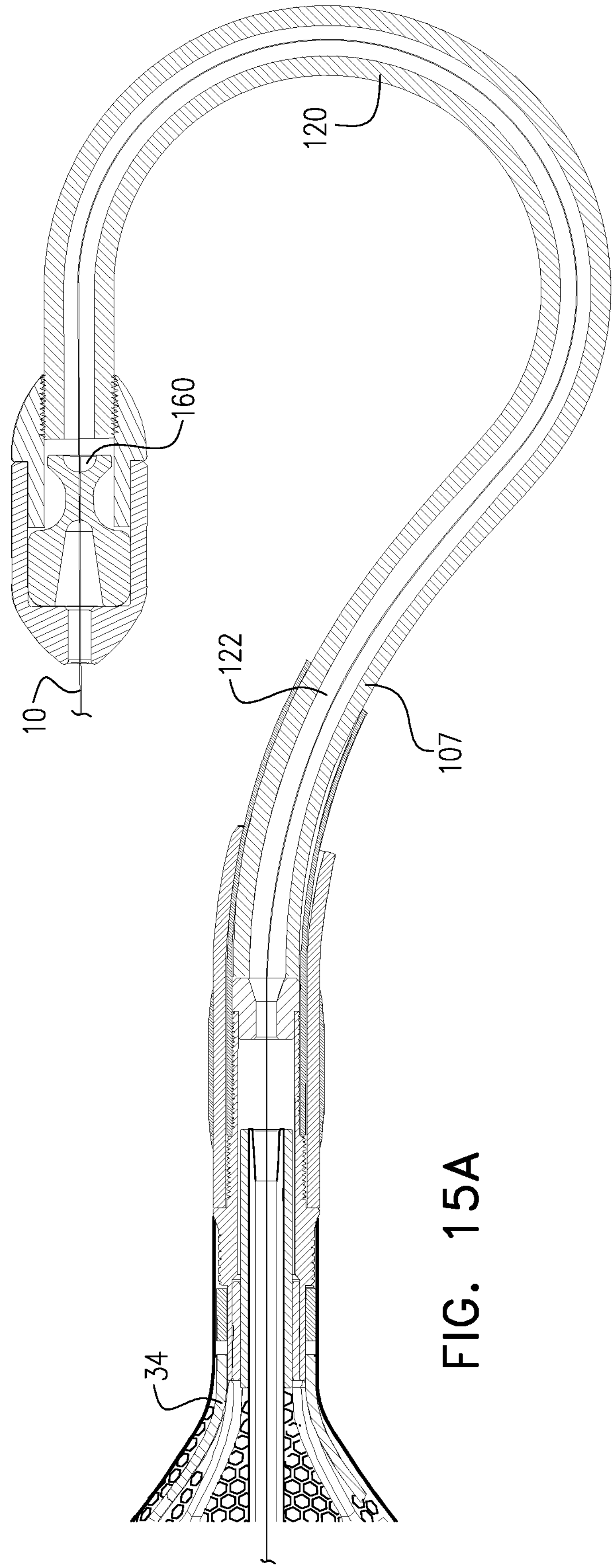
FIGS. 15A, 15B, and 15C are schematic illustrations of portions of a continuous lumen defined by a ventricular assist device, in accordance with some applications of the present invention.
Figure 15B:
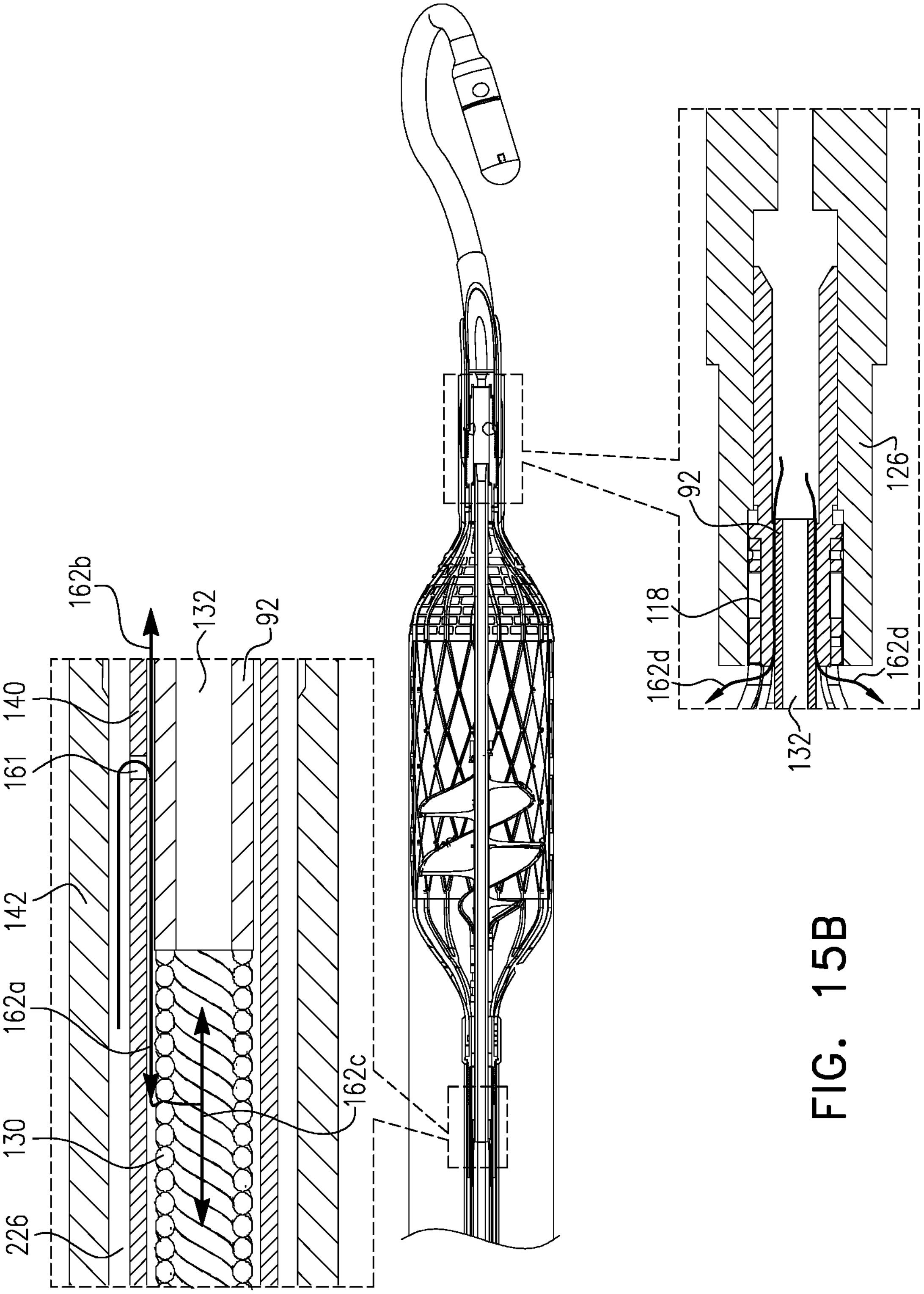
Figure 15C:
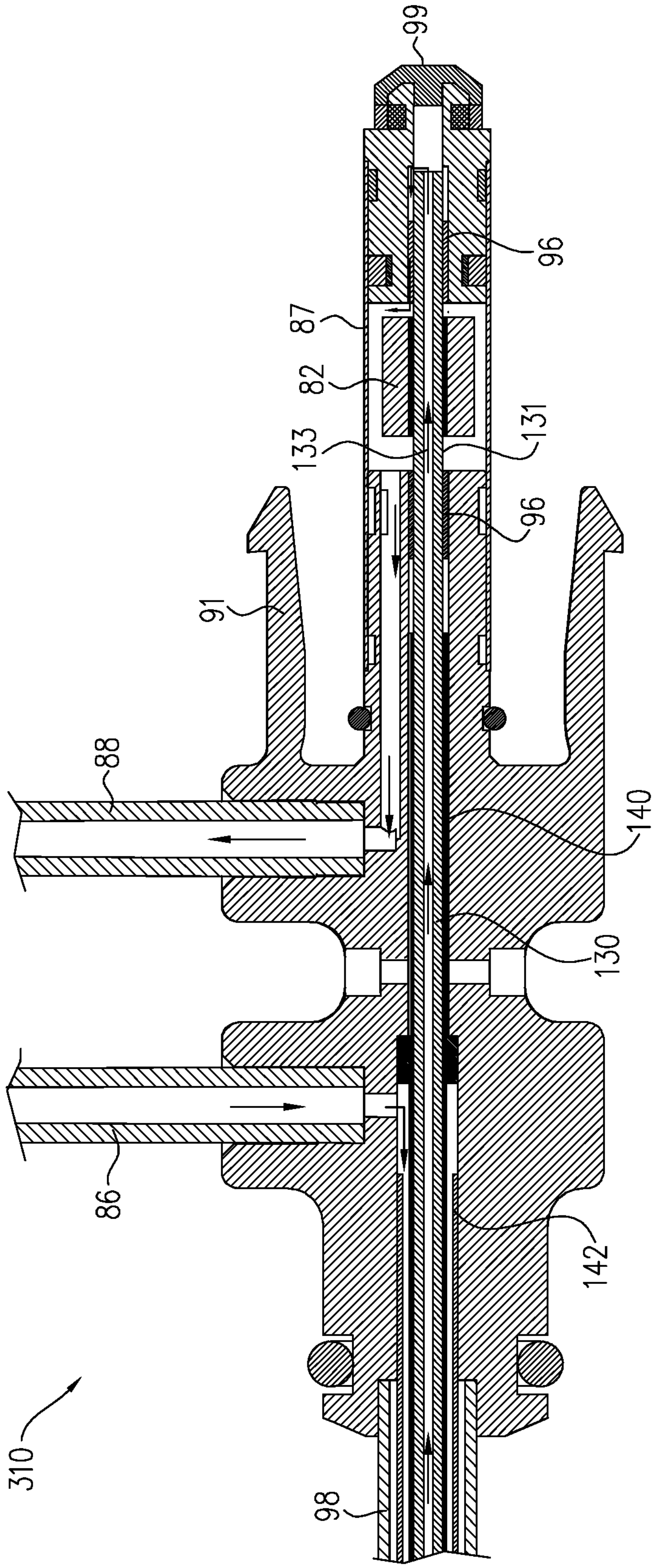

Reference is now made to FIGS. 15A-C, which are schematic illustrations showing a lumen that is used as a guidewire lumen and as a purging fluid lumen, in accordance with some applications of the present invention. For some applications, a continuous lumen extends from the proximal end of the driven-magnet unit 310 (shown in FIG. 15C) to the distal end of distal-tip element 107 (shown in FIGS. 15A-B). Typically, at respective portions along the length of the ventricular assist device, the lumen is defined by respective components. Further typically, starting from its proximal end, the lumen is defined by lumen 133 of pin 131 (FIG. 15C), a lumen 132 of drive cable 130 and axial shaft 92 (FIG. 15B), and then lumen 122 of distal-tip element 107 (FIG. 15A).

Referring to FIG. 15A, for some such applications, the ventricular device is guided to the aorta and to the left ventricle over guidewire 10. Typically, a valve 160 (such as a duckbill valve) is disposed at the distal end of lumen 122, within distal-tip element 107, and the guidewire is inserted through the valve. The guidewire passes through lumen 122 (of the distal-tip portion), and then passes into lumen 132 which is defined by the axial shaft at that point. The guidewire then continues to pass through lumen 132 all the way until the proximal end of the drive cable. From the proximal end of the drive cable, the guidewire passes through lumen 133 defined by pin 131, which is disposed outside of the subject's body even after insertion of the distal end of ventricular assist device 20 into the subject's left ventricle. Typically, as shown in FIG. 15C, a valve 99 (such as a duckbill valve) is disposed at the proximal end of lumen 133 within driven-magnet unit 310, and the guidewire passes out of the proximal end of the driven-magnet unit via the valve. Typically, when the distal end of the ventricular assist device is disposed inside the subject's left ventricle, the guidewire is retracted from the subject's body by pulling the guidewire out of the proximal end of lumen 133. Subsequently, the axial position of driven magnet 82 (within which pin 131 is disposed) is fixed such as to be disposed between driving magnets 77, as shown in FIG. 7A. For example, a portion of motor unit 23 in which the driven magnet is disposed may be coupled to a portion of the motor unit in which driving magnets 77 are disposed using snap-fit prongs 91 (FIG. 15C).

For some applications, by using lumen 132 of the axial shaft and the cable in the above-described manner, it is not necessary to provide an additional guidewire guide to be used during insertion of left-ventricular assist device 20. For some applications, the axial shaft and the drive cable each have outer diameters of more than 0.6 mm (e.g., more than 0.8 mm), and/or less than 1.4 mm (e.g., less than 1 mm), e.g., 0.6-1.4 mm, such as 0.6-1.2 mm or 0.8-1 mm. For some applications, the diameter of lumen 132, defined by the shaft and the cable, is more than 0.3 mm (e.g., more than 0.4 mm), and/or less than 0.7 mm (e.g., less than 0.6 mm), e.g., 0.3-0.7 mm, or 0.4-0.6 mm. For some applications, drive cable 130 has a total length of more than 1 m (e.g., more than 1.1 m), and/or less than 1.4 m (e.g., less than 1.3 m), e.g., 1-1.4 m, or 1.1-1.3 m. Typically, the diameters of lumen 122 and lumen 133 are generally similar to that of lumen 132.

For some applications, the continuous lumen is additionally used by purging system 29 (shown in FIG. 1A) of the ventricular assist device. Typically, both the first and second outer tubes 140, 142 remain stationary, during rotation of the drive cable. For some applications, purging system 29 controls the flow of a purging fluid (e.g., a fluid containing glucose or dextrose) via inlet port 86 and outlet port 88 (FIG. 15C). The fluid is configured to remove air from the space between the drive cable and first outer tube 140, and/or to reduce frictional forces between drive cable 130 (which rotates), and first outer tube 140 (which remains stationary during rotation of the drive cable), and/or to reduce frictional forces between axial shaft 92 and proximal bearing 116 (FIG. 5A) and/or distal bearing 118.

Referring to FIG. 15B, for some applications, the purging fluid is pumped between the first and second outer tubes 140, 142, and there is an opening 161 within the first outer tube in the vicinity of the proximal bearing. For some applications, the purging fluid is pumped via a purging-fluid channel 226 defined between the first and second outer tubes. For some applications, the purging fluid flows between first outer tube 140 and drive cable 130 via opening 161, as indicated by a purging-fluid-flow arrow 162*a* in FIG. 15B. In this manner, the interface between drive cable 130 (which rotates), and first outer tube 140 (which acts as the drive-cable-bearing tube and remains stationary, during rotation of the drive cable) is purged. For some applications, some of the purging fluid additionally flows to the interface between the axial shaft and proximal bearing 116, thereby purging the interface (and/or reducing frictional forces at the interface), as indicated by another purging-fluid-flow arrow 162*b* in FIG. 15B. Typically, the flow of the purging fluid in the direction of arrow 162*b* also prevents blood from flowing into the interface between the axial shaft and the proximal bearing.

As described hereinabove, typically, the drive cable includes a plurality of coiled wires. For some applications, purging fluid passes into lumen 132 defined by the drive cable via gaps in the coiled wires. Once the purging fluid is disposed within lumen 132 it flows in both proximal and distal directions, as indicated by a bidirectional purging-fluid-flow arrow 162*c* of FIG. 15B. The purging fluid that flows in the distal direction typically flows out of the distal end of lumen 132 and toward lumen 122 defined by distal-tip portion 120 (FIG. 15A). At the end of distal-tip portion, the purging fluid is typically prevented from flowing out of the distal-tip portion by valve 160. Therefore, some of the purging fluid typically flows to the interface between the axial shaft and distal bearing 118, thereby purging the interface (and/or reducing frictional forces at the interface), as indicated by purging-fluid-flow arrows 162*d* in FIG. 15B. Typically, the flow of the purging fluid in the direction of arrows 162*d* also prevents blood from flowing into the interface between the axial shaft and the distal bearing.

As described above, once the purging fluid is disposed within lumen 132 it flows in both proximal and distal directions, as indicated by arrow 162*c* of FIG. 15B. Referring now to FIG. 15C, typically, the purging fluid is pumped into the channel between the first and second outer tubes 140, 142 via inlet port 86. Typically, purging fluid flows back toward the proximal end of the device via the drive cable. Further typically, at the proximal end of the device, the purging fluid flows out of the proximal end of lumen 132 and then out of the proximal end of lumen 133 defined by pin 131. Typically, the purging fluid flows such as to purge interfaces between pin 131 and radial bearing 96, thereby reducing frictional forces at these interfaces. For some applications, the purging fluid flows around driven magnet 82, such as to reduce frictional forces that the driven magnet is exposed to. For some applications, the purging fluid then flows out of outlet port 88. Typically, the purging fluid is then disposed of. Alternatively, the purging fluid is pumped back into the device, via inlet port 86.

Referring again to FIG. 7D, for some applications, ventricular assist device 20 includes an additional purging fluid inlet port 89, which is typically used to pump purging fluid into channel 224 (FIG. 12A) between delivery catheter 143 and second outer tube 142. For some applications, rather than continuously pumping purging fluid into channel 224, fluid is pumped into this channel periodically, in order to flush the channel. For some applications, port 89 and channel 224 are used for aortic pressure sensing. For example, a pressure sensor 216 (which is illustrated schematically in FIG. 1A) may be configured to measure pressure within channel 224, within port 89, and/or at a different location that is in fluid communication with channel 224.

Figure 16A:
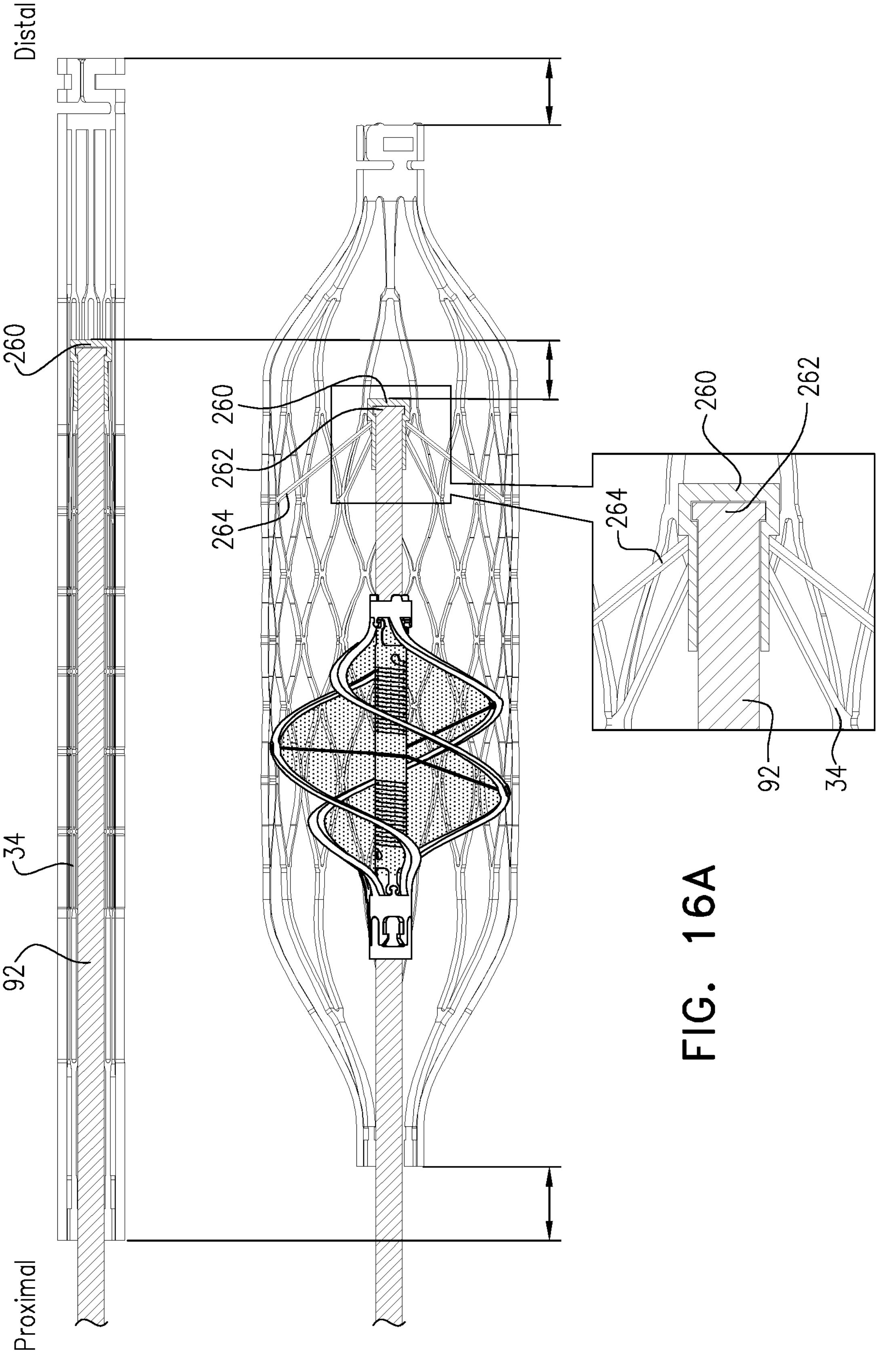
FIG. 16A is a schematic illustration of a pump-head portion of a ventricular assist device that includes a thrust bearing, in accordance with some applications of the present invention.

Reference is now made to FIG. 16A, which is a schematic illustration of a pump-head portion of a ventricular assist device that includes a distal thrust bearing 260, in accordance with some applications of the present invention. Typically, bearing 260 functions as both a distal radial bearing and a distal thrust bearing. The upper view of the ventricular device shown in FIG. 16A shows the device in its radially-constrained (i.e., crimped) configuration, while the lower view shows the device in its non-radially constrained configuration, with the arrows representing the movement of respective portions of the device between these two configurations.

Some applications of the present invention are described hereinabove as being directed toward a ventricular assist device that does not include any thrust bearing disposed within the subject's body and that is configured to allow axial back-and-forth motion of impeller 50 and axial shaft 92. For some alternative applications, the ventricular assist device does include a thrust bearing that is disposed distally from axial shaft 92 so as to inhibit distal movement of the axial shaft beyond the thrust bearing. Optionally, the thrust bearing may further inhibit proximal movement of the axial shaft, such that the thrust bearing may prevent any axial movement of the axial shaft. For example, in some embodiments, thrust bearing 260 prevents axial shaft 92 from undergoing axial motion in response to variations in the pressure gradient against which the impeller is pumping (thereby, typically, preventing the impeller from undergoing axial motion in response to variations in the pressure gradient against which the impeller is pumping).

For some applications, thrust bearing 260 is disposed within frame 34 as shown. For example, the thrust bearing may be disposed within the cylindrical portion of the frame or within the distal conical portion of the frame. For some applications, at a distal end of axial shaft, the axial shaft defines a widened portion 262 that is configured to engage the thrust bearing and to prevent the axial shaft (and thereby prevent the impeller) from undergoing axial motion. (In addition, the widened portion of the axial shaft is constrained radially by bearing 260, such that the bearing also functions as a distal radial bearing.) For some applications, the thrust bearing is coupled to the frame via connecting struts 264, which extend radially inwardly from the frame to the thrust bearing. Typically, in order to manufacture frame 34, the frame is cut from a tube of a shape-memory alloy, such as nitinol. For some applications, connecting struts 264 are cut from the tube from which the frame is cut, such that the frame and the connecting struts form a single integral body, without requiring coupling to each other (e.g., via adhesive, welding, etc.). In general, for some applications, the frame and the connecting struts are cut from a single piece of a material such as to form a single integral body. For some applications, connecting struts 264 as well as thrust bearing 260 itself are cut from the tube from which the frame is cut, such that the frame, the connecting struts, and the thrust bearing form a single integral body, without requiring coupling to each other (e.g., via adhesive, welding, etc.). In general, for some applications, the frame, the connecting struts, and thrust bearing 260 itself are cut from a single piece of a material such as to form a single integral body.

Figure 16B:
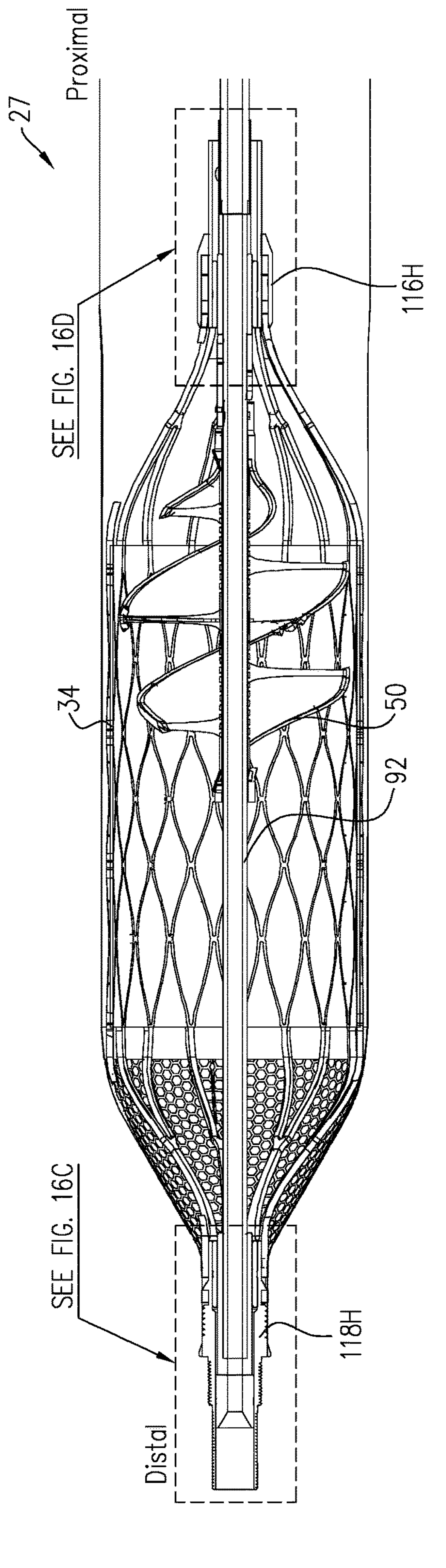
FIG. 16B is a schematic illustration of a pump-head portion of a ventricular assist device, in accordance with some embodiments of the present invention.

Reference is now made to FIG. 16B, which is a schematic illustration of pump-head portion 27 of ventricular assist device 20, in accordance with some embodiments of the present invention. As indicated in FIG. 16B, a distal portion of pump-head portion 27 is enlarged in FIG. 16C, while a proximal portion of pump-head portion 27 is enlarged in FIG. 16D.

Figure 16C:
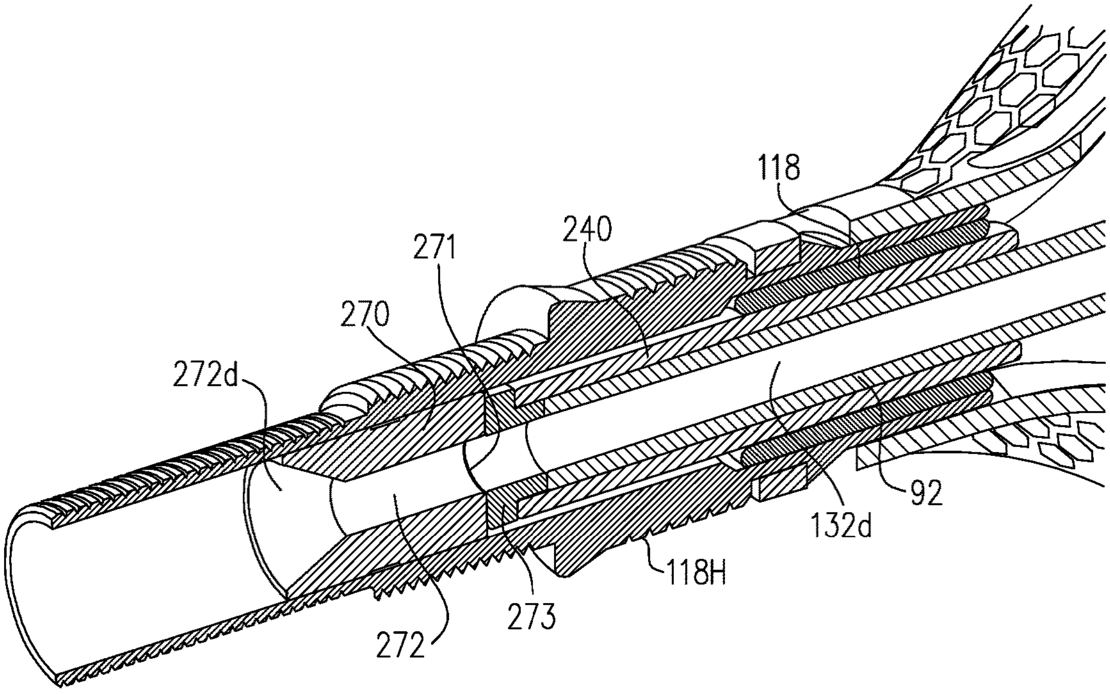
FIG. 16C is a schematic illustration of a distal portion of the pump-head portion shown in FIG. 16B, in accordance with some embodiments of the present invention.
Figure 16D:
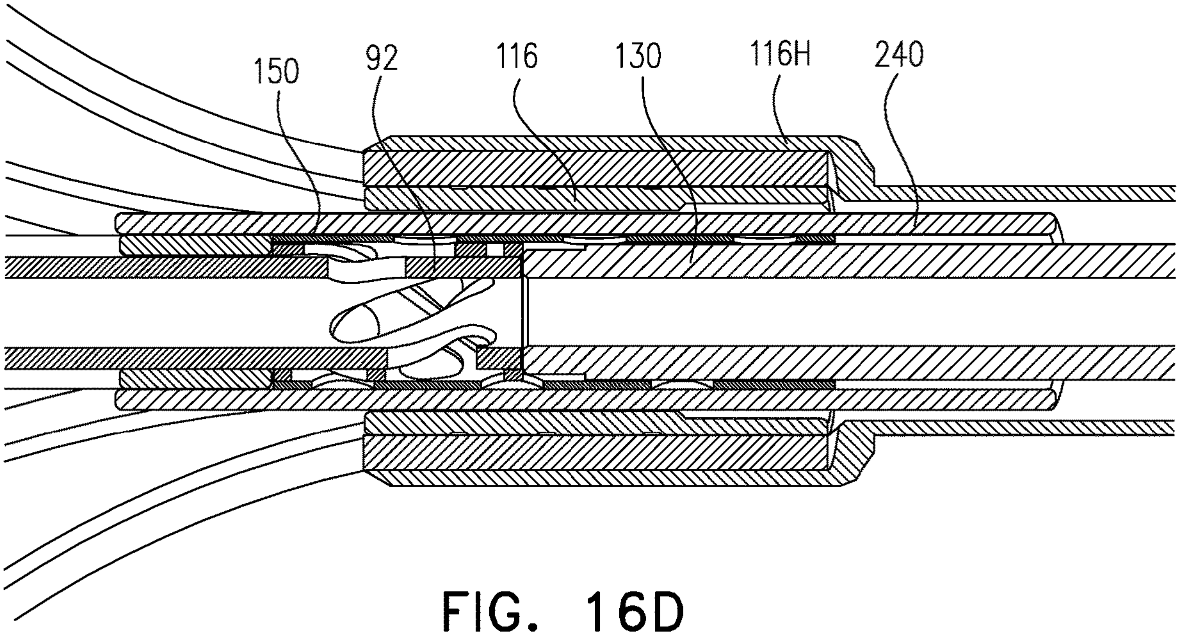
FIG. 16D is a schematic illustration of a proximal portion of the pump-head portion shown in FIG. 16B, in accordance with some embodiments of the present invention.

Reference is now made to FIG. 16C. As stated with reference to FIG. 16A, although some applications of the present invention are described hereinabove as being directed toward a ventricular assist device that does not include any thrust bearing disposed within the subject's body and that is configured to allow axial back-and-forth motion of impeller 50 and axial shaft 92, for some alternative applications, the ventricular assist device does include a thrust bearing that is configured to reduce or prevent axial motion of axial shaft 92 in response to variations in the pressure gradient against which the impeller is pumping (and, typically, to thereby prevent the impeller from undergoing axial motion in response to variations in the pressure gradient against which the impeller is pumping).

For some applications, a thrust bearing 270 is disposed within distal bearing housing 118H, adjacent to the distal end of axial shaft 92. Typically, the distal end of the axial shaft is configured to be in contact with the distal thrust bearing. When the impeller pumps blood in the proximal direction, this causes the axial shaft to be biased in the distal direction. The thrust bearing prevents distal movement of the axial shaft, such that the axial shaft and the impeller typically remain in axially fixed positions within frame 34.

In some embodiments, thrust bearing 270 comprises a proximally-facing ceramic surface 271 comprising, for example, zirconia. A distally-facing ceramic cover 273, comprising zirconia for example, covers the distal end of axial shaft 92, such that ceramic cover 273 contacts ceramic surface 271 as the axial shaft rotates. Thus, advantageously, there is a low-friction interface between the axial shaft and the thrust bearing.

For some applications, the thrust bearing is made of a ceramic material (e.g., zirconia), i.e., the thrust bearing comprises a piece of ceramic comprising proximally-facing ceramic surface 271. In other embodiments, the thrust bearing is made of a different material but is coated with a ceramic material, i.e., the thrust bearing comprises the proximally-facing ceramic surface by virtue of being coated with a ceramic coating.

It is noted that thrust bearing 270 differs from thrust bearing 260 of FIG. 16A, in that thrust bearing 270 is entirely distal to the distal end of the axial shaft. Nonetheless, the features described herein with reference to thrust bearing 270, such as a low-friction ceramic-ceramic interface, may likewise be implemented for thrust bearing 260.

As described hereinabove, for some such applications, the axial shaft is covered with ceramic sleeves 240 (e.g., zirconia sleeves) along regions of the axial shaft that come into contact with either of the proximal and distal bearings 116, 118 during operation of the ventricular assist device. In this manner, the radial interfaces between the axial shaft and the proximal and distal bearings are ceramic-ceramic interfaces. For some applications, the ceramic sleeve at the distal end of the axial shaft extends around the distal end of the axial shaft, such that the axial interface between the axial shaft and thrust bearing 270 is a ceramic-ceramic interface. In other words, a ceramic cap, which comprises ceramic cover 273, fits around the distal end of the axial shaft, such that the ceramic cap covers both the distal end and side wall of the axial shaft. (Thus, in effect, ceramic cover 273 and ceramic sleeve 240 are combined into a single element.) In other embodiments, as shown in FIG. 16C, a separate ceramic covering is applied to the distal end of the axial shaft, such that the axial interface between the axial shaft and thrust bearing 270 is a ceramic-ceramic interface. In other words, ceramic cover 273 covers the distal end of the axial shaft, while ceramic sleeve 240 covers the side wall of the axial shaft. (Typically, in such embodiments, ceramic cover 273 is coupled to ceramic sleeve 240.)

In some embodiments, axial shaft 92 is shaped to define a shaft lumen 132*d*, which is the distal portion of lumen 132 (FIG. 15B), which extends through the drive cable and axial shaft. For some applications, the thrust bearing defines a bearing lumen 272 therethrough. Typically, bearing lumen 272 functions as a portion of the continuous lumen through the device that is used for guidewire insertion and/or as a purging fluid channel, as described hereinabove with reference to FIG. 15A. In other words, bearing lumen 272 is continuous with shaft lumen 132*d*.

For some applications, at least a portion of bearing lumen 272 is frustoconically-shaped, with a wider end of the bearing lumen facing distally. In other words, at its distal end 272*d*, the lumen defines a portion of a cone, with a wide end of the cone-portion facing the distal direction. Typically, the frustoconical portion of the lumen facilitates the advancement of the guidewire through the thrust bearing in the distal-to-proximal direction.

For some applications, thrust bearing 270 is configured such as to allow proximal (or "reverse") flow of fluid (in particular, purging fluid) into the interface between the distal end of the axial shaft and the thrust bearing (e.g., between ceramic cover 273 and proximally-facing ceramic surface 271). For some such applications, the thrust bearing defines at least one additional bearing lumen (not shown) for proximal flow of the purging fluid, through the additional bearing lumen, into the interface. In other words, to facilitate the flow of purging fluid in the distal-to-proximal direction and through the interface between the thrust bearing and the axial shaft, the thrust bearing may define one or more additional flow channels.

Reference is now made to FIG. 16D.

Typically, when the ventricular assist device includes a thrust bearing within the pump-head portion, the impeller and the axial shaft do not undergo axial back-and-forth motion. This is because, when the impeller pumps blood in the proximal direction, this causes the axial shaft to be biased in the distal direction. The thrust bearing prevents distal movement of the axial shaft, such that the axial shaft and the impeller remain in axially fixed positions within frame 34.

For some such applications, and even for some applications in which there is no thrust bearing (such that proximal bearing housing 116H houses proximal radial bearing 116 but no thrust bearing, and the impeller and axial shaft undergo axial motion), drive cable 130 is coupled to axial shaft 92 within the proximal bearing housing. In other words, the interface between the distal end of drive cable 130 and the proximal end of axial shaft 92 (i.e., the location at which the drive cable and the axial shaft are coupled to each other) is within the proximal bearing housing 116H. Typically, the proximal bearing housing is rigid, such that the proximal bearing housing protects the location at which the drive cable and the axial shaft are coupled to each other from being exposed to forces, such as bending forces, that could weaken the coupling and thereby damage the ventricular assist device. For example, the proximal bearing housing may inhibit bending of the drive cable within the bearing housing.

Typically, in such embodiments, the radial separation between the proximal bearing housing and the distal end of the drive cable, which is within the proximal bearing housing, is less than 2 mm, e.g., less than 1 mm. Advantageously, this small radial separation may help inhibit bending of the drive cable.

For some applications, the drive cable and the axial shaft are coupled to each other using the apparatus and methods described with reference to FIGS. 14A-H. Thus, for example, FIG. 16D shows coupling tube 150 disposed partly within the proximal bearing housing. For some applications, coupling tube 150 (which is used to couple the drive cable to the axial shaft) is itself made out of ceramic (e.g., zirconia) and is configured to provide the function of sleeve 240, thereby typically obviating the need for sleeve 240 in addition to coupling tube 150.

As described above, proximal radial bearing 116 surrounds the axial shaft and is configured to radially stabilize the axial shaft while the axial shaft rotates. A proximal sleeve 240 is disposed around the axial shaft such that proximal sleeve 240 contacts proximal radial bearing 116 as the axial shaft rotates. Similarly, distal radial bearing 118 (FIG. 16C) surrounds the axial shaft distally from the proximal radial bearing and is configured to radially stabilize the axial shaft while the axial shaft rotates. A distal sleeve 240 is disposed around the axial shaft distally from the proximal sleeve such that the distal sleeve contacts the distal radial bearing as the axial shaft rotates.

For some applications, when the ventricular assist device includes a thrust bearing within the pump-head portion (and therefore the impeller and axial shaft do not undergo axial back-and-forth motion), sleeves 240 (which are placed around the axial shaft at the interfaces between the axial shaft and the proximal and distal radial bearings) are shorter than in cases in which the ventricular assist device does not include a thrust bearing within the pump-head portion (and in which the impeller and axial shaft undergo axial back-and-forth motion). This is because the portion of the axial shaft that is located at the interfaces with the proximal and distal radial bearings is relatively fixed. For some applications, the length of each of the proximal and distal radial bearings are between 2 and 4 mm (e.g., approximately 3 mm) and the length of each of the sleeves is between 2.5 and 4.5 mm (e.g., approximately 3.5 mm). For some applications, the length of each of the sleeves is between 4 and 6 mm (e.g., approximately 5 mm), in order to provide a larger margin at the ends of the radial bearings.

For some applications, the axial shaft is more flexible than the sleeves. For example, the sleeves may be made of a ceramic material (e.g., zirconia), and the axial shaft may be made of a material more flexible than ceramic, such as nitinol or another shape-memory alloy. Typically, it is desirable for the axial shaft to be sufficiently flexible as to pass through curved portions of the vasculature during delivery of the device to the left ventricle, but also sufficiently rigid to be able to provide support to the impeller during the operation of the impeller without the axial shaft undergoing vibration.

For some such applications, the lengths of the sleeves relative to the length of the shaft is configured to provide a desired overall flexibility to the axial shaft and/or to provide a desired flexibility to respective portions of the axial shaft. For example, the ratio between the length of the axial shaft and the combined length of the proximal and distal sleeves may be more than 2:1 (e.g., more than 3:1) and/or less than 6:1 (e.g., less than 5:1), for example between 2:1 and 6:1 or between 3:1 and 5:1. For some such applications, the length of the axial shaft is between 30 and 50 mm, e.g., between 35 mm and 45 mm. As described hereinabove, the length of each of the proximal and distal sleeves may be between 4 and 6 mm (e.g., approximately 5 mm), such that the combined length of the sleeves is 8-12 mm, in order to provide a larger margin at the ends of the radial bearings.

Figure 16E:
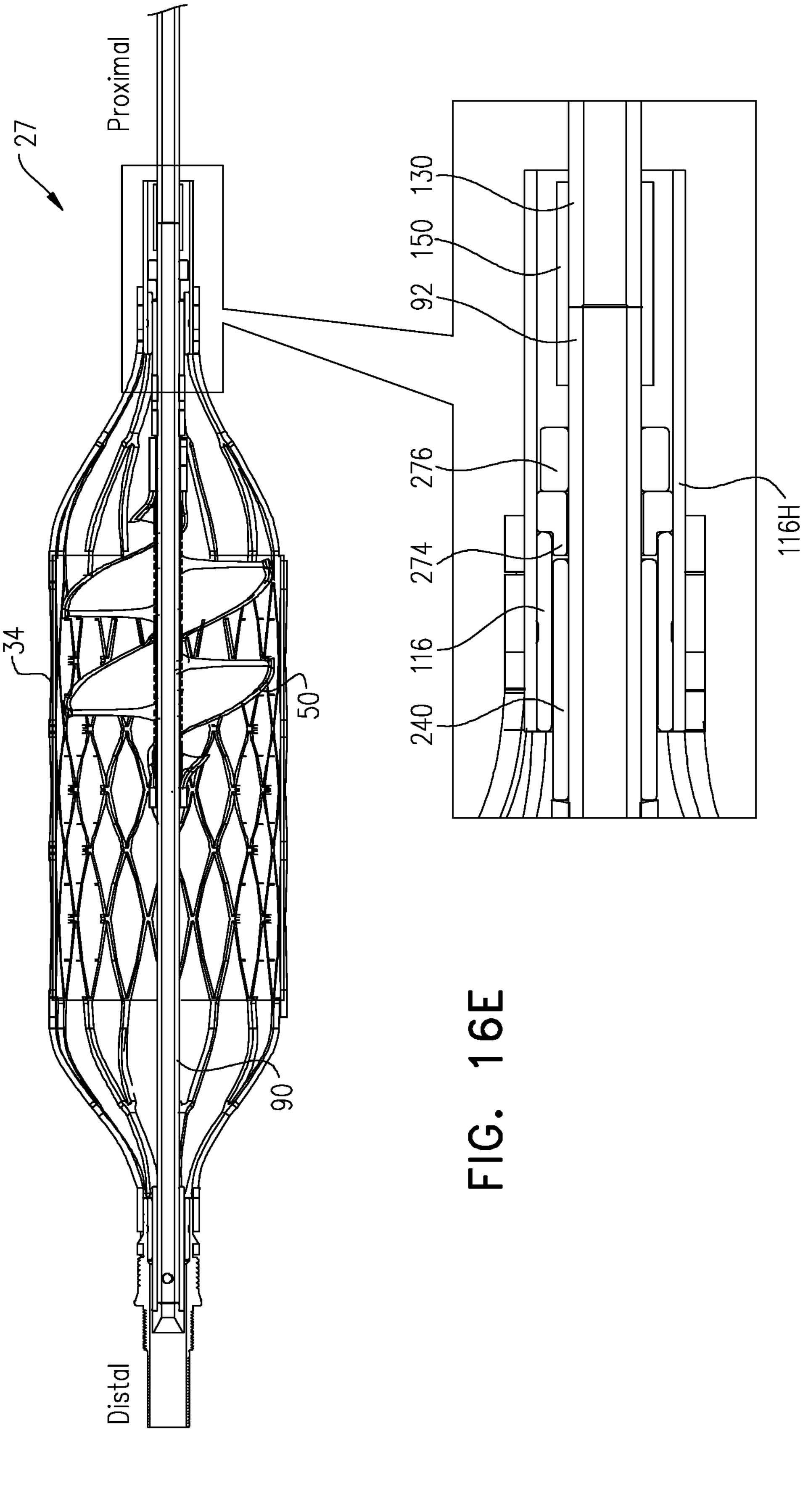
FIG. 16E is a schematic illustration of a pump-head portion of a ventricular assist device, a proximal portion of which includes a thrust bearing, in accordance with some embodiments of the present invention.

Reference is now made to FIG. 16E, which is a schematic illustration of pump-head portion 27 of ventricular assist device 20 that includes a thrust bearing 274, in accordance with some applications of the present invention, in accordance with some applications of the present invention. For some applications, thrust bearing 274 is disposed within proximal bearing housing 116H, adjacent to the proximal portion of axial shaft 92. For some such applications, a flange 276 extends radially from the proximal portion of axial shaft 92. For some applications, the thrust bearing is made of a ceramic material (e.g., zirconia). For some such applications, flange 276 is coated with (or made of) a ceramic material (e.g., zirconia). Thus, the interface between the flange and the thrust bearing is a ceramic-ceramic interface. Typically, the flange is configured to be in contact with the proximal thrust bearing. When the impeller pumps blood in the proximal direction, this causes the axial shaft to be biased in the distal direction. The thrust bearing prevents distal movement of the axial shaft, by holding the flange in place, such that the axial shaft and the impeller remain in axially fixed positions within frame 34. For some applications, thrust bearing 274 comprises a first portion of a shaped element (e.g., a shaped ceramic element), with the shaped element defining a second portion that functions as proximal radial bearing 116.

Figure 17A:
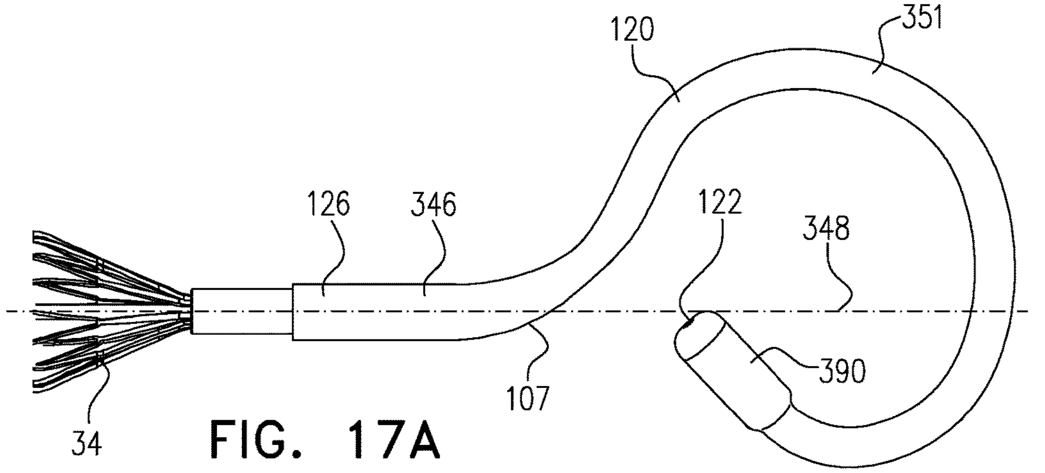
FIGS. 17A, 17B, 17C, and 17D are schematic illustrations of a distal-tip portion of a ventricular assist device, in accordance with some applications of the present invention.

Reference is now made to FIGS. 17A, 17B, 17C, and 17D, which are schematic illustrations of a distal-tip portion 120 of ventricular assist device 20, in accordance with some applications of the present invention. As described hereinabove, distal-tip portion 120 typically forms a portion of distal-tip element 107 which also includes axial-shaft-receiving tube 126. Typically, distal-tip element 107 is configured such that in its non-constrained configuration (i.e., in the absence of any forces acting upon the distal-tip portion), the distal-tip element is at least partially curved. Referring to FIG. 17A, for some applications, within a given plane, distal-tip element 107 has a proximal, straight portion 346 (at least a portion of which typically comprises axial-shaft-receiving tube 126). The proximal straight portion of distal-tip element 107 defines a longitudinal axis 348. The curved portion of distal-tip element 107 curves away from longitudinal axis 348 in a first direction, and then passes through an inflection point and curves in the opposite direction with respect to longitudinal axis 348. For example, as shown in FIG. 17A, within the plane of the page, the distal-tip element first curves to the top of the page, then curves to the bottom of the page. Typically, when shaped as shown in FIG. 17A, the distal-tip element defines an overall curvature that is similar to that of a question mark or a tennis-racket, the distal-tip element defining a bulge 351 on one side of the longitudinal axis of the straight proximal straight portion of the distal-tip element. For some applications, the bulge is generally shaped as a semi-ellipse. (It is noted that in this context, the term "semi-ellipse" includes a semi-circle. It is further noted that in some cases, the tip does not define a precise semi-ellipse, but rather a bulged shape that is substantially similar to a semi-ellipse) Typically, upon being deployed within the subject's left ventricle, the curvature of the curved portion of distal-tip element 107 is configured to provide an atraumatic tip to ventricular assist device 20. Further typically, the distal-tip element is configured to space the inlet openings 108 of the ventricular assist device from walls of the left ventricle.

Figure 17B:
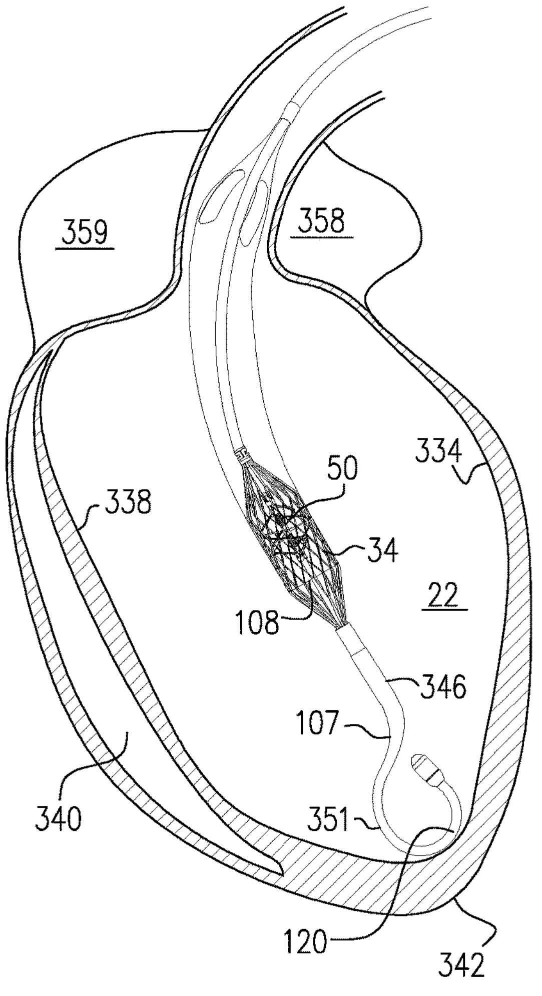
Figure 17C:
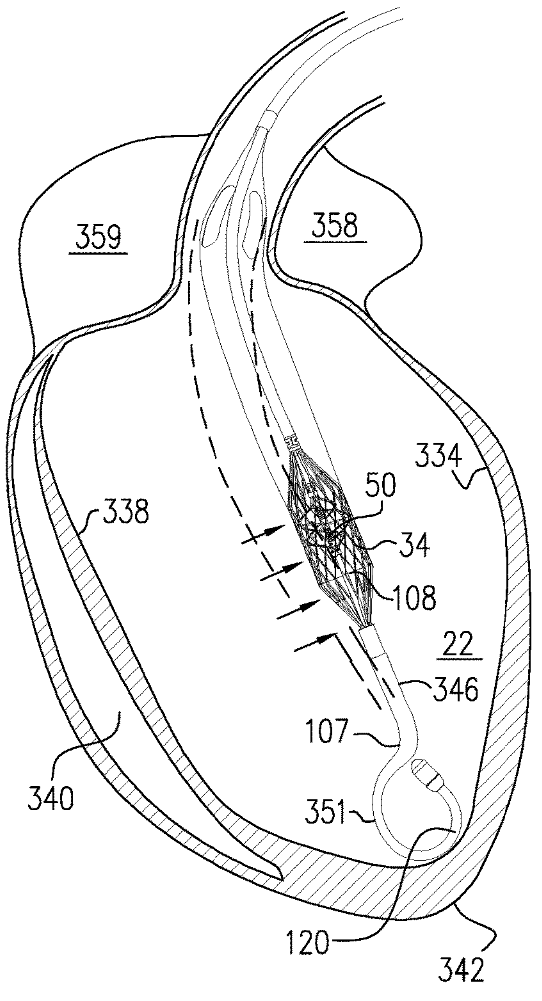

Referring now to FIGS. 17B and 17C, it is first noted that these figures show a cross-sectional view of the left ventricle 22 in which septal wall 338 is disposed on the left of the page and free wall 334 is disposed on the right of the page. In this view, the left atrium 359, and left atrial appendage 358 are visible above the left ventricle, and right ventricle 340 is visible to the left of the left ventricle. It is noted that the view of the aorta and the left ventricle as shown in FIGS. 17B and 17C is different to that shown, for example, in FIG. 1B. FIG. 1B is a schematic illustration, provided for illustrative purposes, and does not properly depict the scale and orientation of the ventricular assist device with respect to the anatomy.

For some applications, distal-tip element 107 is configured to separate the blood inlet opening from a posterior wall of the subject's left ventricle when the distal-tip element is placed against the apex of the subject's left ventricle. Typically, the distal-tip element is configured to separate the blood-inlet opening from a septal wall of the subject's left ventricle as the distal-tip element contacts the apex of the subject's left ventricle.

Typically, distal-tip element 107 is inserted into the left ventricle, such that bulge 351 bulges toward the septal wall 338. When disposed in this configuration, in response to distal-tip element 107 being pushed against the apex (e.g., due to a physician advancing the device or in response to movement of the left ventricle), blood inlet openings 108 typically get pushed in the direction of free wall 334 and away from the septal wall 338 (in the direction of the arrows shown in FIG. 17C). Typically, this is due to proximal straight portion 346 pivoting about the curved portion of the question mark shape, as shown. By contrast, other shapes of tips, if disposed in a similar orientation, may result in the blood inlet openings being pushed toward the septal wall. For example, if the distal-tip element were to have a pigtail tip (in which the tip curves in a single direction of curvature) that is oriented such that the pigtail curve is on the free wall side of the longitudinal axis of the straight portion of the distal-tip element, then pushing the tip distally would typically cause the blood inlet openings to move toward the septal wall due to the loop of the pigtail curve tightening. Notwithstanding the above, however, it is noted that in some embodiments, distal-tip element 107 has a pigtail shape.

Figure 17D:
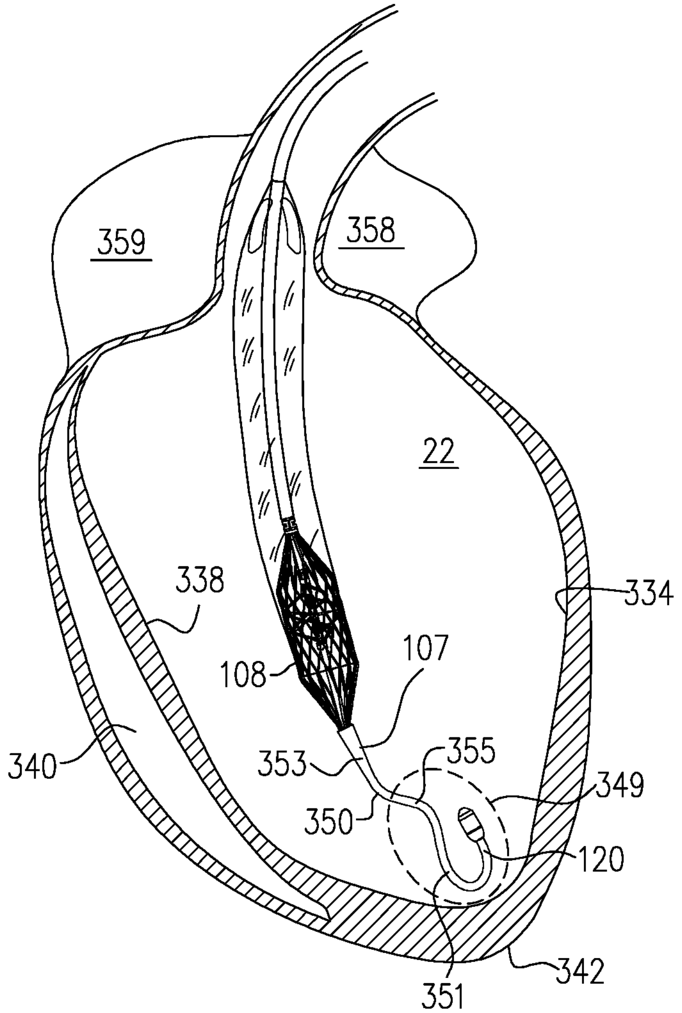

Referring now to FIG. 17D, for some applications, in addition to the above-described curvature of the distal-tip portion, the distal-tip portion has an additional curvature in a different plane from the above-described curvature. In particular, in addition to a distal curved portion 349, the distal-tip portion comprises a proximal curved portion 350, which does not lie in the same plane as the distal curved portion. (The two planes are different in the sense that they are not parallel to one another.)

In some embodiments, the tip portion further comprises a straight portion 353 proximal to proximal curved portion 350. Straight portion 353 may be configured to receive the axial shaft while the axial shaft rotates, as described above, with reference to FIG. 17A, for straight portion 346. Alternatively or additionally, purging fluid may flow through straight portion 353. For some applications, purging fluid flows until the distal end of the distal-tip portion, at which point valve 160 (FIG. 15A, e.g., a duckbill valve) as described herein prevents the purging fluid from flowing out of the distal end of the distal-tip portion.

In some embodiments, the angle between the distal end of the proximal curved portion and the axial shaft is between 100 and 170 degrees. Alternatively or additionally, the angle between the distal end of the proximal curved portion and the plane in which distal curved portion 349 lies is between 25 and 65 degrees, such as between 35 and 55 degrees. For some applications, the angle between the distal end of the proximal curved portion and the plane in which distal curved portion 349 lies is 60 and 120 degrees.

For example, as shown in FIG. 17D, proximal curved portion 350 may curve toward the apex 342 of the left ventricle, otherwise known as the apex of the heart. In other words, the proximal curved portion may be curved such that, following the insertion of the axial shaft into the left ventricle via the aorta, the distal end of the proximal curved portion (where the proximal curved portion meets distal curved portion 349) points toward apex 342.

In some embodiments, distally to proximal curved portion 350, the distal-tip portion undergoes the above-described curvature (i.e., the curvature that is similar to that of a question mark or a tennis-racket) in a second plane. In other words, distal curved portion 349 comprises a straight segment 355 (analogous to straight portion 346 of FIG. 17A) that defines a longitudinal axis, and a curved segment that is distal to straight segment 355 and curves in a first direction with respect to the longitudinal axis before passing through an inflection point and curving in a second direction with respect to the longitudinal axis, such that the curved segment defines bulge 351 on one side of the longitudinal axis. In other embodiments, distal curved portion 349 has a pigtail shape. For some applications, the proximal curved portion and the distal curved portion are continuous with each other. Typically, for such applications, the distal-tip portion does not include straight segment 355 between the proximal curved portion and the distal curved portion.

Typically, lumen 122 (FIG. 15A) passes through proximal curved portion 350 and distal curved portion 349. Also typically, valve 160 (FIG. 15A) is at the distal end of distal curved portion 349.

In some embodiments, the impeller of the blood pump is rotated (i.e., the blood pump is operated) while distal curved portion 349 pushes against apex 342. For some applications, the proximal curved portion is configured such that if the tip is pushed against apex 342, then even in the event that distal curved portion 349 curls up, the distal blood-inlet openings 108 are still pushed in the direction of free wall 334 and away from the septal wall 338, by the tip flexing about proximal curved portion 350.

Figure 18:
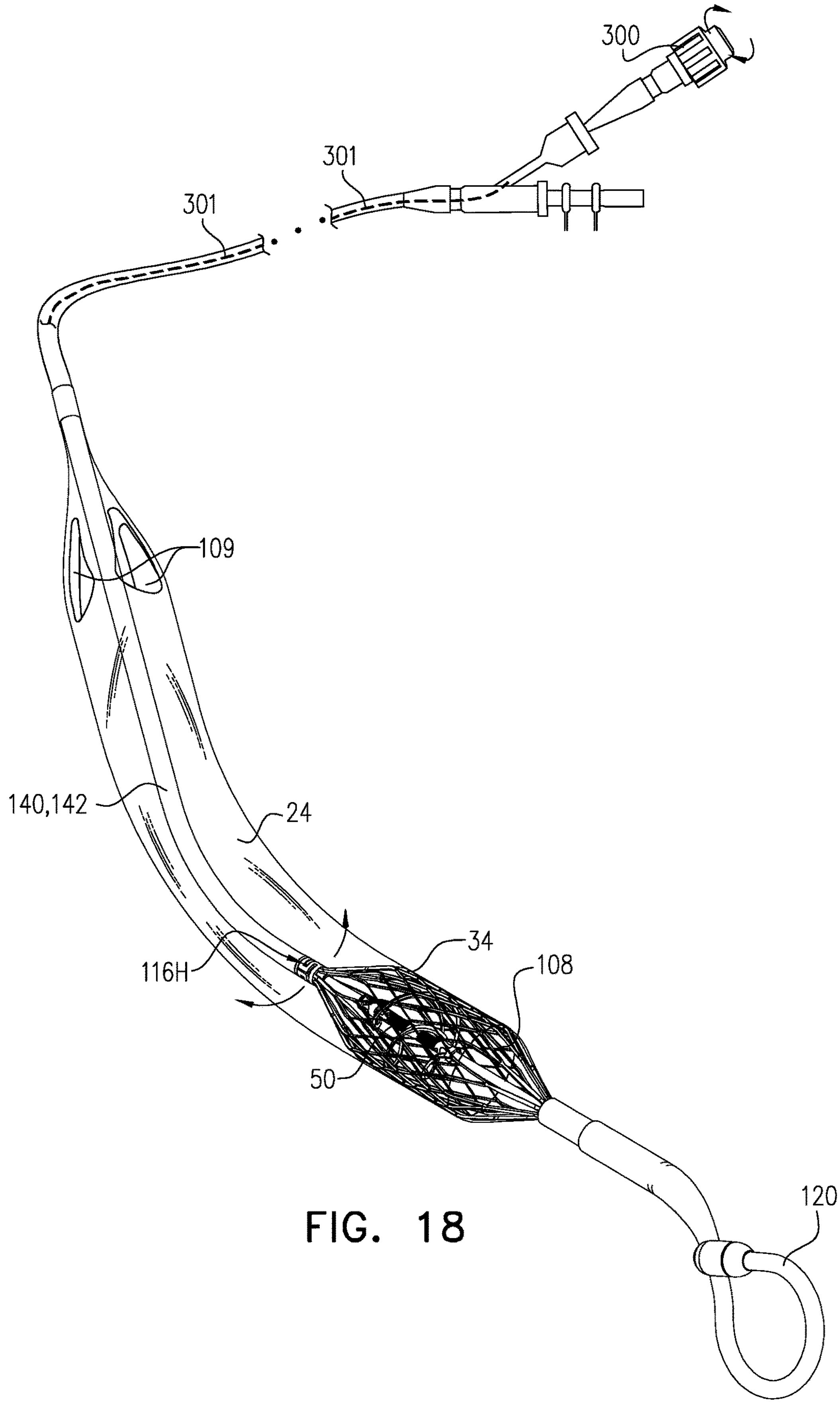
FIG. 18 is a schematic illustration of a steering mechanism that is used to steer a frame of a ventricular assist device with respect to a portion of the device disposed proximally thereto, in accordance with some applications of the present invention.

Reference is now made to FIG. 18, which is a schematic illustration of a steering mechanism that is used to steer frame 34 with respect to a portion of the device disposed proximally thereto, in accordance with some applications of the present invention.

In some embodiments, one or more steering wires 301 are coupled to frame 34 and are configured to extend from the frame, to outside the body of the subject, while the frame is within the body. In some embodiments, steering wires 301 pass through delivery tube 142. For example, the steering wires may be disposed between drive-cable-bearing tube 140 and the delivery tube.

In some embodiments, one of the steering wires is coupled to the proximal end of frame 34. Alternatively or additionally, one of the steering wires may be coupled to the distal end of frame 34. This coupling may be via proximal bearing housing 116H or distal bearing housing 118H, i.e., the steering wire may be coupled to the frame by virtue of being coupled to the proximal or distal bearing housing.

Typically, for such applications, handle 149 of the ventricular assist device comprises a steering control 300, and the steering wires are coupled to steering control 300 so as to be controllable via the steering control.

Advantageously, steering wires 301 may be configured for orienting the frame, e.g., prior to rotating the impeller so as to pump blood of the subject. For example, the steering wires may be configured to extend from the frame while the frame is within the left ventricle of the subject's heart, and the steering wires may be configured for orienting the frame within the left ventricle, e.g., such that the frame extends toward the apex of the left ventricle. The frame may be oriented by applying a force to a steering wire coupled to the proximal end of the frame while applying a counterforce to the delivery tube or to another steering wire coupled to the distal end of the frame.

For some such applications, a controller steers the proximal end of the frame with respect to a portion of the device disposed proximally thereto, for example, in order to direct the distal end of the frame to extend in the direction of the apex of the left ventricle. Typically, upon releasing the pump head within the left ventricle, the operator steers the proximal end of the frame in the above-described manner, in order to conform with the anatomy (e.g., the shape of the left ventricle) of the subject.

As described hereinabove with reference to FIG. 9B, for some applications, the ventricular assist device includes optical fibers 228 for blood-pressure measurement, which extend from a proximal end of the device to, for example, the proximal end of the frame. For some applications, optical fibers 228 are additionally used as steering wires, in the above-described manner. (In other words, the steering wires comprise respective optical fibers.) In other embodiments, one or more of the steering wires comprises an elongation-resistant fiber, such as an aramid fiber.

Figure 19A:
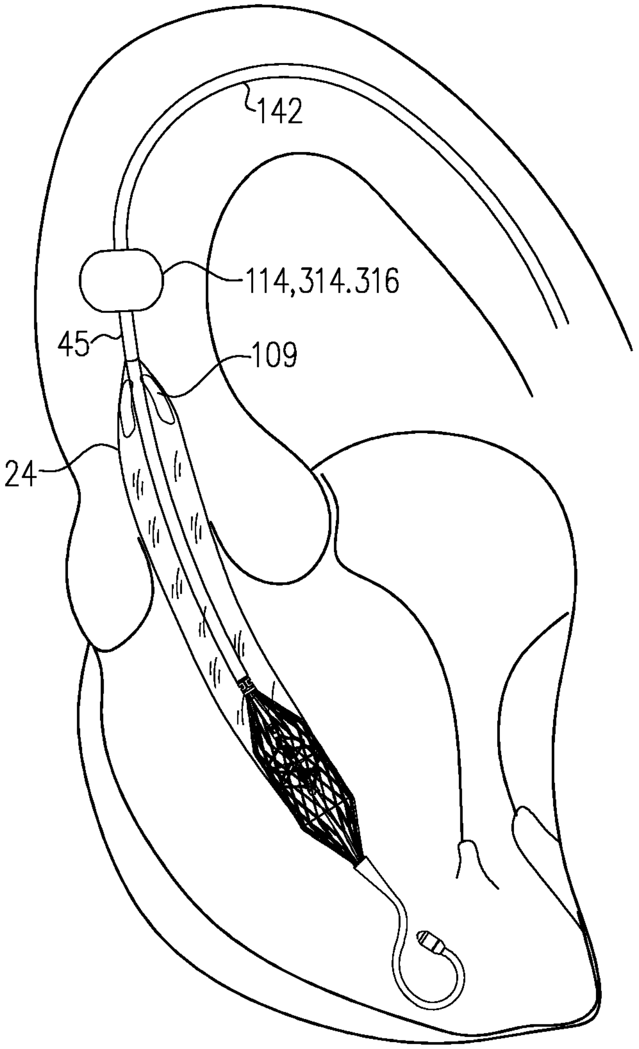
FIGS. 19A and 19B are schematic illustrations of an expandable element surrounding a delivery tube of a ventricular assist device, in accordance with some applications of the present invention.
Figure 19B:
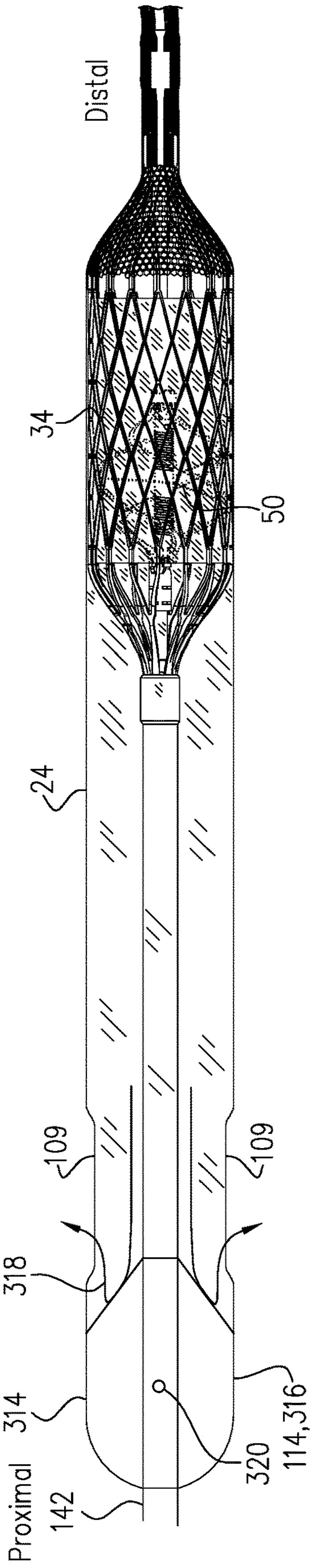

Reference is now made to FIGS. 19A-B, which are schematic illustrations of an expandable element surrounding delivery tube 142, in accordance with some applications of the present invention.

In some embodiments, an expandable element 314, such as an expandable stent, an expandable braided element, or an inflatable element 316 (e.g., a balloon 114), surrounds delivery tube 142 proximally to blood-outlet openings 109, with the length of the delivery tube between expandable element 314 and the blood-outlet openings being less than 30 mm. For example, expandable element 314 may be disposed in the vicinity of the interface between delivery tube 142 and the region at which the proximal end of pump-outlet tube 24 is coupled to the delivery tube (as shown in FIG. 19A).

In some embodiments, as shown in FIG. 19A, expandable element 314 is entirely proximal to the pump-outlet tube. In other embodiments, as shown in FIG. 19B, expandable element 314 is an inflatable element 316 (e.g., balloon 114), which when inflated, is disposed at least partly within, e.g., entirely within, pump-outlet tube 24.

Typically, expandable element 314, whether configured as shown in FIG. 19A, FIG. 19B (or FIG. 20A or FIG. 20B) is configured to center a portion of the ventricular assist device (e.g., a portion of delivery tube 142 and, in particular, the portion of the delivery tube near pump-outlet tube 24) within the aorta, by contacting the aorta wall or, if the expandable element is within the pump-outlet tube, by pushing the wall of the pump-outlet tube against the aorta wall.

In some embodiments, expandable element 314 is an inflatable element 316 that is shaped to direct the blood through blood-outlet openings 109, as indicated in FIG. 19B by blood-flow arrows 318. For example, the distal end of the inflatable element may have a width that decreases moving distally, e.g., the distal end may be frustoconical, such that the blood is directed by the distal end of the inflatable element, at an angle, through the blood-outlet openings.

For some applications, the inflatable element (e.g., balloon) is inflated using a fluid (e.g., a purging fluid), which is pumped through the ventricular-assist device. For example, as shown in FIG. 19B, the wall of the delivery tube may be shaped to define one or more openings 320, and inflatable element 316 may surround openings 320 such that a fluid flowing, via the openings, from the delivery tube into the inflatable element inflates the inflatable element. This fluid may include purging fluid, which, distally to openings 320, purges the interface between the axial shaft and the radial bearings, which don't rotate with the axial shaft.

It is noted that expandable element 314 may be combined with any of the embodiments of pump-outlet tube 24 described below with reference to FIGS. 33A-C.

As shown in FIG. 19A, for some applications, regardless of whether the ventricular assist device comprises expandable element 314, proximally to the proximal conical portion of the pump-outlet tube, the pump-outlet tube defines a tubular coupling portion 45, via which the proximal end of the pump-outlet tube is coupled (e.g., via an adhesive) to second outer tube 142 of the ventricular assist device. For some applications, the pump-outlet tube is manufactured using a single continuous tube, with respective portions of the pump-outlet tube being molded to define the tubular coupling portion, the proximal conical portion, the distal conical portion, and the cylindrical central portion. Typically, in such cases, the blood-inlet openings and the blood-outlet openings are cut (e.g., laser cut) from the tube. For some applications, rather than molding the tube to define the proximal conical section and the tubular coupling portion, initially the portion of the tube that will form the proximal conical section and the tubular coupling portion are shaped as a cylinder (which is typically continuous with the cylinder shape of the central portion). At its proximal end, strips are then cut (e.g., laser cut) from the tube, leaving other strips still attached to, and extending proximally from, the central cylindrical portion of the tube. The proximal ends of the strips are then adhered to outer tube 142 of the ventricular assist device, in such a manner that they define a conical portion of the pump-outlet tube that defines blood-outlet openings. (For some applications, some of the blood-outlet openings are laser cut from the tube, and other blood-outlet openings are formed by adhering the above-described strips to second outer tube 142 of the ventricular assist device.) For some applications, by forming the conical portion of the pump-outlet tube and the blood-outlet openings using the latter method, the thickness of the layer of the pump-outlet tube that is coupled to outer tube 142 is less than the thickness of the tubular coupling portion as formed by the former method. For some applications, this reduces the sharpness of the diameter change at the interface between the outer tube 142 and the region at which the proximal end of the pump-outlet tube is coupled to the outer tube.

For some applications, the pump-outlet tube is manufactured using a single continuous tube, with respective portions of the pump-outlet tube being molded to define the tubular coupling portion, the proximal conical portion, the distal conical portion, and the cylindrical central portion, as in the former method described in the above paragraph.

However, before adhering the tubular coupling portion to outer tube 142 of the ventricular assist device, the tubular coupling is cut (e.g., in a tapered manner), so as to reduce the thickness of the layer of the pump-outlet tube that is coupled to outer tube 142 and/or to prevent folds forming in the tubular coupling portion of the pump-outlet tube.

Typically, (a) blood-outlet openings 109 are defined by portions of the wall of the blood outlet tube that at least partially extends into the proximal conical portion of the pump-outlet tube, e.g., as shown in FIG. 19A, and/or (b) blood-outlet openings 109 are laterally facing, by virtue of being defined by the central cylindrical portion of pump-outlet tube 24, e.g., as shown in FIG. 19B. (As noted hereinabove, "laterally-facing blood-outlet openings" should be interpreted to mean that the blood-outlet openings are disposed laterally with respect to the longitudinal axis of the pump-outlet tube, by virtue of being defined by the central cylindrical portion of the pump-outlet tube. This is in contrast to blood-inlet openings that are described as "lateral blood-inlet openings," which are typically not oriented entirely laterally with respect to the longitudinal axis of the pump-outlet tube. Rather, they are obliquely disposed with respect to the longitudinal axis of the pump-outlet tube.) Examples of each type of blood-outlet openings are shown in respective figures in the present application. The scope of the present disclosure includes combining other features of the pump-outlet tube and/or other portions of the ventricular assist device with any configuration of blood-outlet openings that are described and/or shown in the present application.

Reference is now made to FIGS. 20A, 20B, 20C, and 20D, which are schematic illustrations of ventricular assist device 20, in accordance with some applications of the present invention.

Figure 20A:
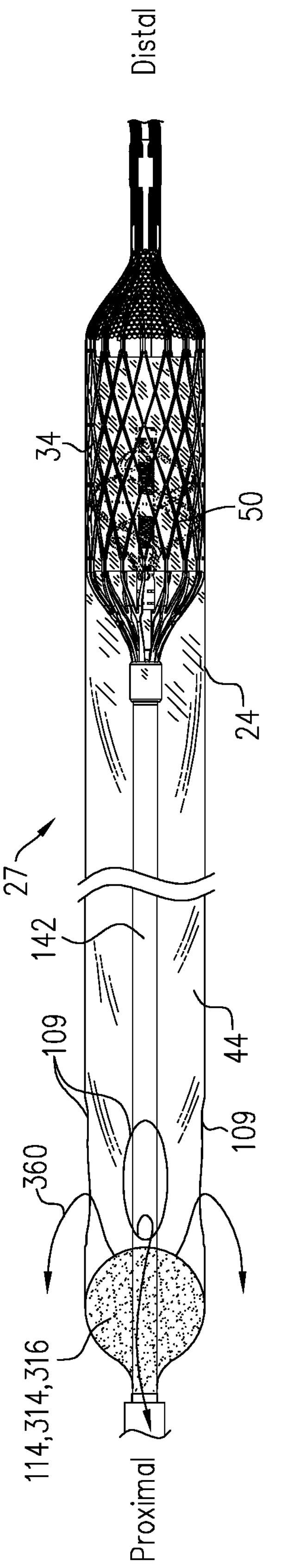
FIGS. 20A, 20B, 20C, 20D, and 20E are schematic illustrations of a pump-outlet tube of a ventricular assist device, in accordance with some applications of the present invention.

FIG. 20A is similar to FIG. 19B, in that FIG. 20A shows expandable element 314 disposed within pump-outlet tube 24, typically in the vicinity of the blood-outlet openings. For some such applications, the blood-outlet openings are configured as described hereinabove. In accordance with some applications, the expandable element is an inflatable element 316, e.g., balloon 114, as shown in FIG. 20A. For some applications, the balloon is inflated using purging fluid, which is pumped through the ventricular-assist device. Alternatively or additionally, the balloon is inflated with a different fluid, e.g., a dedicated supply of fluid (such as air or saline) for inflating the balloon.

For some applications, the expandable element is configured to act as a blood flow director, by directing blood from the proximal end of the pump-outlet tube through the blood outlet openings, as indicated by blood-flow arrows 360. For some applications, the expandable element is shaped such as to direct the blood flow in this manner. For example, the expandable element may have an angled and/or a curved surface that is configured to direct the blood flow in this manner. For some applications, by directing blood flow in this manner, the overall pumping efficiency of the device is increased relative to if the device does not include an expandable element.

As described hereinabove, typically, expandable element 314 is configured to center a portion of the ventricular assist device (e.g., a portion of delivery tube 142 and, in particular, the portion of the delivery tube near pump-outlet tube 24) within the aorta, by contacting the aorta wall or, if the expandable element is within the pump-outlet tube, by pushing the wall of the pump-outlet tube against the aorta wall.

Figure 20B:
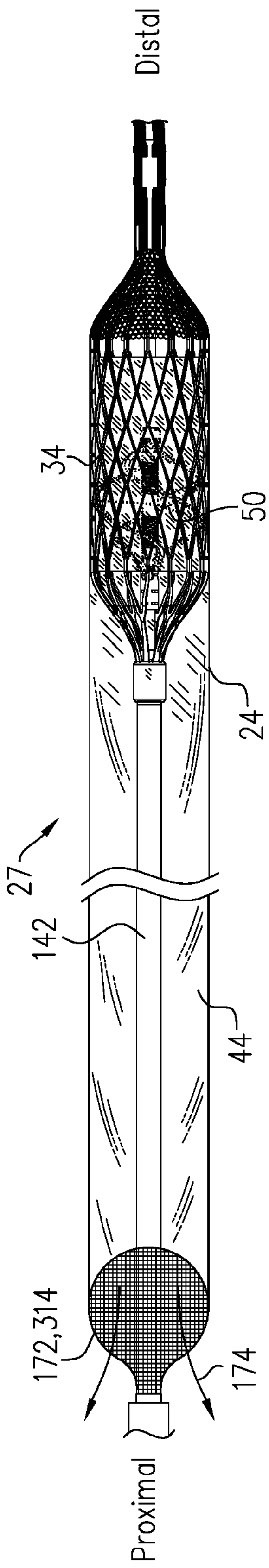

Referring to FIG. 20B, for some applications, expandable element 314 is a porous expandable element, such as an expandable cage or stent 172, surrounds delivery tube 142 within, or at the proximal end of, the pump-outlet tube, such that the blood is pumped through the porous expandable element. For example, the porous expandable element may be disposed at the proximal end of the pump-outlet tube, and the proximal end of the pump outlet tube may be coupled to delivery tube 142 via the porous expandable element. For some such applications, the pump-outlet tube does not define blood-outlet openings 109 (FIG. 20A). Rather, blood flows out of the pump-outlet tube exclusively via the porous expandable element, as indicated by blood-flow arrows 174. For some applications, the porous expandable element comprises a structure made of a shape-memory alloy, such as a laser-cut shape-memory alloy and/or a braided shape-memory alloy.

As described hereinabove, typically, the porous expandable element is configured to center a portion of the ventricular assist device (e.g., a portion of delivery tube 142 and, in particular, the portion of the delivery tube near pump-outlet tube 24) within the aorta, by contacting the aorta wall or, if the expandable element is within the pump-outlet tube, pushing the wall of the pump-outlet tube against the aorta wall.

Figures 20C, 20D, 20E:
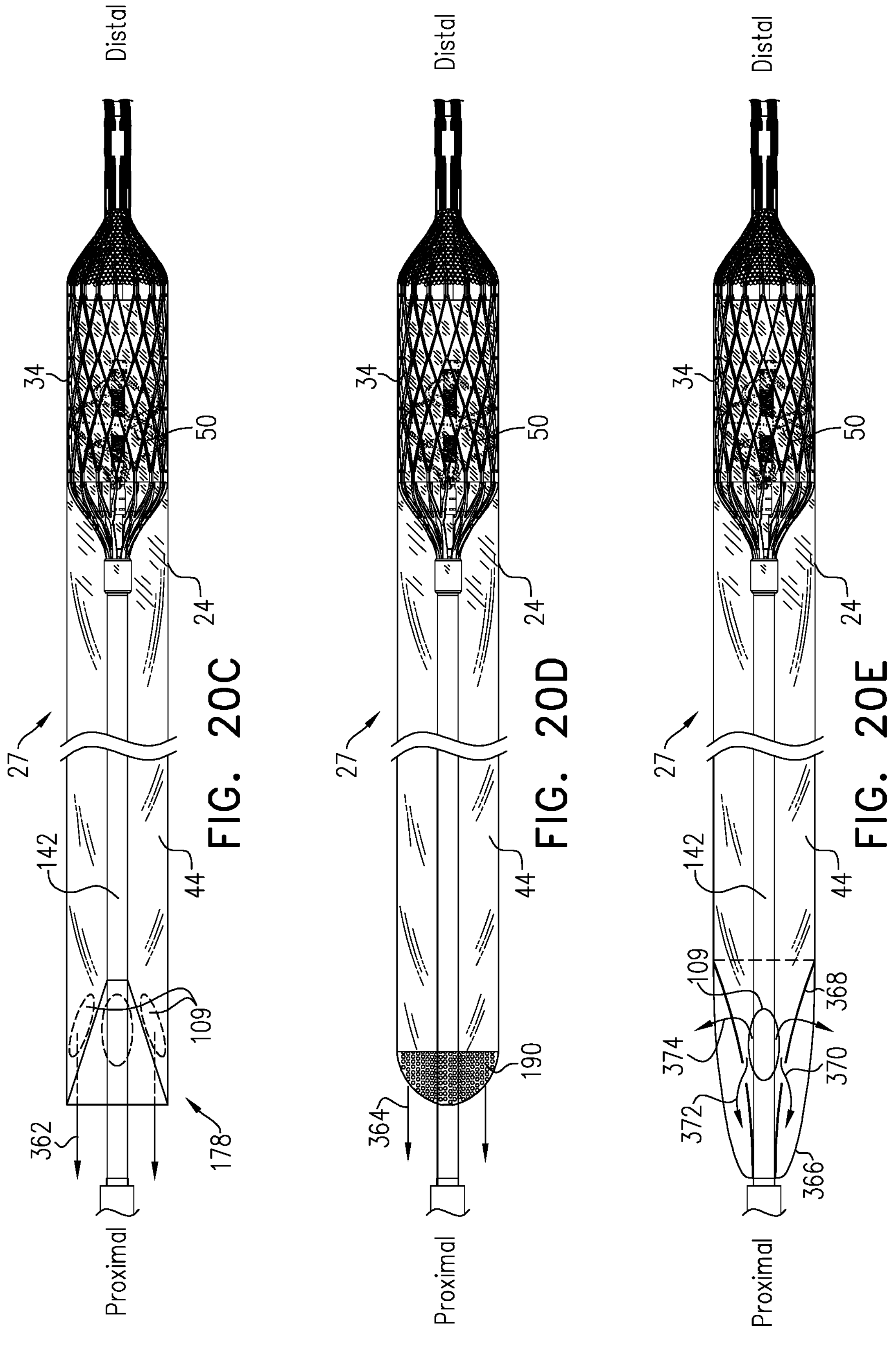

Referring to FIG. 20C, for some applications, a proximal portion 178 of pump-outlet tube 24, which defines blood-outlet openings 109, is folded inwardly toward the distal end of the pump-outlet tube. Typically, as shown, proximal portion 178 is folded inwardly such that the blood-outlet openings direct blood proximally (substantially parallel to the axis of outer tube 142) rather than radially outwardly (away from the axis of outer tube 142), as indicated by blood-flow arrows 362. For some applications, proximal portion 178 is folded inwardly such that the blood-outlet tube forms a protective layer between blood flowing out of the blood-outlet openings and the walls of the subject's aorta.

Referring to FIG. 20D, for some applications, the blood-outlet openings 109 are defined by a substantially proximally-facing surface 190 of the pump-outlet tube, rather than being defined by a lateral surface of the pump-outlet tube. Typically, for such applications, blood flow from the pump-outlet tube is axially directed, as indicated by blood-flow arrows 364.

Reference is now made to FIG. 20E, which is a schematic illustration of pump-outlet tube 24 that defines a blood-flow chamber 366 at its proximal end, in accordance with some applications of the present invention. For some applications, the blood-flow chamber is defined by an internal membrane 368 that is disposed within the proximal end of the pump-outlet tube and that defines holes 370 therethrough. Blood flows into the blood-flow chamber via the holes, as indicated by blood-flow arrows 372. Subsequently, the blood flows out of the blood-flow-chamber and into the subject's aorta via blood-outlet openings 109 (which are generally as described hereinabove), as indicated by blood-flow arrows 374. Typically, by virtue of the blood flowing through the blood-flow chamber, the blood-flow chamber inflates such as to center a portion of the left-ventricular assist device (e.g., the delivery tube, and in particular, the portion of the delivery tube near pump-outlet tube 24) within the aorta, by contacting the aorta wall. Typically, the internal membrane is shaped so as to direct the blood flow out of the blood-outlet openings.

For some applications, internal membrane 368 is a continuation of pump-outlet tube 24, and the internal membrane is covered with an external membrane, which defines blood-outlet openings, and which forms the external surface of blood-flow chamber 366. For such applications, the proximal end of the blood-outlet tube is shaped so as to direct the blood flow out of the blood-outlet openings.

Typically, the combination of the proximal end of the blood-outlet tube and an additional membrane (whether an internal membrane or an external membrane) are configured to define blood-flow chamber 366, which typically functions as described above. In general, the scope of the present disclosure includes any structure that provides a blood-flow chamber disposed at a proximal end of the pump-outlet tube, the blood-flow chamber defining (a) holes 370 via which blood is pumped into the blood-flow chamber and (b) blood-outlet openings 109 configured to be disposed with within the aorta via which the blood flows out of the blood-flow chamber and into the aorta.

Figure 21A:
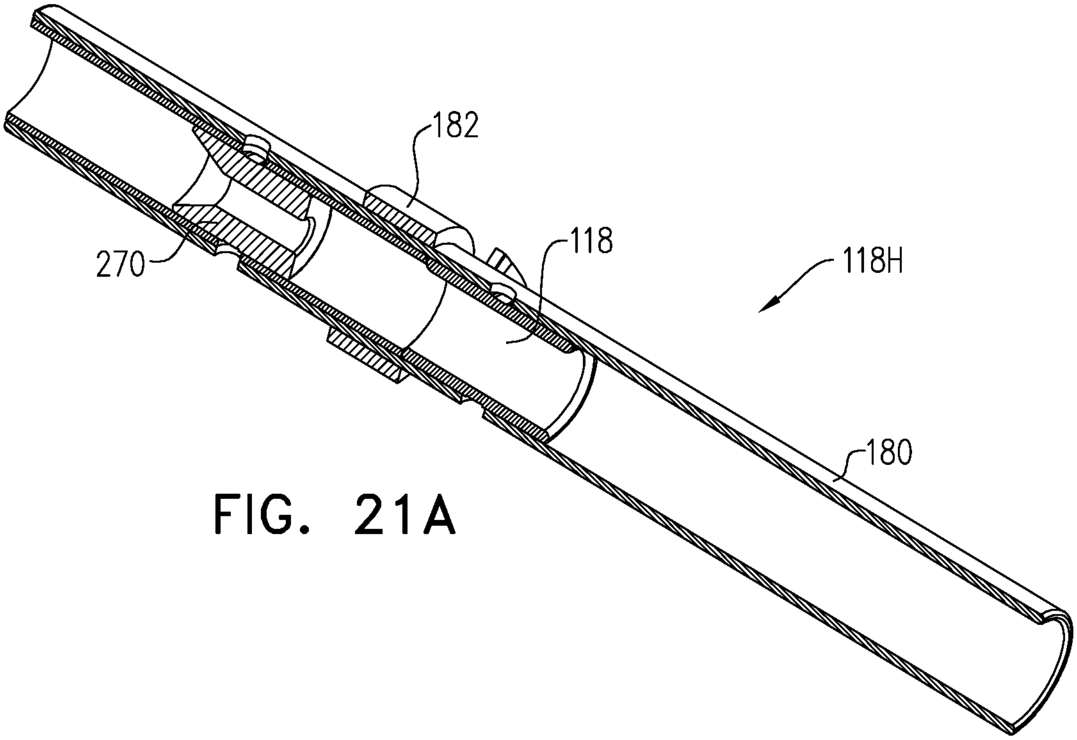
FIGS. 21A and 21B are schematic illustrations of a distal bearing housing of a ventricular assist device, in accordance with some applications of the present invention.
Figure 21B:
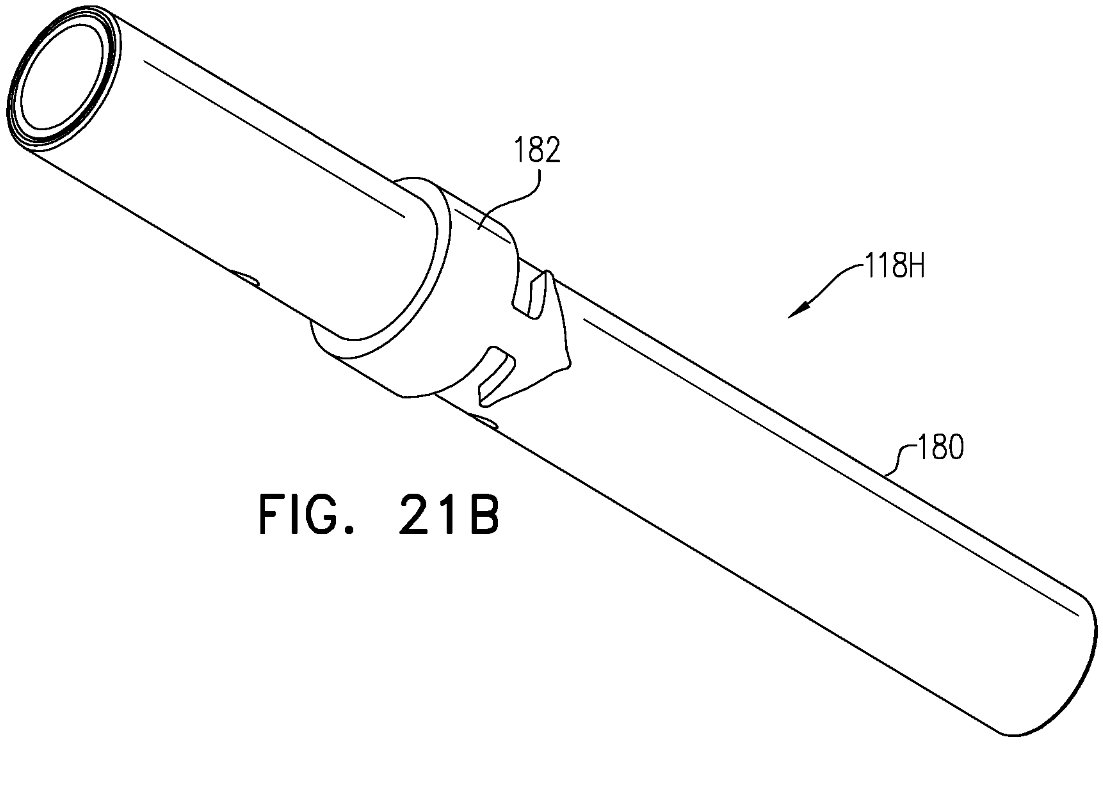

Reference is now made to FIGS. 21A and 21B, which are schematic illustrations of distal bearing housing 118H of ventricular assist device 20, in accordance with some applications of the present invention. For some applications, the bearing housing is constructed using a cylindrical tube 180 that has substantially smooth outer and inner surfaces and a uniform thickness (i.e., without the various regions on the surfaces and varying thicknesses described with reference to FIG. 11E). Typically, the cylindrical tube is made from an alloy or a metal, such as cobalt chrome and/or stainless steel. For some applications, a coupling element 182 is coupled to the outer surface of the cylindrical tube and the distal end of frame 34 is coupled to the bearing housing via the coupling element. (For example, the distal end of the frame may become coupled to the coupling element via a snap-fit mechanism.) For some applications, distal bearing 118 itself comprises an inner cylindrical element that is coupled to the inner surface of the distal bearing housing. As described hereinabove, typically, the bearing is made of a ceramic material such as zirconia. For some applications, distal thrust bearing 270 is disposed inside distal bearing housing 118H, as shown. The distal thrust bearing is generally as described hereinabove. For some applications, the proximal bearing housing also comprises a cylindrical tube that has substantially smooth outer and inner surfaces and a uniform thickness, as described with respect to the distal bearing housing mutatis mutandis.

Reference is now made to FIGS. 22A, 22B, 22C, and 22D, which are schematic illustrations of portions of ventricular assist device 20, the device including an inlet guard 400 disposed inside frame 34, in accordance with some applications of the present invention. Inlet guard 400 is shaped to define one or more holes 402, shown enlarged in FIG. 22D, which are disposed around the axial shaft and within frame 34 distally to the impeller, such that the blood flows to the impeller via holes 402. The inlet guard may be coupled to the struts of frame 34, to inner lining 39 (FIG. 4) of the frame, to the inner wall of pump-outlet tube 24, and/or to distal bearing housing 118H.

For some applications, inlet guard 400 is flat and/or is disposed such that it is perpendicular to the axial shaft (i.e., to the longitudinal axis of the frame). Thus, advantageously, the inlet guard may occupy relatively little space, and/or may provide an advantageous flow direction for the blood. Typically, the inlet guard is toric.

As described hereinabove (with reference to FIGS. 16A-E), for some applications, the ventricular assist device includes a thrust bearing in pump-head portion 27. Typically, for such applications, the impeller does not move distally of cylindrical portion 38 of frame 34 (either during delivery of the device to the left ventricle or during operation of the device).

For some applications, the inlet guard is placed within the frame at the distal end of the central cylindrical portion of the frame or in the vicinity thereof, e.g., within 1 mm of the distal end of the cylindrical portion. This placement may simplify the assembly of the blood pump.

Typically, the inlet guard is polymeric, i.e., is made of a polymeric material (such as polyurethane (e.g., Pellethane®), polyethylene terephthalate ("PET"), ultra-high-molecular-weight polyethylene ("UHMWPE"), and/or polyether block amide (e.g., Pebax®)) that is shaped to define holes 402. For some applications, the thickness of the inlet guard is more than 40 microns (e.g., more than 50 microns), and/or less than 100 microns (e.g., less than 80 microns), for example, 40-100 microns or 50-80 microns. Thus, the inlet guard may be configured to withstand pressure yet be crimpable.

Typically, for applications in which ventricular assist device 20 includes inlet guard 400 disposed inside frame 34, pump-outlet tube 24 does not extend until the distal end of distal conical portion 40 of frame 34. Moreover, pump-outlet tube 24 may have an open distal end, rather than terminating in a distal conical portion. (Thus, the inlet guard may simplify the manufacture of the blood pump.) The distal end of the pump-outlet tube may be proximal to the distal end of the distal conical portion of the frame. For example, the distal end of the pump-outlet tube may be within 1 mm of the distal end of the central cylindrical portion of frame 34, i.e., the pump-outlet tube may extend only until the end of the cylindrical portion of frame 34, or the vicinity thereof. Blood may thus flow into frame 34 via openings defined by the distal conical portion of the frame.

For some applications, holes 402 of inlet guard 400 are sized such as (a) to allow blood to flow from the subject's left ventricle into pump-outlet tube 24 and (b) to block structures from the subject's left ventricle from entering into the pump-outlet tube. Typically, for such applications, the inlet guard is configured to reduce a risk of structures from the left ventricle (such as chordae tendineae, trabeculae carneae, and/or papillary muscles) entering into pump-outlet tube 24 and potentially being damaged by the impeller and/or the axial shaft, and/or causing damage to the ventricular assist device.

For some applications, inlet guard 400 defines more than 10 holes, more than 50 holes, more than 100 holes, or more than 150 holes, e.g., 50-100 holes, 100-150 holes, or 150-200 holes. For some applications, the holes are sized such as (a) to allow blood to flow from the subject's left ventricle into the tube and (b) to block structures from the subject's left ventricle from entering into the frame. Typically, for such applications, the inlet guard is configured to reduce a risk of structures from the left ventricle (such as chordae tendineae, trabecular carneae, and/or papillary muscles) entering into the cylindrical portion of frame 34 and potentially being damaged by the impeller and/or the axial shaft, and/or causing damage to the left ventricular assist device. Therefore, for some applications, the holes are shaped such that, for each of the holes, the span of the hole in at least one direction is less than 1 mm, e.g., 0.1-1 mm, or 0.3-0.8 mm. By defining such a small width (or span), it is typically the case that structures from the left ventricle (such as chordae tendineae, trabeculae carneae, and/or papillary muscles) are blocked from entering into the cylindrical portion of frame 34.

For some applications, each of the holes defines an area of more than 0.05 square mm (e.g., more than 0.1 or 0.3 square mm), and/or less than 5 square mm (e.g., less than 3 or 1 square mm), e.g., 0.05-5, 0.05-3, 0.1-1, 0.1-5, or 0.3-1 square mm.

Typically, the inlet guard has a porosity of at least 40 percent, e.g., more than 50 percent, or more than 60 percent (where porosity is defined as the percentage of the area of this portion that is porous to blood flow). Thus, on the one hand, the holes are relatively small (in order to prevent structures of the left ventricular from entering the frame), but on the other hand, the porosity of the portion of the pump-outlet tube that defines the holes is relatively high, such as to allow sufficient blood flow into the pump-outlet tube.

For some applications, each of the holes has a circular or a polygonal shape. For some applications, each of the holes has a hexagonal shape, as shown most clearly in FIG. 22D. Typically, using openings having a hexagonal shape allows the inlet guard to have a relatively high porosity (e.g., as described hereinabove), while providing the inlet guard with sufficient material between the holes to prevent tearing and/or stretching of the material.

Figure 22A:
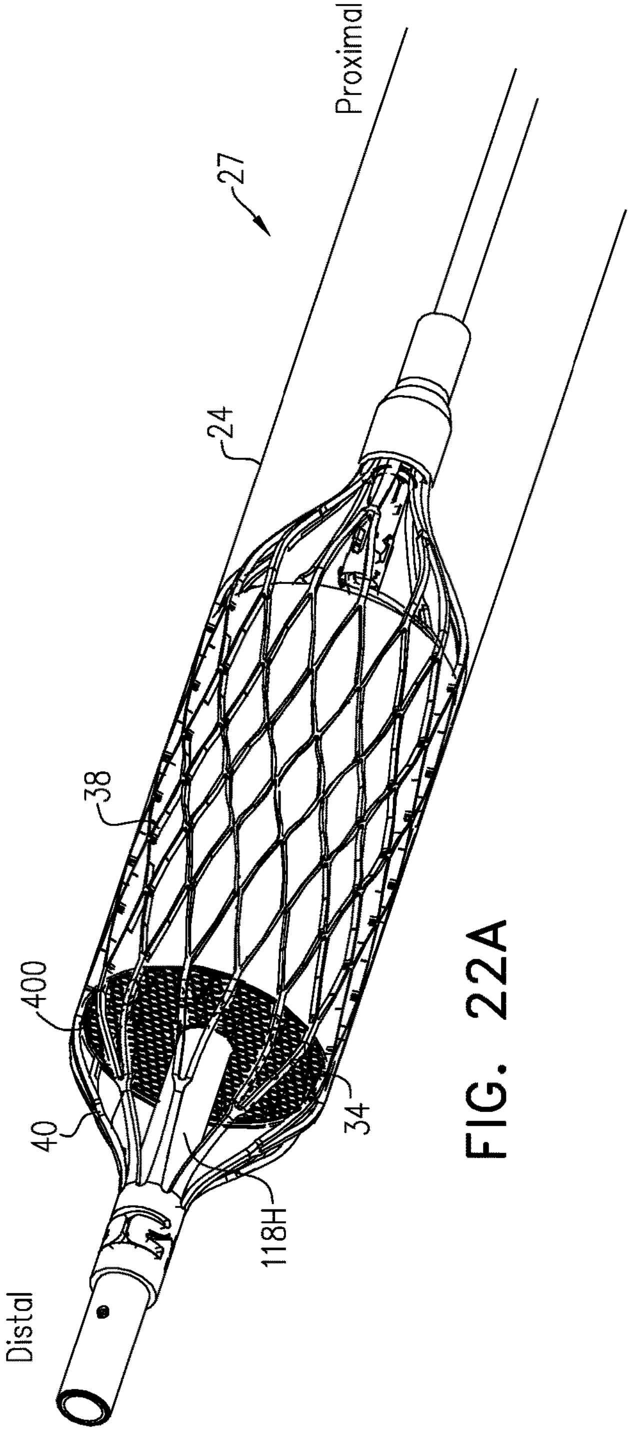
FIGS. 22A, 22B, 22C, and 22D are schematic illustrations of portions of a ventricular assist device that includes an inlet guard disposed within a frame of the pump-head portion of the device, in accordance with some applications of the present invention.
Figure 22B:
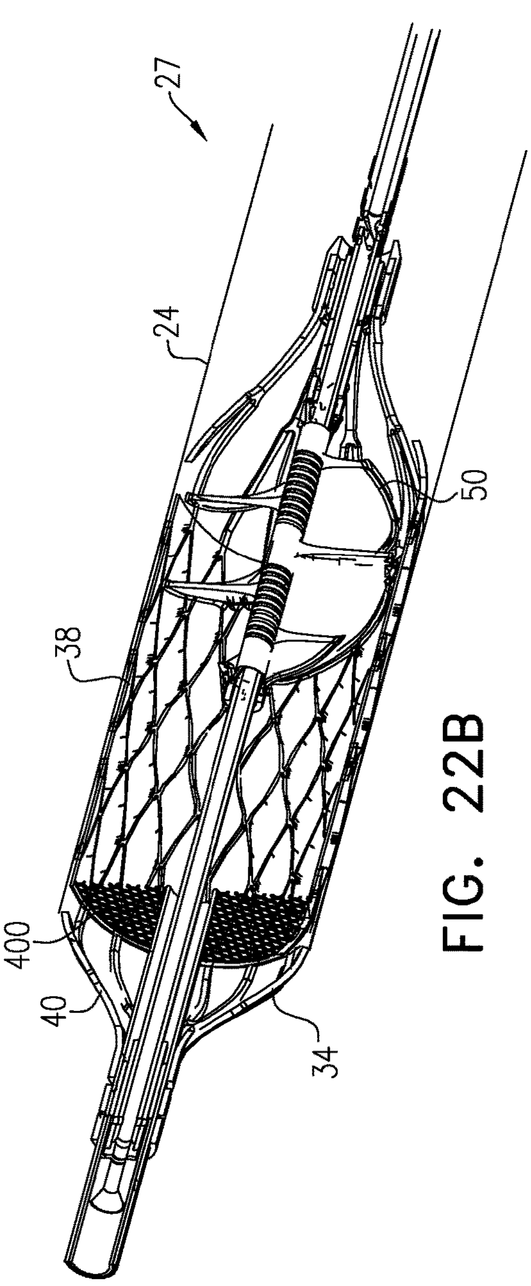
Figure 22C:
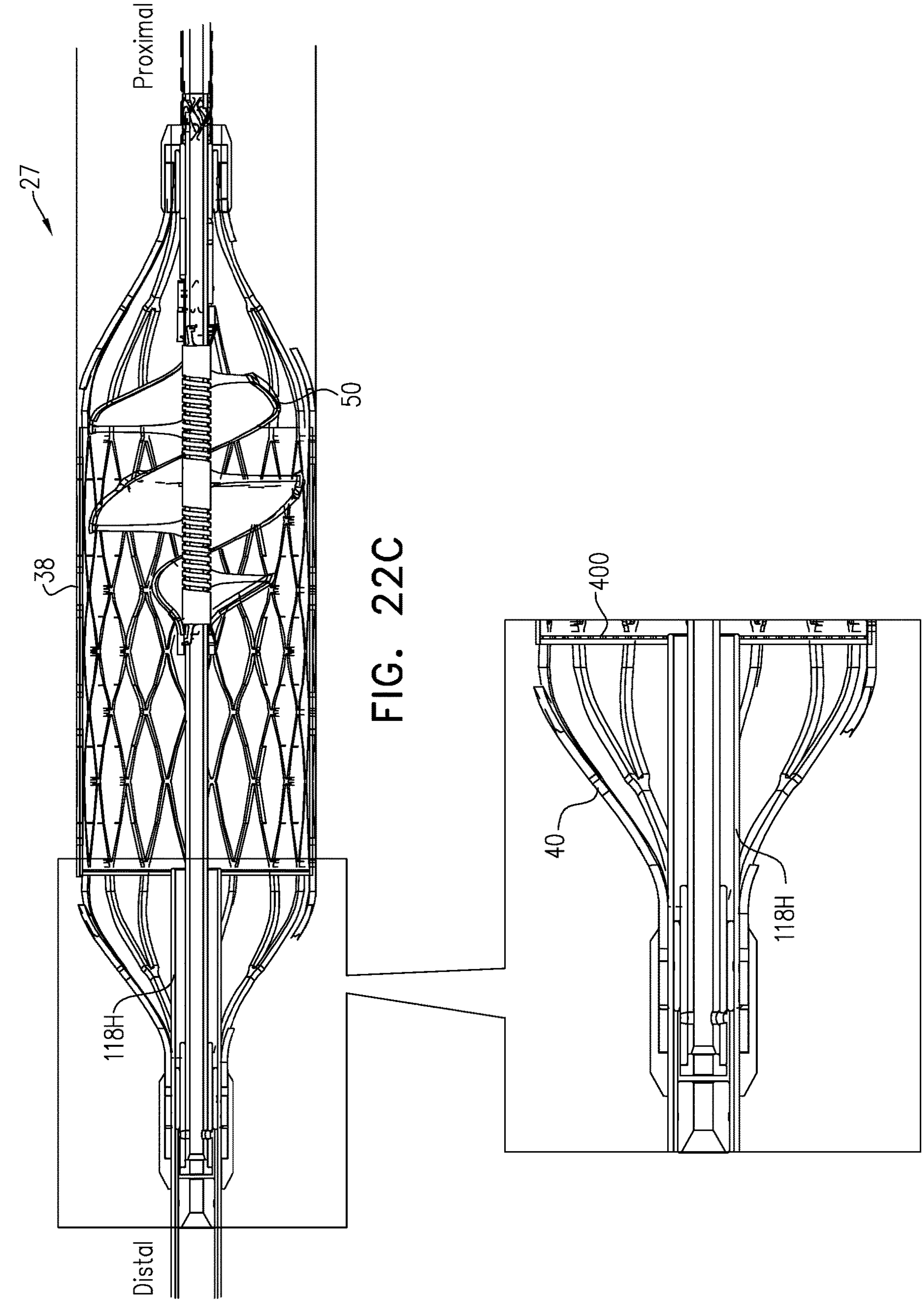
Figure 22D:
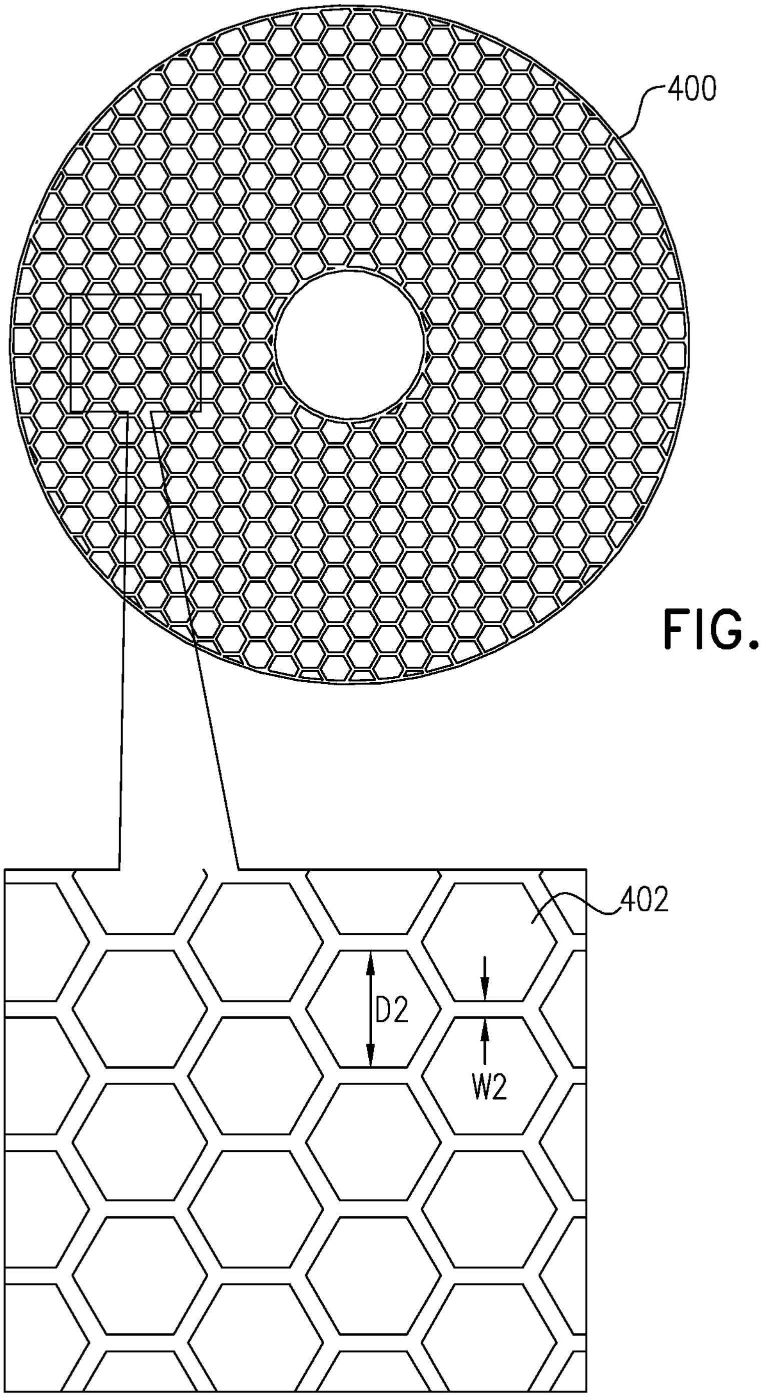

As shown in FIG. 22D, for some applications, a width W2 of gaps between adjacent holes 402 (i.e., the distance between each pair of adjacent holes) is more than 0.01 mm (e.g., more than 0.04 mm), and/or less than 0.1 mm (e.g., less than 0.08 mm), for example, 0.01-0.1 mm, or 0.04-0.08 mm.

As further shown in FIG. 22D, for some applications, the distance D2 between opposing sides of each of the hexagons (or other types of polygons) is more than 0.2 mm (e.g., more than 0.4 mm) and/or less than 0.8 mm (e.g., less than 0.6 mm), e.g., 0.2-0.8 mm, or 0.4-0.6 mm. Typically each of the polygons encloses a circle (such that any structure that cannot pass through such a circle would be unable to pass through the polygon). Typically, the diameter of the circle enclosed by the polygon is the equivalent of distance D2, e.g., more than 0.2 mm (e.g., more than 0.4 mm) and/or less than 0.8 mm (e.g., less than 0.6 mm), e.g., 0.2-0.8 mm, or 0.4-0.6 mm.

For some applications, the frame is assembled with the inlet guard inside in the following manner. As described hereinabove, during assembly of the pump-head portion, the proximal end of frame 34 is typically open. For some applications, the inlet guard is placed through the open proximal end of the frame while being supported upon a rod (e.g., a mandrel). The inlet guard typically has an overall torus shape, with the edges of the shape defining inner and outer circles, as shown in FIG. 22D. The inner circle defined by the inlet guard is typically coupled to the axial shaft (or to the distal bearing housing) and the outer circle is coupled to struts of frame 34, to pump-outlet tube 24 and/or to inner lining 39. For some applications, the aforementioned coupling of the inlet guard to other portions of the device is performed via suturing, via hooks, via adhesive, and/or via heat fusion.

As noted above, in some embodiments, the inlet guard is coupled to the distal bearing housing, which may house a radial and/or thrust bearing. In such embodiments, typically, the distal bearing housing is partly or entirely disposed within frame 34. For example, at least 10%, 50%, or 80% of the length of the bearing housing may be disposed within the frame. Moreover, the distal bearing housing may extend into the frame even for applications in which the blood pump does not comprise inlet guard 400.

Figure 23:
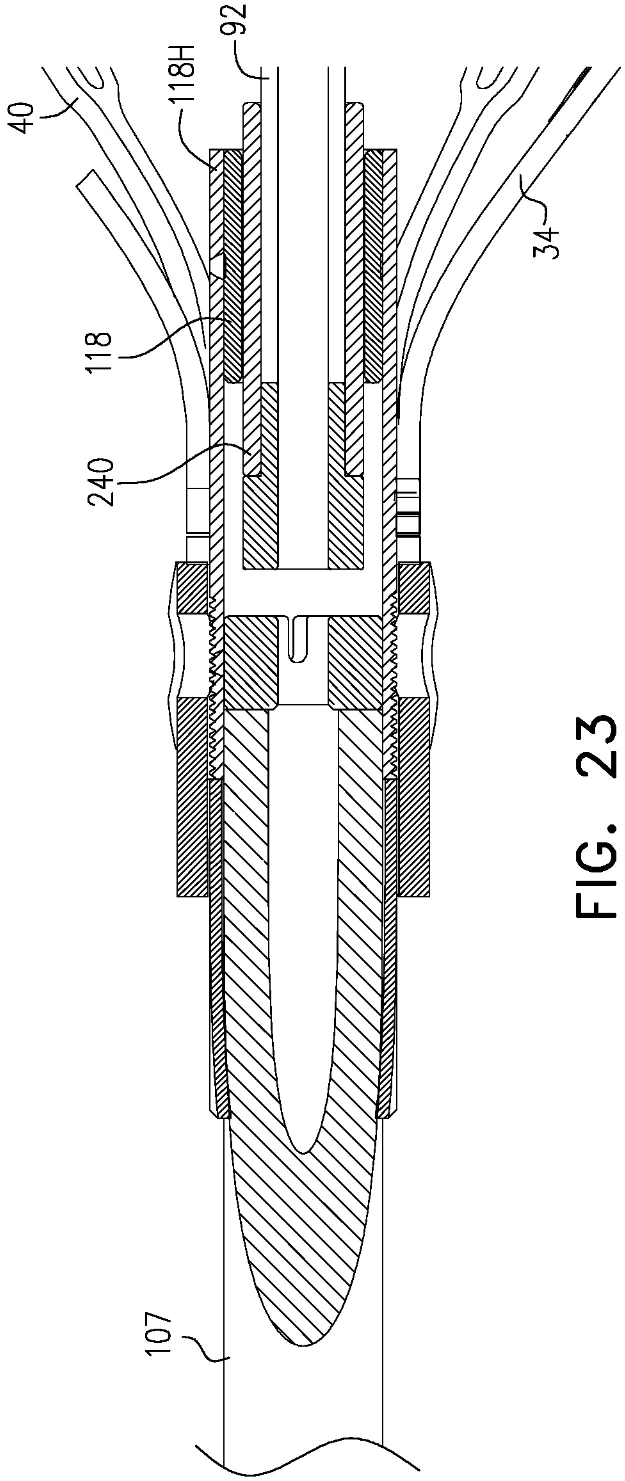
FIG. 23 is a schematic illustration of a distal bearing housing of a ventricular assist device that extends into the frame of the pump-head portion, in accordance with some applications of the present invention.

For further details in this regard, reference is now made to FIG. 23, which is a schematic illustration of ventricular assist device 20 in which distal bearing housing 118H is disposed at least partly within, i.e., extends proximally at least partially into distal conical portion 40 of frame 34. Reference is also made again to FIGS. 22A-C, which similarly show distal bearing housing 118H extending proximally at least partially into the distal conical portion of frame 34.

Typically, it is desirable for the relatively rigid portions of the pump-head portion of the device (such as the frame, the impeller, and the bearing housings) to have a combined length that is as short as possible, in order to safely navigate the device through curved vasculature of the subject (such as the aortic arch). For some applications, by configuring the device such that distal bearing housing 118H extends at least partially into the distal conical portion of frame 34, the combined length of the relatively rigid portions of the pump-head portion of the device (such as the frame, the impeller, and the bearing housings) is shortened relative to if the device were configured such distal bearing housing 118H would not extend proximally at least partially into the distal conical portion of frame 34.

In some embodiments, the bearing housing occupies at least 10% of the length of the distal conical portion of the frame. For some applications, the distal bearing housing extends until, or even at least partially into, cylindrical portion 38 of frame 34.

As noted above, distal bearing housing 118H houses a radial and/or thrust bearing, which is adjacent to the axial shaft and is configured to stabilize the axial shaft (radially and/or axially) while the axial shaft rotates. An advantage of a thrust bearing is that the impeller does not advance into the distal conical portion of the frame (or into a portion thereof) either during operation of the device or during delivery of the device to the left ventricle (when the impeller is in a radially constrained configuration within the frame), such that it may be easier to configure distal bearing housing 118H to extend proximally into the distal conical portion of frame 34. However, the scope of the present disclosure includes a distal bearing housing that extends into frame 34 in the manner described above, but which houses only distal radial bearing 118 and does not house a thrust bearing.

Likewise, the proximal bearing housing, which houses a radial and/or thrust bearing adjacent to the axial shaft and configured to stabilize the axial shaft (radially and/or axially) while the axial shaft rotates, may be disposed partly or entirely within the proximal conical portion of the frame. For example, at least 10%, 50%, or 80% of the length of the proximal bearing housing may be disposed within the frame. Alternatively or additionally, the proximal bearing housing may occupy at least 10% of the length of the proximal conical portion of the frame; for example, the proximal bearing housing may be disposed at least partly within the cylindrical portion of the frame. The scope of the present disclosure includes a proximal bearing housing that extends into frame 34 in the manner described above, but which houses only proximal radial bearing 116 and does not house a thrust bearing.

In some embodiments, both the proximal and distal bearing extend into the frame as described above. In such embodiments, the distance between the proximal end of the proximal bearing housing and the distal end of the distal bearing housing may be less than 10% greater than the length of the frame, thus reducing the total length of the more rigid elements of the blood pump.

Figure 24:
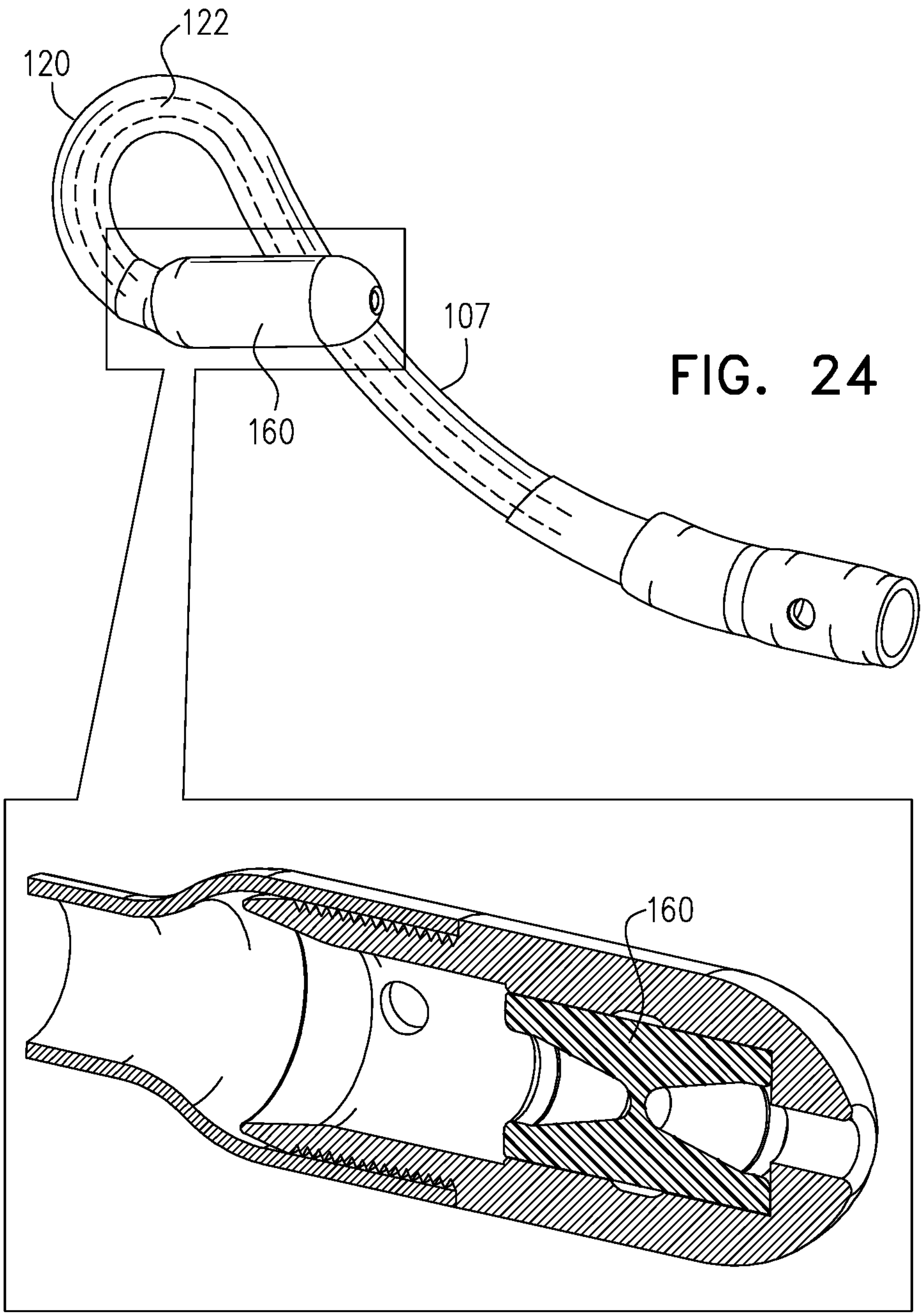
FIG. 24 is a schematic illustration of a distal-tip portion of a ventricular assist device that includes a bidirectional valve, in accordance with some applications of the present invention.

Reference is now made to FIG. 24, which is a schematic illustration of valve 160 disposed at the distal end of lumen 122 of distal-tip portion 120, in accordance with some applications of the present invention. As described hereinabove, in some embodiments, the valve is a duckbill valve. For some applications, the duckbill valve is configured to facilitate insertion of a guidewire both via the distal end of the duckbill valve and via the proximal end of the duckbill valve. For some applications, at both the proximal and the distal end, the valve narrows from a wide opening to a self-scaling central portion, such as to guide the guidewire toward the self-sealing central portion from either end of the valve. Typically, a guidewire is inserted into the distal-tip portion from the distal end of the distal-tip portion in advance of the initial delivery of the ventricular assist device to the left ventricle over the guidewire. In some cases, it is desirable to insert a guidewire from the proximal end of the ventricular assist device to the distal end of the device at some stage thereafter. The shape of the duckbill valve that is shown in FIG. 24 typically facilitates both the distal-to-proximal insertion and the proximal-to-distal insertion of the guidewire.

Figure 25A:
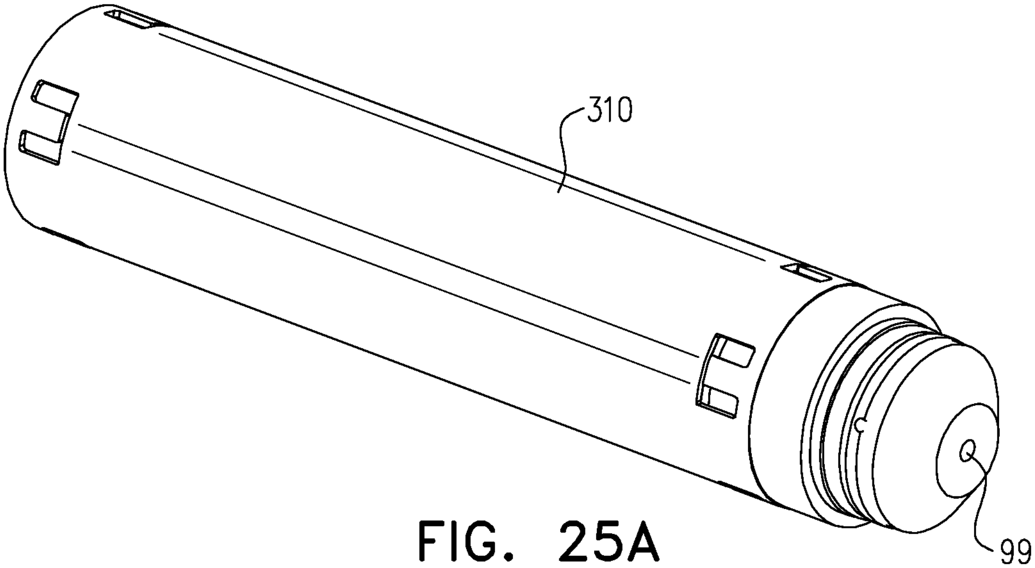
FIGS. 25A and 25B are schematic illustrations of a driven-magnet unit that includes a bidirectional valve, in accordance with some applications of the present invention.
Figure 25B:
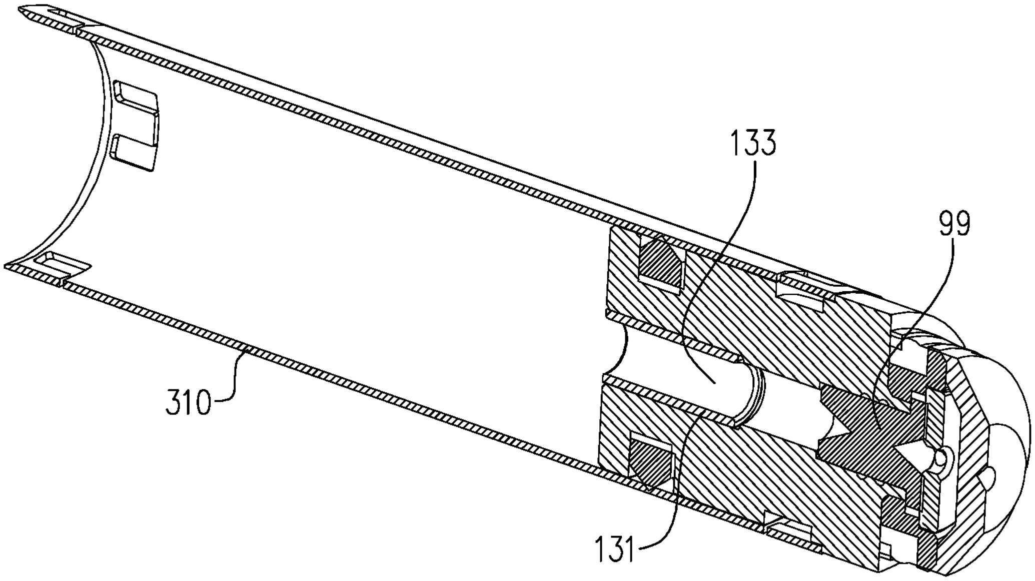

Reference is now made to FIGS. 25A-25B, which are schematic illustrations of valve 99 disposed at the proximal end of lumen 133 defined by pin 131 of driven-magnet unit 310, in accordance with some applications of the present invention. As described hereinabove, in some embodiments, the valve is a duckbill valve. For some applications, the duckbill valve is configured to facilitate insertion of a guidewire via both the distal end of the duckbill valve and via the proximal end of the duckbill valve. For some applications, at both the proximal and the distal end the valve narrows from a wide opening to a self-scaling central portion, such as to guide the guidewire toward the self-sealing central portion from either end of the valve. Typically, a guidewire is inserted through valve 99 from the distal end of the driven-magnet unit in advance of the initial delivery of the ventricular assist device to the left ventricle over the guidewire. In some cases, it is desirable to insert a guidewire from the proximal end of the ventricular assist device to the distal end of the device at some stage thereafter. The shape of the duckbill valve that is shown in FIGS. 25A-B typically facilitates both the distal-to-proximal insertion and the proximal-to-distal insertion of the guidewire.

Figure 26A:
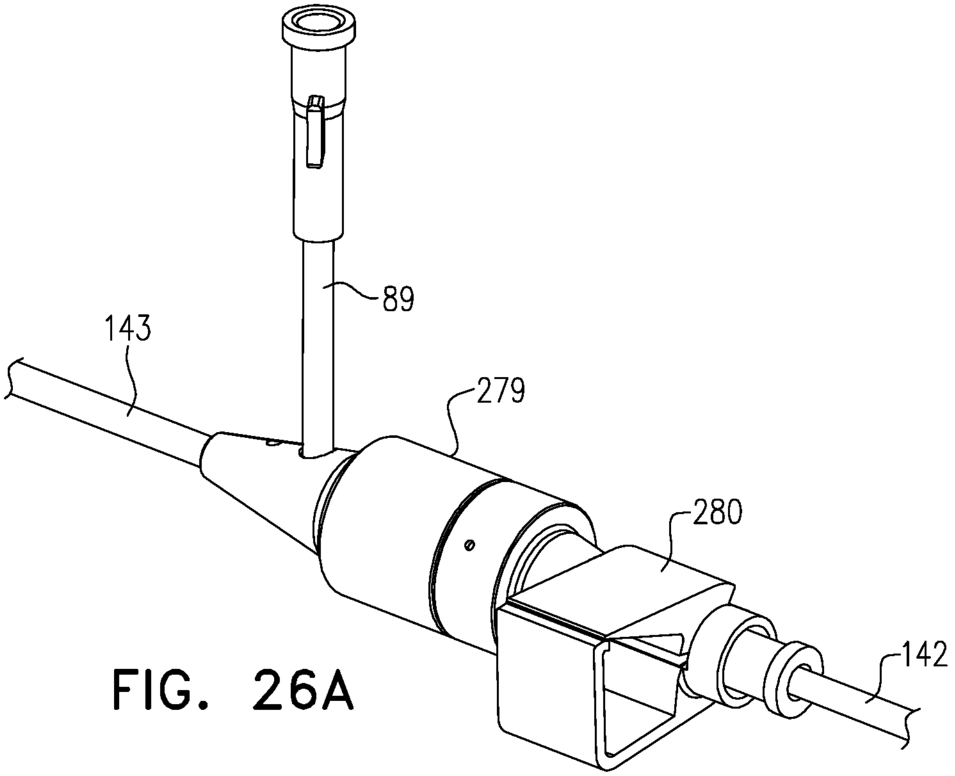
FIGS. 26A and 26B are schematic illustrations of a locking unit for securing a delivery tube to a delivery catheter, in accordance with some applications of the present invention.
Figure 26B:
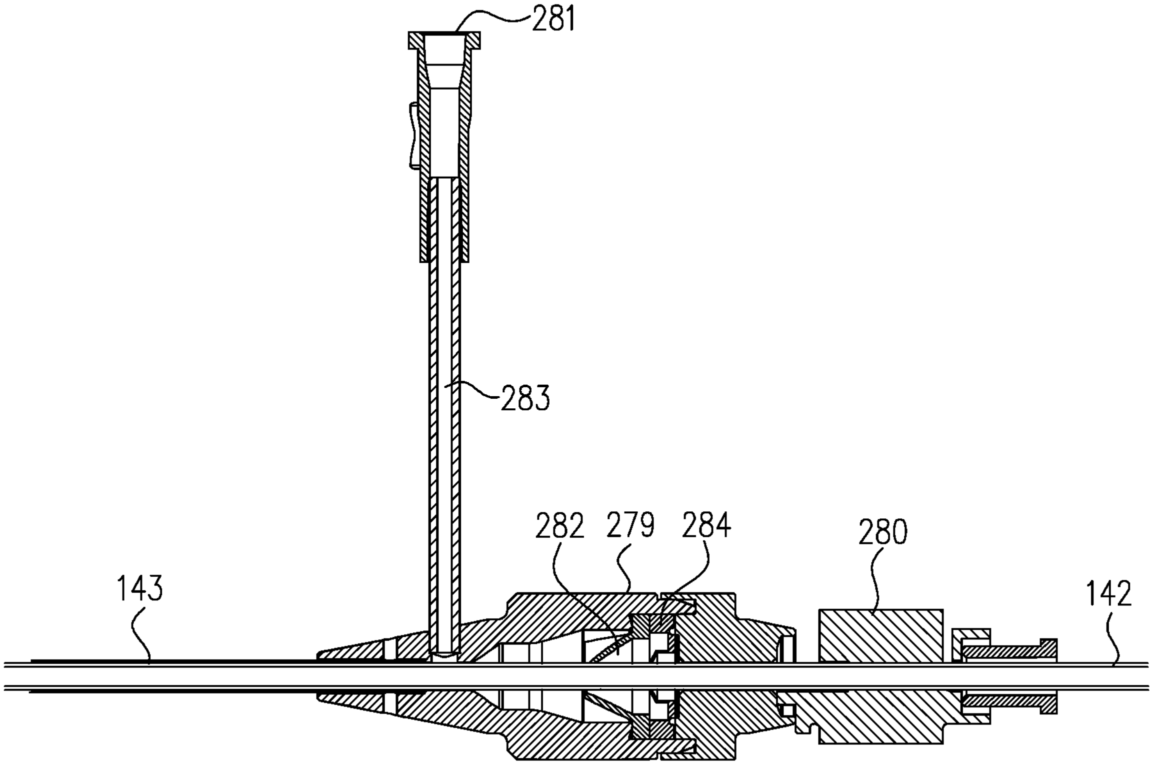

Reference is now made to FIGS. 26A and 26B, which are schematic illustrations of, respectively, an oblique view and a cross-sectional view of a locking unit 279 for securing delivery tube 142 to delivery catheter 143, in accordance with some applications of the present invention.

For some applications, once the ventricular assist device has been deployed within the left ventricle, and the delivery catheter has been retracted to its intraprocedural position (e.g., such that its distal end is disposed within the descending aorta), it is desirable to secure delivery tube 142 and delivery catheter 143 in fixed positions with respect to each other. For some applications, a fixation unit such as fixation unit 97 (shown in FIG. 7D) is used, with the fixation unit being configured such that the position of the driven-magnet unit is fixed or unfixed relative to the proximal end of the delivery catheter by screwing a portion of the fixation unit. For example, the fixation unit may include a Tuohy Borst adapter.

For other applications, locking unit 279, which is configured to couple to the proximal end of the delivery catheter and comprises a clip 280, is used instead of a fixation unit such as that shown in FIG. 7D. For such applications, delivery tube 142 extends from outside the body of the subject into the left ventricle through locking unit 279 and delivery catheter 143. Clip 280 is configured such that it has only two states (or “positions”): a closed state, in which the clip grips the delivery tube so as to inhibit movement of the delivery tube relative to the delivery catheter, and an open state, in which the clip does not grip the delivery tube. This differs from a fixation unit such as that shown in FIG. 7D, which typically has varying degrees of closedness depending on how tightly the screw mechanism is activated. Typically, clip 280 is an external component of the locking unit, such that the state of clip 280 is readily visible to the user.

As shown in FIG. 26B, the locking unit typically comprises at least one internal seal configured to surround the delivery tube and to inhibit backflow of blood of the subject, from the delivery catheter, through the locking unit, while the delivery tube passes through the locking unit. For example, the locking unit may comprise a duckbill seal 282 and an additional seal 284.

Typically, as shown in FIG. 26B, the locking unit further comprises a fluid port 281 and is shaped to define a channel 283 in fluid communication with fluid port 281 and delivery catheter 143. Thus, channel 224 (FIG. 12A) between the delivery catheter and the delivery tube may be purged with a purging fluid. (Fluid port 281 and channel 283 may be collectively referred to as purging fluid inlet port 89, as indicated in FIG. 26A and as described above with reference to FIG. 7D.)

Figure 27A:
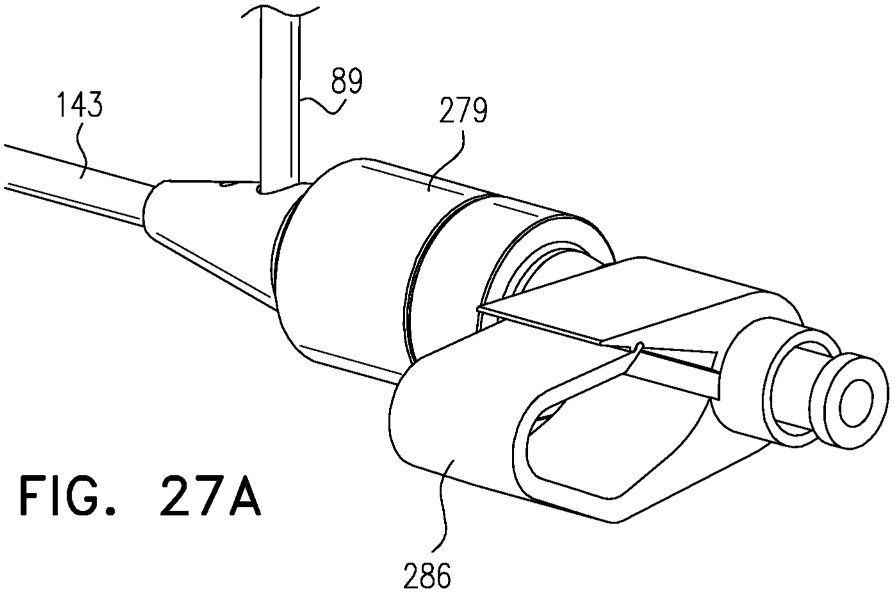
FIGS. 27A and 27B are schematic illustrations of a locking unit for securing a delivery tube to a delivery catheter, in accordance with some alternative applications of the present invention.
Figure 27B:
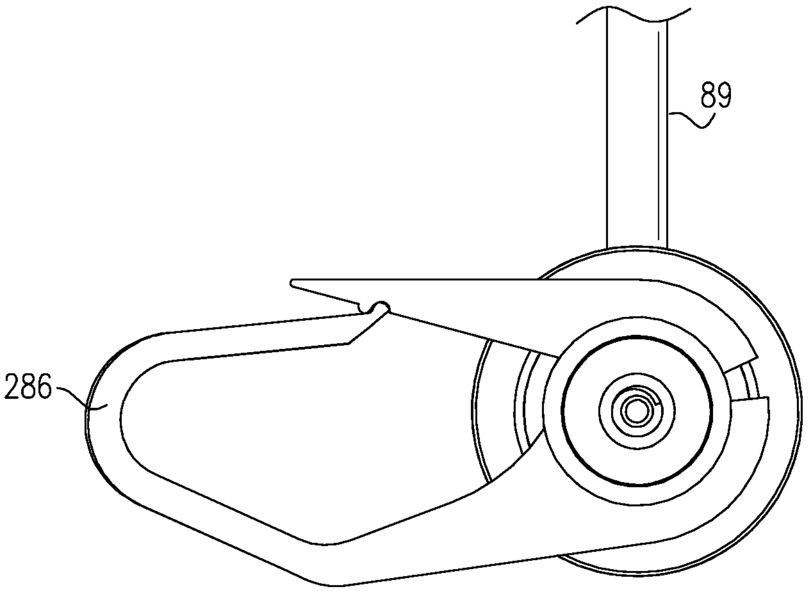

Reference is now made to FIGS. 27A and 27B, which are schematic illustrations of, respectively, an oblique view and a cross-sectional view of a clip 286 for securing delivery tube 142 to delivery catheter 143, in accordance with some alternative applications of the present invention.

In some embodiments, the clip is configured to remain in its open state, following a placement of the clip in its open state, unless the clip is returned to its closed state. In other words, the fixation mechanism can be disengaged by opening the clip, and the user does not then need to actively maintain disengagement of the fixation mechanism.

In other embodiments, the clip is configured to return to its closed state, following a placement of the clip in its open state, unless the clip is held in its open state. In other words, the user needs to actively apply force to the clip in order to maintain disengagement of the fixation mechanism. Clip 286 is an example of such a clip.

Figure 28A:
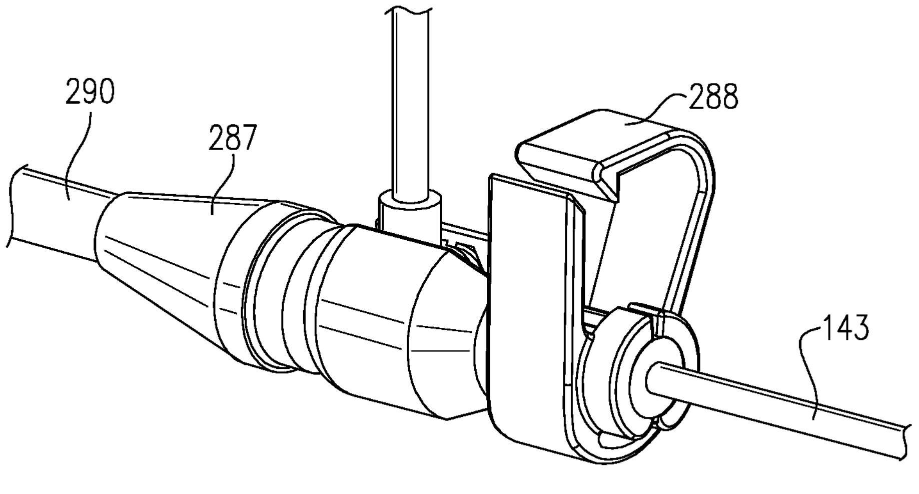
FIGS. 28A and 28B are schematic illustrations of a locking unit for securing a delivery catheter to an introducer sheath, in accordance with some applications of the present invention.
Figure 28B:
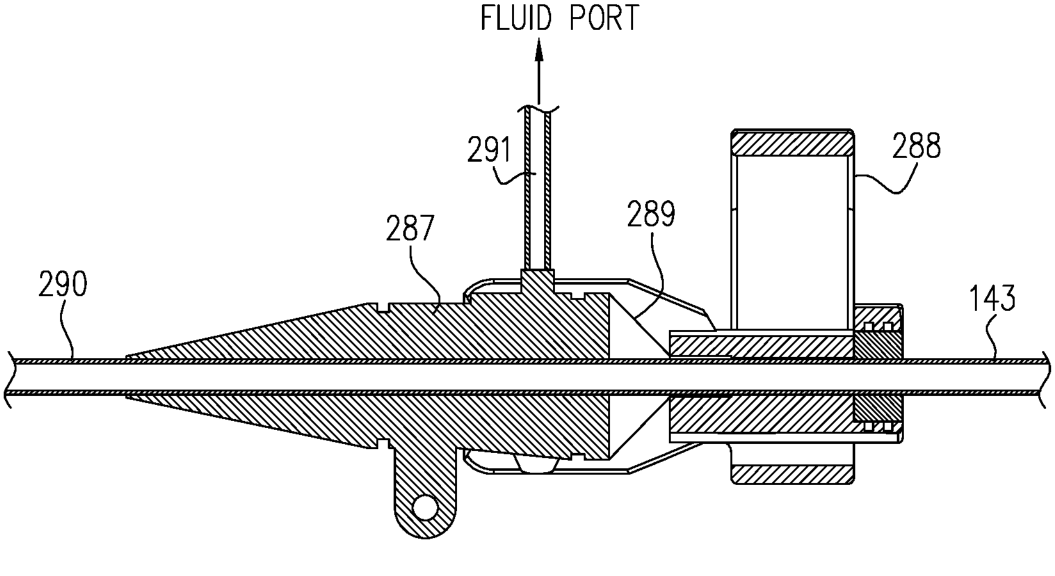

Reference is now made to FIGS. 28A and 28B, which are schematic illustrations of, respectively, an oblique view and a cross-sectional view of another locking unit 287 for securing delivery catheter 143 to an introducer sheath 290, in accordance with some applications of the present invention.

Typically, delivery catheter 143 is inserted from outside the subject's body into the patient's vasculature via introducer sheath 290, which is configured to extend from outside the body of the subject into the body of the subject. For example, the introducer sheath may be used to provide access to the subject's femoral artery, and the delivery catheter may be advanced from the femoral artery to the subject's left ventricle as described hereinabove.

For some applications, locking unit 287 is configured to couple to the proximal end of introducer sheath 290, and delivery catheter 143 is configured to pass through locking unit 287 and introducer sheath 290. Locking unit 287 comprises a clip 288, which is used to fix the position of the delivery catheter with respect to the introducer sheath (typically, once the delivery catheter has been positioned in a desired intraprocedural position). Clip 288 is configured such that it has only two states (or “positions”): a closed state, in which the clip grips the delivery catheter so as to inhibit movement of the delivery catheter relative to the introducer sheath, and an open state, in which the clip does not grip the delivery catheter. This differs from a fixation unit such as that shown in FIG. 7D, which typically has varying degrees of closedness depending on how tightly the screw mechanism is activated. Typically, clip 288 is an external component of locking unit 287, such that the state of the clip is readily visible to the user.

Typically, locking unit 287 comprises at least one internal seal 289 configured to surround the delivery catheter and to inhibit backflow of blood of the subject, from the introducer sheath, through the second locking unit, while the delivery catheter passes through the second locking unit.

Typically, locking unit 287 further comprises a fluid port, and is shaped to define a channel 291 in fluid communication with the fluid port and introducer sheath 290. Thus, the space between the delivery catheter and the introducer sheath may be purged with a purging fluid.

In some embodiments, clip 288 is configured to remain in its open state, following a placement of the second clip in its open state, unless the clip is returned to its closed state. In other embodiments, the clip is configured to return to its closed state, following a placement of the clip in its open state, unless the clip is held in its open state.

Figure 29:
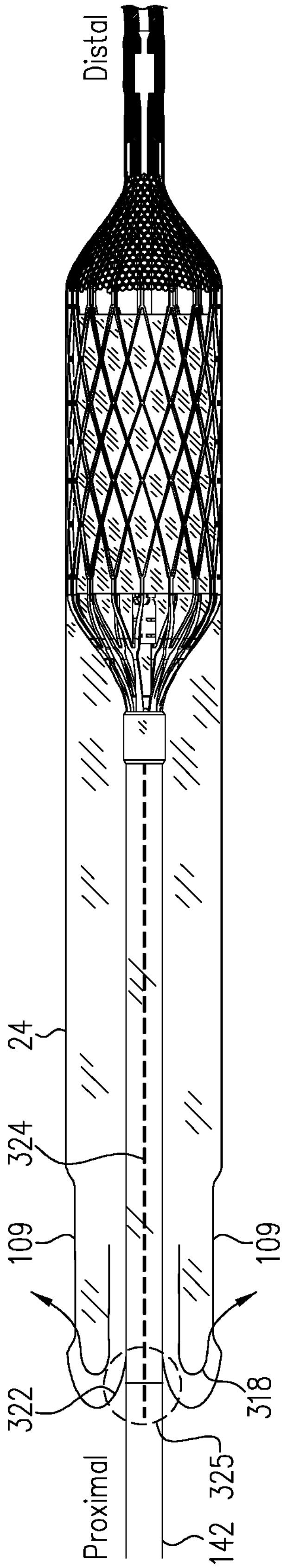
FIG. 29 is a schematic illustration of a left-ventricular assist device, in accordance with some applications of the present invention.

Reference is now made to FIG. 29, which is a schematic illustration of a left-ventricular assist device, in accordance with some applications of the present invention.

In some embodiments, the proximal end of pump-outlet tube 24 is folded inwardly so as to define one or more surfaces 322 configured to direct the blood through blood-outlet openings 109 by virtue of being oblique with respect to the longitudinal axis 324 of the pump-outlet tube.

In some embodiments, surfaces 322 define a projection 325, such as a frustoconical projection, having a width that decreases moving distally. Blood is directed by projection 325, at an angle, through the blood-outlet openings. In such embodiments, typically, projection 325 is distally coupled to the delivery tube.

Figure 30:
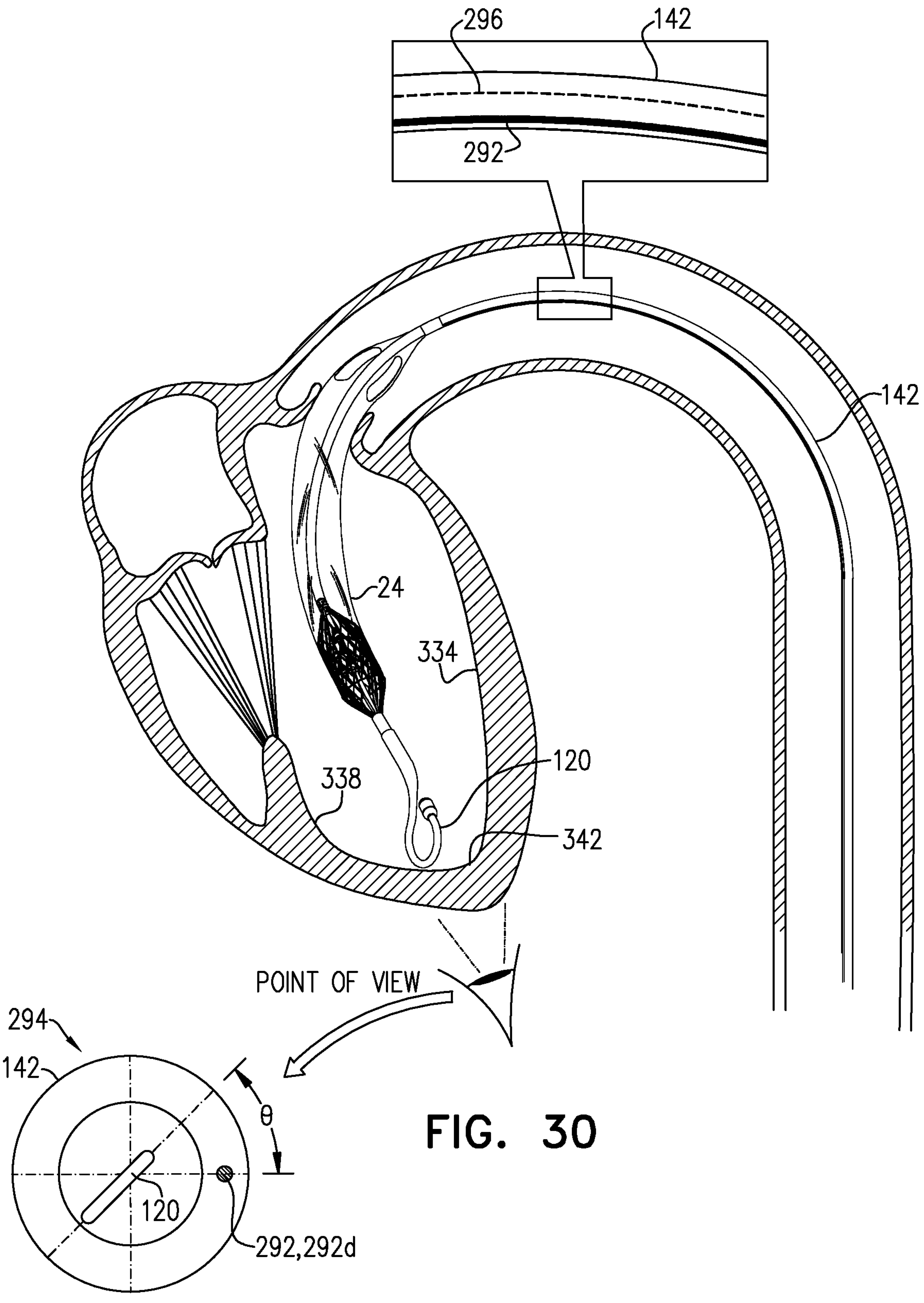
FIG. 30 is a schematic illustration of a ventricular assist device deployed within the body of a subject, in accordance with some applications of the present invention.

Reference is now made to FIG. 30, which is a schematic illustration of a ventricular assist device deployed within the body of a subject, in accordance with some applications of the present invention.

In some embodiments, an elongation-resistant fiber, e.g., an aramid fiber 292 (which may be equivalent to fiber 159 shown in FIG. 13) runs axially along the wall of delivery tube 142. The elongation-resistant properties of aramid fiber 292 cause the delivery tube to adopt an orientation in which the length of the aramid fiber is minimized. Thus, aramid fiber 292 biases the orientation of the delivery tube, typically at least by biasing the roll angle of the delivery tube, while the delivery tube traverses the aortic arch, thereby biasing the orientation of the blood pump. Typically, aramid fiber 292 biases the roll angle of the delivery tube such that the aramid fiber is disposed at the inside of the curve of the aortic arch, such that the length of the aramid fiber is minimized. Typically, aramid fiber 292 extends to the distal end of the delivery tube.

In some embodiments, as shown in the distal-end view 294 of the delivery tube, aramid fiber 292 is disposed within the wall of the delivery tube (e.g., as in FIG. 13). For example, the wall of the delivery tube may comprise a braid, and the aramid fiber may be threaded through the braid or run adjacently to the braid.

As described above, pump-outlet tube 24 is coupled to delivery tube 142. Thus, in addition to biasing the orientation of the blood pump, which is disposed at least partly within the pump-outlet tube, aramid fiber 292 biases the orientation of the pump-outlet tube. Typically, as shown in FIG. 30, the pump-outlet tube is configured to curve within the left ventricle while the blood pump pumps blood from the left ventricle through the pump-outlet tube. For example, the blood pump may be disposed at least partly within the distal portion of the pump-outlet tube, and the proximal portion of the pump-outlet tube may curve.

For example, the delivery tube may be configured to curve (even without aramid fiber 292), and the pump-outlet tube may curve by virtue of the delivery tube curving. Alternatively or additionally, the pump-outlet tube may be configured to curve by virtue of being pre-shaped. Alternatively or additionally, the pump-outlet tube may be shaped to define multiple openings (e.g., blood-inlet openings and/or blood-outlet openings) arranged in a non-axisymmetric arrangement, and the pump-outlet tube may curve by virtue of blood flowing through the openings. For some applications, the pump-outlet tube is configured to curve by virtue of one or more features described with reference to FIGS. 19A-F of US 2022/0226632 to Tuval, which is incorporated herein by reference. Alternatively or additionally, as described below with reference to FIG. 31, the pump-outlet tube may curve by virtue of one or more bands being bonded to the outer wall of the pump-outlet tube.

Due to the curvature of the pump-outlet tube, the orientation-biasing properties of the aramid may be particularly helpful. For example, the aramid fiber may bias the orientation of the delivery tube such that, while the delivery tube traverses the aortic arch (and the aramid fiber biases the roll angle of the delivery tube such that the aramid fiber is disposed at the inside of the curve of the aortic arch), the pump-outlet tube curves away from the posterior wall and/or septal wall 338 of the left ventricle. Alternatively or additionally, the aramid fiber may bias the orientation of the delivery tube such that, while the delivery tube traverses the aortic arch (and the aramid fiber biases the roll angle of the delivery tube such that the aramid fiber is disposed at the inside of the curve of the aortic arch), the pump-outlet tube curves toward apex 342 and/or free wall 334 of the left ventricle.

In some embodiments, the circumferential angle between the aramid fiber and the circumferential position on the pump-outlet tube at the inside of the curve of the pump-outlet tube is close to zero, e.g., between-10 and 10 degrees. In other words, the aramid fiber is positioned at or near the inside of the curve, such that the delivery tube curves in the same direction as the pump-outlet tube. This feature may further help orient the blood pump in the desired orientation.

As described hereinabove, for some applications, distal-tip portion is configured to curve within a plane. For example, within a given plane, the distal tip portion may have a curvature such as that described hereinabove with reference to FIGS. 17A-C. For some applications, the plane in which distal-tip portion 120 curves is disposed at a roll angle theta with respect to a (hypothetical) line extending from a distal end 292*d* of the aramid fiber (which extends out of the page in distal-end view 294). For some applications, the angle theta is between 25 and 65 degrees, such as between 35 and 55 degrees. Typically, the angle theta is selected such that while the delivery tube traverses the aortic arch (and the aramid fiber biases the roll angle of the delivery tube such that the aramid fiber is disposed at the inside of the curve of the aortic arch), the plane in which the distal-tip portion curves is disposed at an orientation with respect to the apex of the left ventricle that is such that the distal-tip portion provides the functionalities of the distal-tip portion that are described hereinabove with reference to FIGS. 17A-C.

FIG. 30 shows an embodiment in which the aramid fiber is parallel to the longitudinal axis 296 of the delivery tube. In other embodiments, at least a portion of the aramid fiber is not parallel to longitudinal axis 296. Thus, in addition to biasing the roll angle of the delivery tube, the aramid fiber may twist the delivery tube. For some applications, this portion of the aramid fiber is configured to twist a portion of the delivery tube that passes through the ascending aorta in the vicinity of the aortic valve, such as to conform with the anatomical twist of this portion of the aorta. For some applications, the length of this non-parallel portion is between 5 and 20 cm (e.g., between 8 and 12 cm), and/or the circumferential span of the portion is between 30 and 60 (e.g., between 35 and 55) degrees.

It is noted that aramid fiber 292 may be used to bias the orientation of delivery tube 142 regardless of the type of device coupled to the distal end of the delivery tube. In fact, the aramid fiber may be used even if no device at all is coupled to the distal end of the delivery tube. Moreover, the delivery tube may extend into any chamber of the heart. Furthermore, it is noted that although some embodiments have been described with reference to an aramid fiber, the scope of the present disclosure includes using other types of elongation-resistant fibers (e.g., polymeric and/or natural fibers) and/or elongation-resistant wires to provide the functionalities described hereinabove both with reference to fiber 159 (shown in FIG. 13) and with reference to fiber 292 (shown in FIG. 30).

Figure 31:
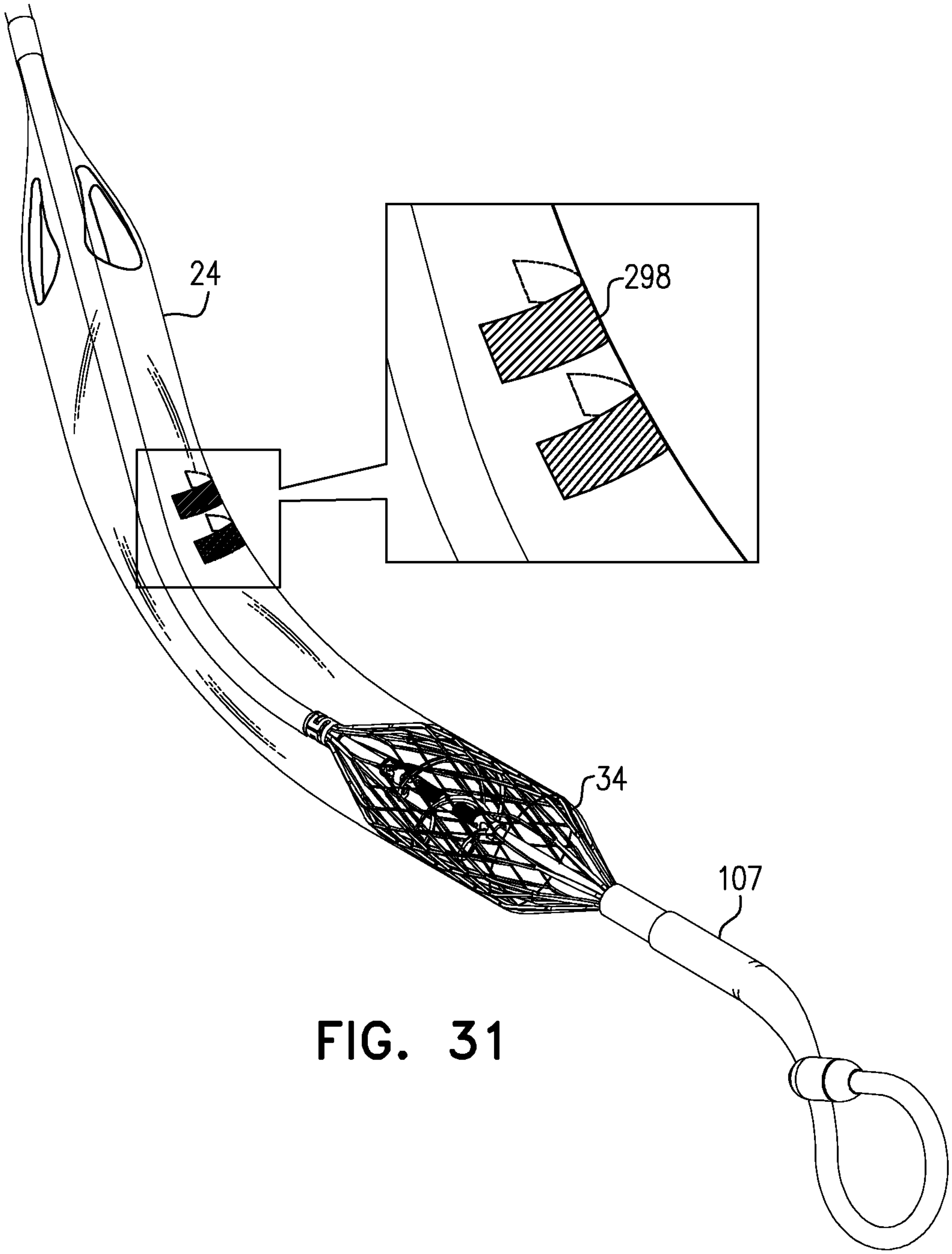
FIG. 31 is a schematic illustration of a left-ventricular assist device that includes bands on a pump-outlet tube, in accordance with some applications of the present invention.

Reference is now made to FIG. 31, which is a schematic illustration of a left-ventricular assist device comprising a curved pump-outlet tube 24, in accordance with some applications of the present invention.

As noted above, frame 34 is disposed at least partly within the distal portion of pump-outlet tube 24 and is configured to hold the distal portion of the pump-outlet tube open. The impeller is disposed within frame 34 and is configured to pump blood of the subject, through the pump-outlet tube, from the left ventricle into the aorta, thereby maintaining the proximal portion of the pump-outlet tube, which is proximal to the frame and traverses the aortic valve, in an open state.

In some embodiments, the left-ventricular assist device comprises one or more (e.g., 1-8) bands 298, each of which is bonded to the outer wall of the proximal portion of the pump-outlet tube, without extending around the full circumference of the pump-outlet tube. For example, each of the bands may extend around 20-80% of the full circumference of the pump-outlet tube. Thus, while the proximal portion of the pump-outlet tube remains open by virtue of the blood flowing proximally through the tube, the proximal portion of the pump-outlet tube curves at respective locations of bands 298.

Advantageously, the curvature of the proximal portion of the pump-outlet tube helps orient the distal portion of the pump-outlet tube. For example, by virtue of the proximal portion of the pump-outlet tube curving at the locations of the bands, the distal portion of the pump-outlet tube may point toward apex 342 or toward free wall 334 (FIG. 30).

In some embodiments, bands 298 are polymeric.

In some embodiments, as described above with reference to FIGS. 9A-B, bands 298 couple blood-pressure-measurement tube 222 and/or optical fiber 228 to the outer wall of the proximal portion of the pump-outlet tube.

In some embodiments, two or more bands 298 are spaced from one other, along the length of the pump-outlet tube, by 1-5 mm. In some embodiments, two or more bands 298 are displaced circumferentially from one another, e.g., by 20-120 degrees. Advantageously, this circumferential displacement may provide a twist to the pump-outlet tube upon blood being pumped through the pump-outlet tube, thus orienting the pump-outlet tube even more precisely. For some applications, the axial spacing between adjacent bands is non-uniform along the length of the pump-outlet tube, in such a manner that it causes different regions of the pump-outlet tube to assume respective degrees of curvature upon blood being pumped through the pump-outlet tube.

Figure 32A:
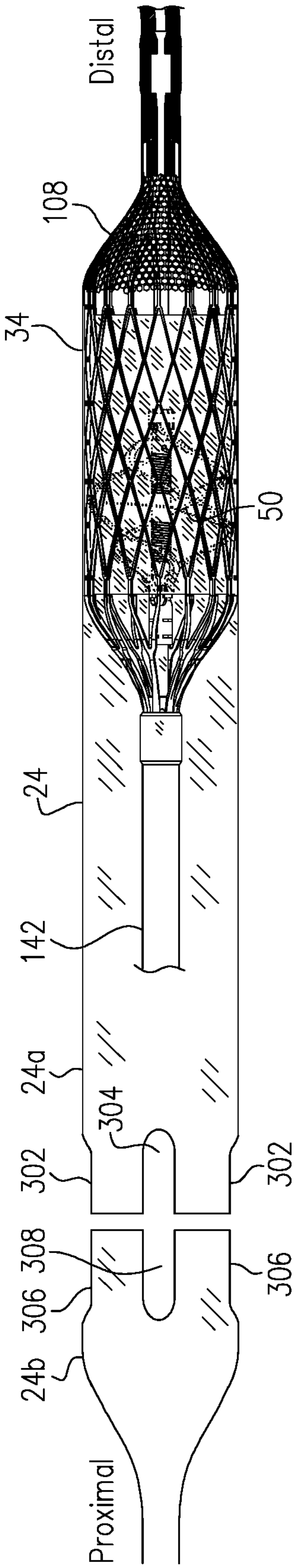
FIGS. 32A and 32B collectively show an assembly of part of a left-ventricular assist device, in accordance with some applications of the present invention.
Figure 32B:
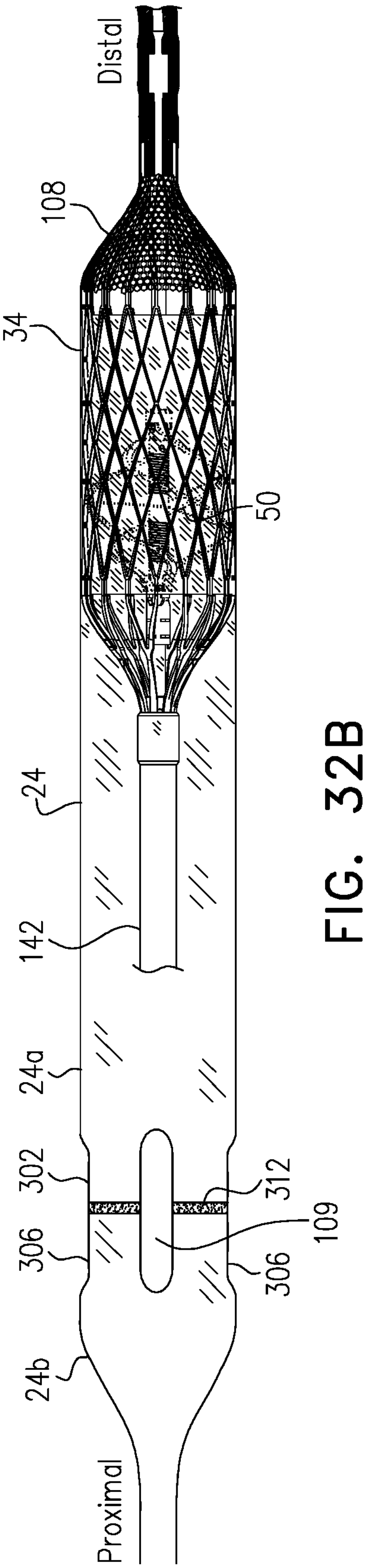

Reference is now made to FIGS. 32A-B, which collectively show an assembly of part of a left-ventricular assist device, in accordance with some applications of the present invention.

In some embodiments, as shown in FIG. 32A, prior to the assembly of the left-ventricular assist device, a first section **24*a* of pump-outlet tube 24 is separate from a second section 24*b* of the pump-outlet tube. The proximal end of first section 24*a* comprises multiple tabs 302, and is shaped to define respective gaps 304 between successive ones of tabs 302. Likewise, second section 24*b* comprises multiple tabs 306 and is shaped to define respective gaps 308 between successive ones of tabs 306**.

To assemble the left-ventricular assist device, impeller 50 (and frame 34) are passed through the proximal end of first section **24*a*, such that impeller 50 (and frame 34) are disposed within first section 24*a*. Next, as shown in FIG. 32B, second section 24*b* is bonded to first section 24*a* such that tabs 306 overlap tabs 302 (either inside or outside tabs 302) and gaps 308 are continuous with gaps 304 so as to define one or more blood-outlet openings 109 that are laterally facing (by virtue of being defined by the central cylindrical portion of pump-outlet tube 24). Advantageously, the overlap 312 between the tabs may help maintain the structural integrity of the pump-outlet tube, even as blood flows through blood-outlet openings 109**. In some embodiments, the first section and second section overlap one another by 0.25-1 mm.

Following the assembly of the left-ventricular assist device, the pump-outlet tube may be inserted, through the aorta of the subject, into the left ventricle of the subject's heart such that the pump-outlet tube traverses the aortic valve of the subject with blood-outlet openings 109 being disposed within the aorta. While the pump-outlet tube is positioned in this manner, the impeller may pump blood of the subject, through blood-outlet openings 109, from the left ventricle into the aorta.

In some embodiments, the blood-outlet openings occupy 20-80% of the circumference of the pump-outlet tube. Advantageously, although overlap 312 between the tabs adds to the minimum diameter to which this region of the pump-outlet tube can be radially constrained, within this region the blood-outlet openings occupy much of the circumference of the pump-outlet tube. Thus, overall this region does not increase the minimum diameter to which the pump-outlet tube can be radially constrained. More generally, typically, overlap 312 between the tabs provides the pump-outlet tube with the right balance between strength and crimpability.

As noted above, the pump-outlet tube may be configured to curve proximally to the impeller, e.g., by virtue of being pre-shaped, by virtue of blood-outlet openings 109 being arranged in a non-axisymmetric arrangement, by virtue of blood-inlet openings 108 being arranged in a non-axisymmetric arrangement, and/or by virtue of bands 298 (FIG. 31) being bonded to the outer wall of the pump-outlet tube. Alternatively or additionally, any of the embodiments described with reference to FIGS. 32A-B may be combined with any of those described with reference to FIGS. 19A-B, FIGS. 20A-D, or FIG. 29.

Figure 33A:
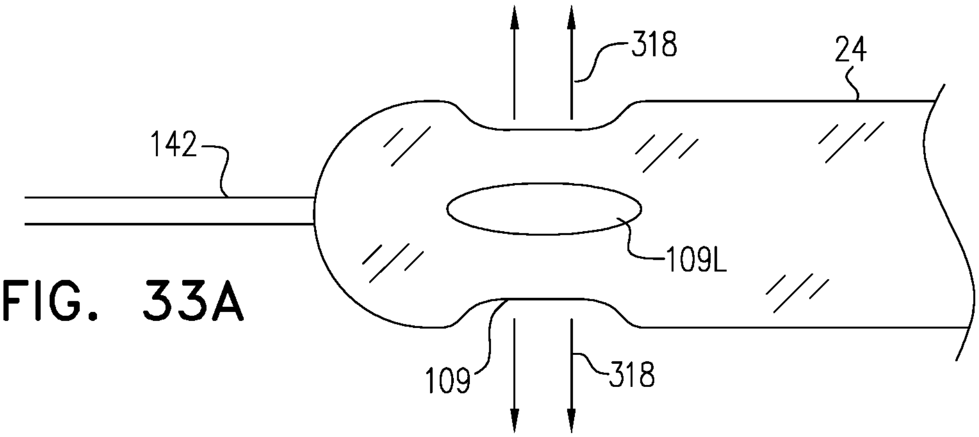
FIGS. 33A, 33B, and 33C are schematic illustrations of a proximal end of a pump-outlet tube, in accordance with some applications of the present invention.
Figure 33B:
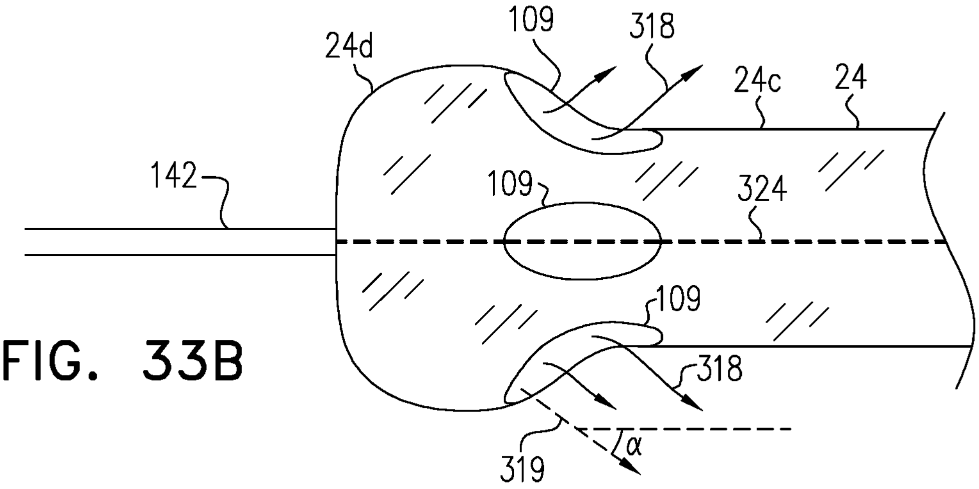
Figure 33C:
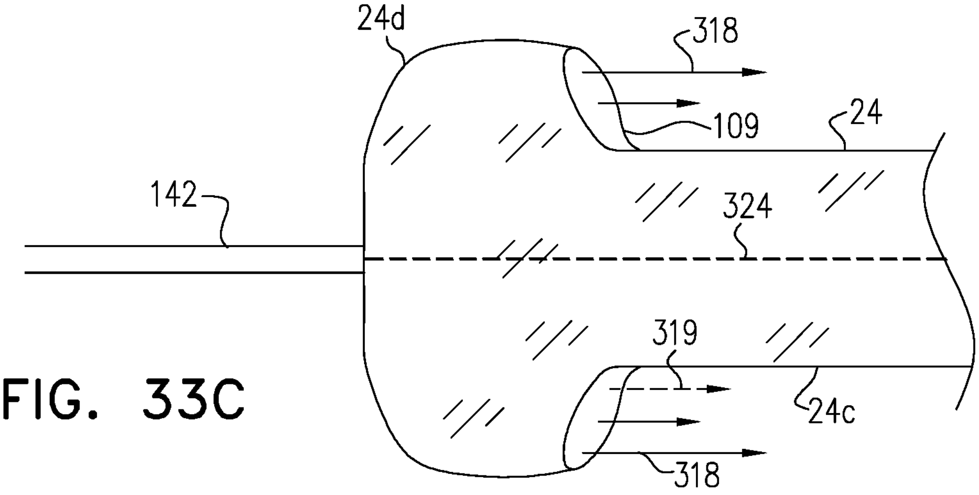

Reference is now made to FIGS. 33A-C, which are schematic illustrations of pump-outlet tube 24, in accordance with different respective applications of the present invention.

Pump-outlet tube 24 may be configured in various ways so as to provide various directions of blood flow from the pump-outlet tube into the aorta.

In FIG. 33A, pump-outlet tube 24 is shaped to define blood-outlet openings 109 that are laterally facing (by virtue of being defined by the central cylindrical portion of pump-outlet tube 24), such that, as indicated by blood-flow arrows 318, blood flows laterally from the tube into the aorta while the blood-outlet openings are disposed within the aorta.

In FIGS. 33B-C, on the other hand, pump-outlet tube 24 comprises a narrower section 24*c*, in which the impeller is disposed, and a wider section 24*d*, which is proximal to and wider than narrower section 24*c*. Wider section 24*d* is shaped to define at least a portion of each blood-outlet opening 109 such that a normal vector 319 to the portion of the blood-outlet opening has a distally-facing component. Thus, as indicated by blood-flow arrows 318, the direction of blood flow from the tube into the aorta has a distal component. Given that the pumping of blood produces a distal thrust on the pump-outlet tube, this distal component may be advantageous in that, by virtue of the distally-facing component, the flow of blood through the blood-outlet openings may produce a proximal thrust on the pump-outlet tube that at least partially cancels the distal thrust.

In some embodiments, each of the blood-outlet openings spans the interface between narrower section 24*c* and wider section 24*d*. In other embodiments, each of the blood-outlet openings is positioned entirely within the wider section.

In some embodiments, as shown in FIG. 33B, the angle α between normal vector 319 and longitudinal axis 324 of the pump-outlet tube at the wider section is between 20 and 80 degrees. In other embodiments, as shown in FIG. 33C, the normal vector is parallel to the longitudinal axis of the pump-outlet tube at wider section 24*d*.

In some embodiments, wider section 24*d* is folded inwardly so as to define one or more surfaces 322 configured to direct the blood through blood-outlet openings 109, as described above with reference to FIG. 29. Alternatively or additionally, the embodiments shown in FIGS. 33B-C may be combined with those shown in FIGS. 32A-B, i.e., first section 24*a* may be identical to narrower section 24*c*, and second section 24*b* may be identical to wider section 24*d*.

With regards to all aspects of ventricular assist device 20 described with reference to FIGS. 1A-33C, it is noted that, although FIGS. 1A and 1B show ventricular assist device 20 in the subject's left ventricle, for some applications, ventricular assist device 20 is placed inside the subject's right ventricle, such that the device traverses the subject's pulmonary valve, and techniques described herein are applied, mutatis mutandis. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. Such aspects may include features of tube 24 (e.g., the curvature of the tube), impeller 50, features of pump-head portion 27, drive cable 130, etc. Alternatively or additionally, device 20 and/or a portion thereof (e.g., impeller 50, even in the absence of tube 24) is placed inside a different portion of the subject's body, in order to assist with the pumping of blood from that portion. For example, device 20 and/or a portion thereof (e.g., impeller 50, even in the absence of tube 24) may be placed in a blood vessel and may be used to pump blood through the blood vessel. For some applications, device 20 and/or a portion thereof (e.g., impeller 50, even in the absence of tube 24) is configured to be placed within the subclavian vein or jugular vein, at junctions of the vein with a lymph duct, and is used to increase flow of lymphatic fluid from the lymph duct into the vein, mutatis mutandis. Since the scope of the present invention includes using the apparatus and methods described herein in anatomical locations other than the left ventricle and the aorta, the ventricular assist device and/or portions thereof are sometimes referred to herein (in the specification and the claims) as a blood pump.

The scope of the present invention includes combining any of the apparatus and methods described herein with any of the apparatus and methods described in one or more of the following applications, all of which are incorporated herein by reference:

- U.S. application Ser. No. 18/447,025 to Tuval, entitled "Ventricular assist device with motion-cushioning spring," which is a continuation of International Application PCT/IB2022/058101 to Tuval (published as WO 23/062453), entitled "Ventricular assist device," filed Aug. 30, 2022, which claims priority from:
  - U.S. Provisional Patent Application 63/254,321 to Tuval, entitled "Ventricular assist device," filed Oct. 11, 2021, and
  - U.S. Provisional Patent Application 63/317,199 to Tuval, entitled "Ventricular assist device," filed Mar. 7, 2022;
- US 2023/0226342 to Tuval, entitled "Ventricular assist device," which is the US national phase of International Application No. PCT/IB2022/051990 to Tuval (published as WO 22/189932), entitled "Ventricular assist device," filed Mar. 7, 2022, which claims priority from:
  - U.S. Provisional Patent Application 63/158,708 to Tuval, entitled "Ventricular assist device," filed Mar. 9, 2021, and
  - U.S. Provisional Patent Application 63/254,321 to Tuval, entitled "Ventricular assist device," filed Oct. 11, 2021;
- US 2023/0137473 to Zipory, entitled "Centrifugal and mixed-flow impellers for use with a blood pump," which is the US national phase of International Application No. PCT/IB2021/052590 to Zipory (published as WO 21/198881), entitled "Centrifugal and mixed-flow impellers for use with a blood pump," filed Mar. 29, 2021, which claims priority from U.S. 63/003,955 to Zipory, entitled "Ventricular assist device," filed Apr. 2, 2020;
- US 2022/0226632 to Tuval, entitled "Ventricular assist device," which is the US national phase of PCT Application No. PCT/IB2021/052857 (published as WO 21/205346), filed Apr. 6, 2021, which claims priority from:
  - U.S. Provisional Patent Application 63/006,122 to Tuval, entitled "Ventricular assist device," filed Apr. 7, 2020,
  - U.S. Provisional Patent Application 63/114,136 to Tuval, entitled "Ventricular assist device," filed Nov. 16, 2020, and U.S. Provisional Patent Application 63/129,983 to Tuval, entitled "Ventricular assist device," filed Dec. 23, 2020;

US 2020/0237981 to Tuval, entitled "Distal tip element for a ventricular assist device," filed Jan. 23, 2020, which claims priority from:

U.S. Provisional Patent Application 62/796,138 to Tuval, entitled "Ventricular assist device," filed Jan. 24, 2019, U.S. Provisional Patent Application 62/851,716 to Tuval, entitled "Ventricular assist device," filed May 23, 2019, U.S. Provisional Patent Application 62/870,821 to Tuval, entitled "Ventricular assist device," filed Jul. 5, 2019, and U.S. Provisional Patent Application 62/896,026 to Tuval, entitled "Ventricular assist device," filed Sep. 5, 2019;

US 2019/0209758 to Tuval, which is a continuation of International Application No. PCT/IB2019/050186 to Tuval (published as WO 19/138350), entitled "Ventricular assist device," filed Jan. 10, 2019, which claims priority from:

U.S. Provisional Patent Application 62/615,538 to Sohn, entitled "Ventricular assist device," filed Jan. 10, 2018, U.S. Provisional Patent Application 62/665,718 to Sohn, entitled "Ventricular assist device," filed May 2, 2018, U.S. Provisional Patent Application 62/681,868 to Tuval, entitled "Ventricular assist device," filed Jun. 7, 2018, and U.S. Provisional Patent Application 62/727,605 to Tuval, entitled "Ventricular assist device," filed Sep. 6, 2018;

US 2019/0269840 to Tuval, which is the US national phase of International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

US 2019/0175806 to Tuval, which is a continuation of International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543,540 to Tuval, filed Aug. 10, 2017;

US 2019/0239998 to Tuval, which is the US national phase of International Patent Application PCT/IL2017/051092 to Tuval (published as WO 18/061002), filed Sep. 28, 2017, entitled "Blood vessel tube," which claims priority from U.S. Provisional Patent Application 62/401,403 to Tuval, filed Sep. 29, 2016;

US 2018/0169313 to Schwammenthal, which is the US national phase of International Patent Application PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump;"

US 2017/0100527 to Schwammenthal, which is the US national phase of International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

U.S. Pat. No. 10,039,874 to Schwammenthal, which is the US national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:

a blood pump, comprising:

an axial shaft configured for insertion into, and rotation within, a body of a subject;

an impeller coupled to the axial shaft such that, as the axial shaft rotates, the impeller pumps blood of the subject;

a thrust bearing comprising a proximally-facing ceramic surface and disposed distally from the axial shaft so as to inhibit distal movement of the axial shaft beyond the thrust bearing; and a distally-facing ceramic cover that covers a distal end of the axial shaft, such that the ceramic cover contacts the ceramic surface as the axial shaft rotates;

a ceramic cap that comprises the ceramic cover and fits around the distal end of the axial shaft;

a distal radial bearing configured to radially stabilize the axial shaft while the axial shaft rotates, wherein the ceramic cap comprises a ceramic sleeve that is configured to cover a distal portion of the axial shaft that rotates within the distal radial bearing as the axial shaft rotates.

2. The apparatus according to claim 1, further comprising a drive cable, wherein the axial shaft is coupled to the drive cable such that the axial shaft rotates with the drive cable.

3. The apparatus according to claim 1, further comprising a drive cable, wherein the axial shaft is a distal portion of the drive cable.

4. The apparatus according to claim 1, wherein the thrust bearing comprises a piece of ceramic comprising the proximally-facing ceramic surface.

5. The apparatus according to claim 1, wherein the thrust bearing is coated with a ceramic coating and wherein the thrust bearing comprises the proximally-facing ceramic surface by virtue of being coated with the ceramic coating.

6. The apparatus according to claim 1, wherein the proximally-facing ceramic surface comprises zirconia.

7. The apparatus according to claim 1, wherein the distally-facing ceramic cover comprises zirconia.

8. The apparatus according to claim 1, wherein the blood pump further comprises a distal bearing housing that houses the thrust bearing and the distal radial bearing that is housed within the distal bearing housing and is configured to radially stabilize the axial shaft while the axial shaft rotates.

9. The apparatus according to claim 1, wherein the axial shaft is configured for insertion, over a guidewire, and is shaped to define a shaft lumen for passage of the guidewire therethrough, and the thrust bearing is shaped to define a bearing lumen that is configured to be continuous with the shaft lumen.

10. The apparatus according to claim 9, wherein at least a portion of the bearing lumen is frustoconically-shaped, a wider end of the bearing lumen facing distally.

11. The apparatus according to claim 9, wherein the bearing lumen is a first bearing lumen, and wherein the thrust bearing is further shaped to define at least one second bearing lumen configured for proximal flow of a purging fluid, through the second bearing lumen, into an interface between the axial shaft and the thrust bearing.

12. The apparatus according to claim 1, wherein the ceramic cover and the ceramic sleeve are combined into a single element.

13. The apparatus according to claim 1, wherein the ceramic cover is separate from the ceramic sleeve, and wherein the ceramic cover is coupled to the ceramic sleeve.

14. An apparatus, comprising:

a blood pump, comprising:

an axial shaft configured for insertion into, and rotation within, a body of a subject, wherein the axial shaft is configured for insertion, over a guidewire, and is shaped to define a shaft lumen for passage of the guidewire therethrough;

an impeller coupled to the axial shaft such that, as the axial shaft rotates, the impeller pumps blood of the subject;

a thrust bearing comprising a proximally-facing ceramic surface and disposed distally from the axial shaft so as to inhibit distal movement of the axial shaft beyond the thrust bearing, wherein the thrust bearing is shaped to define a bearing lumen that is configured to be continuous with the shaft lumen, and wherein at least a portion of the bearing lumen is frustoconically-shaped, a wider end of the bearing lumen facing distally; and a distally-facing ceramic cover that covers a distal end of the axial shaft, such that the ceramic cover contacts the ceramic surface as the axial shaft rotates.

15. The apparatus according to claim 14, further comprising a drive cable, wherein the axial shaft is coupled to the drive cable such that the axial shaft rotates with the drive cable.

16. The apparatus according to claim 14, further comprising a drive cable, wherein the axial shaft is a distal portion of the drive cable.

17. The apparatus according to claim 14, wherein the thrust bearing comprises a piece of ceramic comprising the proximally-facing ceramic surface.

18. The apparatus according to claim 14, wherein the thrust bearing is coated with a ceramic coating and wherein the thrust bearing comprises the proximally-facing ceramic surface by virtue of being coated with the ceramic coating.

19. The apparatus according to claim 14, wherein the proximally-facing ceramic surface comprises zirconia.

20. The apparatus according to claim 14, wherein the distally-facing ceramic cover comprises zirconia.

21. The apparatus according to claim 14, wherein the blood pump further comprises a distal bearing housing that houses the thrust bearing and a distal radial bearing that is housed within the distal bearing housing and is configured to radially stabilize the axial shaft while the axial shaft rotates.

22. The apparatus according to claim 14, wherein the bearing lumen is a first bearing lumen, and wherein the thrust bearing is further shaped to define at least one second bearing lumen configured for proximal flow of a purging fluid, through the second bearing lumen, into an interface between the axial shaft and the thrust bearing.

23. The apparatus according to claim 14, wherein the blood pump comprises a ceramic cap that comprises the ceramic cover and fits around the distal end of the axial shaft.

24. The apparatus according to claim 23, wherein the blood pump comprises a distal radial bearing configured to radially stabilize the axial shaft while the axial shaft rotates and wherein the ceramic cap comprises a ceramic sleeve that is configured to cover a distal portion of the axial shaft that rotates within the distal radial bearing as the axial shaft rotates.

25. An apparatus, comprising:

a blood pump, comprising:

an axial shaft configured for insertion into, and rotation within, a body of a subject, wherein the axial shaft is configured for insertion, over a guidewire, and is shaped to define a shaft lumen for passage of the guidewire therethrough;

an impeller coupled to the axial shaft such that, as the axial shaft rotates, the impeller pumps blood of the subject;

a thrust bearing comprising a proximally-facing ceramic surface and disposed distally from the axial shaft so as to inhibit distal movement of the axial shaft beyond the thrust bearing, wherein the thrust bearing is shaped to define a first bearing lumen that is configured to be continuous with the shaft lumen, and wherein the thrust bearing is shaped to define at least one second bearing lumen configured for proximal flow of a purging fluid, through the second bearing lumen, into an interface between the axial shaft and the thrust bearing; and a distally-facing ceramic cover that covers a distal end of the axial shaft, such that the ceramic cover contacts the ceramic surface as the axial shaft rotates.

* * * * *